(12) United States Patent
Hilton et al.

(10) Patent No.: US 7,049,418 B2
(45) Date of Patent: May 23, 2006

(54) THERAPEUTIC AND DIAGNOSTIC AGENTS COMPRISING A SOCS BOX

(75) Inventors: Douglas J. Hilton, Warrandyte (AU); Warren S. Alexander, Moonee Ponds (AU); Elizabeth M. Viney, Bundoora (AU); Tracy A. Willson, North Balwyn (AU); Rachael T. Richardson, East Brighton (AU); Robyn Starr, Carlton (AU); Sandra E. Nicholson, Newport (AU); Donald Metcalf, Balwyn (AU); Nicos A. Nicola, Mont Albert (AU)

(73) Assignee: The Walter and Eliza Hall Institute of Medical Research, Parkville (AU)

( * ) Notice: Subject to any disclaimer, the term of this patent is extended or adjusted under 35 U.S.C. 154(b) by 479 days.

(21) Appl. No.: 09/908,805

(22) Filed: Jul. 19, 2001

(65) Prior Publication Data

US 2002/0147307 A1 Oct. 10, 2002

Related U.S. Application Data

(60) Division of application No. 09/302,769, filed on Apr. 30, 1999, now Pat. No. 6,323,317, which is a continuation-in-part of application No. 08/962,560, filed on Oct. 31, 1997.

(60) Provisional application No. 60/083,807, filed on May 1, 1998.

(30) Foreign Application Priority Data

Feb. 14, 1997 (AU) .............................................. PO5117

(51) Int. Cl.
*C07H 17/00* (2006.01)

(52) U.S. Cl. .................................................... 536/23.1
(58) Field of Classification Search ................ 536/23.1; 530/350, 300
See application file for complete search history.

(56) References Cited

FOREIGN PATENT DOCUMENTS

| EP | 0 989 186 A1 | 3/2000 |
|---|---|---|
| WO | WO 98/30688 | 7/1998 |
| WO | WO 99/03993 | 1/1999 |

OTHER PUBLICATIONS

Accession No. Z47352, ID: MMPRMGNS (1995), XP–002165867 (Abstract).
Schlüter, G. et al., "Sequence Analysis of the Conserved Protamine Gene Cluster Shows That it Contains a Fourth Expressed Gene", *Molecular Reproduction and Development* 43:1–6 (1996), XP–000993037.
Accession No. Z46940, ID: HSPRMTNP2 (1995), XP–002165868 (Abstract).
Accession No. Z46939; ID: BTPRMTNP2 (1995), XP–002165869 (Abstract).
Yoshimura, A. et al., "A Novel Cytokine–Inducible Gene CIS Encodes an SH2–Containing Protein that Binds to Tyrosine–Phosphorylated Interleukin 3 and Erythropoietin Receptors", *The EMBO Journal* 14(12):2816–2826 (1995), XP–002088456.
Minamoto, S. et al., "Cloning and Functional Analysis of New Members of STAT Induced STAT Inhibitor (SSI) Family: SSI–2 and SSI–3", *Biochemical and Biophysical Research Communications* 237:79–83 (1997), XP–002095406.
Fu, X. et al., "E2a–Pbx1 Induces Aberrant Expression of Tissue–Specific and Developmentally Regulated Genes When Expressed in NIH 3T3 Fibroblasts", *Molecular and Cellular Biology* 17(3):1503–1512 (1997),XP–002172402.
Starr, R et al., "A Family of Cytokine–Inducible Inhibitors of Signalling", *Nature* 387:917–921 (1997), XP–002085491.
Endo, T.A. et al., "A New Protein Containing an SH2 Domain that Inhibits JAK Kinases", *Nature* 387:921–924 (1997), XP–002085492.
Naka, T. et al., "Structure and Function of a New STAT–Inducted STAT Inhibitor", *Nature* 387:924–928 (1997), XP–002088455.
Accession No. AA189608, ID: MMAA81160 (1997), XP–002172404 (Abstract).
Hilton, D.J. et al., "Twenty Proteins Containing a C–Terminal SOCS Box Form Five Structural Classes", *Proceedings of the National Academy of Sciences of USA* 95:114–119 (1998), XP–002085497.
Watson et al., "Molecular Biology of the Gene", 4th edition (1987).
Hilton et al., "Twenty Proteins Containing a C–Terminal SOCS Box Form Five Structural Classes", *Proc Natl. Acad Science USA* 95:114–119 (1998).
Accession No. U72673, ID: MMU72673 (1997), XP–002172403 (Abstract).
W.S. Alexander et al. (1995) "Point Mutations Within a Dimer Interface Homology Domain of c–Mpl Induce Constitutive Receptor Activity and Tumorigenicity" *The Embo Journal* 14: 5569–5578.
S.F. Altschul et al. (1990) "Basic Local Alignment Search Tool" *J. Mol. Biol.* 215: 403–410.

(Continued)

*Primary Examiner*—Karen Cochrane Carlson
(74) *Attorney, Agent, or Firm*—Scully, Scott, Murphy & Presser

(57) ABSTRACT

The present invention relates generally to therapeutic and diagnostic agents. More particularly, the present invention provides therapeutic molecules capable of modulating signal transduction such as but not limited to cytokine-mediated signal transduction. The molecules of the present invention are useful, therefore, in modulating cellular responsiveness to cytokines as well as other mediators of signal transduction such as endogenous or exogenous molecules, antigens, microbes and microbial products, viruses or components thereof, ions, hormones and parasites.

6 Claims, 93 Drawing Sheets

OTHER PUBLICATIONS

J.F. Bazan (1990) "Haemopoietic Receptors and Helical Cytokines" *Immunology Today* 11 (10): 350–354.

R.L. Cutler et al. (1993) "Multiple Cytokines Induce the Tyrosine Phosphorylation of She and its Association With Grb2 . . ." *The Journal of Biological Chemistry* 268 (20): 21463–21465.

J.E. Darnell, Jr. et al. (1984) "Jak–STAT Pathways and Transcriptional Activation in Response to IFNs and Other Extracellular Signaling Proteins" *Science* 264: 1415–1421.

M. David et al. (1995) "Requirement for MAP Kinase (ERK2) Activity in Interferon—alpha and Interferon—beta Stimulated Gene Expression Through STAT Proteins" *Science* 269: 1721–1723.

M. David et al. (1996) "STAT Activation by Epidermal Growth Factor (EGF) and Amphiregulin" *The Journal of Biological Chemistry* 271 (16): 9185–9188.

A. Dugaiczyk et al. (1983) "Cloning and Sequencing of a Deoxyribonucleic Acid Copy of Glyceraldehyde–3–phosphate Dehydrogenase Messenger Ribonucleic Acid . . ." *Biochemistry* 22: 1605–1613.

J.E. Durbin et al. (1996) "Targeted Disruption of the Mouse Stat1 Gene Results in Compromised Innate Immunity to Viral Disease" *Cell* 84: 443–450.

T. Etzold et al. (1996) "SRS: Information Retrieval System for Molecular Biology Data Banks" *Methods in Enzymology* 266: 114–128.

S. Gupta et al. (1996) "The SH2 Domains of Stat1 and Stat2 Mediate Multiple Interactions in the Transduction of IFN–Signals" *The EMBO Journal* 15 (5): 1075–1084.

D.J. Hilton (1994) "An Introduction to Cytokine Receptors" *Guidebook to Cytokines and Their Receptors* Oxford, England: Oxford University Press.

D.J. Hilton et al. (1994) "Cloning of a Murine IL–II Receptor –chain; Requirement for gp130 for High Affinity Binding and Signal Transduction" *The EMBO Journal* 13 (20): 4765–4775.

D.J. Hilton et al. (1996) "Saturation Mutagenesis of the WSXWS Motif of the Erythropoietin Receptor*" *The Journal of Biological Chemistry* 271 (9): 4699–4708.

Y. Ichikawa (1969) "Differentiation of a Cell Line of Myeloid Leukemia" *J. Cell. Physiol.* 74: 223–234.

JN. Ihle (1995) "Cytokine Receptor Signalling" *Nature* 377: 591–594.

M.H. Kaplan et al. (1996) "Stat6 is Required for Mediating Responses to IL–4 and for the Development of Th2 Cells" *Immunity* 4: 313–319.

M.H. Kaplan et al. (1996) "Impaired IL–12 Responses and Enhanced Development of Th2 Cells in Stat4–deficient Mice" *Nature* 382: 174–179.

D.W. Leaman et al. (1996) "Roles of JAKs in Activation of STATs and Stimulation of c–fos Gene Expression by Epidermal Growth Factor" *Mollecular and Cellular Biology* 16 (1): 369–375.

M.A. Meraz et al. (1996) "Targeted Disruption of the Stat1 Gene in Mice Reveals Unexpected Physiologic Specificity in the JAK–STAT Signaling Pathway" *Cell* 84: 431–442.

S. Mizushima and S. Nagata (1990) "pEF–BOS, A Powerful Mammalian Expression Vector" *Nucleic Acids Research* 18 (17): 5322.

M. Murakami et al. (1991) "Critical Cytoplasmic Region of the Interleukin 6 Signal Transducer gp130 is Conserved in the Cytokine Receptor Family" *Proc. Nat'l. Acad. Sci. USA* 88: 11349–11353.

E.J. Neer et al. (1994) "The Ancient Regulatory–protein Family of WD–repeat Proteins" *Nature* 371: 297–300.

N.A. Nicola et al. (1996) "Molecular Cloning of Two Novel Transmembrane Ligands for Eph–related Kinases (LERKS) That Are Related to LERK–2" *Growth Factors* 13: 141–149.

U. Novak et al. (1995) "Colony–stimulating Factor 1–Induced STAT1 and STAT3 Activation Is Accompanied by Phosphorylation of Tyk2 in Macrophages and Tyk2 and JAK1 in Fibroblasts" *Blood* 86 (8): 2948–2956.

W.R. Pearson et al. (1988) "Improved Tools for Biological Sequence Comparison" *Proc. Nat'l. Acad. Sci. USA* 85: 2444–2448.

W.R. Pearson (1990) "Rapid and Sensitive Sequence Comparison With FASTP and FASTA" *Methods in Enzymology* 183: 63–99.

J.R. Rayner and T.J. Gonda (1994) "A Simple and Efficient Procedure for Generating Stable Expression Libraries by cDNA in a Retroviral Vector" *Molecular and Cellular Biology* 14 (2): 880–887.

N. Sato et al. (1993) "Signal Transduction by the High–affinity GM–CSF Receptor: Two Distinct Cytoplasmic Regions of the Common B–Subunit Responsible for Different Signaling" *The EMBO Journal* 12 (11): 4181–4189.

K. Shimoda et al. (1996) "Lack of IL–4–induced Th2 Response and IgE Class Switching in Mice With Disrupted Stat6 Gene" *Nature* 380: 630–633.

K. Shual et al. (1993) "Polypeptide Signalling to the Nucleus Through Tyrosine Phosphorylation of Jak and Stat Proteins" *Nature* 366: 580–583.

S.R. Sprang et al. (1993) "Cytokine Structure Taxonomy and Mechanisms for Receptor Engagement" *Current Opinion in Structural Biology* 3: 815–827.

K. Takeda et al. (1996) "Essential Role of Stat6 in IL–4 Signalling" *Nature* 380: 627–630.

W.E. Thierfelder et al. (1996) "Requirement for Stat4 in Interleukin–12–mediated Responses of Natural Killer and T–Cells" *Nature* 382: 171–174.

H. Wakao et al. (1994) "Mammary Gland Factor (MGF) Is a Novel Member of the Cytokine Regulated Transcription Factor Gene Family and Confers the Prolactin Response" *The EMBO Journal* 13 (9): 2182–2191.

Z. Wen et al. (1995) "Maximal Activation of Transcription by Stat1 and Stat3 Requires Both Tyrosine and Serine Phosphorylation" *Cell* 82: 241–250.

Y. Taolin et al. (1993) "Hematopoietic Cells Phosphatase Associates With the Interleukin–3 (IL–3) Receptor B–Chain and Down–regulates Il–3–Induced Tyrosine Phosphorylation andMitogenesis" *Molecular and Cellular Biology* 13 (12): 7577–7586.

A. Yoshimura et al. (1995) "A Novel Cytokine–Inducible Gene CIS Encodes An SH2–containing Protein That Binds to Tyrosine–phosphorylated Interleukin 3 and Erythropoietin Receptors" *The EMBO Journal* 14 (12): 2816–2826.

```
-159                             cgaggctcaagctccgggcggattctgcgtgccgctctcg
-120   ctccttggggtctgttggccggcctgtgccacccggacgcccggctcactgcctctgtct
 -60   cccccatcagcgcagccccggacgctatggcccaccccctccagctggcccctcgagtagg
```

```
   1   ATGGTAGCACGCAACCAGGTGGCAGCCGACAATGCGATCTCCCCGGCAGCAGAGCCCCGA
   1   MetValAlaArgAsnGlnValAlaAlaAspAsnAlaIleSerProAlaAlaGluProArg

61   CGGCGGTCAGAGCCCTCCTCGTCCTCGTCTTCGTCCTCGCCAGCGGCCCCCGTGCGTCCC
  21   ArgArgSerGluProSerSerSerSerSerSerSerProAlaAlaProValArgPro

121   CGGCCCTGCCCGGCGGTCCCAGCCCCAGCCCCTGGCGACACTCACTTCCGCACCTTCCGC
  41   ArgProCysProAlaValProAlaProAlaProGlyAspThrHisPheArgThrPheArg

181   TCCCACTCCGATTACCGGCGCATCACGCGGACCAGCGCGCTCCTGGACGCCTGCGGCTTC
  61   SerHisSerAspTyrArgArgIleThrArgThrSerAlaLeuLeuAspAlaCysGlyPhe

241   TATTGGGGACCCCTGAGCGTGCACGGGGCGCACGAGCGGCTGCGTGCCGAGCCCGTGGGC
  81   TyrTrpGlyProLeuSerValHisGlyAlaHisGluArgLeuArgAlaGluProValGly

301   ACCTTCTTGGTGCGCGACAGTCGTCAACGGAACTGCTTCTTCGCGCTCAGCGTGAAGATG
 101   ThrPheLeuValArgAspSerArgGlnArgAsnCysPhePheAlaLeuSerValLysMet

361   GCTTCGGGCCCCACGAGCATCCGCGTGCACTTCCAGGCCGGCCGCTTCCACTTGGACGGC
 121   AlaSerGlyProThrSerIleArgValHisPheGlnAlaGlyArgPheHisLeuAspGly

421   AGCCGCGAGACCTTCGACTGCCTTTTCGAGCTGCTGGAGCACTACGTGGCGGCGCCGCGC
 141   SerArgGluThrPheAspCysLeuPheGluLeuLeuGluHisTyrValAlaAlaProArg

491   CGCATGTTGGGGGCCCCGCTGCGCCAGCGCCGCGTGCGGCCGCTGCAGGAGCTGTGTCGC
 161   ArgMetLeuGlyAlaProLeuArgGlnArgArgValArgProLeuGlnGluLeuCysArg

541   CAGCGCATCGTGGCCGCCGTGGGTCGCGAGAACCTGGCGCGCATCCCTCTTAACCCGGTA
 191   GlnArgIleValAlaAlaValGlyArgGluAsnLeuAlaArgIleProLeuAsnProVal

601   CTCCGTGACTACCTGAGTTCCTTCCCCTTCCAGATCtgaccggctgccgctgtgccgcag
 201   LeuArgAspTyrLeuSerSerPheProPheGlnIle*
```

```
 661   cattaagtgggggcgccttattatttcttattattaattattattattttctggaacca
 721   cgtgggagccctccccgcctgggtcggagggagtggttgtggagggtgagatgcctccca
 781   cttctggctggagacctcatcccacctctcaggggtgggggtgctcccctcctggtgctc
 841   cctccgggtccccctggttgtagcagcttgtgtctggggccaggacctgaattccactc
 901   ctacctctccatgtttacatattcccagtatctttgcacaaaccaggggtcggggagggt
 961   ctctggcttcatttttctgctgtgcagaatatcctattttatattttacagccagttta
1021   ggtaataaactttattatgaaagttttttttttaaaagaaaaaaaaaaaaaaaaaaaa
```

```
hsSOCS.1   (98)  VGTFLVRDSRQRNCFFALSVKMASGPTSIRVHFQAGRFHLD......GSR   (141)
rrSOCS.1   (99)  VGTFLVRDSRQRNCFFALSVKMASGPTSIRVHFQAGRFHLD......GNR   (142)
mmSOCS.1   (99)  VGTFLVRDSRQRNCFFALSVKMASGPTSIRVHFQAGRFHLD......GSR   (142)
mmSOCS.2   (67)  EGTFLIRDSSHSDYLTISVKTSAGPTNERIEYQDGKFRLDSIICVKSKL   (116)
mmSOCS.3   (65)  AGTFLIRDSSDQRHFTLSVKTQSGTKNLRIQCEGGSFSLQSDPRSTQPV   (117)
mmCIS      (101) EGTFLVRDSTHPSYLFTLSVKTTRGPTNVRIEYADSSFRLDSNCLSRPRI  (150)

hsSOCS.1   (142) ESFDCLFELLEHYVAAPRRMLGAP..........................   (165)
rrSOCS.1   (143) IETFDCLFELLEHYVAAPRRMLGAP.........................   (166)
mmSOCS.1   (143) ETFDCLFELLEHYVAAPRRMLGAP..........................   (166)
mmSOCS.2   (117) KQFDSVVHLIDYYQMCKOKRTGP...........................   (140)
mmSOCS.3   (115) PRFDCVLKLVHHYMPPPGTPSFSLPPTEPSSEVPEQPPAQALPGSTPKRA   (164)
mmCIS      (151) LAFPDVVSLVQHYVASCAADTRSDSPDPAPTPALPMSKQDAPSDSVLPIP   (200)
```

Figure 3(II)

```
hsSOCS.1  (166)  .................LRQRRVRPLQELCRQRIVATVGR.ENLARIPLNP   (198)
rrSOCS.1  (167)  .................LRQRRVRPLQELCRQRIVAAVGR.ENLARIPLNP   (199)
mmSOCS.1  (167)  .................LRQRRVRPEQELCRQRIVAAVGR.ENLARIPLNP   (199)
mmSOCS.2  (141)  ..EAPRNGTVHLYLTKPLYTSAPTLQHFCRLAINKCTGT...IWGLPLPT     (185)
mmSOCS.3  (165)  YYIYSGGEKIPLVLSRPLSSNVATLQHLCRKTVNGHLDSYEKVTQLPGP.     (213)
mmCIS     (201)  ...VATAVHLKLVQPFVRRSSARSLQHLCRLVIENRLVAD..VDCLPLPR     (244)

hsSOCS.1  (199)  VLRDYLSSFPFQI                                           (211)
rrSOCS.1  (200)  VLRDYLSSFPFQI                                           (212)
mmSOCS.1  (200)  VLRDYLSSFPFQV                                           (212)
mmSOCS.2  (186)  RLKDYLEEYKFQV                                           (198)
mmSOCS.3  (214)  .IREFLDQYDAPL                                           (225)
mmCIS     (245)  RMADYLRQYDFQL                                           (257)
```

Figure 3(III)

| | | |
|---|---|---|
| mmSOCS.1 | SH2 | MVARNQVAADNAISPAAEPRRRSEPSSSSSSPAAPVRP |
| mSOCS.3 | SH2 | MVTHSKFPAAGMSR.................. |
| mSOCS.2 | SH2 | MTLRCLEPSGNGADRTRSQWGTAGLPEEQSPEA...... |
| mCIS | SH2 | MVLCVQGSCPLLAVEQIGRRPLWAQSLELPGPAMQPLPTG |
| mSOCS.5 | SH2 | MDKVGKMWNNLKYRCQNLFSHEGGSRNENVEMNPNRCPSV |
| mSOCS.14 | SH2 | SGGGPWRAGGGSGKSDSGLTVEPGRGLTARPPPGGSRTRS |
| mmSOCS.4 | WD | MASFPPRVNE |
| mmSOCS.6 | WD | ME |
| mmSOCS.15 | WD | MGQTAL |
| | | |
| mSOCS.5 | SH2 | AEIPQVVEISIEKDSDSGATPGTRLARRDSYSRHAPWGGK |
| mSOCS.14 | SH2 | NFLLEKLKNTVFITLEIVKNLFKMAENNSKNVDVRPKTSR |
| | | |
| mSOCS.5 | SH2 | VSSRAVGSRSLRQRLQDTVGLCFPMRTYSKQSKPLFSNKR |
| mSOCS.14 | SH2 | SQERQLSCSSIELDLDHSCGHRFLGRSLKQKLQDAVGQCF |
| | | |
| mSOCS.5 | SH2 | TFFDTFDPSLVSTEDEEDRLRERRRLSIEEGVDPPPNAQI |
| mSOCS.14 | SH2 | IKRHTVPMSPNSDEWVSADLSERKLRDAQLKRRNTEDDIP |
| | | |
| mSOCS.5 | SH2 | SEEDSTTLCLQSRRQKQRQVSGDSHAHVSRQGAWKVHTQI |
| mSOCS.14 | SH2 | SEDEIITLCTSSRKRNKPRWEMEEILQLEAPPKFHTQI |

```
mmSOCS.1    SH2    RPCPAVPAPA
mSOCS.3     SH2    .........
mSOCS.2     SH2    .........
mCIS        SH2    .........
mSOCS.5     SH2    KEKSISLGEAAPQQESSPLRENVALQLGLSPSKTFSRRNQNCA
mSOCS.14    SH2    GSGRASLPRLSERRVMAVMAAGARTAPLELSSERSVQKVPRR
mSOCS.4     WD
mmSOCS.6    WD
mmSOCS.15   WD mSOCS.5     SH2    KKHSCSTKTQSSLDTEKKFGRTRSGLQRRERRYGVSSMQDMDS
mSOCS.14    SH2    SRSADRKDGYVWSGKKLSWSKKSESCSESEAIGTVENVEIPLR mSOCS.5     SH2    KIHLSELMLEKCPFPAGSDLAQKWHLIKQHTAPVS      PHS
mSOCS.14    SH2    PIKNCSGRHSPGLPSKRKIHISELMLDKCPFPPRSDLAFRWHF mSOCS.5     SH2    HTFEATAQVNPEYK         GPKLAPGMTEISGDGSAIPQXNCD
mSOCS.14    SH2    CFSHTNGQPCVITANSASCTGGHITGSMMNLVTNNSIEDSDMD mSOCS.5     SH2    DVLHCLVPDLLQLTGNP
mSOCS.14    SH2    DYVHCLVPDLLQLSNNP
```

Figure 4A(II)

|  |  | Y F H   T | o   Ebal | T   D | T |  |
|---|---|---|---|---|---|---|
| CONSENSUS |  | GWYoG. oS | o Ebal | GSFLoRES | oSo |  |
| mSOCS.1 | SH2 | GFYWGPLSVHGAHERLRAEPVGTFVRDSRQRNCFALSVK |  |  |  |  |
| mSOCS.3 | SH2 | GFYWSAVTGGEANLLSAEPAGTFLRDSSDQRHFTLSVK |  |  |  |  |
| mSOCS.2 | SH2 | GWYWGSMTVNEAKEKLKEAPEGTFLRDSSHSDYLTTSVK |  |  |  |  |
| mCIS | SH2 | GWYWGSITASEARQHLQKMPEGTFLVRDSTHPSYFTSVK |  |  |  |  |
| mSOCS.5 | SH2 | PCYWGVMDRYEAEALLEGKPEGTFLLRDSAQEDYFSVSER |  |  |  |  |
| mSOCS.14 | SH2 | PCYWGVMDXYAAEALLEGKPEGTFLLRDSAQEDYFSVSER |  |  |  |  |
| hSOCS.9 | SH2 | GWYWGPITRWEAEGKLANVPDGSFLVRDSSDDRYLSCDER |  |  |  |  |
| hSOCS.11 | SH2 | GWYWGPMNWEDAEMKLKGKPDGSFLVRDSSDPRYLSESER |  |  |  |  |

Figure 4B(I)

|  | | G | R | | T | | E | | YH |
|---|---|---|---|---|---|---|---|---|---|
| CONSENSUS | | G | oKo | G | FSo | | Doo | | HY |
| mSOCS.1 | SH2 | MASGPTS | FRVHFQAGRF | HLDGSRETF | | DCLFELLEHY |
| mSOCS.3 | SH2 | TQSGTKNLRI | QCEGGSFSL | QSDPRSTQPVPRF | | DCVLKLVHHY |
| mSOCS.2 | SH2 | TSAGPTNLRI | EYQDGKFRL | DSIICVKSKLKQF | | DSVVHLIDYY |
| mCIS | SH2 | TTRGPTNVRI | EYADSSFRL | DSNCLSRPRILAFP | | DVV SLVQHY |
| mSOCS.5 | SH2 | RYNRSLHARI | EQWNHNFSF | DAHDPCVFHSS | | TVTG LLEHY |
| mSOCS.14 | SH2 | RYSRSLHARI | EQWNHNFSF | DAHDPCVFHSP | | DITG L-LEHY |
| hSOCS.9 | SH2 | SHGKTLHTRI | EHSNGRFSF | YEQXDVEGHTSIV | | DLIGAFNQGL |
| hSOCS.11 | SH2 | SQGITHHTRMEHYRGTF | | SLWCHPKFEDRCQSVVEFI | | KRAIMHS |

Figure 4B(II)

```
                              V                    D  D                                         AAA
                              A         S          G  G                                         GGG
                              S         C  C       N  N                 CCCTTT              C
CONSENSUS              GHXXXφXXφxxxXxxxφxxxPxxP.xxxφφφSSSXDXXOX
mmSOCS.4               KEIVRSRTIGELLAPAAPFDKKC GGENWTVAFAPDGSYF
mmSOCS.6               AGEEPLLAELKPGRPHQFDWKS.SCETWSVAFSPDGSWF mmSOCS.4               VPWSQCRKNFLLHGSKNVTNSSCLKLARQNSNGGQKNKPP
mmSOCS.6               VPWPLEEQFIPKGFEAKSRSSKNDPKGRGSLKEKTL mmSOCS.4               GSSVPEKQSRCVNIEWHRFRFGQDQ     LLLATGLNNGRI
mmSOCS.6               SPWPSPPSRKLWARHPQA.P..D..VSCLFEATGLNDGQI mmSOCS.4               AHIEMVRDL     T    F    A  PD     GSLLLVSASRDKTLR
mmSOCS.5               GHQDVVRDL....S...F...TP..SG..     SLLEVSASRDKTLR mmSOCS.4               HQNWVYSC      A    F    SP    D   CS  MLCSVGASKAVF
mmSOCS.6               GHLQWYCC....S...I...SP..D..CS    MLCSAAGEKSVF mmSOCS.4               GHHHDVAC....D...F...SP..D..GA.   LLATASYDTRVY
mmSOCS.6               GHQSSVVSC...D...F...SP..D..SA.   LEVTASYDTSVI
```

Figure 4C(I)

```
mmSOCS.4     GANDRWVRA     VS  F  SH  D   GL  HVASEADDKMVR
mmSOCS.6     VHMSSLRSV...C..F..SP..E..GL..YEATVADDRLLR mmSOCS.4     LSNGLCCAF...S...T...D..G...S.....VLAAGTHDGSVY
mmSOCS.6     MTNGLCCTF.....F.PHG..G..........IEATGTRDGHVQ mmSOCS.15    ARGSSSTPTSQALYSDFSPPEGLEELLSAPPPDLVAQRHH mmSOCS.15    PKDCSENIDVKEGGLCFERRPVAQSTDGVRGKRGYSRGLH mmSOCS.13    LEQRGTH           AVVGVATALAPLQADHYAALLGSNSESW
mmSOCS.15 mmSOCS.13    YHDGK    NQPSKTYPAFLEPDE    TFIVPDSFFVALD
mmSOCS.15    YHQSKGLEAPQYPAGPQGEQLVVPERLLVVLDMEEGTL
```

Figure 4C(II)

```
B — — — — — — — — — — — — — — — B
                    K
                    Y N
                    C F R
CONSENSUS           Q W D
mmSOCS.4            A W S Q G Y R I V K L
mmSOCS.6            A W S Q G H C V V K L mmSOCS.4              E H V I D C G D I V W S L A F
mmSOCS.6                      D C G Q I V W G V A F mmSOCS.4            K I W D V Y T G K L L L L N L V D
mmSOCS.6            K I W E V Q T G L   L L L N L S mmSOCS.4            V W D L K D D G N M V K V L R
mmSOCS.6            I W D L N K H G K Q I Q V L S mmSOCS.4            L W N M D K Y T M I R K L E
mmSOCS.6            L W S M R S Y T L I R K L E mmSOCS.4            V W D P H N G D L L M E F G H L F P S P T P I F A G
mmSOCS.6            M W D P Y T G A R L R S L H H T Q L E P T M D D S D mmSOCS.4            F Y R I D E Q C P V Q V A P
mmSOCS.6            I W A . L E L K A P V A F A P mmSOCS.4            F W A
mmSOCS.6            F W T mmSOCS.15           G W N mmSOCS.15           A W E mmSOCS.13           G W D I S W P L G R N R L
mmSOCS.15           G W D         I G R G K L mmSOCS.13           M X D
mmSOCS.15           G Y S
```

Figure 4C(III)

```
                                    T                         S  LHφAφ         φφφ    G   po          po
CONSENSUS                                                                                                    po
mSOCS.7       ANK  °PCTPLRIAATAGHGNCVDFLIRKGAEVDLVDV
mSOCS.7       ANK   KGQTALYVAVVNGHLESTEILLEAGADPNGSRH
mSOCS.7       ANK   HRSTPVYHAXRVGRDDILKALIRYGADVDVNHHLNSDTRPPFSRRLTS
mSOCS.7       ANK   LVVCPLYISAAYHNLQCFRLLQAGANPDFNCNGPVNTQEFYRGS
mSOCS.7       ANK   PGCVMDAVLRHGCEAAFVSLLVEFGANLN mSOCS.10      ANK  °EETALYLATCREHLDCLLSLLQAGAEPDISNK
mSOCS.10      ANK   SRETPLYKACERKNAEAVRLLVRYNADANHRCN
mSOCS.10      ANK   RGWTALHESVSRNDLEVMELVSGGAKVEAKNV
mSOCS.10      ANK   YSITPLFVAAQSGDLEALRFLAKHGADINTQAS
mSOCS.10      ANK   DSASALYEASKNEHEDVVEFELSQGADANKANK
mSOCS.10      AHK   DGLLPEHVASKKGNYRIVQMLLPVTSRTRVRR
mSOCS.10      ANK   SGISPLHLAAERNHDAVLEALLAARFDVNAPLAPERARLY
mSOCS.10      ANK   EDRRSSALYFAVNNVYATELLLAGADPNR
mSOCS.10      ANK   DVISPLLVAIRHCCLRTMQLLLDHGANIDA°
```

Figure 4D

| | |
|---|---|
| mSOCS.1 | SH2 |
| mSOCS.3 | SH2 | MPPPGTPSFSLPPTEPSSEVPEQPPAQALPGSTPKRAYYI
| mSOCS.2 | SH2 | VQMCKDKRTGPE
| mCIS | SH2 | VASCAADTRSDSPDPAPTPALPMSKQDAPSDSVLPIP
| mSOCS.5 | SH2 | KDP
| mSOCS.14 | SH2 | KDP
| mSOCS.9 | SH2 | CYSRSQLP
| hSOCS.11 | SH2 | KNGKFLYFLRSRVP
| hSOCS.4 | WD |
| mSOCS.6 | WD |
| mSOCS.13 | WD | GTLSFIVDGQYMGVAFRGLKGKKLYPVVSAV
| mSOCS.15 | WD | IGGTYLGPAFRGLKGRTLYPSVSAV
| mSOCS.7 | ANK | LVKWESLGPEARGRRKMDPEALQVFKEARSI

│
                            │
                            │
                            │
                            │
                            │
                            │                         QRR
                            │                         SSN
                            │     SH2  VAAPRRMLGAPLRYTS
mSOCS.1                     │     SH2  YSGGEKIPLVLSRPLRSS
mSOCS.3                     │     SH2  APRNGTVHLVLTKPLRTF
mSOCS.2                     │     SH2  VATAVHLKLVQPFVRRTF
mCIS                        │     SH2  SSCMFFEPLLTISLNFXX
mSOCS.5                     │     SH2  SACMFFEPLSTPLIFSN
mSOCS.14                    │     SH2  GSATYLVRLAKPVSRPRQ
hSOCS.9                     │     WD   GLPPTPVQLLYPPVSRPRV
hSOCS.11                    │     WD                TDPE
mSOCS.4                     │     WD                TAVEE
mSOCS.6                     │     WD   WGHCEIRMRYL NGL
mSOCS.13                    │     ANK  WGQCQVRI RYMGERR
mSOCS.15
mSOCS.7
                            A ────┼─── A
```

Figure 4E(II)

| | | P T H | T | φ | φPφP φ Yφ | F |
|---|---|---|---|---|---|---|
| CONSENSUS | | φ SL YφCR | φ | | | |
| mSOCS.1 | SH2 | VRPLQELCRQRI | VAAVGREN...... | ..LARLPLNPVLRDYL | |
| mSOCS.3 | SH2 | VATLQHLCRKTVNGHLDSYEK...... | ..VTQLPGP IREFL | | | |
| mSOCS.2 | SH2 | APTLQHFCRLAINKCTGT....... | ..IWGLPLPTRLKDYL | | | |
| mCIS | SH2 | ARSLQHLCRLVINRLVAD....... | ..VDCLPLPRRMADYL | | | |
| mSOCS.5 | SH2 | PFSLQYI-CRAVICRCTTYDG..... | ..IDGLPLPSMLQDFL | | | |
| mSOCS.14 | SH2 | PFSLQHI CRTVICNCTTYDG..... | ..IDALPIPSPMKLYL | | | |
| hSOCS.9 | SH2 | VRSLQYLCRFVICQYTRIDL..... | ..DKLPLPNXMKDYL | | | |
| mSOCS.11 | SH2 | VKSLQHLCRFRIRQYTRIDH..... | ..PDLPLPKPLISYI | | | |
| mSOCS.4 | WD | VPSLQHI CRMSIRRVMSTQE..... | ..VQKLPVPSKILAFL | | | |
| mSOCS.6 | WD | LSSLKHLCRKALRSFLTTYQ..... | ..VLAEPIPKKMKEFL | | | |
| mSOCS.13 | WD | PLPLMDLCRRSVRLALGKERLGA... | ..IPAFPLPASLKAYL | | | |
| mSOCS.15 | WD | PQSLLHLSRLCVRHALGDTRLGD... | ..ISTLPLPPAMKRYL | | | |
| mSOCS.7 | ANK | PRTLLSLCRVAVRRALGKYRLHL.. | ..VPSLPLPDPIKKFL | | | |
| mSOCS.10 | ANK | PRPLAHLCRLRVRKAIGKYRIKL.. | ..LDTLPLPGRLIRYL | | | |
| mSOCS.12 | ANK | VPSLTHLCRLEIRASLKAEHLHSDIFIHQLPLPRSLQNYL | | | | |
| mSOCS.8 | ? | PRSLQHLCRCALRSHLEGCLPHA.. | ..LPRLPLPPRMLRFL | | | |

Figure 4F(I)

```
          A-------------------------------------------A
CONSENSUS
mSOCS.1    SH2  SSFPFQI°
mSOCS.3    SH2  DQYDAP°
mSOCS.2    SH2  EEYKFQV°
mCIS       SH2  RQYPFQL°
mSOCS.5    SH2  KEYHYKQKVRVRWLE
mSOCS.14   SH2  KEYHYKSKVRLLRIDLKEAQRQFPNRSKRWNPPRSEGLPAGHHQGHLV°
hSOCS.9    SH2  QEKHY°
hSOCS.11   SH2  RKFYYYDPQEEVYLS
mSOCS.4    WD   SYRG°
mSOCS.6    WD   TYRTF°
mSOCS.13   WD   LYQ°
mSOCS.15   WD   LY°
mSOCS.7    ANK  YE°
mSOCS.10   ANK  KYENTQ°
mSOCS.12   ANK  LYEEVLRMNEILEPA
mSOCS.6    ?    QLDFEDLLY°
```

Figure 4F(II)

```
cgaattccgggcgggctgtgtgagtctgtgagtggaaggcgcgccggctcttttgtct
gagtgtgacccggtggctttgttccaggcattccggtgatttcctccgggcagtccgc
agaagccgcagcggccgcccgcgctctctctgcagtctccacacccgggagagcctga
gcccgcgtcacgcccctcagccccgctgagtcccttctctgttgtcgcgtccgaatc
gagttcccggaatcagacggtgccccatagATGGCCAGCTTTCCCCCGAGGGTTAACG
AGAAAGAGATCGTGAGATCACGTACTATAGGGGAACTCTTGGCTCCAGCAGCTCCTTT
TGACAAGAAATGTGGTGGTGAGAACTGGACGGTTGCTTTTGCTCCTGATGGTTCCTAC
TTTGCGTGGTCACAAGGATATCGCATAGTGAAGCTTGTCCCGTGGTCCCAGTGCCGTA
AGAACTTTCTTTTGCATGGTTCCAAAAATGTTACCAATTCAAGCTGTCTAAAATTGGC
AAGACAAAACAGTAATGGTGGTCAGAAAAACAAGCCTCCTGAGCACGTTATAGACTGT
GGAGACATAGTCTGGAGTCTTGCTTTTGGGTCTTCAGTTCCAGAAAAACAGAGTCGTT
GCGTTAATATAGAATGGCATCGGTTCCGATTTGGACAGGATCAGCTACTCCTTGCCAC
AGGATTAAACAATGGTCGCATCAAAATCTGGGATGTATATACAGGAAAACTCCTCCTT
AATTTGGTAGACCACATTGAAATGGTTAGAGATTTAACTTTTGCTCCAGATGGGAGCT
TACTCCTTGTATCAGCTTCAAGAGACAAAACTCTAAGAGTGTGGGACCTGAAAGATGA
TGGAAACATGGTGAAAGTATTGCGGGCACATCAGAATTGGGTGTACAGTTGTGCATTC
TCTCCCGACTGTTCTATGCTGTGTTCAGTGGGCGCCAGTAAAGCAGTTTTCCTTTGGA
ATATGGATAAATACACCATGATTAGGAAGCTGGAAGGTCATCACCATGATGTTGTAGC
TTGTGACTTTTCTCCTGATGGAGCATTGCTAGCTACTGCATCCTATGACACTCGTGTG
TATGTCTGGGATCCACACAATGGAGACCTTCTGATGGAGTTTGGGCACCTGTTTCCCT
CGCCCACTCCAATATTTGCTGGAGGAGCAAATGACCGATGGGTGAGAGCTGTGTCTTT
CAGTCATGATGGACTGCATGTTGCCAGCCTTGCTGATGATAAAATGGTGAGGTTCTGG
AGAATCGATGAGGATTGTCCGGTACAAGTTGCACCTTTGAGCAATGGTCTTTGCTGTG
CCTTTTCTACTGATGGCAGTGTTTTAGCTGCTGGGACACATGATGGAAGTGTGTATTT
TTGGGCCACTCCAAGGCAAGTCCCTAGCCTTCAACATATATGTCGCATGTCAATCCGA
AGAGTGATGTCCACCCAAGAAGTCCAAAAACTGCCTGTTCCTTCCAAAATATTGGCGT
TTCTCTCCTACCGCGGTtagactgaagactgcctttcctggtaggcctgccagacaga
gcgcccttttacaagacacctcaagctttacctcgtgccgaatt
```

FIGURE 5

MetAlaSerPheProProArgValAsnGluLysGluIleValArgSerArgThrIleGly
GluLeuLeuAlaProAlaAlaProPheAspLysLysCysGlyGlyGluAsnTrpThrVal
AlaPheAlaProAspGlySerTyrPheAlaTrpSerGlnGlyTyrArgIleValLysLeu
ValProTrpSerGlnCysArgLysAsnPheLeuLeuHisGlySerLysAsnValThrAsn
SerSerCysLeuLysLeuAlaArgGlnAsnSerAsnGlyGlyGlnLysAsnLysProPro
GluHisValIleAspCysGlyAspIleValTrpSerLeuAlaPheGlySerSerValPro
GluLysGlnSerArgCysValAsnIleGluTrpHisArgPheArgPheGlyGlnAspGln
LeuLeuLeuAlaThrGlyLeuAsnAsnGlyArgIleLysIleTrpAspValTyrThrGly
LysLeuLeuLeuAsnLeuValAspHisIleGluMetValArgAspLeuThrPheAlaPro
AspGlySerLeuLeuLeuValSerAlaSerArgAspLysThrLeuArgValTrpAspLeu
LysAspAspGlyAsnMetValLysValLeuArgAlaHisGlnAsnTrpValTyrSerCys
AlaPheSerProAspCysSerMetLeuCysSerValGlyAlaSerLysAlaValPheLeu
TrpAsnMetAspLysTyrThrMetIleArgLysLeuGluGlyHisHisHisAspValVal
AlaCysAspPheSerProAspGlyAlaLeuLeuAlaThrAlaSerTyrAspThrArgVal
TyrValTrpAspProHisAsnGlyAspLeuLeuMetGluPheGlyHisLeuPheProSer
ProThrProIlePheAlaGlyGlyAlaAsnAspArgTrpValArgAlaValSerPheSer
HisAspGlyLeuHisValAlaSerLeuAlaAspAspLysMetValArgPheTrpArgIle
AspGluAspCysProValGlnValAlaProLeuSerAsnGlyLeuCysCysAlaPheSer
ThrAspGlySerValLeuAlaAlaGlyThrHisAspGlySerValTyrPheTrpAlaThr
ProArg<u>GlnValProSerLeuGlnHisIleCysArgMetSerIleArgArgValMetSer</u>
<u>ThrGlnGluValGlnLysLeuProValProSerLysIleLeuAlaPheLeuSerTyrArg</u>
Gly*

FIGURE 6 h4.1
| | |
|---|---|
| CTGTCTTCCTCCGCAGCGCGAGGCTGGGTACAGGGTCTATTGTCTGTGGTTGACTCCGTA | 60 |
| CTTTGGTCTGAGGCCTTCGGGAGCTTTCCCGAGGCAGTTAGCAGAAGCCGCAGCGACCGC | 120 |
| CCCCGCCCGTCTCCTCTGTCCCTGGGCCCGGGAGACAAACTTGGCGTCACGCCCTCAGCG | 180 |
| GTCGCCACTCTCTTCTCTGTTGTTGGGTCCGCATCGTATTCCCGGAATCAGACGGTGCCC | 240 |
| CATAGATGGCCAGCTTTCCCCCGAGGGTCAACGAGAAAGAGATCGTGAGATCACGTACTA | 300 |
| TAGGTGAACTTTTAGCTCCTGCAGCTCCTTTTGACAAGAAATGTGGTCGTGAAAATTGGA | 360 |
| CTGTTGCTTTTGCTCCAGATGGTTCATACTTTGCTTGGTCACAAGGACATCGCACAGTAA | 420 |
| AGCTTGTTCCGTGGTCCCAGTGCCTTCAGAACTTTCTCTTGCATGGCACCAAGAATGTTA | 480 |
| CCAATTCAAGCAGTTTAAGATTGCCAAGACAAAATAGTGATGGTGGTCAGAAAAATAAGC | 540 |
| CTCGTGACATATTATAGACTGTGGAGATATAGTCTGGAGTCTTGCTTTTGGGTCATCAGT | 600 |
| TCCAGAAAAACAGAGTCGCTGTGTAAATATAGAATGGCATCGCTTCAGATTTGGACAAGA | 660 |
| TCAGCTACTTCTTGCTACAGGGTTGAACAATGGGCGTATCAAAATATGGGATGTATATCA | 720 |
| GGAAACTCCTCCTTAACTTGGTAGATCATACTGAAGTGGTCAGAGATTTAACTTTTGCTC | 780 |
| CAG | 783 | h4.2
| | |
|---|---|
| CTCTGTATGTCTGAATGAAGCTATAACATTTGCCTTTTTATTGCAGGTTTTCCTTTGGAA | 60 |
| TATGGATAAATACACCATGATACGGAAACTAGAAGGACATCACCATGATGTGGTAGCTTG | 120 |
| TGACTTTTCTCCTGATGGAGCATTACTGGCTACTGCATCTTATGATACTCGAGTATATAT | 180 |
| CTGGGATCCACATAATGGAGACATTCTGATGGAATTTGGGCACCTGTTTCCCCACCTAC | 240 |
| TCCAATATTTGCTGGAGGAGCAAATGACCGGTGGGTACGATCTGTATCTTTTAGCCATGA | 300 |
| TGGACTGCATGTTGCAAGCCTTGCTGATGATAAAATGGTGAGGTTCTGGAGAATTGATGA | 360 |
| GGATTATCCAGTGCAAGTTGCACCTTTGAGCAATGGTCTTTGCTGTGCCTTCTCTACTGA | 420 |
| TGGCAGTGTTTTAGCTGCTGGGACACATGACGGAAGTGTGTATTTTTGGGCCACTCCACG | 480 |
| GCAGGTCCCTAGCCTGCAACATTTATGTCGCATGTCAATCCGAAGAGTGATGCCCACCCA | 540 |
| AGAAGTTCAGGAGCTGCCGATTCCTTCCAAGCTTTTGGAGTTTCTCTCGTATCGTATTTA | 600 |
| GAAGATTCTGCCTTCCCTAGTAGTAGGGACTGACAGAATACACTTAACACAAACCTCAAG | 660 |
| CTTTACTGACTTCAATTATCTGTTTTTAAAGACGTAGAAGATTTATTTAATTTGATATGT | 720 |
| TCTTGTACTGCATTTTGATCAGTTGAGCTTTTAAAATATTATTTATAGACAATAGAAGTA | 780 |
| TTTCTGAACATATCAAATATAAATTTTTTAAAGATCTAACTGTGAAAACATACATACCT | 840 |
| GTACATATTTAGATATAAGCTGCTATATGTTGAATGGACCCTTTTGCTTTTCTGATTTTT | 900 |
| AGTTCTGACATGTATATATTGCTTCAGTAGAGCCACAATATGTATCTTTGCTGTAAAGTG | 960 |
| CAAGGAAATTTTAAATTCTGGGACACTGAGTTAGATGGTAAATACTGACTTACGAAAGTT | 1020 |
| GAATTGGGTGAGGCGGGCAAATCACCTGAGGTCAGCAGTTTGAGACTAGCCTGGCAAACA | 1080 |
| TGATGAAACCCTGTCTCTACTAAAAATACAAAAAAAAAAAA | 1122 |

FIGURE 7 cggcacgagccgggctccgtccggaggaagcgaggctgcgccgccggcccggcaggagcggaggacgg
gamgcgcggcggtcgcgctcgccctgtcgctgactgcgctgccccggcccatccttgcctggccgca
ggtgccctggatgaggccgccgcgcgtgtcccggccgctgagtgtccccgcggtcgcccggcgcctg
ccctcaagcggccgcctctccttgcccgggtccccgttttccccggcgcagtcctcctccggtgggc
gcctccgcacctcggcgcaggcggcacggccctcgggccgggatggatccgcgggaagaggaagaca
agccggggcgttgagccctgcgcacggtgccgccgcgcgtagtgggagcttactcgcagtaggctct
cgctcttctaatcaATGGATAAAGTGGGGAAAATGTGGAACAACTTAAAATACAGATGCCAGAATCTC
TTCAGCCACGAGGGAGGAAGCCGTAATGAGAACGTGGAGATGAACCCCAACAGATGTCCGTCTGTCAA
AGAGAAAAGCATCAGTCTGGGAGAGGCAGCTCCCCAGCAAGAGAGCAGTCCCTTAAGAGAAAATGTT
GCCTTACAGCTGGGACTGAGCCCTTCCAAGACCTTTTCCAGGCGGAACCAAAACTGTGCCGCAGAGAT
CCCTCAAGTGGTTGAAATCAGCATCGAGAAAGACAGTGACTCGGGTGCCACCCCAGGAACGAGGCTTG
CACGGAGAGACTCCTACTCGCGGCACGCCCCGTGGGGAGGAAAGAAGAAACATTCCTGTTCCACAAAG
ACCCAGAGTTCATTGGATACCGAGAAAAAGTTTGGTAGAACTCGAAGCGGCCTTCAGAGGCGAGAGCG
GCGCTATGGAGTCAGCTCCATGCAGGACATGGACAGCGTTTCTAGCCGCGCGGTCGGGAGCCGCTCCC
TGAGGCAGAGGCTCCAGGACACGGTGGGTTTGTGTTTTCCCATGAGAACTTACAGCAAGCAGTCAAAG
CCACTCTTTTCCAATAAAAGAAAAATACATCTTTCTGAATTAATGCTGGAGAAATGCCCTTTTCCTGC
TGGCTCGGATTTAGCACAAAAGTGGCATTTGATTAAACAGCATACCGCCCCTGTGAGCCCACACTCAA
CATTTTTTGATACATTTGATCCATCACTGGTGTCTACAGAAGATGAAGAAGATAGGCTTCGCGAGAGA
AGACGGCTTAGTATCGAAGAAGGGGTGGATCCCCCTCCCAACGCACAAATACACACCTTTGAAGCTAC
TGCACAGGTCAACCCATTGTATAAGCTGGGACCAAAGTTAGCTCCTGGGATGACAGAGATAAGTGGAG
ATGGTTCTGCAATTCCACAAGCSAATTGTGACTCAGAAGAGGATTCAACCACCCTATGTCTGCAGTCA
CGGAGGCAGAAGCAGCGCCAGGTGTCCGGGGACAGCCACGCGCACGTTAGCAGACAGGGAGCTTGGAA
AGTTCATACGCAGATCGATTACATACACTGCCTCGTGCCAGATTTGCTTCAGATCACAGGGAATCCCT
GTTACTGGGGCGTGATGGACCGATACGAGGCCGAAGCCCTTCTAGAAGGGAAACCGGAAGGCACGTTC
TTGCTCAGGGACTCTGCACAGGAGGACTACCTCTTCTCTGTGAGCTTCCGCCGCTACAACAGGTCTCT
GCACGCCCGGATCGAGCAGTGGAACCACAACTTCAGCTTCGATGCCCATGACCCCTGCGTGTTTCACT
CCTCCACWGTCACGGGGCTTCTCGAACACTATAAAGACCCCAGCTCTTGCATGTTTTTTGAACCGTTG
CTAACGATATCACTGAATAGAACTTTCCCTTTCAGCCTGCAGTATATCTGCCGCGCAGTGATCTGCAG
ATGCACTACGTATGATGGGATTGACGGGCTCCCGCTACCGTCGATGTTACAGGATTTTTTAAAAGAGT
ATCATTATAAACAAAAAGTTAGGGTTCGCTGGTTAGAACGAGARCCAGTCAAAGCAAAGtaactcctg
tccccaaagggcactaactaagtctgctcctcccgtgcatcmgaactgcacccataggraggcagtca
gctgctaggatttcccacccagaatgggagcttagtcattagcctctgccctatgggtccgctgttc
ctcagacaaaggtgcctagggacagcaagatggcttgcaggtgttcggtgggctgtgacaactgaggg
aggcaactctggggcatttgctatgaagaattctatttcttaccgaagaacaaattattaatattgga
tgggtatttcaatagtgtgactaatgtttgaaattattttttctaagaattttttctataaccttcaga
aaagtagtgatgtttgtagttactataaatcaagctttgaaagttcaaaacaaacaagttaaataaa
agactaccttccttttagagaaaacaaatgcaagttttcccagccacaggcattgtgcactgttaatg
ttagcttgttatcagctcctttctcctcc

FIGURE 9A

MetAspLysValGlyLysMetTrpAsnAsnLeuLysTyrArgCysGlnAsnLeuPheSerHisGlu
GlyGlySerArgAsnGluAsnValGluMetAsnProAsnArgCysProSerValLysGluLysSer
IleSerLeuGlyGluAlaAlaProGlnGlnGluSerSerProLeuArgGluAsnValAlaLeuGln
LeuGlyLeuSerProSerLysThrPheSerArgArgAsnGlnAsnCysAlaAlaGluIleProGln
ValValGluIleSerIleGluLysAspSerAspSerGlyAlaThrProGlyThrArgLeuAlaArg
ArgAspSerTyrSerArgHisAlaProTrpGlyGlyLysLysLysHisSerCysSerThrLysThr
GlnSerSerLeuAspThrGluLysLysPheGlyArgThrArgSerGlyLeuGlnArgArgGluArg
ArgTyrGlyValSerSerMetGlnAspMetAspSerValSerSerArgAlaValGlySerArgSer
LeuArgGlnArgLeuGlnAspThrValGlyLeuCysPheProMetArgThrTyrSerLysGlnSer
LysProLeuPheSerAsnLysArgLysIleHisLeuSerGluLeuMetLeuGluLysCysProPhe
ProAlaGlySerAspLeuAlaGlnLysTrpHisLeuIleLysGlnHisThrAlaProValSerPro
HisSerThrPhePheAspThrPheAspProSerLeuValSerThrGluAspGluGluAspArgLeu
ArgGluArgArgArgLeuSerIleGluGluGlyValAspProProProAsnAlaGlnIleHisThr
PheGluAlaThrAlaGlnValAsnProLeuTyrLysLeuGlyProLysLeuAlaProGlyMetThr
GluIleSerGlyAspGlySerAlaIleProGlnXaaAsnCysAspSerGluGluAspSerThrThr
LeuCysLeuGlnSerArgArgGlnLysGlnArgGlnValSerGlyAspSerHisAlaHisValSer
ArgGlnGlyAlaTrpLysValHisThrGlnIleAspTyrIleHisCysLeuValProAspLeuLeu
GlnIleThrGlyAsnProCysTyrTrpGlyValMetAspArgTyrGluAlaGluAlaLeuLeuGlu
GlyLysProGluGlyThrPheLeuLeuArgAspSerAlaGlnGluAspTyrLeuPheSerValSer
PheArgArgTyrAsnArgSerLeuHisAlaArgIleGluGlnTrpAsnHisAsnPheSerPheAsp
AlaHisAspProCysValPheHisSerSerXaaValThrGlyLeuLeuGluHisTyrLysAspPro
SerSerCysMetPhePheGluProLeuLeuThrIleSerLeuAsnArgThrPhe<u>ProPheSerLeu</u>
<u>GlnTyrIleCysArgAlaValIleCysArgCysThrThrTyrAspGlyIleAspGlyLeuProLeu</u>
<u>ProSerMetLeuGlnAspPheLeu</u>LysGluTyrHisTyrLysGlnLysValArgValArgTrpLeu
GluArgXaaProValLysAlaLys*

FIGURE 9B

```
GATTAAACAGCATACAGCTCCTGTGAGCCCACATTCAACATTTTTTGATACTTTGATCCATCTTTGGT
TTCTACAGAAGATGAAGAAGATAGGCTTAGAGAGAGAAGGCGGCTTAGTATTGAAGAAGGGGTTGATC
CCCCTCCCAATGCACAAATACATACATTTGAAGCTACTGCACAGGTTAATCCATTATTAAACTGGGAC
CAAAATTAGCTCCTGGAATGACTGAAATAAGTGGGGACAGTTCTGCAATTCCACAAGCTAATTGTGAC
TCGGAAGAGGATACAACCACCCTGTGTTGCAGTCACGGAGGCAGAAGCAGCGTCAGATATCTGGAGAC
AGCCATACCCATGTTAGCAGACAGGGAGCTTGGAAAGTCCACACACAGATTGATTACATACACTGCTT
CGTGCCTGATTTGCTTCAAATTACAGGGAATCCCTGTTACTGGGGAGTGATGGACCGTTATGAAGCAG
AAGCCCTTCTCGAAGGGAAACCTGAAGGCACGTTTTTGCTCAGGGACTCTGCGCAAGAGGACTACTTC
TTCTCTGTGAGCTTCCGCCGATACAACAGATCCCTGCATGCCCGAATTGAGCAGTGGAATCACAACTT
TAGTTTCGACGCCCATGACCCGTGTGTATTTCACTCCTCCACTGTAACGGGACTTTTAGAACATTATA
AAGATCCCAGTTCGTGCATGTTTTTTGAACCATTGCTTACTATATCACTAAATAGGACTTTCCCTTTT
AGCCTGCAGTATATCTGTCGCGCGGTAATCTGCAGGTGCACTACGTATGATGGAATTGATGGGCTCCC
TCTACCCTCAATGTTACAGGATTTTTTAAAAGAGTATCATTATAAACAAAAAGTTAGAGTTCGCTGGT
TGGAACGAGAACCAGTCAAGGCAAAGTAAACTCTCCGGTCCCCAAAGGGTGTTAACTAGGTCCGCTTT
CATGTGCATCAGACAGTACACCTATAGCAAGCACACGTAGCAGTGTTAGGCTTTTTCATACAGTATGT
AAGCTTAGTGTTAGTATCTGTCAGATGCTACCTGCTGTTACTTATTCAGATAAACATGGTGCCTATTG
GAACAATAGCGGATAGAGCTACAGGTGTTCAGTAAGACTACAAAAACATTTTGCCTATTTCGCTAACA
GTTTGGTTTTTAATGGCTGTGGTATTTGAGTGAGGCAACTCTGGGGCATTTGTTATGAAGAAATG
```

FIGURE 10

```
ggcacgaggcggtggtggcggcgggcgcggccgcggccgcgggcgcggaatgaaggcgcggcccacggccctgggggctgaggcgcccgccgcctg
gggggccgccgcgtcctcATGGAGGCCGGAGAGGAGCCGCTGGCTGGCTGCTGCTGGTTCGCCTGGCGGCCCACCAGTTCGACTGGAAGTCAAG
CTGCGAGACCTGGAGCCTTCTCGCCGTTCCTGGTTCTGGGTCTCCAGACGGCTTCCTGGTCTCAAGGACACTGCGTGGTCAAGCTGGTCCCTTAGA
GGAACAGTTCATCTCCCTAAAGGATTCGAAGCCAAGACCAAGAGCAGCAGCCCCTGGGGCTGGCCTTCAGCCCTGGCCTTCAGCCCTGTGGGGCCACGTCACCATCCCCAGGCGCTGACTG
TGGCCAGATTGTGTGGGGGCTGGCCTTCAGCCCTGTGGGGCTGGCTGGCCTTCAGCGATGGGCAGATCAAGATTTGGGAGGTACAGACAGGCCTCCTGCTTCTGAATCTTTCTGGCCACCAGA
TTGCCTGATCCTGGCCACAGGTCTGAGCTTCACGCGCCAGGCGCAGTTTGATTTGGTCTCTGCATCCCGGATAAGACACTTCGAATTTGGGACCTGAATAAACA
CGTCGTGAGAGATCCAGGTGTTATCCGGCCATCTGCAGTGGGTTTACTGCAGTGGTTTACTGCAGTGGTACACTGTAGCATGCTGTGCTCTGCAGCTGGGGA
CGGTAAGCAGATCCAGGTGCTCTTCTGCTGTCACAGCTTCGTGGAGCATGGCGGTCCTACACACCAGTGCTGATTATGTGGGACCCCTAGAAGGCCCACACCCGGCAGCCTACACCGGGTCACCTGGACCCCTATACCCCTGAGTTCACTCATCACACAACT
TTCAGCCTTGCTGTGTCACAGCTTCGTGGAGCATGGCGGTCCTACACACCAGTGCTGATTATGTGGGACCCCTGAGTCCGTGCTCTTCCGATGACCAGTAGAGGCTGAGGTCATCTCGCTACGGTGGCAGATGA
TGAACCCACCATGATGACAGTGACGTCCACATGAGCTCGAACTGAAGGCTCGAACTGAAGGCTCTTTGCCTTTGCCTCCGATGACCAATGGTCTCTCACTGAAGCACTTATGCAGGAAAGCCCTCCG
CAGGCTGCTCAGGATCTGGGCTCTGAACTGAAGGCCCATGTCCAGTTCCCAGCATGGCCATGTCCAGTTCCTGGACAGCTCCTGTCCTCACTGAAGCACTTATGCAGGAAAGCCCTCCG
AATTATTGCCACAGGACGAGAGATGGCCATGTCCAGTTCCTGGACAGCTCCTGTCCTCACTGAAGCACTTATGCAGGAAAGCCCTCCG
AAGTTTCCTGACAACGTATCAAGTCTGACACTGCCAATCCCCAAGAAGATGAAAAGAGTTCCTCACATACAGACTTTCTAGcagtgccggctccc
ccacctcctgcagtaggtctgcctaggaaggactgctaggatggagtcaggcagtcacactggaccagtgtggaccttcctcctccatggcat
gtgcaagtaggtctgcgtgatgttgctgctgtgggtaataaaggcaaggtgacccactcctgtggtgccggccttctcatccgtggttgagcagccttcctcgtcagttcctagtttgttgtgttgaag
ccaagtgcagttgtggatggcatttctgctgctaataaggcaaggtgacccactcctgtggccggccttcctcgtcagttcctagtcagttcctagttgttgt
acctgcctaggacctgcgctgtggactggctgagctcctcaccatacactagtgacgttcctgtgcatgacagagttcttgtgcatgttgcatgtgagaag
tcctgctcagctgcgtgactggctgagctcctcaccatacactagtgacgttcctgtgcatgacagagttcttgtgcatgttgcatgtgagaag
taacaagcagtattcagatcatacgaggaggcgttcctcgaaaaacagaggcgcttcctcgtgatggccattatcagcatatttatttgtattttctcagca
catagtaaggtacaactgtgtgtgtttctcaatgtgtctgtcacatgtgttctctgtcttgacctcatggatgtgcccagttgtgcccagttcaagtctaagtcgtgtggagtca
gtgctgacatcactggcttgtgctgtcgttctttgacagcggtagcagctaccatccaagacgcctcacacaaatctgcctagaaagttaatatttaa
acagcccttcaaagaaactcaacatcttattcttggcctttctttatgctttatgcttattatgctttatgctttatgctttatgctttaa
attattttaaaagaaactcaacatcttattcttggcctttctttatgctttatgctttatgctttatgctttatgctttatgctttaa
agtcctcctatttgaagaacaatgcaaaatgaggctttcattgaagggaaaaaaaaaaaaaaa
```

FIGURE 12A

MetGluAlaGlyGluGluProLeuLeuLeuAlaGluLeuLysProGlyArgProHisGlnPheAsp
TrpLysSerSerCysGluThrTrpSerValAlaPheSerProAspGlySerTrpPheAlaTrpSer
GlnGlyHisCysValValLysLeuValProTrpProLeuGluGluGlnPheIleProLysGlyPhe
GluAlaLysSerArgSerSerLysAsnAspProLysGlyArgGlySerLeuLysGluLysThrLeu
AspCysGlyGlnIleValTrpGlyLeuAlaPheSerProTrpProSerProProSerArgLysLeu
TrpAlaArgHisHisProGlnAlaProAspValSerCysLeuIleLeuAlaThrGlyLeuAsnAsp
GlyGlnIleLysIleTrpGluValGlnThrGlyLeuLeuLeuLeuAsnLeuSerGlyHisGlnAsp
ValValArgAspLeuSerPheThrProSerGlySerLeuIleLeuValSerAlaSerArgAspLys
AsnLysHisGlyLysGlnIleGlnValLeuSerGlyHisLeuGlnTrpValTyrCysCysSerIle
SerProAspCysSerMetLeuCysSerAlaAlaGlyGluLysSerValPheLeuTrpSerMetArg
SerTyrThrLeuIleArgLysLeuGluGlyHisGlnSerSerValValSerCysAspPheSerPro
AspSerAlaLeuLeuValThrAlaSerTyrAspThrSerValIleMetTrpAspProTyrThrGly
AlaArgLeuArgSerLeuHisHisThrGlnLeuGluProThrMetAspAspSerAspValHisMet
SerSerLeuArgSerValCysPheSerProGluGlyLeuTyrLeuAlaThrValAlaAspAspArg
LeuLeuArgIleTrpAlaLeuGluLeuLysAlaProValAlaPheAlaProMetThrAsnGlyLeu
CysCysThrPhePheProHisGlyGlyIleIleAlaThrGlyThrArgAspGlyHisValGlnPhe
TrpThrAlaProArgVal<u>LeuSerSerLeuLysHisLeuCysArgLysAlaLeuArgSerPheLeu</u>
<u>ThrThrTyrGlnValLeuAlaLeuProIleProLysLysMetLysGluPheLeu</u>ThrTyrArgThr
Phe*

FIGURE 12B h6.1
GACACTGCATCGTCAAACTGATCCCCTGGCCGTTGGAGGAGCAGTTCATCCCTAAAGGGTTTGAAGCC
AAAAGCCGAAGTAGCAAAAATGAGACGAAAGGGCGGGGCAGCCCAAAAGAGAAGACGCTGGACTGTGG
TCAGATTGTCTGGGGGCTGGCCTTCAGCCTGTGCTTTCCCCACCCAGCAGGAAGCTCTGGGCACGCCA
CCACCCCCAAGTGCCCGATGTCTCTTGCCTGGTTCTTGCTACGGGACTCAACGATGGGCAGATCAAGA
TCTGGGAGGTGCAGACAGGGCTCCTGCTTTTGAATCTTTCCGGCCACCAAGATGTCGTGAGAGATCTG
AGCTTCACACCCAGTGGCAGTTTGATTTTGGTCTCCGCGTCACGGGATAAGACTCTTCGCATCTGGGA
CCTGAATAAACACGGTAAACAGATTCAAGTGTTATCGGGCCACCTGCAGTGGGTTTACTGCTGTTCCA
TCTCCCCAGACTGCAGCATGCTGTGCTCTGCAGCTGGAGAGAAGTCGGTCTTTCTATGGAGCATGAGG
TCCTACACGTTAATTCGGAAGCTAGAGGGCCATCAAAGCAGTGTTGTCTCTTGTGACTTCTCCCCCGA
CTCTGCCCTGCTTGTCACGGCTTCTTACGATACCAATGTGATTATGTGGGACCCCTACACCGGCGAAA
GGCTGAGGTCACTCCACCACACCCAGGTTGACCCCGCCATGGATGACAGTGACGTCCACATTAGCTCA
CTGAGATCTGTGTGCTTCTCTCCAGAAGGCTTGTACCTTGCCACGGTGGCAGATGACAGACTCCTCAG
GATCTGGGCCCTGGAACTGAAAACTCCCATTGCATTTGCTCCTATGACCAATGGGCTTTGCTGGCACA
TTTTTTCCACATGGTGGAGTCATTGCCACAGGGACAAGAGATGGCCACGTCCAGTTCTGGACAGCTCC
TAGGGTCCTGTCCTCACTGAAGCACTTATGCCGGAAAGCCCTTCGAAGTTTCCTAACAACTTACCAAG
TCCTAGCACTGCCAATCCCCAAGAAAATGAAAGAGTTCCTCACATACAGGACTTTTTAAGCAACACCA
CATCTTGTGCTTCTTTGTAGCAGGGTAAATCGTCCTGTCAAAGGGAGTTGCTGGAATAATGGGCCAAA
CATCTGGTCTTGCATTGAAATAGCATTTCTTTGGGATTGTGAATAGAATGTAGCAAAACCAGATTCCA
GTGTACTAGTCATGGATTTTTC h6.2
ACCATGGTTCCAAGTCCTCTCCCCTGTGGTCAAGTTGCCCGAATGTTGGGCCCAAGTGCCTTTTCCTC
CTTGGGCCTCCCCTTCTGACCTGCAGGACAGTTTTCCGGAGCCCATTTGGTATGAGGTATTAATTAGC
CTTAACTAAATTACAGGGGACTCAGAGGCCGTGCTCCTGACCGATCCAGACACTATTTTTTTTTTTTT
TTTTTAACAATGGTGTGCATGTGCAGGAAATGACAAATTTGTATGTCAGATTATACAAGGATGTATTC
TTAAACCGCATGACTATTCAGATGGCTACTGAGTTATCAGTGGCCATTTATTAGCATCATATTTATTT
GTATTTTCTCAACAGATGTTAAGGTACAACTGTGTTTTCTCGATTATCTAAAAACCATAGTACTTAA
ATTGAAAAAAAAAA

FIGURE 13

```
GGCACGAGGCGGGGTCAGGGCGGAGGCTGAGGACCAAGTAGGCATGGCGGAGGGCGGGACCGGCCCCG
ATGGACGGGCCGGCCCGGGACCCGCAGGTCCTAATCTGAAGGAGTGGCTGAGGGAGCAGTTCTGTGAC
CATCCACTGGAGCACTGTGACGATACAAGACTCCATGATGCAGCCTATGTAGGGGACCTCCAGACCCT
CAGGAACCTACTGCAAGAGGAGAGCTACCGGAGCCGCATCAATGAGAAGTCTGTCTGGTGCTGCGGCT
GGCTTCCCTGCACACCACTGAGGATCGCAGCCACTGCAGGCCATGGGAACTGTGTGGACTTCCTCATA
CGCAAAGGGGCCGAGGTGGACCTGGTGGATGTCAAGGGGCAGACTGCCCTGTATGTGGCTGTAGTGAA
CGGGCACTTGGAGAGCACTGAGATCCTTTTGGAAGCTGGTGCTGATCCCAACGGCAGCCGGCACCACC
GCAGCACTCCTGTGTACCATGCCTYTCGTGTGGGTAGGGACGACATCCTGAAGGCTCTTATCAGGTAT
GGGGCAGATGTTGATGTCAACCATCATCTGAATTCTGACACCCGGCCCCCTTTTTCACGGCGGCTAAC
CTCCTTGGTGGTCTGTCCTCTATACATCAGTGCTGCCTACCATAACCTTCAGTGCTTCAGGCTGCTCT
TGCAGGCTGGGGCAAATCCTGACTTCAATTGCAATGGCCCTGTCAACACCCAGGAGTTCTACAGGGGA
TCCCCTGGGTGTGTCATGGATGCTGTCCTGCGCCATGGCTGTGAAGCAGCCTTCGTGAGTCTGTTGGT
AGAGTTTGGAGCCAACCTGAACCTGGTGAAGTGGGAATCCCTGGGCCCAGAGGCAAGAGGCAGAAGAA
AGATGGATCCTGAGGCCTTGCAGGTCTTTAAAGAGGCCAGAAGTATTCCCAGGACCTTGCTGAGTTTG
TGCCGGGTGGCTGTGAGAAGAGCTCTTGGCAAATACCGACTGCATCTGGTTCCCTCGCTGCCGCTGCC
AGACCCCATAAAGAAGTTTTTGCTTTATGAGTAGcattcacatgcagtgctgactgcaatgtggaagc
cgatcacctgcagtgaaaactgacacagactctggcatcctgggaaccatggcctgtgctgccagctt
gatccttggctgtcagtgaagaaaaaacggctgtgttctcttggactgtgattctatctcaggtgctt
gggccatcgaacgctccttgagtcattgtcaactgagaggcacatacaaacttaattttgttcctctt
cagtctctctgttttggattcttcctggcaatgtgtgcagcatgggctgagcctggtgattgccctag
tggggaaggcttttttctccaggctatgcatctatttatgttcctactttgcaatttattgttcttt
aaggcttgatatcaaaacagaaagagggtttgttaagaaaagatatagggagaaaggaattccggttcc
gtgcacttgctagcctgctttccttgcctgggtttgtctgtctatgctgcctggtgcacatcccttct
ctttgctgccactgttctatttggggagttgtcttccgtctaagatggcttctggggttctatcttat
tgcacagaggtcccagaacagtgttcatagggcaccatctgctctgccaagggttttctgatgtctta
ccctggggatcttcagacagtggttacctttaggagacccacctggaactaaccattaagtgactgcc
cacattcagatcagggaccatcttaatagtactcactgccagtcctcacaagagaagatgacacgggt
gctctcttcagacactcccatacaggaagttggaaaatgtcttggtcacctgggttgttcccaggcta
caacttcttggtgttccactaaaccagratatcctagttttttgggttgactgttccctccccactt
tccttgaacccaatgcccntttgtktnggttgcttccctaaaaktt
```

FIGURE 15A

AlaArgGlyGlyValArgAlaGluAlaGluAspGlnValGlyMetAlaGluGlyGlyThrGlyPro
AspGlyArgAlaGlyProGlyProAlaGlyProAsnLeuLysGluTrpLeuArgGluGlnPheCys
AspHisProLeuGluHisCysAspAspThrArgLeuHisAspAlaAlaTyrValGlyAspLeuGln
ThrLeuArgAsnLeuLeuGlnGluGluSerTyrArgSerArgIleAsnGluLysSerValTrpCys
CysGlyTrpLeuProCysThrProLeuArgIleAlaAlaThrAlaGlyHisGlyAsnCysValAsp
PheLeuIleArgLysGlyAlaGluValAspLeuValAspValLysGlyGlnThrAlaLeuTyrVal
AlaValValAsnGlyHisLeuGluSerThrGluIleLeuLeuGluAlaGlyAlaAspProAsnGly
SerArgHisHisArgSerThrProValTyrHisAlaXaaArgValGlyArgAspAspIleLeuLys
AlaLeuIleArgTyrGlyAlaAspValAspValAsnHisHisLeuAsnSerAspThrArgProPro
PheSerArgArgLeuThrSerLeuValValCysProLeuTyrIleSerAlaAlaTyrHisAsnLeu
GlnCysPheArgLeuLeuLeuGlnAlaGlyAlaAsnProAspPheAsnCysAsnGlyProValAsn
ThrGlnGluPheTyrArgGlySerProGlyCysValMetAspAlaValLeuArgHisGlyCysGlu
AlaAlaPheValSerLeuLeuValGluPheGlyAlaAsnLeuAsnLeuValLysTrpGluSerLeu
GlyProGluAlaArgGlyArgArgLysMetAspProGluAlaLeuGlnValPheLysGluAlaArg
SerIle<u>ProArgThrLeuLeuSerLeuCysArgValAlaValArgArgAlaLeuGlyLysTyrArg
LeuHisLeuValProSerLeuProLeuProAspProIleLysLysPheLeuLeuTyrGlu</u>

FIGURE 15B h7.1
GCATCCATGGCGGAGGGCGGCAGCACGACGGGCGGGCAGGGCCGGGCTCCGCAGGTCGTAATCTGAAG
GAGTGGCTGAGGGAGCAATTTTGTGATCATCCGCTGGAGCACTGTGAGGACACGAGGCTCCATGATGC
AGCTTACGTCGGGGACCTCCAGACCCTCAGGAGCCTATTGCAAGAGGAGAGCTACCGGAGCCGCATCA
ACGAGAAGTCTGTCTGGTGCTGTGGCTGGCTCCCCTGCACACCGTTGCGAATCGCGGCCACTGCAGGC
CATGGGAGCTGTGTGGACTTCCTCATCCGGAAGGGGGCCGAGGTGGATCTGGTGGACGTAAAAGGACA
GACGGCCCTGTATGTGGCTGTGGTGAACGGGCACCTAGAGAGTACCCAGATCCTTCTCGAAGCTGGCG
CGGACCCCAAC h7.2
GAGGAAGAAGAAAAGTGGACCCTGAGGCCTTGCAGGTCTTTAAAGAGGCCAGAAGTGTTCCCAGAACC
TTGCTGTGTCTGTGCCGTGTGGCTGTGAGAAGAGCTCTTGGCAAAACCGGCTTCATCTGATTCCTTCG
CTGCCTCTGCCAGACCCCATAAAGAAGTTTCTACTCCATGAGTAGACTCCAAGTGCTGCGGTTGATTC
CAGTGAGGGAGAAAGTGATCTGCAGGGAGGTGGACACCGAGCCCTGAGTGCTGTGCTGCTGCTGGTCT
CCTGATGGCTGTTGCTGCAGAAGATGTCCTCGTAGACTGTCATTGCTCCTCAGGTGCCTGGGCCGCTG
AACAGTCCTTGGGTCATTGTCAGCTGAGAGGCTTATACTAAAGTTATTATTGTTTTTCCCAAGTTCTC
TGTTCTGGATTTTCAGTTGCATATTAATGTAACGGGCCATGGGGTATGTACATGTAGGGGCTGAGGTT
GGAGGCCTACTAATTTCCTGTAGGGAAGACTCCCAGCACTTCTGGAACTGTGCTTCTCTTTATTTTTC
TACTTCTCAATTTGATGGTTCGATTAAAGCCTTCTAGTATCTCAATGAAAA

FIGURE 16

```
ctgATGTCCGCAATTCTGAAGGTTGGACACCACTGCTGGCTGCCTGTGACATCCGCTGTCAATCCCCA
AAGGATGCTGAGGCCACCACCAACCGCTGTTTTCAACTGTGCCGCTTGCTGCTGTCTGTGGGGCAGA
TGCTGATGAATACATACCGTGTAGTTCAGCTTCCTGAGGAGGCCAAGGGCTTGGTGCCACCAGAGATT
CTACAGAAGTACCATGGATTCTACTCTTCCCTCTTTGCCTTGGTGAGGCAGCCCAGGTCGCTGCAGCA
TCTCTGCCGTTGTGCGCTCCGCAGTCACCTGGAGGGCTGTCTGCCCCATGCACTACCGCGCCTTCCCC
TGCCACCGCGCATGCTCCGCTTTCTGCAGCTGGACTTTGAGGATCTGCTCTACTAGgcttgctgccct
gtgaacaaagcagaccccaccccacccaagggcatctctcagcaatgaatgatgcaaggcggtctg
tcttcaagtcaggagtggacgccttgatccacacttgagagaagaggccagatcagcaccyggctggt
agtgatngcagagggcacctgtgcagatctgtgtgcgcactggaaatctctaggctgaaggcyagagc
aaatggtgcargtgttagtccttgggangagagacaganggtgagaaagcaagacagaggtgagagtg
cacatgtcaagtggtagattgccttaaaagaaagctaaaaaagaaaaagattcgggcgaacttcttt
agggtaatgctgcagcgtgttaaactgactgaccagcgtccatatctttggacccttcccgggtgaa
aaagccccttcatcctccagcgctccccaagggtgcttagcaataccgggtgcttttctgccgcaaag
tgagttaccaaa
```

FIGURE 18A

...MetSerAlaIleLeuLysValGlyHisHisCysTrpLeuProValThrSerAlaVal
AsnProGlnArgMetLeuArgProProThrAlaValPheAsnCysAlaAlaCysCys
CysLeuTrpGlyGlnMetLeuMetAsnThrTyrArgValValGlnLeuProGluGluAla
LysGlyLeuValProProGluIleLeuGlnLysTyrHisGlyPheTyrSerSerLeuPhe
AlaLeuValArg<u>GlnProArgSerLeuGlnHisLeuCysArgCysAlaLeuArgSerHis</u>
<u>LeuGluGlyCysLeuProHisAlaLeuProArgLeuProLeuProProArgMetLeuArg</u>
<u>PheLeu</u>GlnLeuAspPheGluAspLeuLeuTyr*

FIGURE 18B

```
GTGGGGGCGTCATCATGACCTCCTCTAGGGCTCTGCAACATGACTCCTGTGGTGCAAATCAACAAATT
GTTCACTGATGAATCCACAAGGATCTCTGGGCCTACAACCAGGTCCTGGTCCACATGACTGTCGTCTT
CGGAGAAGGCACCACTCGCCCCCGGCAGGTACGGCTGACACCTCCATGGGAGAAGACGTATCCAGGCA
GCAGCTGCGCGGCCCTTCAAGAGGGCACATCCCGTCATCTAAAGGCACGGTGTACTGAAGGTAGTCCT
GAGACATGAGTCCGATTACTACAGGCACGTGTTCCTCCAGGTGGAGGCTCAGGTCCCCGGGTGAGCTG
GGGCTGCAGCGGGACTCAGGGCGCGGCTCTGGCTGCAGGTCTCGCAGCTCCCTGGGCTGTAGCTCCCG
CAGATCCTTGCGCACACCGTTGACTGGT
```

FIGURE 20

TTAATAGTACCTACATAGTAGAAAATTATAACTCCACTTTAAAAATCAATGTTTCTTTCTATTCAAATCAATTTAAAACTTTTTATAAACATTAATGTTGCAAGAG
AATCCAGTCCATTATGAAATTAGTTGACAATCAAGTTCACCCAAGAAATGTTGACTAAGCTAAAGAAATCACAGATAAAACATTTTACCAAAAGGATAGGTA
ACACACAAAAAAATGCTATCACAGGAAGCTATGATCATCTAATATTTCTTTAATAATAATTCTAGTTCCATAGGTTTTCATGTTATGCCAATTTGTACCCGAGTT
TAATTACAGAAAAGGCAACAATTTCTAAATTGGTAGTAGTATACATTTCTTTACAATTTTTTAATGTAAGGCCATTTATTAAAATAGACAAACTAGAAGATGAAAACG
AAGGCAACAACAGAAAAATTCAACTTTTCACAACCAAAAGAATTAGCACAACCTTAGAAATAATTTAGAAAAAAGTGTTGTTAAAAGATATGTGCAGATCCGTTC
CATTACCCAAGATTATGTCAATTCACGATTCTAAATAAATCTTTTTAAGTAAGAGATTAAAAACTCATCTTCAGTGTATATGTAAATTCCGTGGTTTATCACA
CAGGTATGTTTATTCAACACTGCTTTGGAAATGGACCATTTAAAAGGACAATTTCCATTCTGTTAAGTTTCATTCAACCTTTACTTAGGGTGATTACC
ACATGAAATGTGCTTTTAATGCATAAAAATCACAGTAGCCAGCAAAAGGACTGGGCGGGGGCATTGAGGAGAATTGATAATTCACATTGTGATTA
TTCTGCACATTGATGAAACATAATTCACACCTCTAAAACCTCAAGACTTCCCTTTTTTAAAGAACCAAAATAAACCAAGACACCTTGCTGACACTTCCCACCC
CTAAACAAACTGATGACTCTCTTTTACACATAAAACTGAAATAGTTATGGCAGCAAAAGATTTTGATGCAATGAAAGTTTGTAAACTGTATTTCAATCTCTTGTTC
TTATTCCCAAAGTGCAAGATGCAGGTTCTCAATCTTTCAGTAGTCTTCAGTAGTGTGCAAAGGCAGTTCTGAATTAAGTCTA
TTCTGGTATACTGACGTATAACAAAACGACACAGTACTGCAACGAGCGCACCTATGAACCCCGAACACTGGTTGGCAAGTTCTGACGGAAGTGCAGATTCCAG
GCAGCGAGACCTTGAATAACAAAAAGCTCCCATTTTCAGAGTCCCTGATTGAATGCTCCAATTAGATCAACTATGACGTATGTCCTTCCACATCGGCTGTTCAT
AAAAGCTAAACCTACCATTGAGTGCTGCTCAATTCTAGTGTGAAGTGTTTTACCATGGGAGCGAAAGTCACAGCTTAAAAGGTAACGGTCGTCAGAACTGTCCCGAA
CAAGAAAAGAACCATCTGGCACGTTTGCTAGCTTCCCTTCTGCCCTCAGTCAGTCATAAAACTCTTGCAACCCCAGGAGCAGAGTTCGGATCAAAATTCAAATGACAGCGCATAACTT
TAAGGCTTGTCACAACCATGGGACCACTACTTTGCACTGAGTCACTGAGTTCCCCTTTGGATTATTCCTGCATTGGAATAACCAATGGTGAAGATTGGAGGGACAT
TCAGCCACGTGGGCTTTCTGTCCAGTGAGTTCTGCACTCAACAGCCATTCACCGGACTGATCCACGAAGATCTCTGGGCGACAACTAG
CCATCGTGAACCCGCTCTCCGGGGTTCTGCAACATGACTCCCGTGGTGCCAATCAACAAGCCATTCACCGGACTTCCATGGGAGAGAACCGCAGAGTGTCCAGACAATAGCTCCG
GTCCTGGTCTACCTGACTCTCATCCTCGGGGAAAGCGCGCCCTCCACTTGAGGAGGAACCGCAGAGACTTCCATGGGAGAGAACCGCAGACAATAGCTCCG
TGATCCTTCCAAAGGATACATCCCCTCATCTGAATGGCTTGCTCCTGGCACGTGGTCTCAGACTGGTCGT
ATGCAGGTCTCCATTATGAGAAGCCGAGCTCTTCAGTGAATTGCTCCTGGCACGTGGTCTCAGACTCCAGGTGAAG

CCTCCTGAGAGTTCGCCGGCCCGGGCCCAATGGGTTGTTCCAAGGGGTCATGCAGAAATACAGCAGCA
GCTTGTTCAAGACCTCCCAGCTGGCGCCTGCGGACCCCTTGATAAAGGCCATCAAGGATGCGATGAAG
AGGCCTTGAAGACCATGATCAAGGAAGGGAAGAATCTCGCAGAGCCCAACAAGGAGGGCTGGCTGCCG
CTGCACGAGGCCGCATACTATGGCCAGGTGGGCTGCCTGAAAGTCCTGCAGCGAGCGTACCCAGGGAC
CATCGACCAGCGCACCCTGCAGGAGGAAACAGCCGTTTACTTGGCAACGTGCAGGGGCCACCTGGACT
GTCTCCTGTCACTGCTCCAAGCAGGGGCAGAGCGGGACATCTCCAACAAATCCCGAGAGAACCGCTCT
ACAAAGCCTGTGAGCGCAAGAACGCGGAAGCCGTGAAGATTCTTGGTGCAGCACAACGCAGACACCAA
CAACGCTGCAACCGGGCTG h10.2

GTGCAGCTCTGCTCGCGGCTGAAGGAACACATCGACAGCTTTGAGGACTGGGCCGTCATCAAGGAGAA
GGCAGAACCTCCAAGACCTCTGGCTCACCTTTGCCGACTGCGGGTTCGAAAGGCCATTGGGAAATACC
GTATAAAACTCCTAGACACCTTGCCGCTCCCAGGCAGGCTGATTAGATACCTGAAATACGAGAACACC
CAGTAACTGGGGCCACGGGGAGAGAGGAGTAGCCCCTCAGACTCTTCTTACTAAGTCTCAGGACGTCG
GTGTTCCCAACTCCAAGGGGACCTGGTGACAGACGAGGCTGCAGGCTGCCTCCCTCTCAGCCTGGACA
GCTACCAGGATCTCACTGGGTCTCAGGGCCCAGAGCTTTGGCCAGAGCAGAGAACAGAATGTGTCAAG
GAGAAGAATCATTTGTTTACAAACTGATGAGCAGATCCCAGACCTTCTCTACCTTCAGGAATGGCAGA
AACCTCTATTCCTGGGGCCAGGGCAGAGCTTGAGGTGTTCTGGGGAAGGTGGTGCTCAGAGCCTTCCC
TGTGCCCCTCCACTTGTTCTGGAAAACTCACCACTTGACTTCAGAGCTTTCTCTCCAAAGACTAAGAT
GAAGACGTGGCCCAAGGTAGGGGTAGGGGGAGCCTGGGTCTTGGAGGGCTTTGTTAAGTATTAATAT
AATAAATGTTACACATGTGAAAAAAAAAA

FIGURE 24

```
TTGGAGAAGTGTGGTTGGTATTGGGGGCCAATGAATTGGGAAGATGCAGAGATGAAGCTGAAAGGGAA
ACCAGATGGTTCTTTCCTGGTACGAGACAGTTCTGATCCTCGTTACATCCTGAGCCTCAGTTTCCGAT
CACAGGGTATCACCCACCACACTAGAATGGAGCACTACAGAGGAACCTTCAGCCTGTGGTGTCATCCC
AAGTTTGAGGACCGCTGTCAATCTGTTGTAGAGTTTATTAAGAGAGCCATTATGCACTCCAAGAATGG
AAAGTTTCTCTATTTCTTAAGATCCAGGGTTCCAGGACTGCCACCAACTCCTGTCCAGCTGCTCTATC
CAGTGTCCCGATTCAGCAATGTCAAATCCCTCCAGCACCTTTGCAGATTCCGGATACGACAGCTCGTC
AGGATAGATCACATCCCAGATCTCCCACTGCCTAAACCTCTGATCTCTTATATCCGAAAGTTCTACTA
CTATGATCCTCAGGAAGAGGTATACCTGTCTCTAAAGGAAGCGCAGCGTCAGTTTCCAAACAGAAGCA
AGAGGTGGAACCCTCCACGTAGCGAGGGGCTCCCTGCTGGTCACCACCAAGGGCATTTGGTTGCCAAG
CTCCAGCTTTGAagaaccaaattaagctaccatgaaaagaagaggaaaagtgagggaacaggaaggtt
gggattctctgtgcagagactttggttccccacgcaagccctggggcttggaagaagcacatgaccgt
actctgcgtggggctccacctcacacccacccctgggcatcttaggactggaggggctccttggaaaa
ctggaagaagtctcaacactgtttcttttca
```

FIGURE 25A

...LeuGluLysCysGlyTrpTyrTrpGlyProMetAsnTrpGluAspAlaGluMetLysLeuLys
GlyLysProAspGlySerPheLeuValArgAspSerSerAspProArgTyrIleLeuSerLeuSer
PheArgSerGlnGlyIleThrHisHisThrArgMetGluHisTyrArgGlyThrPheSerLeuTrp
CysHisProLysPheGluAspArgCysGlnSerValValGluPheIleLysArgAlaIleMetHis
SerLysAsnGlyLysPheLeuTyrPheLeuArgSerArgValProGlyLeuProProThrProVal
GlnLeuLeuTyrProValSerArgPheSerAsn<u>ValLysSerLeuGlnHisLeuCysArgPheArg
IleArgGlnLeuValArgIleAspHisIleProAspLeuProLeuProLysProLeuIleSerTyr
Ile</u>ArgLysPheTyrTyrTyrAspProGlnGluGluValTyrLeuSerLeuLysGluAlaGlnArg
GlnPheProAsnArgSerLysArgTrpAsnProProArgSerGluGlyLeuProAlaGlyHisHis
GlnGlyHisLeuValAlaLysLeuGlnLeu*

FIGURE 25B

```
GTTCCAAGCCTAACCCATCTTTGTCGTTTGGAAATTCGGGCCAGTCTAAAAGCAGAGCACCTTCACTC
TGACATTTTCATCCATCAGTTGCCACTTCCCAGAAGTCTGCAGAACTATTTGCTCTATGAAGAGGTTT
TAAGAATGAATGAGATTCTAGAACCAGCAGCTAATCAGGATGGAGAAACCAGCAAGGCCACCTGAcac
aggtcctttaattctgtttagtcacaaaagacggcttgtgtgactgtttggatttggtgatcaaatgt
ccatgtttacagttgcttttcccagtttgtgtctttcccaatattgtgaaccttatccatcttgcctt
actcagttttatttctagtgcactttgttgtgtattatttgtttacctgaccattttctactttattc
tgctaataaactgtaattctgaaaaaaaaaaaaaaaaaaaaaaaaaaaaaaaaaa
```

FIGURE 28 h12.1

GGGGATCGAAAGCGGGGGCTTCTGGGACGCAGCTCTGGAGACGCGGCCTCGGACCAGCCATTTCGGTG
TAGAAGTGGCAGCACGGCAGACTGGTCAAACAAATGGATTTTACAGAGGCTTACGCGGACACGTGCTC
TACAGTTGGACTTGCTGCCAGGGAAGGCAATGTTAAAGTCTTAAGGAAACTGCTCAAAAAGGGCCGAA
GTGTCGATGTTGCTGATAACAGGGGATGGATGCCAATTCATGAAGCAGCTTATCACAACTCTGTAGAA
TGTTTGCAAATGTTAATTAATGCAGATTCATCTGAAAACTACATTAAGATGAAGACCTTTGAAGGTTT
CTGTGCTTTGCATCTCGCTGCAAGTCAAGGACATTGGAAAATCGTACAGATTCTTTTAGAAGCTGGGG
CAGATCCTAATGCAACTACTTTAGAAGAAACGACACCATTGTTTTTAGCTGTTGAAAATGGACAGATA
GATGTGTTAAGGCTGTTGCTTCAACACGGAGCAAATGTTAATGGATCCCATTCTATGTGTGGATGGAA
CTCCTTGCACCAGGCTTCTTTTCAGGAAAATGCTGAGATCATAAAATTGCTTCTTAGAAAAGGAGCAA
ACAAGGAATGCCAGGATGACTTTGGAATCACACCTTTATTTGTGGCTGCTCAGTATGGCCAAGCTAGA
AAGCTTTGAAGCATACTTATTTCATCCGGGTGCAAATGTCAATTGTCAAGCCTTGGACAAAGCTACC h12.2

CACAAATGGGACCATACAAAAATCTTGGACTTGTTAATAACCACTTACTAACCGGGACCTGTGACACT
GGGCTAAACAAAGTAAGTCCCTGTTTACTCAGCAGTGTTTGGGGGACATGAAGGATTGCCTAGAAATA
TTACTCCGGAATGGTCTACAGCCCAGACGCCCAGGCGTGCCTTGTTTTGGATTCAGTTCTCCTGTGT
GCATGGCTTTCCAAAAGGAGGTGGAGCTGTAGTTCTTTGGAATTGTGAACATTCTTTTGAAATATGGA
GCCCAGATAAATGAACTTCATTTGGCATACTGCCTGAAGTACGAGAAGTTTTCGATATTTCGCTACTT
TTTGAGGAAAGGTTGCTCATTGGGACCATGGAACCATATATATGAATTTGTAAATCATGCAATTAAAG
CACAAGCAAAATATAAGGAGTGGTTGCCACATCTTCTGGTTGCTGGATTTGACCCACTGATTCTACTG
TGCAATTCTTGGATTGACTCAGTCAGCATTGACACCCTTATCTTCACTTTGGAGTTTACTAATTGGAA
GACACTTGCACCAGCTGTTGAAAGGATGCTCTCTGCTCGTGCCTCAAACGCTTGGATTCTACAGCAAC
ATATTGCCCACTGTTCCATCCCTGACCCATCTTTGTCGTTTGGAAATTCGGTCCAGTCTAAAATCAGA
ACGTCTACGGTCTGACAGTTATATTAGTCAGCTGCCACTTCCCAGAAGCCTACATAATTATTTGCTCT
ATGAAGACGTTCTGAGGATGTATGAAGTTCCAGAACTGGCAGCTATTCAAGATGGATAAATCAGTGAA
ACTACTTAACACAGCTAATTTTTTCTCTGAAAAATCATCGAGACAAAAGAGCCACAGAGTACAAGTT
TTTATGATTTTATAGTCAAAAGATGATTATTGATTGTCAGATAGGTTAGGTTTTGGGGGGCCAGTAGT
TCAGTGAGAATGTTTATGTTTACAACTAGCCTTCCCAGTAAAAAAAAAAAAAAAAAAAAAAAAAA

FIGURE 29

```
CGGGGGGCTGGGACCTGGGGCGTAACCGTCTCTACCACGACGGCAAGAACCAGCCAAGTAAAACATAC
CCAGCCTTTCTGGAGCCGGACGAGACATTCATTGTCCCTGACTCCTTTTTCGTGGCCCTGGACATGRA
TGATGGGACCTTAAGTTTCATCGTGGATGGACAGTACATGGGAGTGGCTTTCCGGGGACTCAAGGGTA
AAAAGCTGTATCCTGTAGTGAGTGCCGTCTGGGCCACTGTGAGATCCGCATGCGCTACTTGAACGGA
CTTGATCCTGAGCCCCTGCCACTCATGGACCTGTGCCGGCGTTCGGTGCGCCTAGCGCTGGGAAAAGA
GCGCCTGGGTGCCATCCCCGCTCTGCCGCTACCTGCCTCCCTCAAAGCCTACCTCCTCTACCAGTGAt
ccacatcccaggaccgccatacgacagccatctggtgccaartcactgagccgttggggtccgccga
ccctgcgcctgggatggaagcccacctcagccatgggcagacgtgcccctcatcctaccggctgcc
tctgctgggggaacctatgccaacggacttctcccttcccaacactggctgaagcagcagcacccagg
cccttccctgaaccagatgcagagaataaactatgaaaacctctctcaggcgccttctgctctcaggt
ggagtgggctgcccccactctctgcagagagaggctacacccacctggggggtcctgggaggtaaga
ctagtaggaggtgccagggctgartccaaaagcaggaatggccaggamcaggccatacagatgaagct
caggatgtcacataccatggacamtgagacagaaccccaggttggamttcccttgggccaacgagtgc
cagctttaatgtcagctgcmggtgctctgtggcctgtatttattctttaaacagtagcaaaggccatt
tatttattccacttagaaaggaaaccttggtgggtggyttccctcgatgtgctttcccccacctccct
ggaatgtgtgtgccacacctgtccttgtcccaggccaggactgtggcacatgagctggtgtgcacaga
tacacgtatgtcgtcgtgcatgaccctgactagttcctaagtagccctgcaccaagcaccagagcag
accccaagagaggcccgtgcaagtccccatgtccccaggtcctgcttctgttgccttgggactcata
caccggcacacgtgtttcagcctcttgacttccatgagcttcgaattttgccccgattcttctgata
tttcccattggcatcctccaaagctctgggcctggagggcattaggacacatggaatgagtggggtct
ccagcccctgggaaagccactggcaaggcaggattagaaagaccaagagcagggtggggcgccatgaa
gcctgtatgcctctcaggctcaagaccccgccacacacccactcaagcctcagaagtggtgtgtaggg
cagccccaggagaggaatgcctgtcctagcagcacgtacatggagcacccacatgtgctccagccct
ctggctgtttctcttgctctagaatcaactccctacattgggaatgtagccatttggtagaggacttg
cctagcctgcaggaagctcacgttccatcccctgcaccaaggagaatcaaagctcaggaggctgaggc
aggaggattgctgtcagtggtgtacagaggtcatggccatcctgggctatattaaaccttgtccttta
agaaaaagaaaagaaatcaacttccattgaatctgagttctgctcatttctgcacaggtacaatagat
gacttkatttgttgaaaaatgkttaatatatttacmtatatatatatttgtaagaagcatt
```

FIGURE 31A

...GlyGlyTrpAspLeuGlyArgAsnArgLeuTyrHisAspGlyLysAsnGlnProSerLysThr
TyrProAlaPheLeuGluProAspGluThrPheIleValProAspSerPhePheValAlaLeuAsp
MetXaaAspGlyThrLeuSerPheIleValAspGlyGlnTyrMetGlyValAlaPheArgGlyLeu
LysGlyLysLysLeuTyrProValValSerAlaValTrpGlyHisCysGluIleArgMetArgTyr
LeuAsnGlyLeuAspProGlu<u>ProLeuProLeuMetAspLeuCysArgArgSerValArgLeuAla</u>
<u>LeuGlyLysGluArgLeuGlyAlaIleProAlaLeuProLeuProAlaSerLeuLysAlaTyrLeu</u>
LeuTyrGln*

FIGURE 31B

```
AAGGGTAAAAAACTGTATCCTGTAGTGAGTGCCGTCTGGGGCCACTGTAGATCCGAATGCGCTACTTG
AACGGACTCGATCCCGAGACTGCCGCTCATGGATTTGTGCCGTCGCTCGGTGCGCCTGGCCCTGGGGA
GGGAGCGCCTGGGGGAGAACCACACCTGCCGCTGCCGGCTTCCCTCAAGGCCTACCTCCTCTACCAGT
GACGTTCGCCATCATACCGCCAGCGCGACAGCCACCTGGTGCCAACTCACTGAGCCGCCTG
```

FIGURE 32

```
...AAGTGGCGGCGGTCCCTGGAGAGCAGGCGGAGGCAGGCAAGTCTGACTCTGGGCTGACTCGTGAGCCGGGCGGGGGGGCTGACAGCCAGGCCT
CCGCCTGGCGGGAGCCGGCGCACGAGCTCCGCTTGAGCTGAGCTCGGAGAGATGGCCGGGGCCCTCTCTTCCAGAAGTGCCCAGAAGAAACTTCCTCTTAGAAGTGCCGGTGATGGCGGTGGTGATGGCGGCAGGC
GCTCGGACAGTCCGCTTGTAAAGAATTTGTTGTTAAAGATTGGCTGAGAAATGCTGAAAAGATACGGCCTAAAACAAGTCGGAGTCGAAGTGCT
ATAACACTGGAAATTGTATGTGTGGAGTGGAAGAAGAAGAAGTTGTCTGGTCCAAAAAGAGTGAGAGTTGTTCTGAATCTGAAGCCATAGGTACTGTTGAG
GACAGGAAGGATGGTTATGTGTGGAGTGGAAGAAGCCAAGATGCGGTGGGGCAGTGTTTTCCATTGAGATCATTCCTGTGGGCATAGATTTTTAGGC
AATGTTGAAATTCCTCTAAGAACAGAAACTGCAAGATGCGGTGGGGCAGTGTTTTCCAATAAAGAATTGTAGTGGCCGACACTCTCCAGGCTTCCATCTAAAAGA
CGATCCCTTAAACAGAACTGAACTCATGTTAGATAAGTGCCCTTTCAGATTTAGCCTTTAGGTGGCATTTTATTAAACGACACACTGTT
AAGATTCATATCAGTCCCAACTCAGATACCAACTGCCAACTGCTCAGCTGCAGACCTGTCTGTCATAACCAGAAACGAAGAAACACAGAAGATGAC
CCTATGAGTCCCAACTCAGATACCAACTGCCAATGCCAACTGCTCAGCTGCAGACCTGTCTGTCATAACCAGTGCTTCGTCACATAACGAAGATGAAC
ATACCCTGTTTCTCACATACCAACTGCCAATGCCAACAGTGAAGACATGGATTCAGAGGATGAAATTATAACGCTGTGCACAAGCTCCAAGCTCCACTACGTCGACTCGAGATCGACTACGCTCCAGACCTCCTTCAG
TTGGTCACAAACAACAGCATAGAAGAGACAGTGAAGACATGGATTCAGAGGATGAAATTATAACGCTGTGCACAAGCTCCACTACGTCGACTCGAGATCGACTACGCTCCAGACCTCCTTCAG
TGGGAAATGGAAGAGGAGATCCTGCAGTTGGAGGCACCTGCTAAGTTCCACACCCAGTCCACCTAAGTTCCACACCCAAGCTCTGCTGGAAGGAAAGCCAGAGGGCACCTTTTACTTCGAGAT
ATCAGTAACAATCCGTGCTACTGGGGTGTCATGGACAACAAATATGCAGCCGAAGCTCGTTCCTTCCATGCTAGAATTGAGCAGTGGAATCATAACTTTAGCTTT
TCAGCGCAGGAGATTATTATTCTGTCTTCCATTCTCCTGATATTACTGGGCTCCTGAACACTATAAGGACCCCAGTGCCTGCCTGTATGTTCTTTGAGCCGCTC
GATGCCCATGATCCTCGCCTAAATCCGGACGTTCCCCTTTTCCCCTATGAAATTGTATCTGAAGAATACCATTATAATATCAAAAGTTAGTTAGTTACTCAGGATTGATGTGCCAGAGCAGCAGTGA
CTTCCATTCCTTCGCCTATGAAATTGTATCTGAAGAATACCATTATAATATCAAAAGTTAGTTAGTTACTCAGGATTGATGTGCCAGAGCAGCAGTGA
tgcggagaggttagaatgtcgacctgtgaatctgacctcttgaattttgtacaaaggcagttgaat
caaataaaactgtgccctaagttgcctaagttgcctagttttaaatattttttatgatcacactgttatatattttttaagcaggtgttggttttgttt
ttaccatataaattacatatggtccaggcattgcatatatctgtatatccgaatcattgaatatctgtattttttaatatctttgt
tctttcctatgtgtgaaatatttgctaatcatatgctaatattttcttgtatgaccgaatagtagttgatctatcgatttttaaaatgatttaaaatgaaatta
gtaaagagtgttgtaatcaatcattataatgtaattgacttttgtaatttgccattgccaatagtagagttgtgttaaacaacaaaatgatttaaaaatgaaactta
atgtatttcattttaaatattaactaaccaagtttgtttttttgtgtgcaataactgaaccctagcatcctagaggtgtatttg
ttctgcagtttggcaggaccgtcagttgtccaaataaacatcccctcagcgtggaggcgaatgaaccctgtgctcctttctttacggagcttggt
caaagcaaaatagcaggttacaagcttggagttgtttaaggcaactagagttttcctatttaattatagactgttgttgttgcacctactagctctt
tttggaactctagttccccagggaaaataccctcgtgcc
```

FIGURE 34A

...SerGlyGlyGlyProTrpArgAlaGlyGlyGlySerGlyLysSerAspSerGlyLeuThrVal
GluProGlyArgGlyLeuThrAlaArgProProProGlyGlySerArgThrArgSerGlySerGly
ArgAlaSerLeuProArgLeuSerGluArgArgValMetAlaValValMetAlaAlaGlyAlaArg
ThrAlaProLeuGluLeuSerSerGluArgSerValGlnLysValProArgArgAsnPheLeuLeu
GluLysLeuLysAsnThrXaaPheIleThrLeuGluIleValLysAsnLeuPheLysMetAlaGlu
AsnAsnSerLysAsnValAspValArgProLysThrSerArgSerArgSerAlaAspArgLysAsp
GlyTyrValTrpSerGlyLysLysLeuSerTrpSerLysLysSerGluSerCysSerGluSerGlu
AlaIleGlyThrValGluAsnValGluIleProLeuArgSerGlnGluArgGlnLeuSerCysSer
SerIleGluLeuAspLeuAspHisSerCysGlyHisArgPheLeuGlyArgSerLeuLysGlnLys
LeuGlnAspAlaValGlyGlnCysPheProIleLysAsnCysSerGlyArgHisSerProGlyLeu
ProSerLysArgLysIleHisIleSerGluLeuMetLeuAspLysCysProPheProProArgSer
AspLeuAlaPheArgTrpHisPheIleLysArgHisThrValProMetSerProAsnSerAspGlu
TrpValSerAlaAspLeuSerGluArgLysLeuArgAspAlaGlnLeuLysArgArgAsnThrGlu
AspAspIleProCysPheSerHisThrAsnGlyGlnProCysValIleThrAlaAsnSerAlaSer
CysThrGlyGlyHisIleThrGlySerMetMetAsnLeuValThrAsnAsnSerIleGluAspSer
AspMetAspSerGluAspGluIleIleThrLeuCysThrSerSerArgLysArgAsnLysProArg
TrpGluMetGluGluGluIleLeuGlnLeuGluAlaProProLysPheHisThrGlnIleAspTyr
ValHisCysLeuValProAspLeuLeuGlnIleSerAsnAsnProCysTyrTrpGlyValMetAsp
LysTyrAlaAlaGluAlaLeuLeuGluGlyLysProGluGlyThrPheLeuLeuArgAspSerAla
GlnGluAspTyrLeuPheSerValSerPheArgArgTyrSerArgSerLeuHisAlaArgIleGlu
GlnTrpAsnHisAsnPheSerPheAspAlaHisAspProCysValPheHisSerProAspIleThr
GlyLeuLeuGluHisTyrLysAspProSerAlaCysMetPhePheGluProLeuLeuSerThrPro
LeuIleArgThrPheProPheSerLeuGlnHisIleCysArgThrValIleCysAsnCysThrThr
TyrAspGlyIleAspAlaLeuProIleProSerProMetLysLeuTyrLeuLysGluTyrHisTyr
LysSerLysValArgLeuLeuArgIleAspValProGluGlnGln*

FIGURE 34B

```
ccctctgggcaagccgcccccccaccatctaccacacacacacacacattcagacccttgggcaaaaacaaagcaaaa
taacaacaaaaacactgcctgtggaaagtccttacttcaggaaggttggcagatgaggagcaaggaacatttatcaggactgccacaagg
agtcttttttttaatggtttttcagacagggtttctgttcctggagctcactttgtagaccaggctggcctcgaactca
gaattcgcctgcctctgcctcctgagtgctgggattaaaggcgtgcagcaccatgtccaactggcattttctcaattaaggttcgttcctttcag
ataactctaggttctgggtcaagctgacacaagctacacagtttgtatgccacattcagttcagaagacacccaacctccctgaactgg
aacttatgcacatttgtgagcttccacttgggagtgggaacctgaactggtcctctgcaagagcagccgtgctcttaactgctgagccatttcag
cagcctcacatcagaattaagttagccgggtatgaatcatacccttagaatcctagcatctgaaagcatctccaaacaacaataactacaacaacaa
caagaccagctcttggctacagagcccgtcctgtcctaggatgggctacaagagactatttcaaagccatcagaggcagcaggctgatcagtgtgagtttcaacgt
caaggttaaaattaggctgggcacagggtacacacctttaatgccaacactcaggaggcaggcaggctgatcagtgtgagtttgagttcaacgt
ggtctacataggagttctaggccagcagaggttacagtctctctctctctctgtctctagccctggcatagattcactctgtagactaggctag
acacacacacacacacacacacggtggccattatggcctctgcctctgcctcccaagtgctggattatagtgttgcaccactgcctaa
cctgaactcagagatccgcctgcctctgcctcccaagtgctggattatagtgttgccaccactgcctggattttgaactg
tatcaagaggctttcgaggaggtcaaacttcaacagcaactctccatgatagtctcatgataatgtagctcaaacgacactcaaacttaaccttaaa
gcacacatccaccagacagcgtgcccactcgtagttccattactcctgaacagaggcaggagactaaggctcagcaacctaggag
ccgcaggggacagtagtctcaatcctacatttcctgaacacagaggagagttcaggaaggtgtcaaggccgcttactgatcttaggcctc
aggaatgactagctcaggcagagagaagagcaaaggtctccagtgctgagaagtctacacacacacacacacacacacagaat
ccaaggcgatgacgtcatcaaaggttaattctagtctgggatgggggaggtgggcacgcagctgtcaggtggcttggaaaaataaactgc
```

FIGURE 36A(i)

```
tgaagagtctgacgcgccaggagtcctggaggacaagaggttaccactcaaagagtgtgctcccacaaagcatgcgcgcttgtccacgtctggag
tcgtcacttattttttgcctgattcttgtagccggtggggttctcaaggcggtaagtggtccgcgtggctctggaggtgacgataggtt
aatcgtccacagagcccaggggcggagcgcggggcggtccgcagccccgctggagcagcagtgcgtggctgctgtcagggggcgcttctagccttcc
ctatctgtacttccacagaggtctctgcgagctaggggacagtgaggtgcgggtagggcccgcgttagagccagcaaggacgttcacgg
taaggtctgaggagagagctcctgagaaacttgggggcgcgacacagataggtgaaagcagagtgatagaccgggatggttaggggacca
agggaagaccaggctggttggcatacaccggtgaacggatgggagtcctagggaaagatgatgcgcctaacagtcctttctgtctccacaccactc
cagggacgatccggagctcaacttcaaaagcgagacgcccagcaagcctgttttgagaagttcttcagcggctctcctcATGGGCCAGACGGC
CCTGGCAAGGGGCAGCAGCAGCACCCCTACCTCGGACTTCTCTCCCGAGAACATCGATGTCACGCCTGGAGGAGCTCCTGTCTGCTTTGAGCGGCG
TCCTGACCTGGTTGCCCAGAGACACTGATGGAGTCCGGGCTCTATTCGCAGGTGACCTCGACGCGCCGAAACGGGGCTCTTGGGCCCCTGGAGCAAAGGGG
CACACACGCCGTGGTGGGCGTGGCCACCGCCCCTCGCCCGCTGACCACTATGCGGCGCCTTTTGGGCAGCAACAGCGAGTCCTGGGCTG
GGATATTGGGCGGGGAAAATTGTATCATCAGAGTAAGGGGACTCTTGGCTCTTGGCGACCTCAGGTGAGCAGCAGCTCCGTGGTGCCAGA
GAGACTGCTGGTGGTTCTGGACATGGAGGAGGGGACTCTTGGCGCCAGTGCCAGGTCCGCATCCGCTACATGGGCGAAAGAAGAGtgagatacgactaggtgtgg
GACCCTCTATCCCTCTGTAAGTGCTGTTTGGGGCCAGTGCCAGGAGGTAGGCTTCTTGTCACTTTGGCCTGTCACTTAGATGGC
ggagtcactactcttggcaatggttgggctgaaactcatgttggagcacaggaagtaggcttcttgtcactttggcctgtcacttagatggc
cttggatctagcttcactcccaatccctattggatgtgatgcacaaattcagagcctttggtctccctcagctgagtgcggtggaaatggagg
aagagaaggggtgcctgagcgcaggatctcaagttcaaggagttgcttacttaccttgtcttcctcctctccgcagTGGAGGAACCA
```

FIGURE 36A(ii)

CAATCCCTTCTGCACCTGAGCCGCCTGTGTGTGCGCCATGCTCTCTGGGGACACCCGGCTGTGGGTCAAATATCCACTCTGCCTTTGCCCCTGCCATG
AAGCGCTATCTGCTTCTACAAATGAcccagtagtacagggtgtgctgacccagtgggacaggtggagaggcacccgctgcctagacaact
ttaaaagctggtgaagctgggggggggctgacccttcacctccccttctcacaggagcaagacatatagaaatgatattaaacaccatgg
cagcctgggacaaagaggtttttgaagtaaaaatgagatgtattgtcacaacctgtttcattattgttttttgttttacactccccacc
ccaggctagagcccatcactgtcttaaggaattatgacaaccccacaaagctcaggcccagtgtgtttattccccttacatgtaggatggttcacaa
acacaatacagggcgtttgcacccgtggggagggactatcccaggcctcttaggtctcatgtatacgaattcagacccgaaagctctgaatt
tctgcatcagacatccagtagaacttgggagtgaagctagagccaaggccatctaagtgacaggcccaaagtgacacgaagcccacttcctgtgctc
caaccatgagtttccagcccaaaccaatggaaggtgatttcacttgtcagggcccagtcagttctactccctccctcactaggagcc
acctttgtgacagttgattctaccactgtaagtggtaaaggggattggctgtcccaaccataataggcggtgaaacggctcaggaggtaca
gcgtggattaggccacaagatggggcagatgggcagatgctcatcagaagcatgtgaccggtgggagcagttactaaacttctgggcaacctagtccatgct
atgcaggcagtagagggatgggcagtgcttgctctcattgtttgcagttggctgctgatgatgtccacaaattcaggcttgagagatgcgccaccacaaggaagccg
tccacgtccaggctggcttgccacctctctgtgcaaggcagccagtctcttagcgtacaggaaccaagaagacagtttggtcaggtctatgatcag
aacacttaagcctgctcctgagccaccccatctctccatatatctcatcaaggagtaaaaaccactggttctcacatagagttgagtttcagaagggaggcagag
ctactaagtaagctccttgagccaatccaccaggcttgaatgaacatttttggcaaagtcactctccttggtagttacctgggtagttacctgcgtcttgccagtccc
gtggcaagctccaatccaccaggcttgaatgaacatttttggcaaagtcactctccttggtagttacctgcgtcttgccagtccc
tggatgggctccatagctgtgtgagtctgttaaagccggacaggctgaggagctctgggtagttacctgcgtcttgccagtccc
aatgcccacacaggttcataggccaggaccaccttgctccagtcttcacattatctgtgggcagagagaggagtgagtaggaaggagctgacc
cgccaagc FIGURE 36A(iii)

MetGlyGlnThrAlaLeuAlaArgGlySerSerSerThrProThrSerGlnAlaLeuTyrSe
rAspPheSerProProGluGlyLeuGluGluLeuLeuSerAlaProProProAspLeuValA
laGlnArgHisHisGlyTrpAsnProLysAspCysSerGluAsnIleAspValLysGluGly
GlyLeuCysPheGluArgArgProValAlaGlnSerThrAspGlyValArgGlyLysArgGl
yTyrSerArgGlyLeuHisAlaTrpGluIleSerTrpProLeuGluGlnArgGlyThrHisA
laValValGlyValAlaThrAlaLeuAlaProLeuGlnAlaAspHisTyrAlaAlaLeuLeu
GlySerAsnSerGluSerTrpGlyTrpAspIleGlyArgGlyLysLeuTyrHisGlnSerLy
sGlyLeuGluAlaProGlnTyrProAlaGlyProGlnGlyGluGlnLeuValValProGluA
rgLeuLeuValValLeuAspMetGluGluGlyThrLeuGlyTyrSerIleGlyGlyThrTyr
LeuGlyProAlaPheArgGlyLeuLysGlyArgThrLeuTyrProSerValSerAlaValTr
pGlyGlnCysGlnValArgIleArgTyrMetGlyGluArgArgValGluGluProGlnSerL
euLeuHisLeuSerArgLeuCysValArgHisAlaLeuGlyAspThrArgLeuGlyGlnIle
SerThrLeuProLeuProProAlaMetLysArgTyrLeuLeuTyrLys

FIGURE 36B

```
gtactttctttatatctccataatttattactatacatgatacattatttataaagtctttgtaacctccttaaggattcactgctta
atctccagtgcttagcacaaatcattaaatgcgaaccagaaactcttcatatagtgttacatctatatacctcattgattctcactaccaaccca
tgcaatagatactaatgtgatctctgtcttacagaggaagaaacaggcacaggaggttcagtaatttgcccaagtcatacacactggccttc
aggtattcatgccgggagtctggtcccacagctgcatgtttgccattatattattgcctccttatagtgtcggcactcattaagcacattg
acagctatgctggtgagtgactactatgtaccagctctgtgctgctacatgctttacctgattattcaactgcacaacaccctgtgaggtaact
accatcattgctccctatttacataacagaaatctgggcgtagtggctcatgcctgaaatcccagcactttgggagaccc
tgtcctcaaaaaattttttttggccggtggtggctcacacctgtaatctcagcactttggagctaaggcaggcagatcacaaggtcag
gagttctagaccagcctggccaacatgcgaaaacccctgtctctactaaaaatacaaaaatagctaggcgtggtggcaggtgcctgtaatcccagc
tactcaggaggctgaggcaggagaatcccctgaacctgggagatgaggttacagagagccgagatcgtgccgctgcactccagcctgggcaacaa
gagcaagactctgtctcgaaaaaataaaataaaatatttttaaaaataattagctgggtgtgtagcacatgcctgtagtcccagcta
cttgggaggctgaggctaggaggatcacttgagccaggaggtcaaggctgtgatggcgccactgcactctagcctggtgacagca
agaccctgtctcaaaaaaaaagagaaatcgggctcaactcccccagatcgcgcagttaactagtgcatagcttcactcaaactcgaagtct
taatcaggacactctaccaaatgagatcttcacagcctcagaggtggcacaggagaactatgatgcgtaca
gcctagagcctgaagcagaatggaacaggagacccatgaacaaccgggacagcaggagaaagggaccagcgcaggagttagtcgctcagc
aatcacagggaagtagaaatgggattcggcacaatgaagcccctccttgacccatgctccttaccctcaggggcgcaggagttagtcgctcagc
ggctcaaaggtcttgacggtggagaacaccatcccccaggattccgacgcggtgatgccatcaaagcgttaatctgagatgggcctgcccggt
gcggactctgccgcagcaagagagaagggttaactgccccggcctcgccgtggggcggggcctcggggaggtcacagcccggactgagaccccg
```

FIGURE 37A(i)

```
aggttaaccgcgcccggggtggctccacggggctgggctccacggggctggggctgctctccgcggtctgccggtatagagcggtaactgcccagagagggggcggggcc
ccaagggggcgtggcctcgagctgcacggccgtgggcggccgtgggcggcgatgagaggttaagcccagaggggcccctgagggggcgggcgcgggacgggct
cggcccaagggaggagctgggggcggaagcggccggcgttgcgccggcctggctcgcgcctcttccgccgctccttcagaggccggcgac
ctccagggctgggaagtcaaccgagttcggggcagcggcgagggctccggcgagtaaggggatggtccatgctgaggcccaaatggggcgaa
ctcgcgagagtctctggcgacctggatcagatggggcgaggggcagatgaaggggcaggagctttggggcagcgaggaggagcgggccgtt
ggcaaacttggtgaaaggatgggtacctggtgacgagcccccgccaggatctgctctcaccgcccctttctccagctccctctccaggtca
atccaaactggagctcaactttcagaagagaaagacgccccagcaagcctcttcggggagtcctctagctcctcaccctccATGGGCCAGACAGCT
CTGGCAGGGGCAGCAGCACCCCCAGCGCCCAGCGCGGGGCGCCCGTGTACCCTGTACCCTCTCCTGACCTCTCCTGTCCCGAGAGTCCTGTCTGCCCCCT
CCTGACCTGGGGCCCAGAGCACTGATGGGCCCGGGTTGGAACATCGAGGTCTATTCAAGGGCCTTGGAAGAGGAGGGGTTGTACTTTGAGCGGCGG
CCCGTGGCCCAGAGCACTGATGGGCCGTGGCGGGGAAGCTGTACCATCAGAGACATCAGGCCTGCTGCAGCAACAGCGAGTCGTGGGGCTGG
ACGCATGCCGTGGGCGTGGCCACGCCTGGGCGGCGGTGCAGCCCCCCAGTATCCAGCGGAACTCAGGGTGAGCAGCTCAGGGTGAGCAGCAGG
GACATCGGGGGAAGCTGTACCATCAGAGCAGGAGCAACTCTGGGCACCTACCTGGGCCAGCATTCCGCGGACTGAAGGGCAGG
AGACTGCTGGTGGTTCTGGACATGGAGGAGGAACTCTGGGCTACGTCTGGGGCCAGTCCGACCATCCGCTACCTGGGCGAAAGGAGAGGTgaggcctgggcagacgtggg
ACCCTCTATCCGGCAGTAAGCGCTGTCTGGGGCAGTGGTTTGGATGGAAACTCTTCTGACAAGAGCAGAGGGGATGGACCTTCATCCAGCTGCCTCAACCTCTG
gagaactttctgtccctgtgcagtgggtcttcacagtcgttatttaattaaccaacagcaatagaggtgaaacaggcttgagaaagcaacttttctca
ttcagtgctgggaaaggctaggggtcttcacagtgcttgaaccttttcacagcgtaaatgtgaaccttttgcatatgtaaatgcaaggacaggaagagagcagg
agttctcttggccagtaatggtgaacttcagaatgaggaagaactgcaggatgagagaattcaggagatatcaaccccctgagcaagaggtg
```

FIGURE 37A(ii)

```
caaagcgttaggtactgggtttgatgtacaggtccaaaagaaggatgggcagagagccaggtacccaggctgtataccggattccctggctctaacc
tgtctctgtgccacatacctacttcctcctcagccacacctctgatgagacacctgggcacccaggaggagagcagtggaggagc
agggccttagggtggggcagcaggggagccctcccagaactgggtccagggcttggagctgctctctgcagttgtgggctgtagag
tggagggccatccctcctcacctcagccagcccagtcccagtccaccactgtcagagccaccttggcctgt
tgtttagagggcctagcagctcttcaccccagctctgactagggatgtgtgaaatcttatctgggaggcagaacttccggtatctcaaattc
cccttcagccaggtgggcacactcgaagcaggaaagcagaaagcatctgagtaggacccgtagttgaggacatctggctgtgctgcaccc
atacttacattccctcctcttctctcccagCGGAGCCACACTCCCTTCTGCACCTGCTCTACCAGTGAgccctgtgataccacagactgctgaggtctt
CTCGGCCAGGTGTCTGCCCTGCCCTGCCCCTTGCCCCTGGGAGGTGGGAGGCACTGCTGCCTAGACCAGCTGCTGAAAGCTGGTGAGGCTGAGCCCTACCCAACCCAAGCT
gccaccacccctccccttggggagtgggaggcactgcttgaggaggaagaaaggagccggttcaaggctatgacagtctgctacgcaaaacatttttca
ctgcggaaatcaacagccccagagatgtgttatagaaacctgtctgttcttgttttttcttgcacaaatgatcattttatagctgcctcaaaaggaa
agtaaaaatagtaggcaagtccagtgaagggcagacagaaaccacagacctagtgccagtttattccctcacatgggtggttcacatacacagagg
gattatctgggcaagtccagtggagagggcagcaggagcagcaaatcctcctgccttgggaggggccctgcgttttattccctctcacatgggtggttcacatacacagagg
cacgggcaccatgggagagggcagcaggagcaaatcctcactccgccttccatctctcagccaaggaggaagccacctggtgacgtttagttccaaccattata
ctagggcctagggaacccaggagcaaatcccaccattacaggtgaagatataaacagtaaaggaagatacagtttgatgagccacaggaaggag
gtaagtgagaaggatgggctggtccccacccactacaggtgaagatataaacagtaaaggaagatacagtttgatgagccacaggaaggag
cagatgacaccatcagaagcatatgcaggagaagggcagtactggcttctgggctgcttagtccctgctgcaggaagggtaggaagatgg
```

FIGURE 37A(iii)

atgggctcattgtttggcattgatgatgtccacgaattcgggcttgagggaagcaccacccacaaggaagccatccacatcaggctggctgctggcca
gctccttgcaggttgccccagtcacagagcctgggaagggagcagaacaagggcttgtcaagaatggatgagtctgccccatcccacctccat
gtccgagggctcagtctagtcctcagcccactccacctccagccgggaaccaaagccactcacctccataaatgatacgggtgctctgagccaccgc
atcagagacgttggacttcagccatcctcggagcttctcgtgtacttcctgggcctagaacaagaagctggcctaagtagacctttctgcctct
ctaagaggaaaaatcactggcaccagtggacacttagtggtttctgactgagtcagagtaccaggctctgatccagccaggccctgactgg
atgccccttgacaagtcactgtctctgggttcaaggtctctgtgtctttgaaataagggttgccccatgtgggctgtgtctgtccaaacctattg
aggcaggctgggatgagggcagggctcctgggcccggttacctgttgggggtgttgcagtcttgccagtaccaatggcccacacaggctcataggcc
aggacgacccttgctccagtcctcacgttatctgcagggcagagatacagatggaggaaggtgaacaagaaagagctctccagccaggttctcc
ggagtacgaagaaacggtggcctactgccccctagtggacattgggg FIGURE 37A(iv)

MetGlyGlnThrAlaLeuAlaGlyGlySerSerSerThrProThrProGlnAlaLeuTyrProAsp
LeuSerCysProGluGlyLeuGluGluLeuLeuSerAlaProProProAspLeuGlyAlaGlnArg
ArgHisGlyTrpAsnProLysAspCysSerGluAsnIleGluValLysGluGlyGlyLeuTyrPhe
GluArgArgProValAlaGlnSerThrAspGlyAlaArgGlyLysArgGlyTyrSerArgGlyLeu
HisAlaTrpGluIleSerTrpProLeuGluGlnArgGlyThrHisAlaValValGlyValAlaThr
AlaLeuAlaProLeuGlnThrAspHisTyrAlaAlaLeuLeuGlySerAsnSerGluSerTrpGly
TrpAspIleGlyArgGlyLysLeuTyrHisGlnSerLysGlyProGlyAlaProGlnTyrProAla
GlyThrGlnGlyGluGlnLeuGluValProGluArgLeuLeuValValLeuAspMetGluGluGly
ThrLeuGlyTyrAlaIleGlyGlyThrTyrLeuGlyProAlaPheArgGlyLeuLysGlyArgThr
LeuTyrProAlaValSerAlaValTrpGlyGlnCysGlnValArgIleArgTyrLeuGlyGluArg
ArgAlaGluProHisSerLeuLeuHisLeuSerArgLeuCysValArgHisAsnLeuGlyAspThr
ArgLeuGlyGlnValSerAlaLeuProLeuProProAlaMetLysArgTyrLeuLeuTyrGln*

FIGURE 37B

| atg | gta | gca | cgc | aac | cag | gtg | gca | gcc | gac | aat | gcg | atc | tcc | ccg | gca | 48 |
| Met | Val | Ala | Arg | Asn | Gln | Val | Ala | Ala | Asp | Asn | Ala | Ile | Ser | Pro | Ala | |
| 1 | | | | 5 | | | | | 10 | | | | | 15 | | |

| gca | gag | ccc | cga | cgg | cgg | tca | gag | ccc | tcc | tcc | tcg | tcg | tct | tcg | tcc | 96 |
| Ala | Glu | Pro | Arg | Arg | Arg | Ser | Glu | Pro | Ser | Ser | Ser | Ser | Ser | Ser | Ser | |
| | 20 | | | | | 25 | | | | 30 | | | | | | |

| tcg | cca | gcg | ccc | gtg | cgt | ccc | cgg | ccc | tgc | tcg | ccg | gcg | gtc | cca | gcc | 144 |
| Ser | Pro | Ala | Pro | Val | Arg | Pro | Arg | Pro | Cys | Ser | Pro | Ala | Val | Pro | Ala | |
| | | 35 | | | | 40 | | | | | 45 | | | | | |

| cca | gcc | cct | ggc | gac | act | cgg | ttc | cac | ccc | acc | ttc | ctg | cgc | tcc | gat | 192 |
| Pro | Ala | Pro | Gly | Asp | Thr | Arg | Phe | His | Pro | Thr | Phe | Leu | Arg | Ser | Asp | |
| | 50 | | | | | 55 | | | | 60 | | | | | | |

| tac | cgg | atc | cgc | acg | cgg | acc | agc | gcg | ggg | cac | ctc | gag | gcc | tcc | ttc | 240 |
| Tyr | Arg | Ile | Arg | Thr | Arg | Thr | Ser | Ala | Gly | His | Leu | Glu | Ala | Ser | Phe | |
| 65 | | | | | 70 | | | | 75 | | | | | | 80 | |

| tat | tgg | gga | ccc | ctg | agc | gtg | cac | gtg | gcg | cac | gag | cgg | ctg | cgt | gcc | 288 |
| Tyr | Trp | Gly | Pro | Leu | Ser | Val | His | Gly | Ala | His | Glu | Arg | Leu | Arg | Ala | |
| | | | | 85 | | | | 90 | | | | | | 95 | | |

Figure 41A

| | | | | | | | | | | | | | | | | |
|---|---|---|---|---|---|---|---|---|---|---|---|---|---|---|---|---|
| gag | ccc | gtg | ggc | acc | ttc | ttg | gtg | cgc | gac | agt | cgt | caa | cgg | aac | tgc | 336 |
| Glu | Pro | Val | Gly | Thr | Phe | Leu | Val | Arg | Asp | Ser | Arg | Gln | Arg | Asn | Cys | |
| | | | | 100 | | | | 105 | | | | | 110 | | | |
| ttc | ttc | gcg | ctc | agc | gtg | aag | atg | gct | tcg | ggc | ccc | acg | agc | atc | cgc | 384 |
| Phe | Phe | Ala | Leu | Ser | Val | Lys | Met | Ala | Ser | Gly | Pro | Thr | Ser | Ile | Arg | |
| | | 115 | | | | | 120 | | | | | 125 | | | | |
| gtg | cac | cag | ttc | gcc | ggc | cgc | ctg | ttc | gac | ggc | agc | agc | gcg | gag | acc | 432 |
| Val | His | Gln | Phe | Ala | Gly | Arg | Leu | Phe | Asp | Gly | Ser | Ser | Ala | Glu | Thr | |
| 130 | | | | | | 135 | | | | 140 | | | | | | |
| ttc | gac | tgc | ctt | ttc | gag | gcc | ctg | ctg | cac | tac | gtg | gcg | gcg | ccg | cgc | 480 |
| Phe | Asp | Cys | Leu | Phe | Glu | Ala | Leu | Leu | His | Tyr | Val | Ala | Ala | Pro | Arg | |
| 145 | | | | | 150 | | | | 155 | | | | | | 160 | |
| cgc | atg | ttg | ggg | gcc | ccg | ctg | cgc | cag | cgc | cgc | gtg | cgg | ccg | ctg | cag | 528 |
| Arg | Met | Leu | Gly | Ala | Pro | Leu | Arg | Gln | Arg | Arg | Val | Arg | Pro | Leu | Gln | |
| | | | | 165 | | | | | 170 | | | | | 175 | | |

| gag | ctg | tgt | cgc | cag | cgc | atc | gtg | gcc | gtg | ggt | cgc | gag | aac | ctg | 576 |
| Glu | Leu | Cys | Arg | Gln | Arg | Ile | Val | Ala | Val | Gly | Arg | Glu | Asn | Leu | |
| | | | | 180 | | | | 185 | | | | 190 | | | |

| gcg | cgc | atc | cct | ctt | aac | ccg | gta | ctc | cgt | gac | tac | ctg | agt | tcc | 624 |
| Ala | Arg | Ile | Pro | Leu | Asn | Pro | Val | Leu | Arg | Asp | Tyr | Leu | Ser | Ser | |
| | | 195 | | | | | 200 | | | | | 205 | | | |

| ccc | ttc | cag | atc | tga | | | | | | | | | | | 639 |
| Pro | Phe | Gln | Ile | | | | | | | | | | | | |
| | | 210 | | | | | | | | | | | | | |

```
GGGTGGTACTGGGGTTCTATTACAGCCAGCGAGGCCCGGCAGCACCTACAGAAGATGCCGGAGGTACATTCCTAGTTAAAGAC        CIS
 G  W  Y  W  G  S  I  T  A  S  E  A  R  Q  H  L  Q  K  M  P  E  G  T  F  L  V  K  D

GGCTTCTATTGGGGACCCCTGAGCGTGCACGGGGCGCACGAGCGGCTGCGTGCCGAGCCCGTGGGCACCTTCTTGGTGAAAGAC        SOCS1
 G  F  Y  W  G  P  L  S  V  H  G  A  H  E  R  L  R  A  E  P  V  G  T  F  L  V  K  D

GGATGGTACTGGGGAAGTATGACTGTTAATGAAGCCAAAGAGAAATTAAAGGAGGCTCCAGAAGGAACTTTCTTGATTAAAGAT        SOCS2
 G  W  Y  W  G  S  M  T  V  N  E  A  K  E  K  L  K  E  A  P  E  G  T  F  L  I  K  D

GGATTCTACTGGAGCGCCGTGACCGGCGGCGAGGCGAACCTGCTCTCAGCGCCCGAGCCCGCGGGCACCTTTCTTATCAAGGAC        SOCS3
 G  F  Y  W  S  A  V  T  G  G  E  A  N  L  L  L  S  A  E  P  A  G  T  F  L  I  K  D
```

FIGURE 42

```
ATGGGTCAGAAGGTCACGGGAGGGATCAAGACTGTGGACATGCGGGACCCCACATACCGACC
TCTGAAGCAGGAACTCCAGGGGCTGGATTACTGCAAGCCCACCCGGCTGGACCTGCTGCTCG
ACATGCCCCCCGTGTCCTACGATGTGCAGCTGCTCCACTCCTGGAACAATAACGACCGTTCG
CTCAACGTCTTCGTGAAGGAAGATGACAAGTTGATCTTTCACCGGCATCCGGTGGCCCAGAG
CACGGACGCCATCAGGGGCAAAGTTGGGTACACACGTGGACTGCACGTATGGCAGATCACAT
GGGCCATGAGGCAGCGAGGCACGCATGCCGTGGTGGGGGTGGCCACAGCAGATGCCCCTTTG
CACTCCGTTGGGGACACAACCCTTGTAGGAAATAACCATGAATCCTGGGGCTGGGACCTGGG
GCGTAACCGTCTCTACCACGACGGCAAGAACCAGCCAAGTAAAACATACCCAGCCTTTCTGG
AGCCGGACGAGACATTCATTGTCCCTGACTCCTTTCTCGTGGCCCTGGACATGGATGATGGG
ACCTTAAGTTTCATCGTGGATGGACAGTACATGGGAGTGGCTTTCCGGGGACTCAAGGGTAA
AAAGCTGTATCCTGTAGTGAGTGCCGTCTGGGGCCACTGTGAGATCCGCATGCGCTACTTGA
ACGGACTTGATCCTGAGCCCCTGCCACTCATGGACCTGTGCCGGCGTTCGGTGCGCCTAGCG
CTGGGAAAGGAGCGCCTGGGTGCCATCCCCGCTCTGCCGCTACCTGCCTCCCTCAAAGCCTA
CCTCCTCTACCAGTGA
```

FIGURE 49

MetGlyGlnLysValThrGlyGlyIleLysThrValAspMetArgAspProThrTyrArg
ProLeuLysGlnGluLeuGlnGlyLeuAspTyrCysLysProThrArgLeuAspLeuLeu
LeuAspMetProProValSerTyrAspValGlnLeuLeuHisSerTrpAsnAsnAsnAsp
ArgSerLeuAsnValPheValLysGluAspAspLysLeuIlePheHisArgHisProVal
AlaGlnSerThrAspAlaIleArgGlyLysValGlyTyrThrArgGlyLeuHisValTrp
GlnIleThrTrpAlaMetArgGlnArgGlyThrHisAlaValValGlyValAlaThrAla
AspAlaProLeuHisSerValGlyTyrThrThrLeuValGlyAsnAsnHisGluSerTrp
GlyTrpAspLeuGlyArgAsnArgLeuTyrHisAspGlyLysAsnGlnProSerLysThr
TyrProAlaPheLeuGluProAspGluThrPheIleValProAspSerPheLeuValAla
LeuAspMetAspAspGlyThrLeuSerPheIleValAspGlyGlnTyrMetGlyValAla
PheArgGlyLeuLysGlyLysLysLeuTyrProValValSerAlaValTrpGlyHisCys
GluIleArgMetArgTyrLeuAsnGlyLeuAspProGluProLeuProLeuMetAspLeu
CysArgArgSerValArgLeuAlaLeuGlyLysGluArgLeuGlyAlaIleProAlaLeu
ProLeuProAlaSerLeuLysAlaTyrLeuLeuTyrGln*

FIGURE 50

```
ATGGATAAAGTGGGGAAAATGTGGAACAACTTAAAATACAGATGCCAGAATCTCTTCAGCCA
CGAGGGAGGAAGCCGTAATGAGAACGTGGAGATGAACCCCAACAGATGTCCGTCTGTCAAAG
AGAAAAGCATCAGTCTGGGAGAGGCAGCTCCCCAGCAAGAGAGCAGTCCCTTAAGAGAAAAT
GTTGCCTTACAGCTGGGACTGAGCCCTTCCAAGACCTTTTCCAGGCGGAACCAAAACTGTGC
CGCAGAGATCCCTCAAGTGGTTGAAATCAGCATCGAGAAGACAGTGACTCGGGTGCCACCC
CAGGAACGAGGCTTGCACGGAGAGACTCCTACTCGCGGCACGCCCGTGGGGAGGAAAGAAG
AAACATTCCTGTTCCACAAAGACCCAGAGTTCATTGGATACCGAGAAAAGTTTGGTAGAAC
TCGAAGCGGCCTTCAGAGGCGAGAGCGGCGCTATGGAGTCAGCTCCATGCAGGACATGGACA
GCGTTTCTAGCCGCACGGTCGGGAGCCGCTCCCTGAGGCAGAGGCTCCAGGACACGGTGGGT
TTGTGTTTTCCCATGAGAACTTACAGCAAGCAGTCAAAGCCACTCTTTTCCAATAAAAGAAA
AATACATCTTTCTGAATTAATGCTGGAGAAATGCCCTTTTCCTGCTGGCTCGGATTTAGCAC
AAAAGTGGCATTTGATTAAACAGCATACCGCCCCTGTGAGCCCACACTCAACATTTTTTGAT
ACATTTGATCCATCACTGGTGTCTACAGAAGATGAAGAAGATAGGCTTCGCGAGAGAAGACG
GCTTAGTATCGAAGAAGGGGTGGATCCCCCTCCCAACGCACAAATACACACCTTTGAAGCTA
CTGCACAGGTCAACCCATTGTATAAGCTGGGACCAAAGTTAGCTCCTGGGATGACAGAGATA
AGTGGAGATGGTTCTGCAATTCCACAAACGAATTGTGACTCAGAAGAGGATTCAACCACCCT
ATGTCTGCAGTCACGGAGGCAGAAGCAGCGCCAGGTGTCCGGGGACAGCCACGCGCACGTTA
GCAGACAGGGAGCTTGGAAAGTTCATACGCAGATCGATTACATACACTGCCTCGTGCCAGAT
TTGCTTCAGATCACAGGGAATCCCTGTTACTGGGGCGTGATGGACCGATACGAGGCCGAAGC
CCTTCTAGAAGGGAAACCGGAAGGCACGTTCTTGCTCAGGGACTCTGCACAGGAGGACTACC
TCTTCTCTGTGAGCTTCCGCCGCTACAACAGGTCTCTGCACGCCCGGATCGAGCAGTGGAAC
CACAACTTCAGCTTCGATGCCCATGACCCCTGCGTGTTTCACTCCTCCACAGTCACGGGGCT
TCTCGAACACTATAAAGACCCCAGCTCTTGCATGTTTTTTGAACCGTTGCTAACGATATCAC
TGAATAGAACTTTCCCTTTCAGCCTGCAGTATATCTGCCGCGCAGTGATCTGCAGATGCACT
ACGTATGATGGGATTGACGGGCTCCCGCTACCGTCGATGTTACAGGATTTTTTAAAAGAGTA
TCATTATAAACAAAAAGTTAGGGTTCGCTGGTTAGAACGAGAGCCAGTCAAAGCAAAGTAA
```

FIGURE 51A

```
MetAspLysValGlyLysMetTrpAsnAsnLeuLysTyrArgCysGlnAsnLeuPheSer
HisGluGlyGlySerArgAsnGluAsnValGluMetAsnProAsnArgCysProSerVal
LysGluLysSerIleSerLeuGlyGluAlaAlaProGlnGlnGluSerSerProLeuArg
GluAsnValAlaLeuGlnLeuGlyLeuSerProSerLysThrPheSerArgArgAsnGln
AsnCysAlaAlaGluIleProGlnValValGluIleSerIleGluLysAspSerAspSer
GlyAlaThrProGlyThrArgLeuAlaArgArgAspSerTyrSerArgHisAlaProTrp
GlyGlyLysLysLysHisSerCysSerThrLysThrGlnSerSerLeuAspThrGluLys
LysPheGlyArgThrArgSerGlyLeuGlnArgArgGluArgArgTyrGlyValSerSer
MetGlnAspMetAspSerValSerSerArgThrValGlySerArgSerLeuArgGlnArg
LeuGlnAspThrValGlyLeuCysPheProMetArgThrTyrSerLysGlnSerLysPro
LeuPheSerAsnLysArgLysIleHisLeuSerGluLeuMetLeuGluLysCysProPhe
ProAlaGlySerAspLeuAlaGlnLysTrpHisLeuIleLysGlnHisThrAlaProVal
SerProHisSerThrPhePheAspThrPheAspProSerLeuValSerThrGluAspGlu
GluAspArgLeuArgGluArgArgArgLeuSerIleGluGluGlyValAspProProPro
AsnAlaGlnIleHisThrPheGluAlaThrAlaGlnValAsnProLeuTyrLysLeuGly
ProLysLeuAlaProGlyMetThrGluIleSerGlyAspGlySerAlaIleProGlnThr
AsnCysAspSerGluGluAspSerThrThrLeuCysLeuGlnSerArgArgGlnLysGln
ArgGlnValSerGlyAspSerHisAlaHisValSerArgGlnGlyAlaTrpLysValHis
ThrGlnIleAspTyrIleHisCysLeuValProAspLeuLeuGlnIleThrGlyAsnPro
CysTyrTrpGlyValMetAspArgTyrGluAlaGluAlaLeuLeuGluGlyLysProGlu
GlyThrPheLeuLeuArgAspSerAlaGlnGluAspTyrLeuPheSerValSerPheArg
ArgTyrAsnArgSerLeuHisAlaArgIleGluGlnTrpAsnHisAsnPheSerPheAsp
AlaHisAspProCysValPheHisSerSerThrValThrGlyLeuLeuGluHisTyrLys
AspProSerSerCysMetPhePheGluProLeuLeuThrIleSerLeuAsnArgThrPhe
ProPheSerLeuGlnTyrIleCysArgAlaValIleCysArgCysThrThrTyrAspGly
IleAspGlyLeuProLeuProSerMetLeuGlnAspPheLeuLysGluTyrHisTyrLys
GlnLysValArgValArgTrpLeuGluArgGluProValLysAlaLys*
```

FIGURE 51B

```
ATGAAGAAAATCAGTCTGAAGACCTTCAGGAAATCTTTTAACCTGAGTAAAAGCAAAGACGA
AACTGAGTTCATGGTGGTTCAGCCCCAGTCCCTTGCTGGTGACTTCGTGAAGATGACTCTT
TATTCGGGAGCTGTTATGGCAAAGACATGGCCAGTTGTGACATTGGCAGCGAGGATGAGAAA
GGGAAGAACAGATCCAAAAGCGAGAGCCTGATGGGCACTTTGAAGAGGCGGTTGTCCGCCAA
GCAGAAGACCAAGGGCAAGGGCGGCACTGCGTCTACAGATGAGGACACCTTCTCCTCAGCTT
CAGCTCCTGGTGGGCTCAAGGATGTGCGTGCTCCGCGGCCCATCCGCTCCACATCACTGAGA
AGCCACCATTATAGCCCCACGCCCTGGCCGCTGCGTCCCACCAGCTCGGAGGAGACGTGCAT
CAAGATGGAGATGCGAGTGAAAGCACTGGTGCATGCTGCCAGCCCAGGACCAGTCAACGGTG
TGCGCAAGGATCTGCGGGAGCTACAGCCCAGGGAGCTGCGAGACCTGCAGCCAGAGCCGCGC
CCTGAGTCCCGCTGCAGCCCCAGCTCACCCGGGGACCTGAGCCTCCACCTGGAGGAACACGT
GCCTGTAGTAATCGGACTCATGTCTCAGGACTACCTTCAGTACACCGTGCCTTTAGATGACG
GGATGTGCCCTCTTGAAGGGCCGCGCAGCTGCTGCCTGGATACGTCTTCTCCCATGGAGGTG
TCAGCCGTACCCCTGCCGGGGGCGAGTGGTGCCTTCTCCGAAGACGACAGTCATGTGGACCA
GGACCTGGTTGTAGGCCCAGAGATCCTTGTGGATTCATCAGTGAACAATTTGTTGATTGGCA
CCACAGGAGTCATGTTGCAGAGCCCTAGAGGAGGTCATGATGACGCCCCTCCCCTCTCACCA
TTGCTACCTCCAATGCAGAATAACCCAATCCAAAGGAACTTCAGTGGCCTCTCGGGCCCAGA
CTTGCACATGGCCGAAAGTGTTCGCTGTCATTTGAATTTCGATCCCAACTCTGCGCCTGGGG
TTGCTAGAGTTTATGACTCGGTGCAAAGTAGTGGCCCCATGGTTGTTACAAGTCTTACGGAG
GAGCTGAAGAAGCTTGCAAAACAGGGGTGGTATTGGGGCCCCATCACACGCTGGGAGCAGAG
GGGAAGTTGGCAAATGTGCCAGATGGTTCTTTTCTTGTAAGGGATAGTTCTGATGACCGTTA
CCTTTTAAGCCTGAGCTTTCGTTCCCATGGTAAAACACTTCACACTAGAATTGAGCACTCAA
ATGGTAGATTCAGCTTTTATGAACAGCCAGATGTGGAAGGGCATACATCTATAGTTGACTTA
ATCGAGCATTCAATCAGGGACTCTGAAAATGGAGCATTTTGTTATTCAAGATCTCGATTGCC
TGGATCAGCAACTTACCCAGTCAGACTGACCAATCCAGTGTCACGATTCATGCAGGTGCGCT
CGCTGCAGTACCTGTGCCGCTTTGTTATCCGTCAGTACACCAGAATAGACTTAATTCAGAAA
CTGCCTTTGCCAAACAAAATGAAGGATTATTTGCAGGAGAAGCACTACTG
```

FIGURE 52A

MetLysLysIleSerLeuLysThrPheArgLysSerPheAsnLeuSerLysSerLysAsp
GluThrGluPheMetValValGlnProGlnSerLeuAlaGlyAspPheValLysAspAsp
SerLeuPheGlySerCysTyrGlyLysAspMetAlaSerCysAspIleGlySerGluAsp
GluLysGlyLysAsnArgSerLysSerGluSerLeuMetGlyThrLeuLysArgArgLeu
SerAlaLysGlnLysThrLysGlyLysGlyGlyThrAlaSerThrAspGluAspThrPhe
SerSerAlaSerAlaProGlyGlyLeuLysAspValArgAlaProArgProIleArgSer
ThrSerLeuArgSerHisHisTyrSerProThrProTrpProLeuArgProThrSerSer
GluGluThrCysIleLysMetGluMetArgValLysAlaLeuValHisAlaAlaSerPro
GlyProValAsnGlyValArgLysAspLeuArgGluLeuGlnProArgGluLeuArgAsp
LeuGlnProGluProArgProGluSerArgCysSerProSerSerProGlyAspLeuSer
LeuHisLeuGluGluHisValProValValIleGlyLeuMetSerGlnAspTyrLeuGln
TyrThrValProLeuAspAspGlyMetCysProLeuGluGlyProArgSerCysCysLeu
AspThrSerSerProMetGluValSerAlaValProLeuProGlyAlaSerGlyAlaPhe
SerGluAspAspSerHisValAspGlnAspLeuValValGlyProGluIleLeuValAsp
SerSerValAsnAsnLeuLeuIleGlyThrThrGlyValMetLeuGlnSerProArgGly
GlyHisAspAspAlaProProLeuSerProLeuLeuProProMetGlnAsnAsnProIle
GlnArgAsnPheSerGlyLeuSerGlyProAspLeuHisMetAlaGluSerValArgCys
HisLeuAsnPheAspProAsnSerAlaProGlyValAlaArgValTyrAspSerValGln
SerSerGlyProMetValValThrSerLeuThrGluGluLeuLysLysLeuAlaLysGln
GlyTrpTyrTrpGlyProIleThrArgTrpGluAlaGluGlyLysLeuAlaAsnValPro
AspGlySerPheLeuValArgAspSerSerAspAspArgTyrLeuLeuSerLeuSerPhe
ArgSerHisGlyLysThrLeuHisThrArgIleGluHisSerAsnGlyArgPheSerPhe
TyrGluGlnProAspValGluGlyHisThrSerIleValAspLeuIleGluHisSerIle
ArgAspSerGluAsnGlyAlaPheCysTyrSerArgSerArgLeuProGlySerAlaThr
TyrProValArgLeuThrAsnProValSerArgPheMetGlnValArgSerLeuGlnTyr
LeuCysArgPheValIleArgGlnTyrThrArgIleAspLeuIleGlnLysLeuProLeu
ProAsnLysMetLysAspTyrLeuGlnGluLysHisTyr*

FIGURE 52B

THERAPEUTIC AND DIAGNOSTIC AGENTS COMPRISING A SOCS BOX

CROSS-REFERENCE TO RELATED APPLICATIONS

This application is a divisional of patent application Ser. No. 09/302,769, filed Apr. 30, 1999, now U.S. Pat. No. 6,323,317, which is a continuation-in-part of patent application Ser. No. 08/962,560, filed Oct. 31, 1997, which claims benefit to provisional application Ser. No. 60/083,807, filed May 1, 1998. Foreign priority is claimed to Austrian patent application PO5117/97 filed Feb. 14, 1997.

FIELD OF THE INVENTION

The present invention relates generally to therapeutic and diagnostic agents. More particularly, the present invention provides therapeutic molecules capable of modulating signal transduction such as but not limited to cytokine-mediated signal transduction. The molecules of the present invention are useful, therefore, in modulating cellular responsiveness to cytokines as well as other mediators of signal transduction such as endogenous or exogenous molecules, antigens, microbes and microbial products, viruses or components thereof, ions, hormones and parasites.

Bibliographic details of the publications referred to in this specification by author are collected at the end of the description. The subject specification contains nucleotide and amino acid sequence information prepared using the programme PatentIn Version 2.0, presented hereinafter the bibliography. Each nucleotide or amino acid sequence is identified in the sequence listing by the numeric indicator <210> followed by the sequence identifier (e.g. <210>1, <210>2, etc.). The length, type of sequence (DNA, protein (PRT), etc.) and source organism for each nucleotide or amino acid sequence are indicated by information provided in the numeric indicator fields <211 >, <212> and <213>, respectively. Nucleotide and amino acid sequences referred to in the specification are defined by the information provided in numeric indicator field <400> followed by the sequence identifier leg, <400>1, <400>2, etc.).

The designation of nucleotide residues referred to herein are those recommended by the IUPAC-IUB Biochemical Nomenclature Commission, wherein A represents Adenine, C represents Cytosine, G represents Guanine, T represents thymine, Y represents a pyrimidine residue, R represents a purine residue, M represents, Adenine or Cytosine, K represents Guanine or Thymine, S represents Guanine or Cytosine, W represents Adenine or Thymine, H represents a nucleotide other than Guanine, B represents a nucleotide other than Adenine, V represents a nucleotide other than Thymine, D represents a nucleotide other than Cytosine and N represents any nucleotide residue. A summary of the sequence listing is given in Table 1.

BACKGROUND OF THE INVENTION

Cells continually monitor their environment in order to modulate physiological and biochemical processes which in turn affects future behaviour. Frequently, a cell's initial interaction with its surroundings occurs via receptors expressed on the plasma membrane. Activation of these receptors, whether through binding endogenous ligands (such as cytokines) or exogenous ligands (such as antigens), triggers a biochemical cascade from the membrane through the cytoplasm to the nucleus.

Of the endogenous ligands, cytokines represent a particularly important and versatile group. Cytokines are proteins which regulate the survival, proliferation, differentiation and function of a variety of cells within the body [Nicola, 1994]. The haemopoietic cytokines have in common a four-alpha helical bundle structure and the vast majority interact with a structurally related family of cell surface receptors, the type I and type II cytokine receptors [Bazan, 1990; Sprang, 1993]. In all cases, ligand-induced receptor aggregation appears to be a critical event in initiating intracellular signal transduction cascades. Some cytokines, for example growth hormone, erythropoietin (Epo) and granulocyte-colony-stimulating factor (G-CSF), trigger receptor homodimerisation, while for other cytokines, receptor heterodimersation or heterotrimerisation is crucial. In the latter cases, several cytokines share common receptor subunits and on this basis can be grouped into three subfamilies with similar patterns of intracellular activation and similar biological effects [Hilton, 1994]. Interleukin-3 (IL-3), IL-5 and granulocyte-macrophage colony-stimulating factor (GM-CSF) use the common β-receptor subunit (βc) and each cytokine stimulates the production and functional activity of granulocytes and macrophages. IL-2, IL-4, IL-7, IL-9, and IL-15 each use the common γ-chain (γc), while IL-4 and IL-13 share an alternative 7-chain (γ'c or IL-13 receptor a-chain). Each of these cytokines plays an important role in regulating acquired immunity in the lymphoid system. Finally, IL-6, IL-11, leukaemia inhibitory factor (LIF), oncostatin-M (OSM), ciliary neurotrophic factor (CNTF) and cardiotrophin (CT) share the receptors subunit gp 130. Each of these cytokines appears to be highly pleiotropic, having effects both within and outside the haemopoietic system [Nicola, 1994].

In all of the above cases at least one subunit of each receptor complex contains the conserved sequence elements, termed box1 and box2, in their cytoplasmic tails [Murakami, 1991]. Box1 is a proline-rich motif which is located more proximal to the transmembrane domain than the acidic box 2 element. The box-1 region serves as the binding site for a class of cytoplasmic tyrosine kinases termed JAKs (Janus kinases). Ligand-induced receptor dimerisation serves to increase the catalytic activity of the associated JAKs through cross-phosphorylation. Activated JAKs then tyrosine phosphorylate several substrates, including the receptors themselves. Specific phosphotyrosine residues on the receptor then serve as docking sites for SH2-containing proteins, the best characterised of which are the signal transducers and activators of transcription (STATs) and the adaptor protein, shc. The STATs are then phosphorylated on tyrosines, probably by JAKs, dissociate from the receptor and form either homodimers or heterodimers through the interaction of the SH2 domain of one STAT with the phosphotyrosine residue of the other. STAT dimers then translocate to the nucleus where they bind to specific cytokine-responsive promoters and activate transcription [Darnell, 1994; Ihle, 1995; Ihle, 1995]. In a separate pathway, tyrosine phosphorylated shc interacts with another SH2 domain-containing protein, Grb-2, leading ultimately to activation of members of the MAP kinase family and in rum transcription factors such as fos and jun (Sato, 1993; Cutler, 19931. These pathways are not unique to members of the cytokine receptor family since cytokines that bind receptor tyrosine kinases also being able to activate STATs and members of the MAP kinase family [David, 1996; Leaman, 1996; Shual, 1993; Sato, 1993; Cutler, 1993].

Four members of the JAK family of cytoplasmic tyrosine kinases have been described, JAK1, JAK2, JAK2 and TYK2, each of which binds to a specific subset of cytokine receptor subunits. Six STATs have been described (STAT1 through STAT6), and these too are activated by distinct cytokine/receptor complexes. For example, STAT1 appears to be functionally specific to the interferon system, STAT2 appears to be specific to IL-12, while STATE appears to be specific for IL-4 and IL-13. Thus, despite common activation mechanisms some degree of cytokine specificity may be achieved through the use of specific JAKs and STATs [Thierfelder, 1996; Kaplan, 1996; Takeda, 1996; Shimoda, 1996; Meraz,1996; Durbin, 1996].

In addition to those described above, there .are clearly other mechanisms of activation of these pathways. For example, the JAK/STAT pathway appears to be able to activate MAP kinases independent of the shc-induced pathway [David, 1995] and the STATs themselves can be activated without binding to the receptor, possibly by direct interaction with JAKs [Gupta, 1996]. Conversely, full activation of STATS may require the action of MAP kinase in addition to that of JAKs [David, 1995; Wen, 1995].

While the activation of these signalling pathways is becoming better understood, little is known S of the regulation of these pathways, including employment of negative or positive feedback loops. This is important since once a cell has begun to respond to a stimulus, it is critical that the intensity and duration of the response is regulated and that signal transduction is switched off. It is likewise desirable to increase the intensity of a response systemically or even locally as the situation requires.

In work leading up to the present invention, the inventors sought to isolate negative regulators of signal transduction. The inventors have now identified a new family of proteins which are capable of acting as regulators of signalling. The new family of proteins is defined as the suppressor of cytokine signalling (SOCS) family based on the ability of the initially identified SOCS molecules to suppress cytokine-mediated signalling. It should be noted, however, that not all members of the SOCS family need necessarily share suppressor function nor target solely cytokine mediated signalling. The SOCS family comprises at least three classes of protein molecules based on amino acid sequence motifs located N-terminal of a C-terminal motif called the SOCS box. The identification of this new family of regulatory molecules permits the generation of a range of effector or modulator molecules capable of modulating signal transduction and, hence, cellular responsiveness to a range of molecules including cytokines. The present invention, therefore, provides therapeutic and diagnostic agents based on SOCS proteins, derivatives, homologues, analogues and mimetics thereof as well as agonists and antagonists of SOCS proteins.

SUMMARY OF THE INVENTION

Throughout this specification and the claims which follow, unless the context requires otherwise, the word "comprise", or variations such as "comprises" or "comprising", will be understood to imply the inclusion of a stated integer or group of integers but not the exclusion of any other integer or group of integers.

The present invention provides inter alia nucleic acid molecules encoding members of the SOCS family of proteins as well as the proteins themselves. Reference hereinafter to "SOCS" encompasses any or all members of the SOCS family. Specific SOCS molecules are defined numerically such as, for example, SOCS1, SOCS2 and SOCS3. The species from which the SOCS has been obtained may be indicated by a preface of a single letter abbreviation where "h" is human, "m" is murine and "r" is rat. Accordingly, "mSOCS1" is a specific SOCS from a murine animal. Reference herein to "SOCS" is not to imply that the protein solely suppresses cytokine-mediated signal transduction, as the molecule may modulate other effector-mediated signal transductions such as by hormones or other endogenous or exogenous molecules, antigens, microbes and microbial products, viruses or components thereof, ions, hormones and parasites. The term "modulates" encompasses up-regulation, down-regulation as well as maintenance of particular levels.

One aspect of the present invention provides a nucleic acid molecule comprising a sequence of nucleotides encoding or complementary to a sequence encoding a protein or a derivative, homologue, analogue or mimetic thereofor a nucleotide sequence capable of hybridizing thereto under low stringency conditions at 42° C. wherein said protein comprises a SOCS box in its C-terminal region Another aspect of the present invention provides a nucleic acid molecule comprising a sequence of nucleotides encoding or complementary to a sequence encoding a protein or a derivative, homologue, analogue or mimetic thereof or a nucleotide sequence capable of hybridizing thereto under low stringency conditions at 42° C. wherein said protein comprises a SOCS box in its C-terminal region and a protein:molecule interacting region.

Yet another aspect of the present invention is directed to a nucleic acid molecule comprising a sequence of nucleotides encoding or complementary to a sequence encoding a protein or a derivative, homologue, analogue or mimetic thereof or a nucleotide sequence capable of hybridizing thereto under low stringency conditions at 42° C. wherein said protein comprises a C-terminal region and a protein:molecule interacting region located in a region N-terminal of the SOCS box.

Preferably, the protein:molecule interacting region is a protein:DNA or protein:protein binding region.

Still a further aspect of the present invention provides a nucleic acid molecule comprising a sequence of nucleotides encoding or complementary to a sequence encoding a protein or a derivative, homologue, analogue or mimetic thereof or a nucleotide sequence capable of hybridizing thereto under low stringency conditions at 42° C. wherein said protein comprises a SOCS box in its C-terminal region and one or more of an SH2 domain, WD-40 repeats or ankyrin repeats N-terminal of the SOCS box.

Even still a further aspect of the present invention is directed to a nucleic acid molecule comprising a sequence of nucleotides encoding or complementary to a sequence encoding a protein or a derivative, homologue, analogue or mimetic thereof or a nucleotide sequence capable of hybridizing thereto under low stringency conditions at 42° C. wherein said protein comprises a SOCS box in its C-terminal region wherein the SOCS box comprises the amino acid sequence:

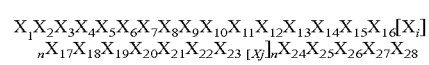

wherein $X_1$ is L, I, V, M, A or P;

$X_2$ is any amino acid residue;

$X_3$ is P, T or S;

$X_4$ is L, I, V, M, A or P;

$X_5$ is any amino acid;

$X_6$ is any amino acid;

$X_7$ is L, I, V, M, A, F, Y or W;

$X_8$ is C, T or S;
$X_9$ is R, K or H;
$X_{10}$ is any amino acid;
$X_{11}$ is any amino acid;
$X_{12}$ is L, I, V, M, A or P;
$X_{13}$ is any amino acid;
$X_{14}$ is any amino acid;
$X_{15}$ is any amino acid;
$X_{16}$ is L, I, V, M, A, P, G, C, T or S;
$[X_i]_n$ is a sequence of n amino acids wherein n is from 1 to 50 amino acids and wherein the sequence $X_i$ may comprise the same or different amino acids selected from any amino acid residue;
$X_{17}$ is L, I, V, M, A or P;
$X_{18}$ is any amino acid;
$X_{19}$ is any amino acid;
$X_{20}$ L, I, V, M, A or P;
$X_{21}$ is P;
$X_{22}$ is L, I, V, M, A, P or G;
$X_{23}$ is P or N;
$[X_j]_n$ is a sequence of n amino acids wherein n is from 0 to 50 amino acids and wherein the sequence $X_j$ may comprise the same or different amino acids selected from any amino acid residue;
$X_{24}$ is L, I, V, M, A or P;
$X_{25}$ is any amino acid;
$X_{26}$ is any amino acid;
$X_{27}$ is Y or F;
$X_{28}$ is L, I, V, M, A or P;
and a protein:molecule interacting region such as but not limited to one or more of an SH2 domain, WD-40 repeats and/or ankyrin repeats N-terminal of the SOCS box.

Another aspect of the present invention is directed to a nucleic acid molecule comprising a sequence of nucleotides encoding or complementary to a sequence encoding a protein or a derivative, homologue, analogue or mimetic thereof or a nucleotide sequence capable of hybridizing thereto under low stringency conditions at 42° C. wherein said protein exhibits the following characteristics:

(i) comprises a SOCS box in its C-terminal region having the amino acid sequence:

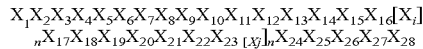

wherein:
$X_1$ is L, I, V, M, A or P;
$X_2$ is any amino acid residue;
$X_3$ is P, T or S;
$X_4$ is L, I, V, M, A or P;
$X_5$ is any amino acid;
$X_6$ is any amino acid;
$X_7$ is L, I, V, M, A, F, Y or W;
$X_8$ is C, T or S;
$X_9$ is R, K or H;
$X_{10}$ is any amino acid;
$X_{11}$ is any amino acid;
$X_{12}$ is L, I, V, M, A or P;
$X_{13}$ is any amino acid;
$X_{14}$ is any amino acid;
$X_{15}$ is any amino acid;
$X_{16}$ is L, I, V, M, A, P, G, C, T or S;
$[X_i]_n$ is a sequence of n amino acids wherein n is from 1 to 50 amino acids and wherein the sequence $X_i$ may comprise the same or different amino acids selected from any amino acid residue;
$X_{17}$ is L, I, V, M, A or P;
$X_{18}$ is any amino acid;
$X_{19}$ is any amino acid;
$X_{20}$ L, I, V, M, A or P;
$X_{21}$ is P;
$X_{22}$ is L, I, V, M, A, P or G;
$X_{23}$ is P or N;
$[X_j]$ n is a sequence of n amino acids wherein n is from 0 to 50 amino acids and wherein the sequence $X_j$ may comprise the same or different amino acids selected from any amino acid residue;
$X_{24}$ is L, I, V, M, A or P;
$X_{25}$ is any amino acid;
$X_{26}$ is any amino acid;
$X_{27}$ is Y or F;
$X_{28}$ is L, I, V, M, A or P; and
(ii) comprises at least one of a SH2 domain, WD-40 repeats and/or ankyrin repeats or other protein:molecule interacting domain in a region N-terminal of the SOCS box.

Preferably, the SOCS molecules modulate signal transduction such as from a cytokine or hormone or other endogenous or exogenous molecule, a microbe or microbial product, an antigen or a parasite.

More preferably, the SOCS molecule modulate cytokine mediated signal transduction.

Still another aspect of the present invention comprises a nucleic acid molecule comprising a sequence of nucleotides encoding or complementary to a sequence encoding a protein or a derivative, homologue, analogue or mimetic thereof or comprises a nucleotide sequence capable of hybridizing thereto under low stringency conditions at 42° C. wherein said protein exhibits the following characteristics;

(i) is capable of modulating signal transduction;
(ii) comprises a SOCS box in its C-terminal region having the amino acid sequence:

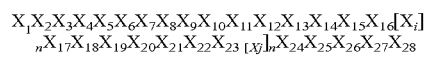

wherein:
$X_1$ is L, I, V, M, A or P;
$X_2$ is any amino acid residue;
$X_3$ is P, T or S;
$X_4$ is L, I, V, M, A or P;
$X_5$ is any amino acid;
$X_6$ is any amino acid;
$X_7$ is L, I, V, M, A, F, Y or W;
$X_8$ is C, T or S;
$X_9$ is R, K or H;
$X_{10}$ is any amino acid;
$X_{11}$ is any amino acid;
$X_{12}$ is L, I, V, M, A or P;
$X_{13}$ is any amino acid;
$X_{14}$ is any amino acid;
$X_{15}$ is any amino acid;
$X_{16}$ is L, I, V, M, A, P, G, C, T or S;

[X$_i$]$_n$ is a sequence of n amino acids wherein n is from 1 to 50 amino acids and wherein the sequence X$_i$ may comprise the same or different amino acids selected from any amino acid residue;

X$_{17}$ is L, I, V, M, A or P;
X$_{18}$ is any amino acid;
X$_{19}$ is any amino acid;
X$_{20}$ L, I, V, M, A or P;
X$_{21}$ is P;
X$_{22}$ is L, I, V, M, A, P or G;
X$_{23}$ is P or N;
[X$_j$] n is a sequence of n amino acids wherein n is from 0 to 50 amino acids and wherein the sequence X$_j$ may comprise the same or different amino acids selected from any amino acid residue;
X$_{24}$ is L, I, V, M, A or P;
X$_{25}$ is any amino acid;
X$_{26}$ is any amino acid;
X$_{27}$ is Y or F;
X$_{28}$ is L, I, V, M, A or P; and
(iii) comprises at least one of a SH2 domain, WD-40 repeats and/or ankyrin repeats or other protein:molecule interacting domain in a region N-terminal of the SOCS box.

Preferably, the signal transduction is mediated by a cytokine such as one or more of EPO, TPO, G-CSF, GM-CSF, IL-3, IL-2, IL-4, IL-7, IL-13, IL-6, LIF, IL-12, IFNα, TNFα, IL-1 and/or M-CSF.

Preferably, the signal transduction is mediated by one or more of Interleukin 6 (IL-6), Leukaemia Inhibitory Factor (LIF), Oncostatin M (OSM), Interferon (IFN)-α and/or thrombopoietin.

Preferably, the signal transduction is mediated by IL-6.

Particularly preferred nucleic acid molecules comprise nucleotide sequences substantially set forth in SEQ ID NO:3 (mSOCS1), SEQ ID NO:5 (mSOCS2), SEQ ID NO:7 (mSOCS3), SEQ ID NO:9 (hSOCS1), SEQ ID NO:11 (rSOCS1), SEQ ID NO:13 (mSOCS4), SEQ ID NOS: 15 and 16 (hSOCS4), SEQ ID NO:17 (mSOCS5), SEQ ID NO:19 (hSOCS5), SEQ ID NO:20 (mSOCS6), SEQ ID NOS: 22 and 23 (hSOCS6), SEQ ID NO:24 (mSOCS7), SEQ ID NOS:26 and 27 (hSOCS7), SEQ ID NO:28 (mSOCS8), SEQ ID NO:30 (mSOCS9), SEQ ID NO:31 (hSOCS9), SEQ ID NO:32 (mSOCS10), SEQ ID NOS: 33 and 34 (hSOCS10), SEQ ID NO: 35 (hSOCS11), SEQ ID NO:37 (mSOCS12), SEQ ID NOS: 38 and 39 (hSOCS12), SEQ ID NO:40 (mSOCS13), SEQ ID NO:42 (hSOCS13), SEQ ID NO:43 (mSOCS14), SEQ ID NO: 45 (mSOCS15) and SEQ ID NO:47 (hSOCS15) or a nucleotide sequence having at least about 15% similarity to all or a region of any of the listed sequences or a nucleotide acid molecule capable of hybridizing to any one of the listed sequences under low stringency conditions at 42° C.

Another aspect of the present invention relates to a protein or a derivative, homologue, analogue or mimetic thereof comprising a SOCS box in its C-terminal region.

Yet another aspect of the present invention is directed to a protein or a derivative, homologue, analogue or mimetic thereof comprising a SOCS box in its C-terminal region and a protein:molecule interacting region.

Even yet another aspect of the present invention provides a protein or a derivative, homologue, analogue or mimetic thereof comprising an interacting region located in a region N-terminal of the SOCS box.

Preferably, the protein:molecule interacting region is a protein:DNA or a protein:protein binding region.

Another aspect of the present invention contemplates a protein or a derivative, homologue, analogue or mimetic thereof comprising a SOCS box in its C-terminal region and a SH2 domain, WD-40 repeats or ankyrin repeats N-terminal of the SOCS box.

Still yet another aspect of the present invention provides a protein or a derivative, homologue, analogue or mimetic thereof exhibiting the following characteristics: (i) comprises a SOCS box in its C-terminal region having the amino acid sequence:

$$X_1X_2X_3X_4X_5X_6X_7X_8X_9X_{10}X_{11}X_{12}X_{13}X_{14}X_{15}X_{16}[X_i]_nX_{17}X_{18}X_{19}X_{20}X_{21}X_{22}X_{23}[X_j]_nX_{24}X_{25}X_{26}X_{27}X_{28}$$

wherein:

X$_1$ is L, I, V, M, A or P;
X$_2$ is any amino acid residue;
X$_3$ is P, T or S;
X$_4$ is L, I, V, M, A or P;
X$_5$ is any amino acid;
X$_6$ is any amino acid;
X$_7$ is L, I, V, M, A, F, Y or W;
X$_8$ is C, T or S;
X$_9$ is R, K or H;
X$_{10}$ is any amino acid;
X$_{11}$ is any amino acid;
X$_{12}$ is L, I, V, M, A or P;
X$_{13}$ is any amino acid;
X$_{14}$ is any amino acid;
X$_{15}$ is any amino acid;
X$_{16}$ is L, I, V, M, A, P, G, C, T or S;
[X$_i$]$_n$ is a sequence of n amino acids wherein n is from 1 to 50 amino acids and wherein the sequence X$_i$ may comprise the same or different amino acids selected from any amino acid residue;
X$_{17}$ is L, I, V, M, A or P;
X$_{18}$ is any amino acid;
X$_{19}$ is any amino acid;
X$_{20}$ L, I, V, M, A or P;
X$_{21}$ is P;
X$_{22}$ is L, I, V, M, A, P or G;
X$_{23}$ is P or N;
[X$_j$] n is a sequence of n amino acids wherein n is from 0 to 50 amino acids and wherein the sequence X$_j$ may comprise the same or different amino acids selected from any amino acid residue;
X$_{24}$ is L, I, V, M, A or P;
X$_{25}$ is any amino acid;
X$_{26}$ is any amino acid;
X$_{27}$ is Y or F;
X$_{28}$ is L, I, V, M, A or P; and
(ii) comprises at least one of a SH2 domain, WD-40 repeats and/or ankyrin repeats or other protein:molecule interacting domain in a region N-terminal of the SOCS box.

Preferably, the proteins modulate signal transduction such as cytokine-mediated signal transduction.

Preferred cytokines are EPO, TPO, G-CSF, GM-CSF, IL-3, IL-2, IL-4, IL-7, IL-13, IL-6, LIF, IL-12, IFNγ, TNFα, IL-1 and/or M-CSF.

A particularly preferred cytokine is IL-6.

Even yet another aspect of the present invention provides a protein or derivative, homologue, analogue or mimetic thereof exhibiting the following characteristics:

(i) is capable of modulating signal transduction such as cytokine-mediated signal transduction;

(ii) comprises a SOCS box in its C-terminal region having the amino acid sequence:

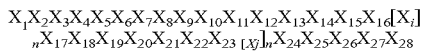

$$X_1X_2X_3X_4X_5X_6X_7X_8X_9X_{10}X_{11}X_{12}X_{13}X_{14}X_{15}X_{16}[X_i]_n X_{17}X_{18}X_{19}X_{20}X_{21}X_{22}X_{23}[X_j]_n X_{24}X_{25}X_{26}X_{27}X_{28}$$

wherein:

$X_1$ is L, I, V, M, A or P;
$X_2$ is any amino acid residue;
$X_3$ is P, T or S;
$X_4$ is L, I, V, M, A or P;
$X_5$ is any amino acid;
$X_6$ is any amino acid;
$X_7$ is L, I, V, M, A, F, Y or W;
$X_8$ is C, T or S;
$X_9$ is R, K or H;
$X_{10}$ is any amino acid;
$X_{11}$ is any amino acid;
$X_{12}$ is L, I, V, M, A or P;
$X_{13}$ is any amino acid;
$X_{14}$ is any amino acid;
$X_{15}$ is any amino acid;
$X_{16}$ is L, I, V, M, A, P, G, C, T or S;
$[X_i]_n$ is a sequence of n amino acids wherein n is from 1 to 50 amino acids and wherein the sequence $X_i$ may comprise the same or different amino acids selected from any amino acid residue;
$X_{17}$ is L, I, V, M, A or P;
$X_{18}$ is any amino acid;
$X_{19}$ is any amino acid;
$X_{20}$ L, I, V, M, A or P;
$X_{21}$ is P;
$X_{22}$ is L, I, V, M, A, P or G;
$X_{23}$ is P or N;
$[X_j]$ n is a sequence of n amino acids wherein n is from 0 to 50 amino acids and wherein the sequence $X_j$ may comprise the same or different amino acids selected from any amino acid residue;
$X_{24}$ is L, I, V, M, A or P;
$X_{25}$ is any amino acid;
$X_{26}$ is any amino acid;
$X_{27}$ is Y or F;
$X_{28}$ is L, I, V, M, A or P; and (iii) comprises at least one of a SH2 domain, WD-40 repeats and/or ankyrin repeats or other protein-molecule interacting domain in a region N-terminal of the SOCS box.

Particularly preferred SOCS proteins comprise an amino acid sequence substantially asset forth in SEQ ID NO:4 (mSOCS1), SEQ ID NO:6 (mSOCS2), SEQ ID NO:8 (mSOCS3), SEQ ID NO:10 (hSOCS1), SEQ ID NO:12 (rSOCS1), SEQ ID NO:14 (mSOCS4), SEQ ID NO:18 (mSOCS5), SEQ ID NO:21 (mSOCS6), SEQ ID NO:25 (mSOCS7), SEQ ID NO:29 (mSOCS8), SEQ ID NO:36 (hSOCS11), SEQ ID NO:41 (mSOCS13), SEQ ID NO:44 (mSOCS14), SEQ ID NO:46 (mSOCS15) and SEQ ID NO:48 (hSOCS15) or an amino acid sequence having at least 15% similarity to all or a region of any one of the listed sequences.

Another aspect of the present invention contemplates a method of modulating levels of a SOCS protein in a cell said method comprising contacting a cell containing a SOCS gene with an effective amount of a modulator of SOCS gene expression or SOCS protein activity for a time and under conditions sufficient to modulate levels of said SOCS protein.

A related aspect of the present invention provides a method of modulating signal transduction in a cell containing a SOCS gene comprising contacting said cell with an effective amount of a modulator of SOCS gene expression or SOCS protein activity for a time sufficient to modulate signal transduction.

Yet a further related aspect of the present invention is directed to a method of influencing interaction between cells wherein at least one cell carries a SOCS gene, said method comprising contacting the cell carrying the SOCS gene with an effective amount of a modulator of SOCS gene expression or SOCS protein activity for a time sufficient to modulate signal transduction.

In accordance with the present invention, n in $[X_i]_n$ and $[X_j]_n$ may, in addition from being 1–50, be from 1–30, 1–20, 1–10 and 1–5.

A summary of the sequence listing referred to in the subject specification is given in Table 1.

TABLE 1

SUMMARY OF SEQUENCE IDENTIFYING NUMBERS

| SEQUENCE | SEQ ID NO |
|---|---|
| PCR Primer | 1 |
| PCR Primer | 2 |
| Mouse SOCS1 (nucleotide) | 3 |
| Mouse SOCS1 (amino acid) | 4 |
| Mouse SOCS2 (nucleotide) | 5 |
| Mouse SOCS2 (amino acid) | 6 |
| Mouse SOCS3 (nucleotide) | 7 |
| Mouse SOCS3 (amino acid) | 8 |
| Human SOCS1 (nucleotide) | 9 |
| Human SOCS1 (amino acid) | 10 |
| Rat SOCS1 (nucleotide) | 11 |
| Rat SOCS1 (amino acid) | 12 |
| nucleotide sequence of murine SOCS4 | 13 |
| amino acid sequence of murine SOCS4 | 14 |
| nucleotide sequence of SOCS4 cDNA human contig 4.1 | 15 |
| nucleotide sequence of SOCS4 cDNA human contig 4.2 | 16 |
| nucleotide sequence of murine SOCS5 | 17 |
| amino acid sequence of murine SOCS5 | 18 |
| nucleotide sequence of human SOCS5 | 19 |
| nucleotide sequence of murine SOCS6 | 20 |
| amino acid of murine SOCS6 | 21 |
| nucleotide sequence of human SOCS6 contig h6.1 | 22 |
| nucleotide sequence of human SOCS6 contig h6.2 | 23 |
| nucleotide sequence of murine SOCS7 | 24 |
| amino acid sequence of murine SOCS7 | 25 |
| nucleotide sequence of human SOCS7 contig h7.1 | 26 |
| nucleotide sequence of human SOCS7 contig 17.2 | 27 |
| nucleotide sequence of murine SOCS8 | 28 |
| amino acid sequence of murine SOCS 8 | 29 |
| nucleotide sequence of murine SOCS9 | 30 |
| nucleotide sequence of human SOCS9 | 31 |
| nucleotide sequence of murine SOCS10 | 32 |
| nucleotide sequence of human SOCS10 contig h10.1 | 33 |
| nucleotide sequence of human SOCS10 contig h10.2 | 34 |
| nucleotide sequence of human SOCS11 | 35 |
| amino acid sequence of human SOCS11 | 36 |
| nucleotide sequence of mouse SOCS12 | 37 |
| nucleotide sequence of human SOCS12 contig h12.1 | 38 |
| nucleotide sequence of human SOCS12 contig h12.2 | 39 |
| nucleotide sequence of murine SOCS13 | 40 |
| amino acid sequence of murine SOCS13 | 41 |
| nucleotide sequence of human SOCS13 cDNA contig h13.1 | 42 |
| nucleotide sequence of murine SOCS14 cDNA | 43 |
| amino acid sequence of murine SOCS14 | 44 |
| nucleotide sequence of murine SOCS15 cDNA | 45 |

TABLE 1-continued

SUMMARY OF SEQUENCE IDENTIFYING NUMBERS

| SEQUENCE | SEQ ID NO |
|---|---|
| amino acid sequence of murine SOCS15 | 46 |
| nucleotide sequence of human SOCS15 | 47 |
| amino acid sequence of human SOCS15 | 48 |
| 5' oliognucleotide sequence (2465) | 49 |
| 3' oligonucleotide sequence (2466) | 50 |
| N-terminal GFP tag | 51 |
| 3' genomic oligonucleotide no. 3243 | 52 |
| 5' genomic oligonucleotide no. 3244 | 53 |
| Amino acid sequence of SEQ ID NO: 53 | 54 |
| 3' cDNA oligonucleotide no. 3245 | 55 |
| Nucleotide sequence of murine SOCS13 | 56 |
| Amino acid sequence of murine SOCS13 | 57 |
| Oligonucleotide no. 3342 | 58 |
| Amino acid sequence of SOCS box | 59 |
| Nucleotide sequence of murine SOCS5 | 60 |
| Amino acid sequence of murine SOCS5 | 61 |
| Nucleotide sequence of murine SOCS9 | 62 |
| Amino acid sequence of murine SOCS9 | 63 |
| SOCS Box Motif in mSOCS-1 and rSOCS-1 | 64 |
| SOCS Box Motif in mSOCS-2 | 65 |
| SOCS Box Motif in mSOCS-3 | 66 |
| SOCS Box Motif in hSOCS-1 | 67 |
| SOCS Box Motif in mSOCS-4 | 68 |
| SOCS Box Motif in mSOCS-5 | 69 |
| SOCS Box Motif in mSOCS-7 | 70 |
| SOCS Box Motif in mSOCS-8 | 71 |
| SOCS Box Motif in hSOCS-9 | 72 |
| SOCS Box Motif in mSOCS-10 | 73 |
| SOCS Box Motif in hSOCS-11 | 74 |
| SOCS Box Motif in mSOCS-12 | 75 |
| SOCS Box Motif in mSOCS-13 | 76 |
| SOCS Box Motif in mSOCS-14 | 77 |
| SOCS Box Motif in mSOCS-15 | 78 |
| SOCS Box Motif in hSOCS-15 | 79 |
| SOCS Box Motif in mSOCS-6 | 80 |
| SOCS Box Motif in mSOCS-9 | 81 |

Single and three letter abbreviations are used to denote amino acid residues and these are summarized in Table 2.

TABLE 2

| Amino Acid | Three-letter Abbreviation | One-letter Symbol |
|---|---|---|
| Alanine | Ala | A |
| Arginine | Arg | R |
| Asparagine | Asn | N |
| Aspartic acid | Asp | D |
| Cysteine | Cys | C |
| Glutamine | Gln | Q |
| Glutamic acid | Glu | E |
| Glycine | Gly | G |
| Histidine | His | H |
| Isoleucine | Ile | I |
| Leucine | Leu | L |
| Lysine | Lys | K |
| Methionine | Met | M |
| Phenylalanine | Phe | F |
| Proline | Pro | P |
| Serine | Ser | S |
| Threonine | Thr | T |
| Tryptophan | Trp | W |
| Tyrosine | Tyr | Y |
| Valine | Val | V |
| Any residue | Xaa | X |

BRIEF DESCRIPTION OF THE DRAWINGS

In some of the Figures, abbreviations are used to denote SOCS proteins with certain binding motifs. SOCS proteins which contain WD-40 repeats are referred to as WSB1–WSB4. SOCS proteins with ankyrin repeats are referred to as ASB1–ASB3. Deletion mutants are "Δ". For example, ΔC is a deletion in the carboxy terminal region and ΔN is a deletion in the amino terminal region.

FIGS. 2A–2B depict the nucleotide sequence and structure of the SOCS1 gene. 2A. The genomic context of SOCS1 in relation to the protamine gene cluster on murine chromosome 16. The accession number of this locus is MMPRMGNS (direct submission; G. Schlueter, 1995) for the mouse and BTPRMTNP2 for the rat (direct submission; G. Schlueter, 1996). 2B. The nucleotide sequence of the SOCS1 cDNA and deduced amino acid sequence. Conventional three letter abbreviations are used for the amino acid sequence and the asterisk indicates the stop colon. The polyadenylation signal sequence is underlined. The coding region is shown in uppercase and the untranslated region is shown in lower case.

FIG. 3 is a representation of a comparison of the amino acid sequences of SOCS1, SOCS2, SOCS3 and CIS. Alignment of the predicted amino acid sequence of mouse (mm), human (hs) and rat (rr) SOCS1, SOCS2, SOCS3 and CIS. Those residues shaded are conserved in three or four mouse SOCS family members. The SH2 domain is boxed in dotted lines, while the SOCS box is bounded by double lines.

FIGS. 4A(I)–4F(II) show a comparison of the amino acid sequence of the SOCS proteins. Schematic representation of structures of SOCS proteins including proteins which contain WD-40 repeats (WSB) and ankyrin repeats (ASB). 4A(I)–4A(II): Alignment of N-terminal regions of SOCS proteins. 4B(I)–4B(II): Alignment of the SH2 domains of CIS, SOCS1,2,3,5,9,11 and 14. 4C(I)–4C(III): Alignment of the WD-40 repeats of SOCS4, SOCS6, SOCS13 and SOCS15. 4D: Alignment of the ankyrin repeats of SOCS2 and SOCS10. 4E(I)–4E(II): Alignment of the regions between SH2, WD-40 and ankyrin repeats and the SOCS box. 4F(I)–4F(II): Alignment of the SOCS box. In each case the conventional one letter abbreviations for amino acids are used, with X denoting residues of uncertain identity and ○○○ denoting the beginning and the end of contigs. Amino acid sequence obtained from conceptual translation of nucleic acid sequence derived from isolated cDNAs is shown in upper case while amino acid sequence obtained by conceptual translation of ESTs is shown in lower case and is approximate only. Conserved residues, defined as (LIVMA), (FYW), (DE), (QN), (C, S, T), (KRH), (PG) are shaded in the SH2 domain, WD-40 repeats, ankyrin repeats and the SOCS box. For the alignment of SH2 domains, WD-40 repeats and ankyrin repeats a consensus sequence is shown above. In each case this has been derived from examination of a large and diverse set of domains (Neer et al, 1994; Bork, 1993).

FIG. 5 is a representation showing the nucleotide sequence of the mouse SOCS4 cDNA. The nucleotides encoding the mature coding region from the predicted ATG "start" codon to the stop codon is shown in upper case, while the predicted 5' and 3' untranslated regions are shown in lower case.

FIG. 6 is a representation showing the predicted amino acid sequence of the mouse SOCS4 protein, derived from the nucleotide sequence in FIG. 5. The SOCS box, which also shown in FIG. 4, is underlined.

FIG. 7 is a representation showing the nucleotide sequence of human SOCS4 cDNA contigs h4.1 and h4.2, derived from analysis of ESTs listed in Table 4.1.

FIG. 9A is a representation showing the nucleotide sequence of the mouse SOCS5 derived from analysis of genomic and cDNA clones. The nucleotides encoding the mature coding region from the predicted ATG "start" codon to the stop codon is shown in upper case, while the predicted 5' and 3' untranslated regions are shown in lowercase. The relationship of mouse cDNA sequence to mouse and human EST contigs is illustrated in FIG. 8.

FIG. 9B is a representation of the predicted amino acid sequence of mouse SOCS5 protein, derived from the nucleotide sequence in is underlined.

FIG. 10 is a representation showing the nucleotide sequence of human SOCS5 CDNA contig h5.1, derived from analysis of cDNA clone 5-94-2 and the ESTs listed in Table 5.2. The relationship of these contigs to the mouse cDNA sequence is illustrated in FIG. 8.

FIG. 12A is a representation showing the nucleotide sequence of the mouse SOCS6 derived from analysis of cDNA clone 64-10A-11. The nucleotides encoding the part of the predicted coding region, ending in the stop codon are shown in upper case, while the predicted 3' untranslated regions are shown in lower case. The relationship of mouse cDNA sequence to mouse and human EST contigs is illustrated in FIG. 11.

FIG. 12B is a representation showing the predicted amino acid sequence of mouse SOCS6 protein, derived from the nucleotide sequence in FIG. 12A. The SOCS box, which also shown in FIG. 4 is underlined.

FIG. 13 is a representation showing the nucleotide sequence of human SOCS6 cDNA contig h6.1 and contig h6.2, derived from analysis of cDNA clone 5-94-2 and the ESTs listed in Table 6.2. The relationship of these contigs to the mouse cDNA sequence is illustrated in FIG. 11.

FIG. 15A is a representation showing the nucleotide sequence of the mouse SOCS7 derived from analysis of cDNA clone 74-10A-11. The nucleotides encoding the part of the predicted coding region, ending in the stop codon are shown in upper case, while the predicted 3' untranslated regions are shown in lower case. The relationship of mouse cDNA sequence to mouse and human EST contigs is illustrated in FIG. 14.

FIG. 15B is a representation showing the predicted amino acid sequence of mouse SOCS7 protein, derived from the nucleotide sequence in FIG. 15A. The SOCS box, which also shown in FIG. 4 is underlined.

FIG. 16 is a representation showing the nucleotide sequence of human SOCS 7cDNA contig h7.1 and h7.2 derived from analysis of the ESTs listed in Table 7.2. The relationship of these contigs to the mouse cDNA sequence is illustrated in FIG. 14.

FIG. 18A is s a representation showing the partial nucleotide sequence of mouse SOCS8 CDNA (contig 8.1) derived from analysis of ESTs. The nucleotides encoding the part of the predicted coding region, ending in the STOP colon are shown in upper case, while the predicted 3' untranslated regions are shown in lowercase.

FIG. 18B is a representation showing the partial predicted amino acid sequence of the mouse SOCS8 protein, derived from the nucleotide sequence in FIG. 18A. The SOCS box, which also shown in FIG. 4 is underlined.

FIG. 20 is a representation showing the partial nucleotide sequence of mouse SOCS9 cDNA (contig m9.1), derived from analysis of the ESTs listed in Table 9.1. The relationship of these contigs to the mouse cDNA sequence is illustrated in FIG. 19.

FIG. 21 is a representation showing the partial nucleotide sequence of human SOCS9 cDNA (contig h9.1), derived from analysis of the ESTs listed in Table 9.2. Although it is clear that contig h9.1 encodes a protein with an SH2 domain and a SOCS box, the quality of the sequence is not high enough to derive a single unambiguous open reading frame.

Figure 19:
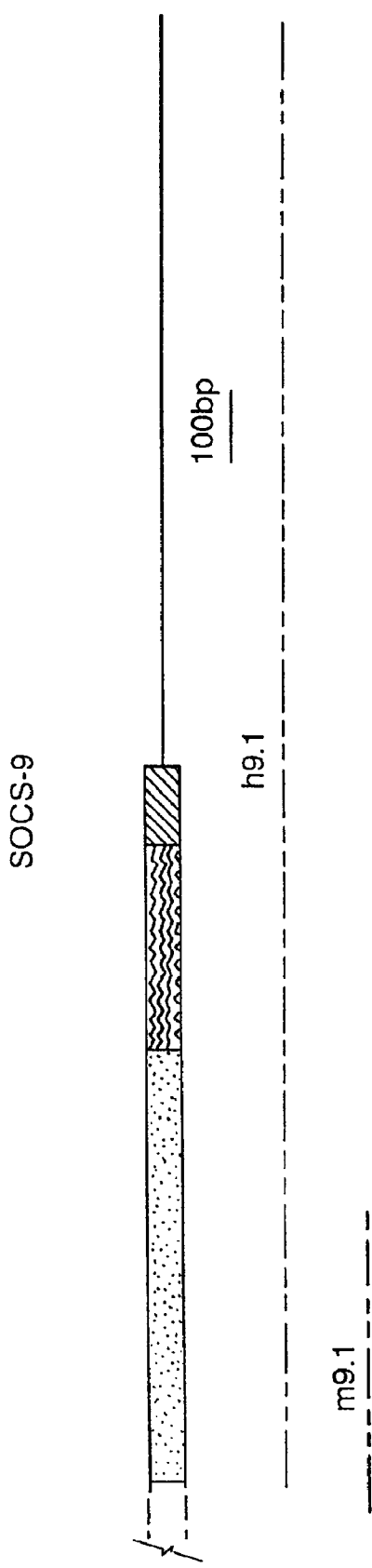
FIG. 19 is a diagrammatic representation showing the relationship of mouse SOCS9 ESTs (Table 9.1) and human SOCS9 ESTs (Table 9.2). The nucleotide sequence of the mouse SOCS2 contig (m9.1) is shown in FIG. 20, with the sequence of human SOCS9 contig (h9.1) being shown in FIG. 21. The deduced amino acid sequence of human SOCS9 is shown schematically, with the SH2 domain indicated by the open white wave box and the SOCS box by the open hatched box. The putative 3' untranslated region is shown by the thin solid line.

The relationship of these contigs to the mouse cDNA sequence is illustrated in FIG. 19.

Figure 22:
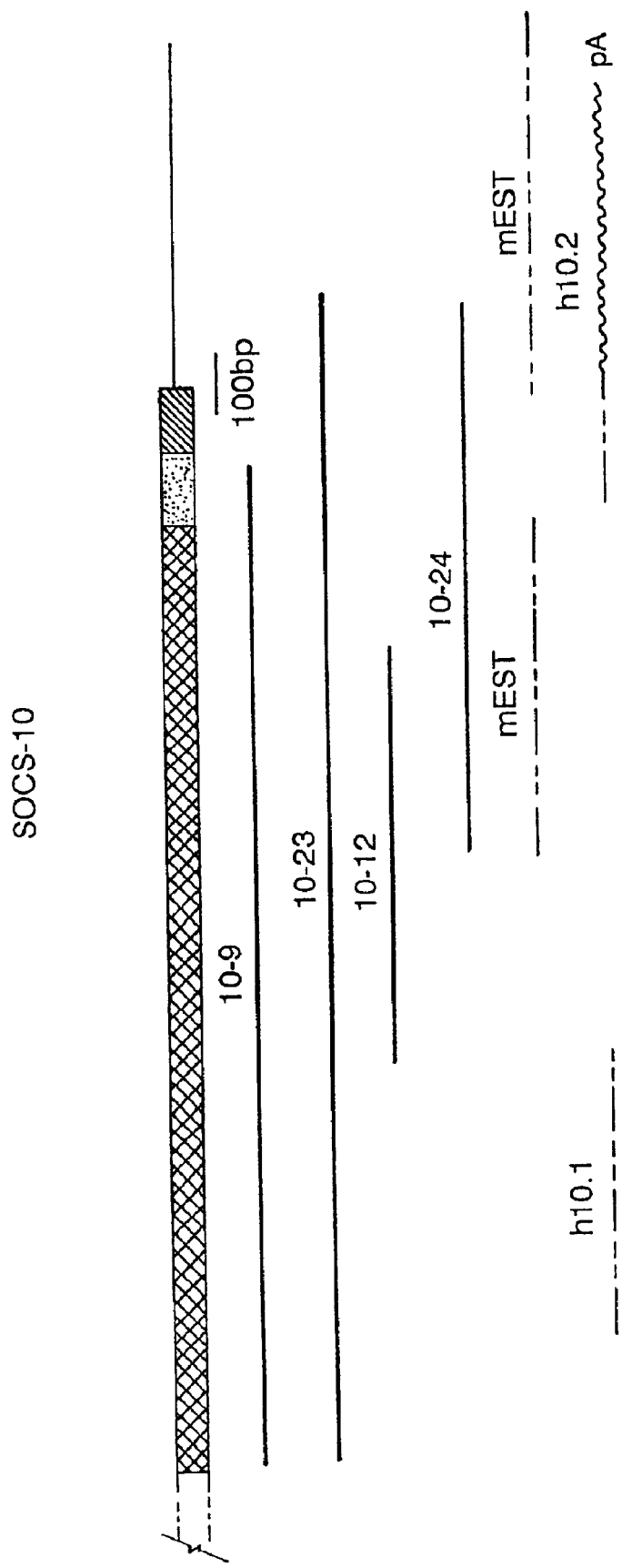

FIG. 22 is a representation showing the relationship of mouse SOCS10 cDNA clones (10-9, 10-12, 10-23 and 10-24) to contigs derived from analysis of mouse ESTs (Table 10.1) and human ESTs (Table 10.2). The nucleotide sequence of the mouse SOCS10 contig is shown in FIG. 23, with the sequence of human SOCS10 contigs (h10.1 and h10.2) being shown in FIG. 24. The predicted structure of the protein is shown schematically, with the ankyrin repeals indicated by the cross hatched box and the SOCS box by open hatched box. The putative 3' untranslated regions is shown by the thin line solid line in the mouse and by the wavy line in h10.2. Based on analysis of clones isolated to date and ESTs the 3' untranslated regions of mSOCS-10 and hSOCS-10 share little similarity.

FIG. 23 is a representation showing the nucleotide sequence of the mouse SOCS10 derived from analysis of cDNA clone 10-9,10-12,10-23 and 10-24. The nucleotides encoding the part of the predicted coding region, ending in the stop codon are shown in upper case, while the predicted 3' untranslated regions are shown in lowercase. Although it is clear that contig m10.1 encodes a protein with a series of ankyrin repeats and a SOCS box, the quality of the sequence is not high enough to derive a single unambiguous open reading frame. The relationship of mouse cDNA sequence to mouse and human EST contigs is illustrated in FIG. 22.

FIG. 24 is a representation showing the nucleotide sequence of human SOCS10 cDNA contig h10.2 and h10.2 derived from analysis of the SSTs listed in Table 10.2. The relationship of these contigs to the mouse cDNA sequence is illustrated in FIG. 22.

FIG. 25A is a representation showing the partial nucleotide sequence of the human SOCS11 cDNA derived from analysis of ESTs listed in Table 11.1. The nucleotides encoding the mature coding region from the predicted ATG "start" codon to the stop codon is shown in upper case, while the predicted 5' and 3' untranslated regions are shown in lower case. The relationship of the partial cDNA sequence, derived from ESTs, to the predicted protein is shown in FIG. 26.

FIG. 25B is a representation showing the partial predicted amino acid sequence of human SOCS11 protein, derived from the nucleotide sequence in FIG. 25A. The SOCS box, which also shown in FIG. 4, is underlined.

Figure 26:
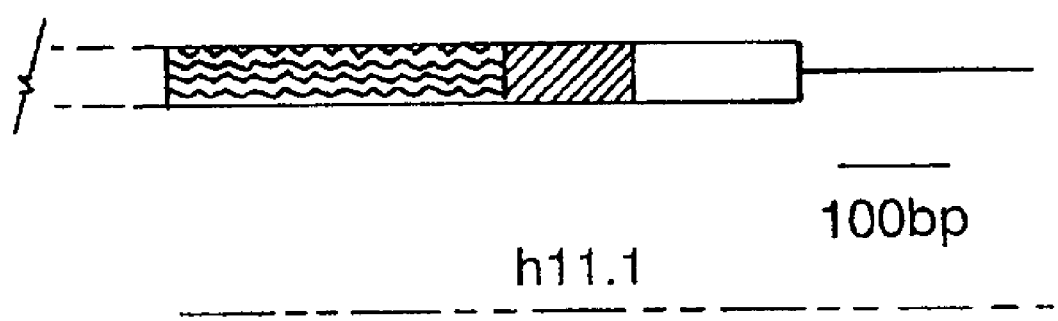

FIG. 26 is a diagrammatic representation showing the relationship of sequence derived from analysis of human SOCS-11 ESTs (Table 11.1) to the predicted protein structure of human SOCS11. The deduced partial amino acid sequence of human SOCS11 is shown in FIG. 25B. The structure of the protein is shown schematically with the SH2 domain shown by the open hatched box and the SOCS box shown by the open white box. The predicted 3' untranslated region is shown by the thin line.

Figure 27:
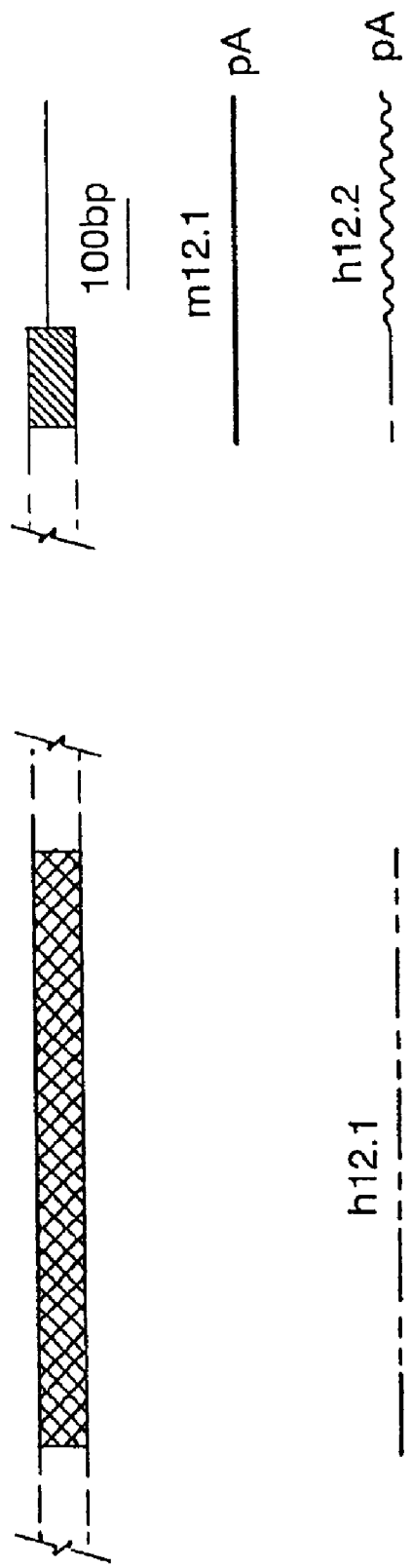

FIG. 27 is a diagrammatic representation showing the relationship of mouse SOCS12 cDNA clones (12-1) to contigs derived from analysis of mouse ESTs (Table 12.1) and human ESTs (Table 12.2). The nucleotide sequence of the mouse SOCS12 contig is shown in FIG. 28, with the sequence of human SOCS12 contigs (h12.1 and h12.2) being shown in FIG. 29. The structure of the protein is shown schematically, with the ankyrin repeats indicated by the cross hatched box and the SOCS box by the open hatched box. The putative 3' untranslated region is shown by the thin line solid line in the mouse and by the wavy line in h12.2. Based on analysis of clones isolated to date and ESTs the 3' untranslated regions of mSOCS12 and hSOCS12 share little similarity.

FIG. 28 is a representation showing the nucleotide sequence of the mouse SOCS12 derived from analysis of cDNA clone 12-1 and the ESTs listed in Table 12.1. The nucleotides encoding the part of the predicted coding region, including the stop codon are shown in uppercase, while the predicted 3' untranslated region is shown in lower case, By homology with human SOCS12 it is clear that contig m12.1 encodes a protein with a series of ankyrin repeats and a SOCS box, the quality of the sequence is not high enough to derive a single unambiguous open reading frame. The relationship of mouse cDNA sequence to mouse and human EST contigs is illustrated in FIG. 27.

FIG. 29 is a representation showing the nucleotide sequence of human SOCS12 cDNA contig h12.1 and h12.2 derived from analysis of the ESTs listed in Table 12.2. The relationship of these contigs to the mouse cDNA sequence is illustrated in FIG. 27.

Figure 30:
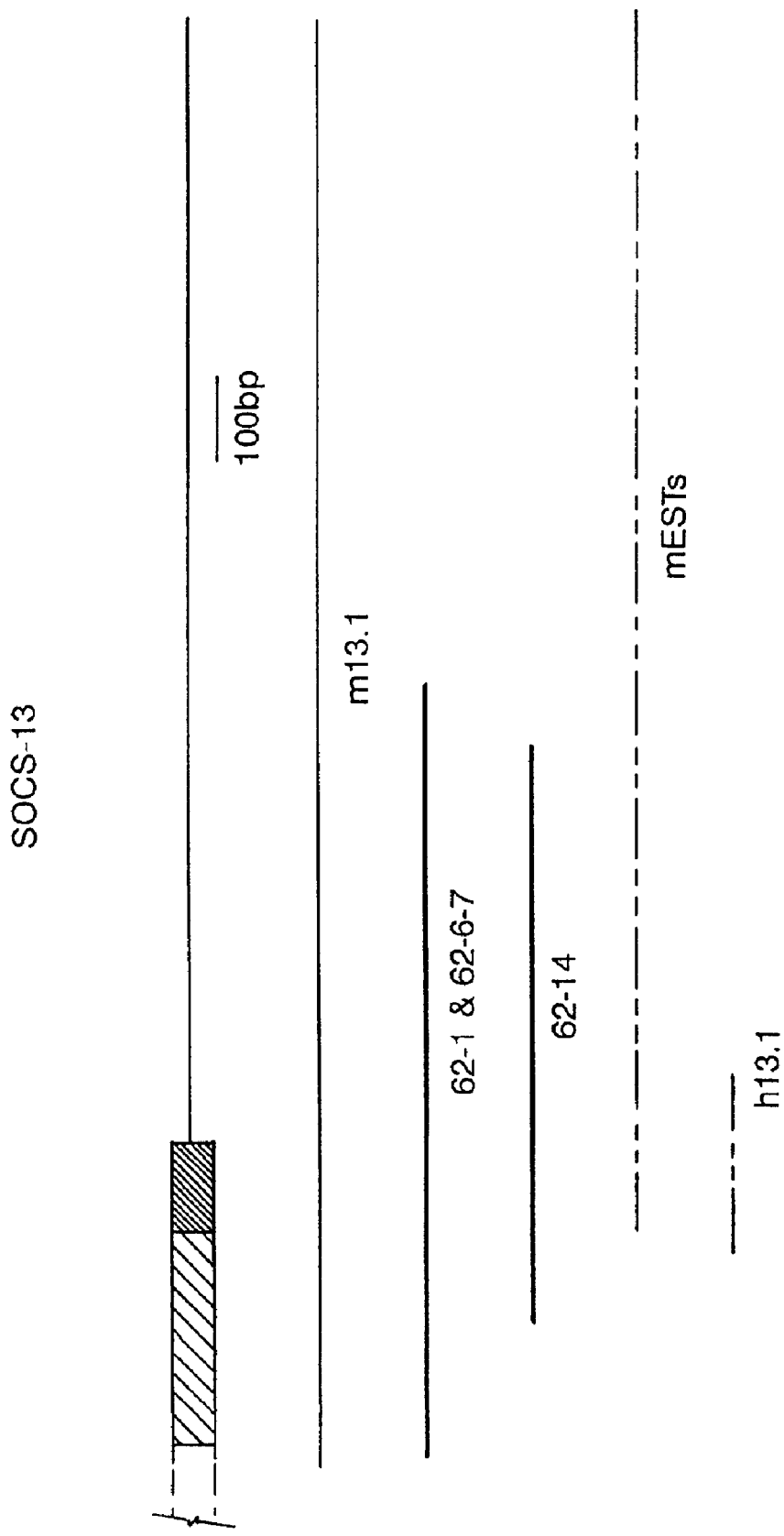

FIG. 30 is a diagrammatic representation showing the relationship of contig m13.1 derived from analysis of mouse SOCS13 cDNA clones (62-1, 62-6-7, 62-14) and mouse ESTs (Table 13.1) to contig h13.1 derived from analysis of human ESTs (Table 13.2). The nucleotide sequence of the mouse SOCS13 contig is shown in FIG. 31A, with the sequence of human SOCS13 contig (h13.1) being shown in FIG. 32. The deduced amino acid sequence of mouse SOCS13 is shown in FIG. 31B. The structure of the protein is shown schematically, with the WD-40 repeats highlighted by the open hatched box and the SOCS box shown by the densely hatched box. The 3' untranslated region is shown by the thin line solid line.

FIG. 31A is a representation showing the nucleotide sequence of the mouse SOCS13 derived from analysis of cDNA clones 62-1, 62-6-7 and 62-14. The nucleotides encoding pan of the predicted coding region, ending in the stop codon are shown in upper case, while those encoding the predicted 3' untranslated regions are shown in lowercase. The relationship of mouse cDNA sequence to mouse and human EST contigs is illustrated in FIG. 30.

FIG. 31B is a representation showing the predicted amino acid sequence of mouse SOCS13 protein, derived from the nucleotide sequence in FIG. 31A. The SOCS box, which also shown in FIG. 4 is underlined.

FIG. 32 is a representation showing the nucleotide sequence of human SOCS 13 cDNA contig h13.1 derived from analysis of the ESTs listed in Table 13.2. The relationship of these contigs to the mouse cDNA sequence is illustrated in FIG. 30.

Figure 33:
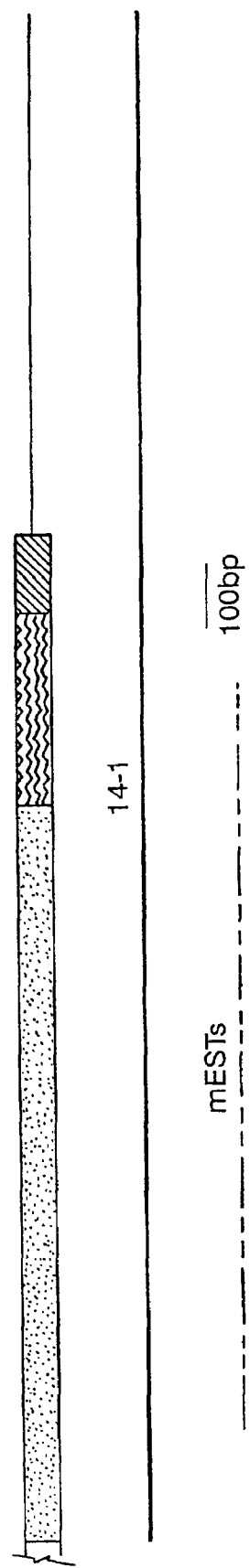

FIG. 33 is a diagrammatic representation showing the relationship of a partial mouse SOCS14 cDNA clone (14-1) to contigs derived from analysis of mouse ESTs (Table 14.1). The nucleotide sequence of the mouse SOCS14 contig is shown in FIG. 34A. The deduced partial amino acid sequence of mouse SOCS14 is shown in FIG. 34B. The structure of the protein is shown schematically, with the SH2 domain indicated by the open wave box and the SOCS box by the densely hatched box. The putative 3' untranslated region is shown by the thin line.

FIG. 34A is a representation showing the nucleotide sequence of the mouse SOCS14 derived from analysis of genomic and cDNA clones. The nucleotides encoding the mature coding region from the predicted ATG "start" codon to the stop codon is shown in upper case, while the predicted 5' and 3' untranslated regions are shown in lower case. The relationship of mouse cDNA sequence to mouse and human EST contigs is illustrated in FIG. 33.

FIG. 34B is a representation showing the predicted amino acid sequence of mouse SOCS14 protein, derived from the nucleotide sequence in FIG. 34A. The SOCS box, which also shown in FIG. 4 is underlined.

Figure 35:
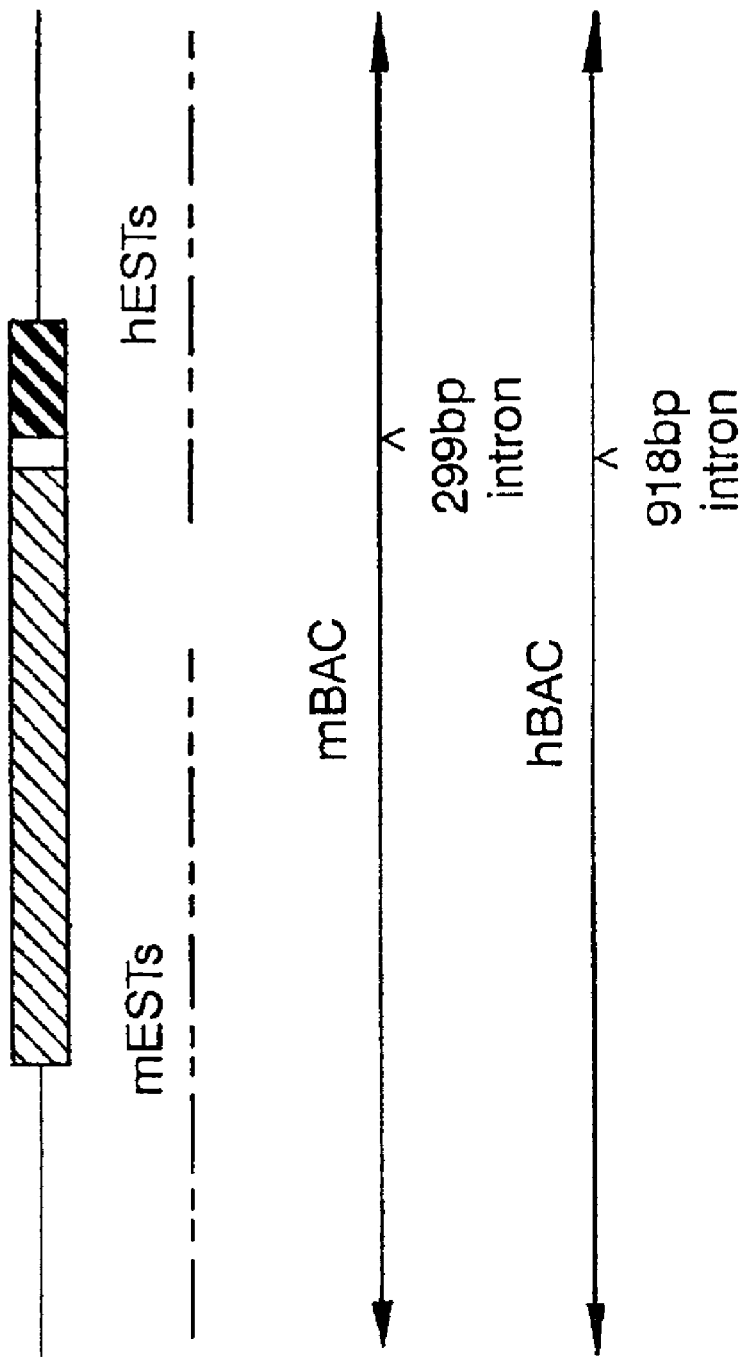

FIG. 35 is a diagrammatic representation showing the relationship of contig m15.1 derived from analysis of mouse BAC and mouse ESTs (Table 15,1) to contig h15.1 derived from analysis of the human BAC and human ESTs (Table 15.2). The nucleotide sequence of the mouse SOCS15 contig is shown in FIG. 36A, with the sequence of human SOCS15 contig (h15.1) being shown in FIG. 38A. The deduced amino acid sequence of mouse SOCS15 is shown in FIG. 36B. The structure of the protein is shown schematically, with the WD-40 repeats highlighted by the open hatched box on the left and the SOCS box highlighted by the (hatched box on the right. The 5' and 3' untranslated region are shown by the thin line solid line. The introns which interrupt the coding region are shown by ^.

FIG. 36A(i)–(iii) is a representation showing the nucleotide sequence covering the mouse SOCS15 gene derived from analysis the mouse BAC listed in Table 15.1. The nucleotides encoding the predicted coding region, beginning with the ATG and ending in the stop codon are shown in upper case, while those encoding the predicted 5' untranslated region, the introns and the 3' untranslated region are shown in lower case. The relationship of mouse BAC to mouse and human ESTs contigs is illustrated in FIG. 35.

FIG. 36B is a representation showing the predicted amino acid sequence of mouse SOCS15 protein, derived from the nucleotide sequence in FIG. 36A. The SOCS box, which also shoe in FIG. 4 is underlined.

FIG. 37A(i)–(iv) is a representation showing the nucleotide sequence covering the human SOCS15 gene derived from analysis the human BAC listed in Table 15.2. The nucleotide encoding the predicted coding region, beginning with the ATG and ending in the stop codon are shown in uppercase, while those encoding the predicted 5' untranslated region, the introns and the 3' untranslated region are shown in lower case. The relationship of the human BAC to mouse and human ESTs contigs is illustrated in FIG. 35.

FIG. 37B is a representation showing the predicted amino acid sequence of human SOCS15 protein, derived from the nucleotide sequence in FIG. 31A. The SOCS box, which also show in FIG. 4 is underlined.

Figure 38:
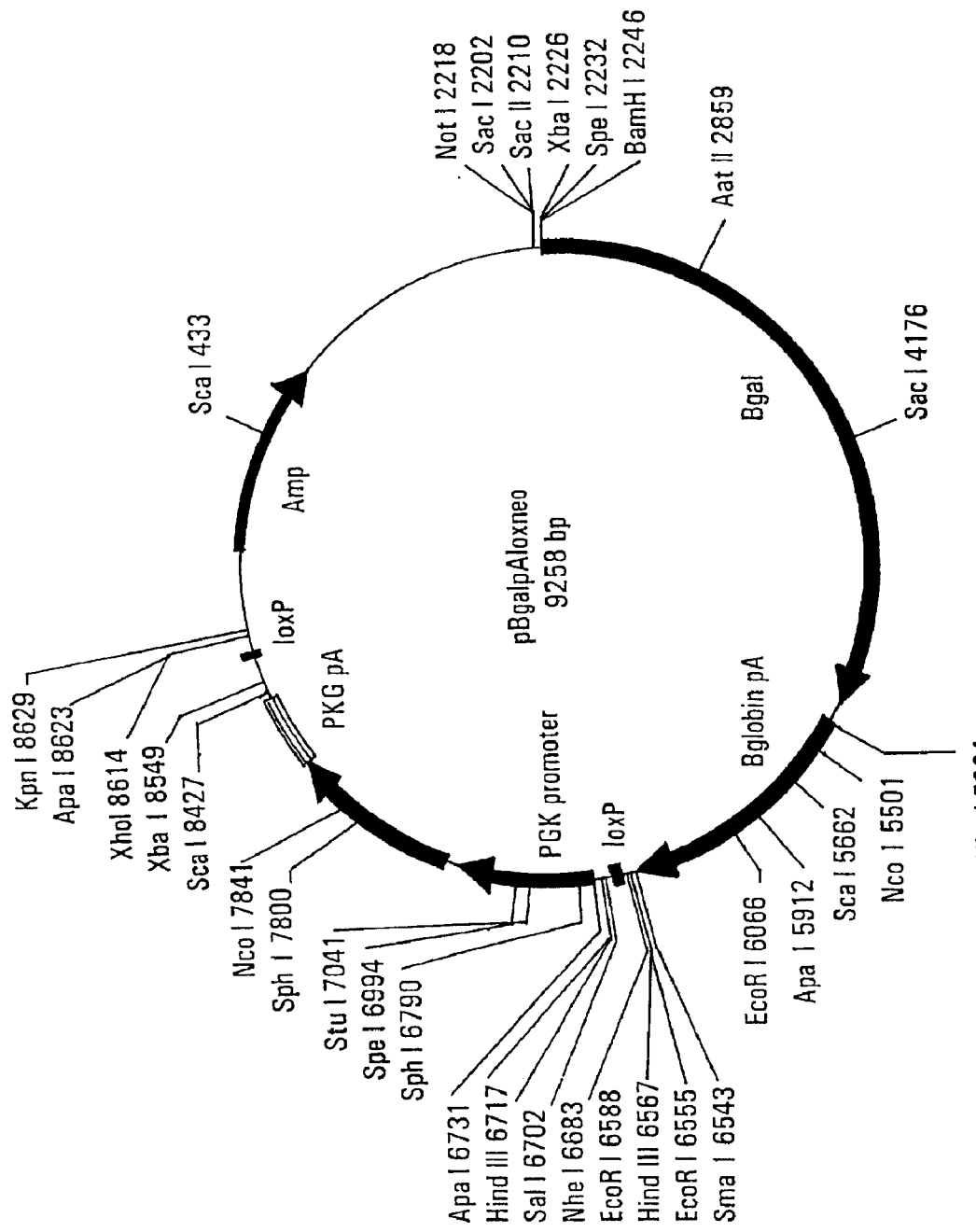

FIG. 38 is a diagrammatic representation of pβgalpAloxnco

Figure 39:
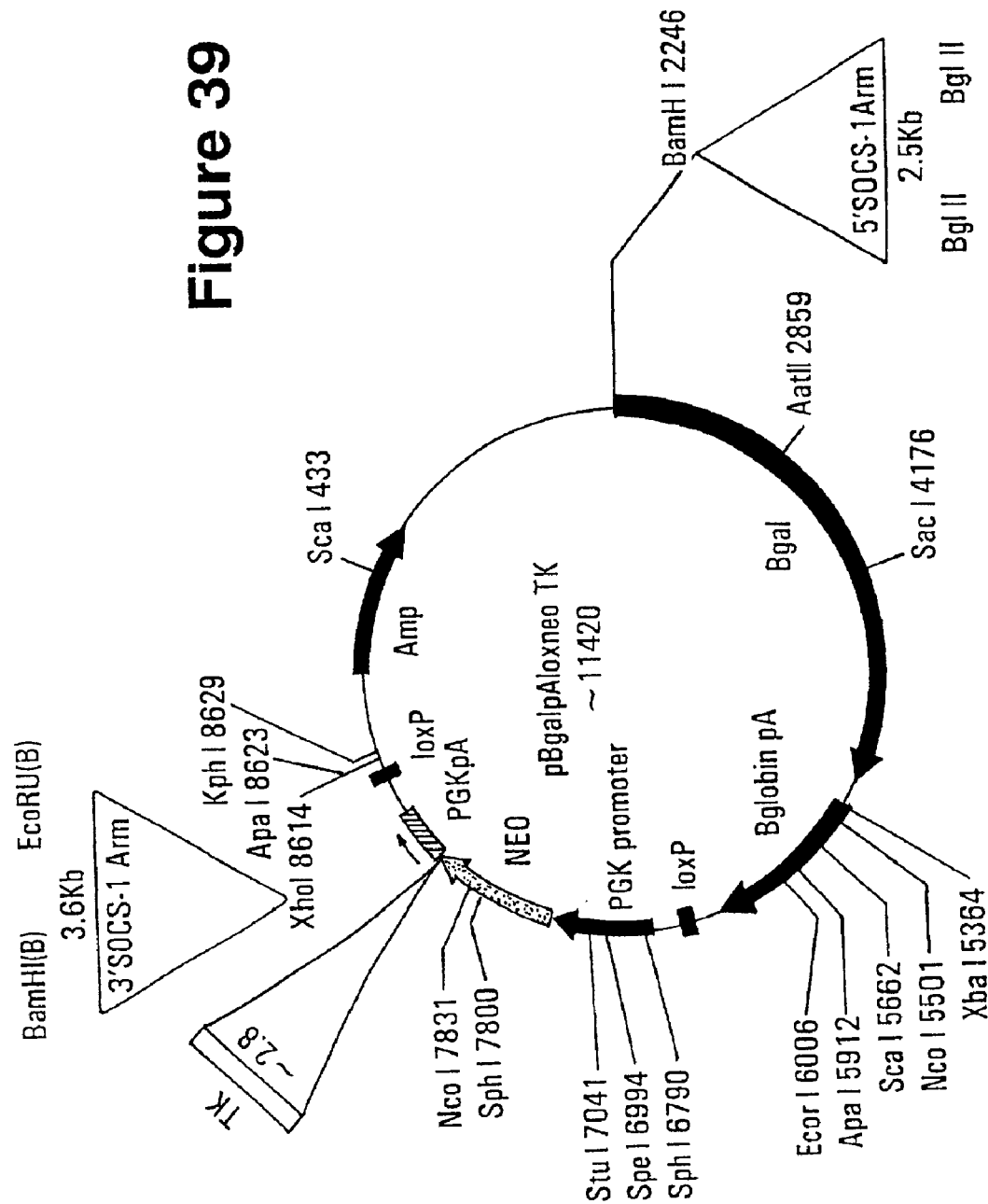

FIG. 39 is a diagrammatic representation of pβgalpAloxneoTK.

Figure 40:
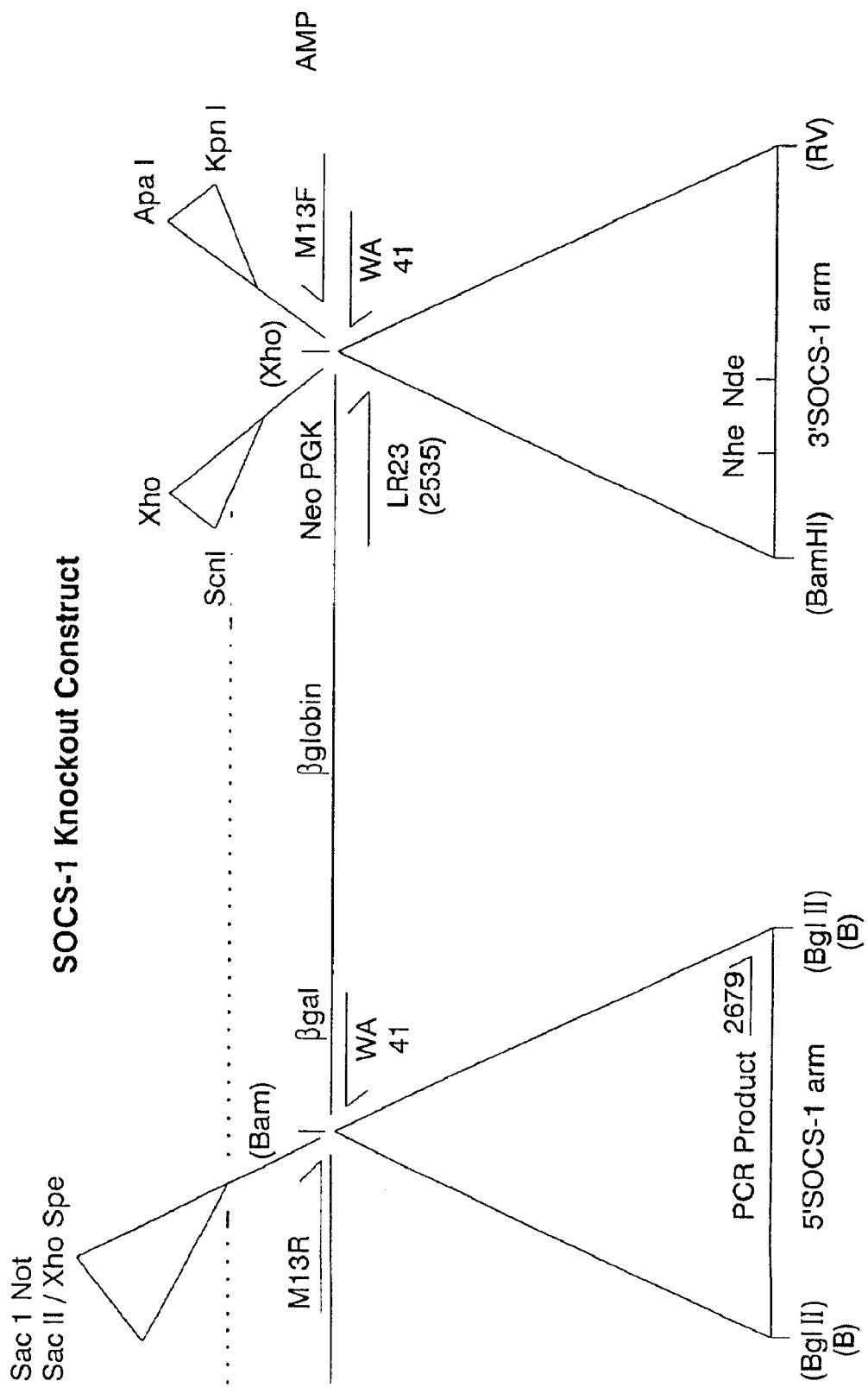

FIG. 40 is a diagrammatic representation of SOCS1 knockout construct.

FIG. 41A–C is the nucleotide sequence and predicted amino acid sequence of the coding region mouse SOCS1 mutXHO FIG. 42 is the alignment of the nucleotide and predicted amino acid sequence of the first 28 amino acids of the SH2 domain of CIS, SOCS1, SOCS2 and SOCS3, introduced nucleotide changes that lead to the R>K amino acid substitution are underlined.

Figure 43A:
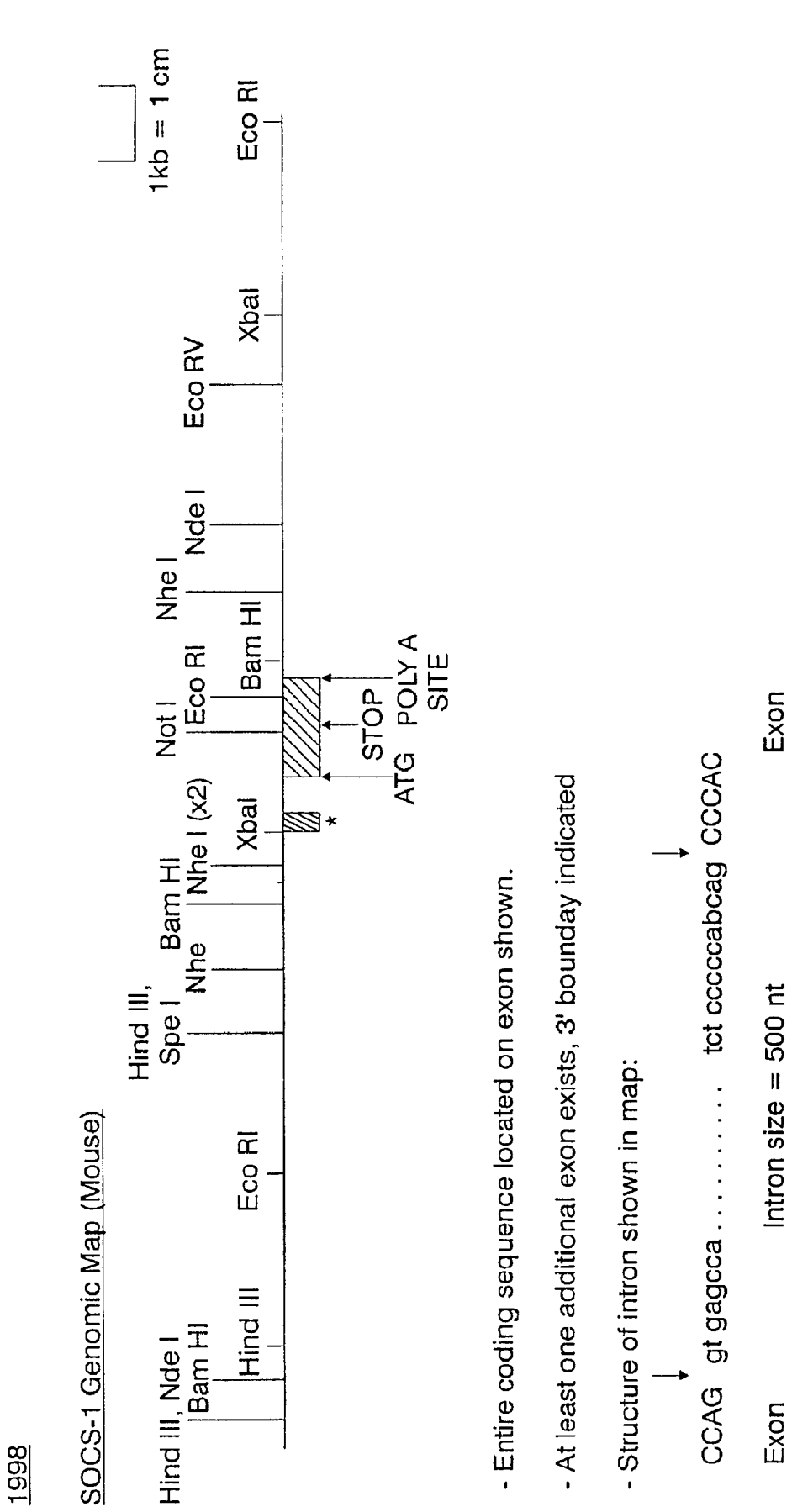

FIG. 43A is a schematic representation of SOCS-1 genomic map in mice.

Figure 43B:
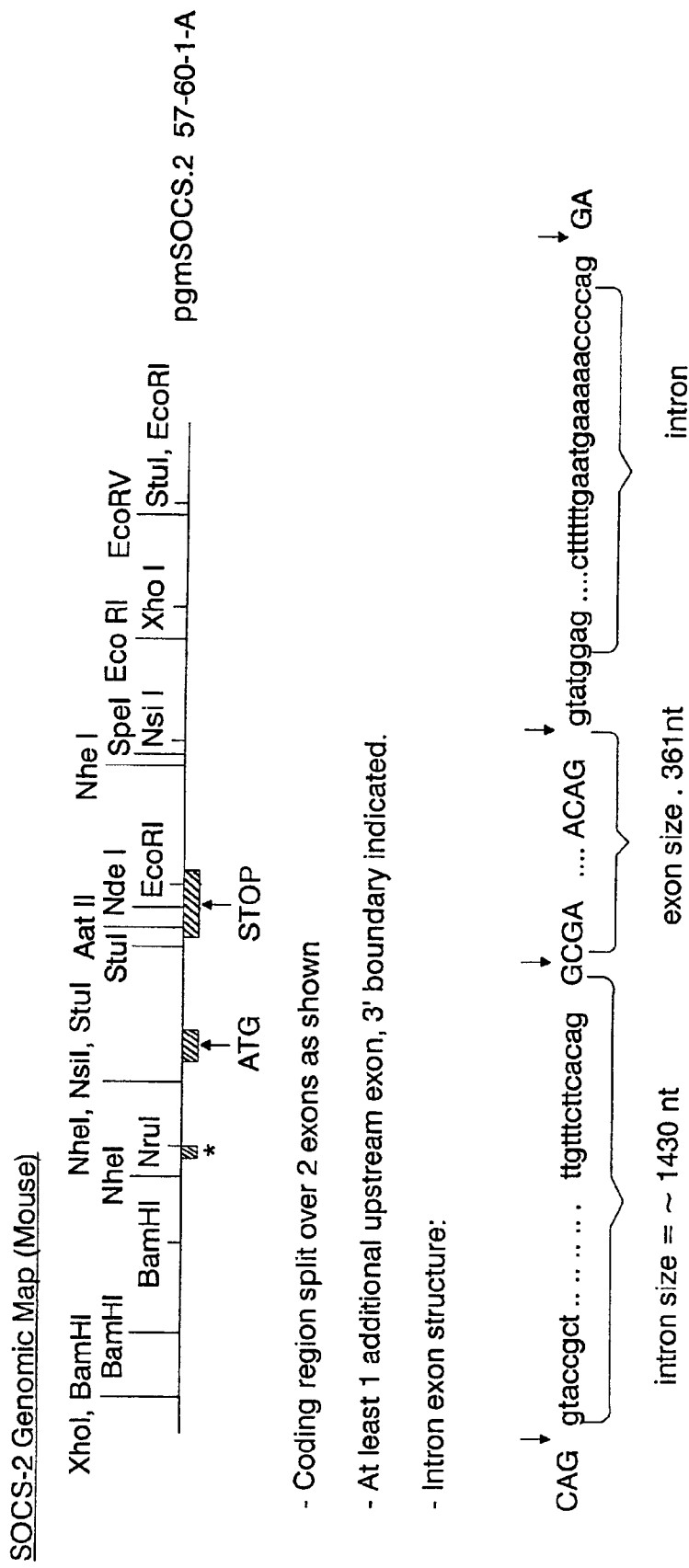

FIG. 43B is a schematic representation of the genomic map in mice.

Figure 43C:
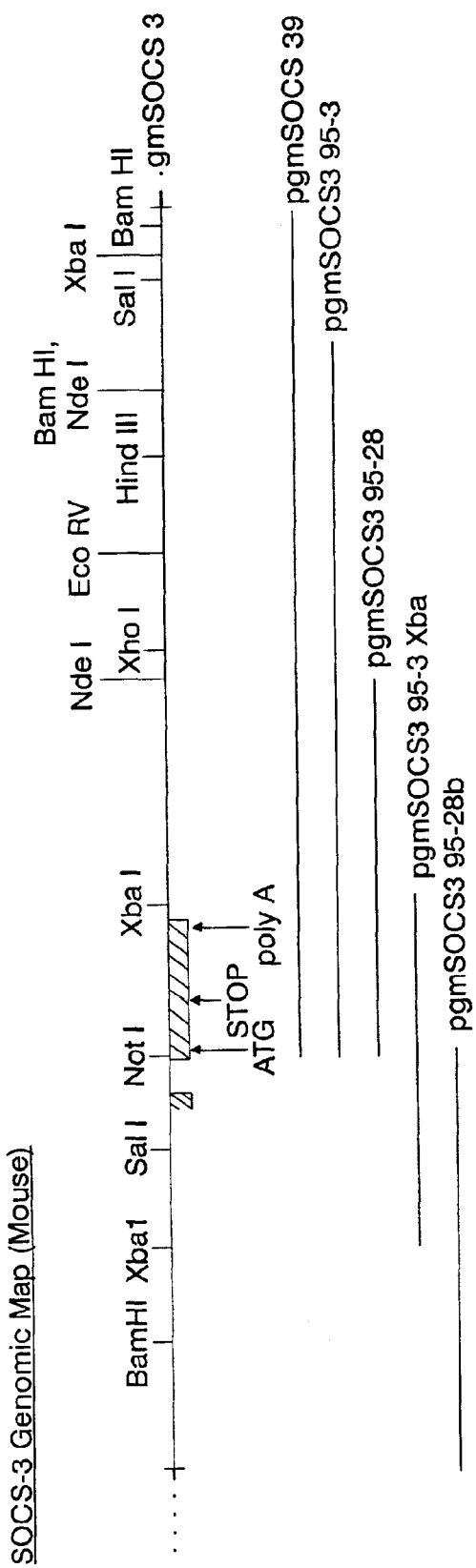

FIG. 43C is a schematic representation of the SOCS-3 genomic map in mice.

Figure 43D:
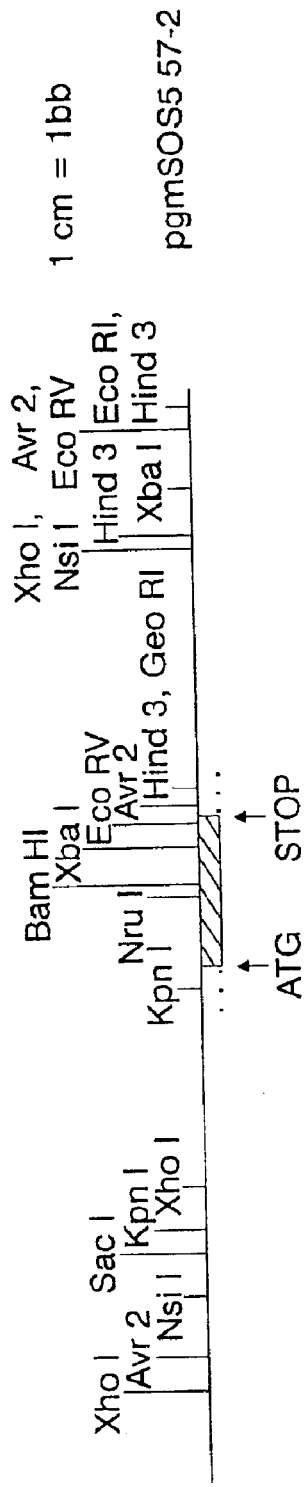

FIG. 43D is a schematic representation of the SOCS-5 genomic map in mice.

Figure 43E:

FIG. 43E is a schematic representation of SOCS-9 genomic map in mice.

Figure 43F:
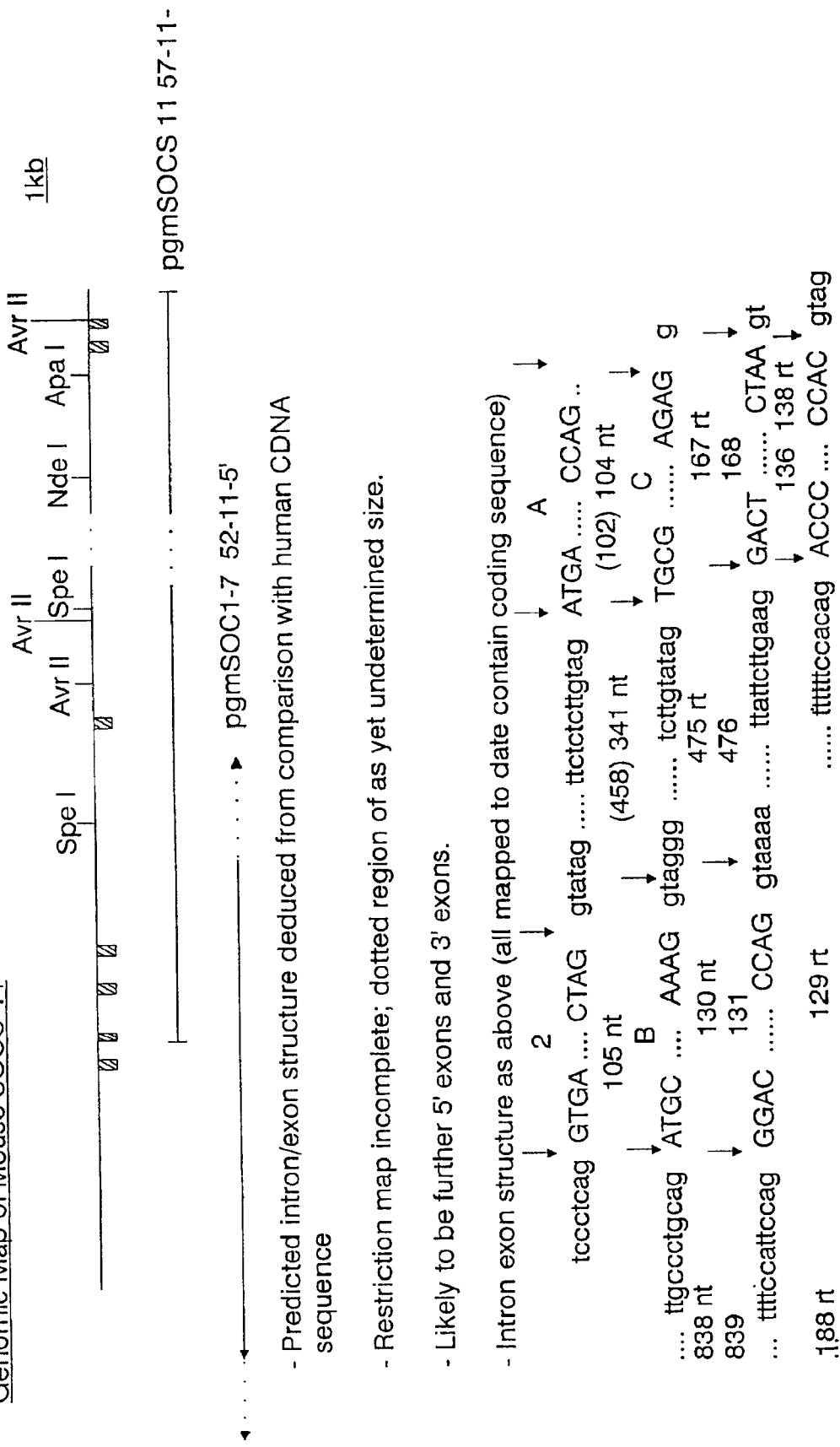

FIG. 43F is a schematic representation of the SOCS-11 genomic map in mice.

Figure 44A:
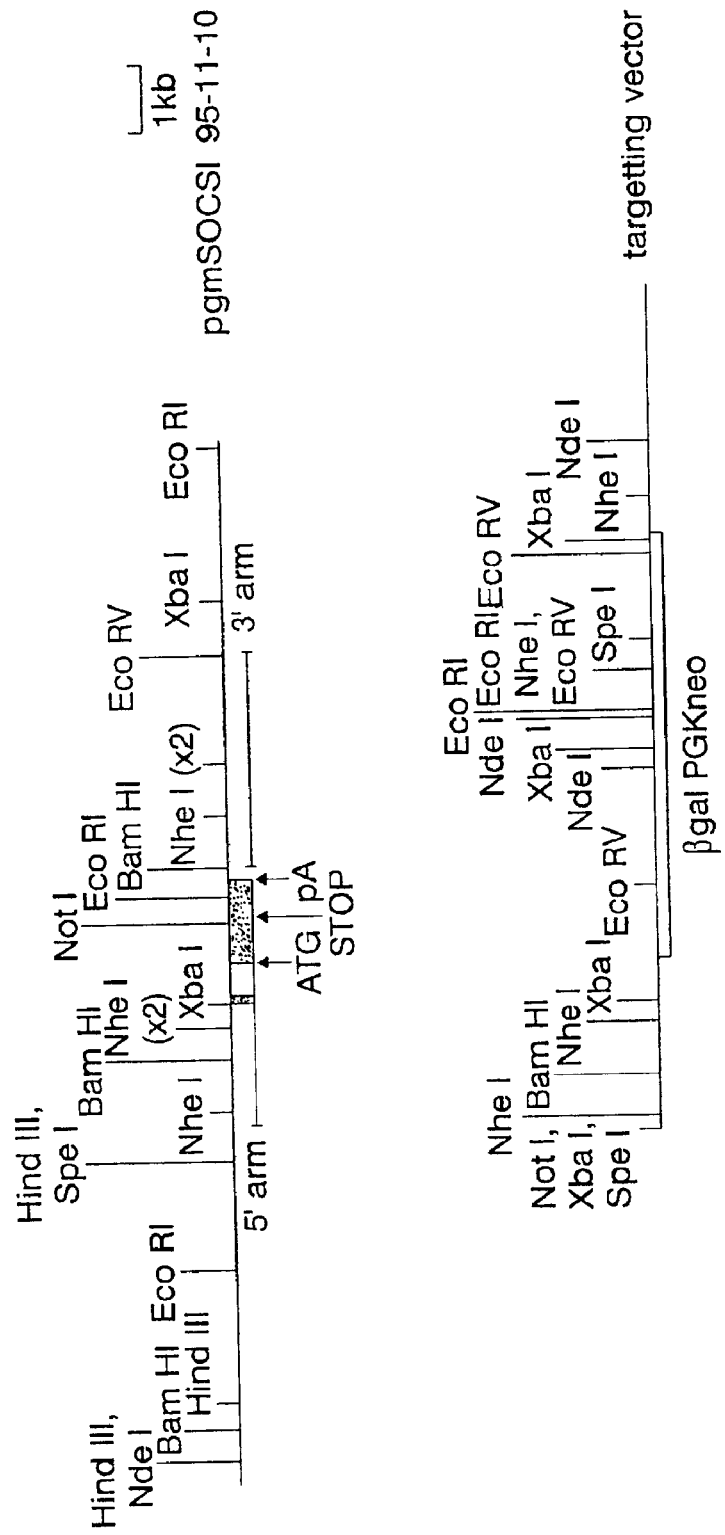
Figure 44B:
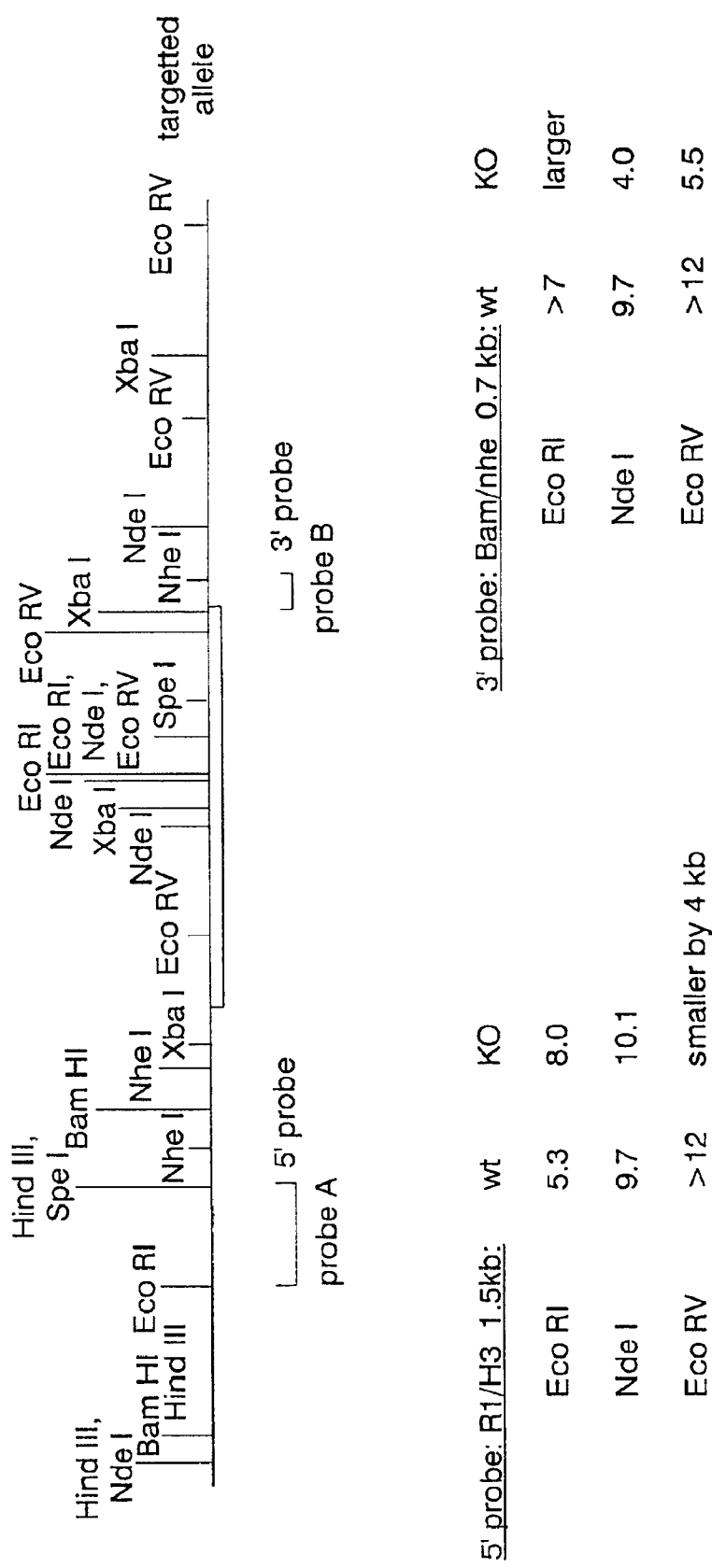

FIG. 44 is a diagrammatic representation of SOCS-1 targeting.

Figure 45A:
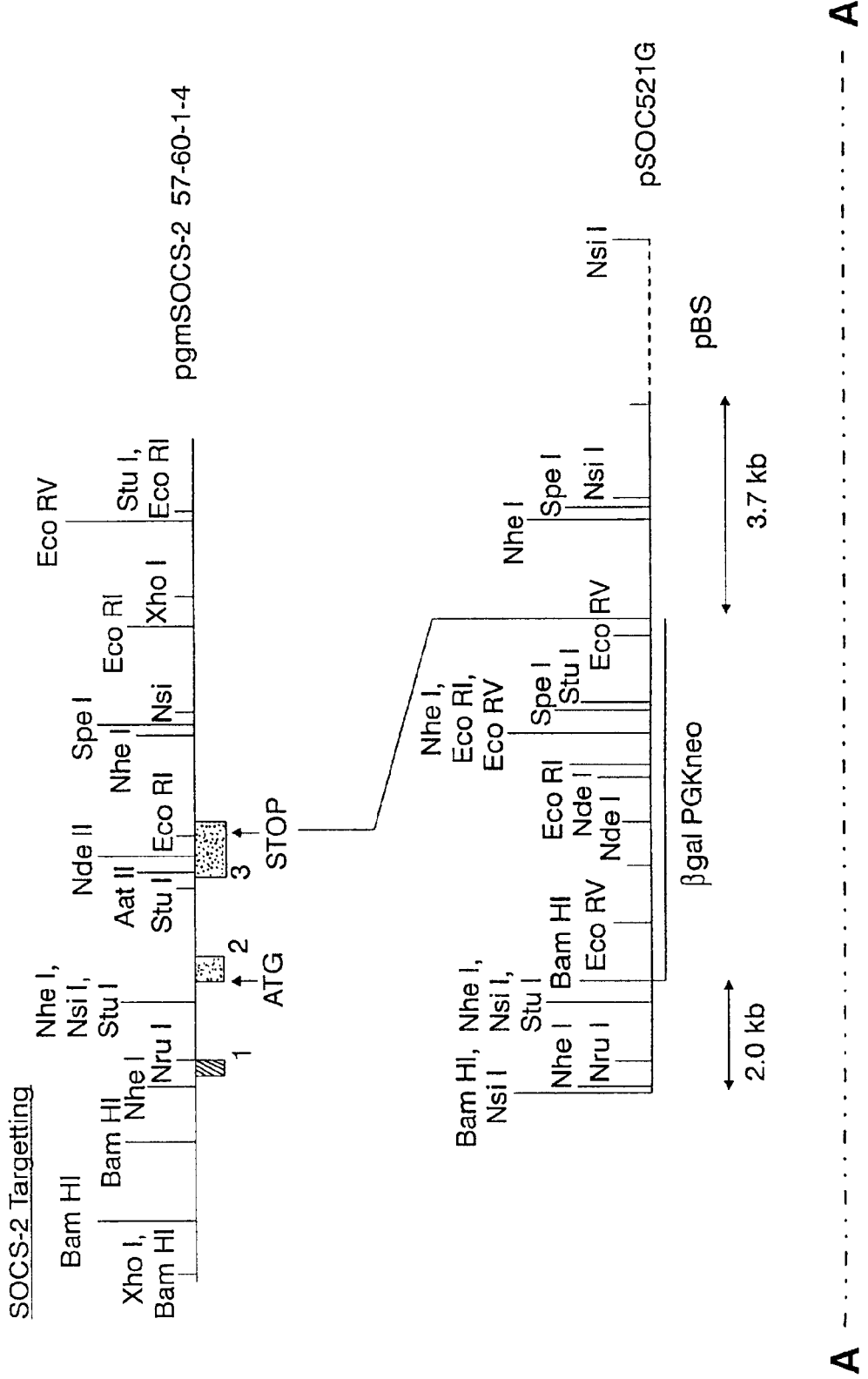
Figure 45B:
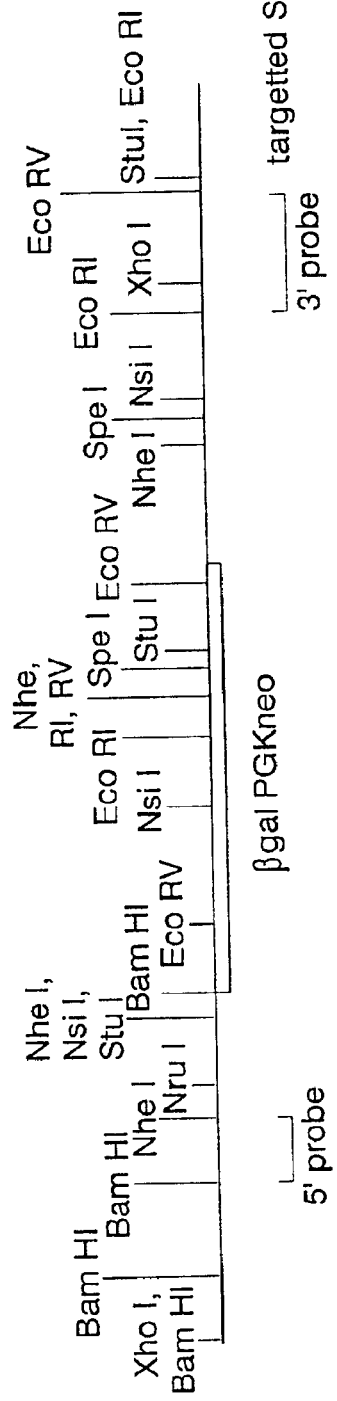

FIG. 45 is a diagrammatic representation of SOCS-2 targeting.

Figure 46A:
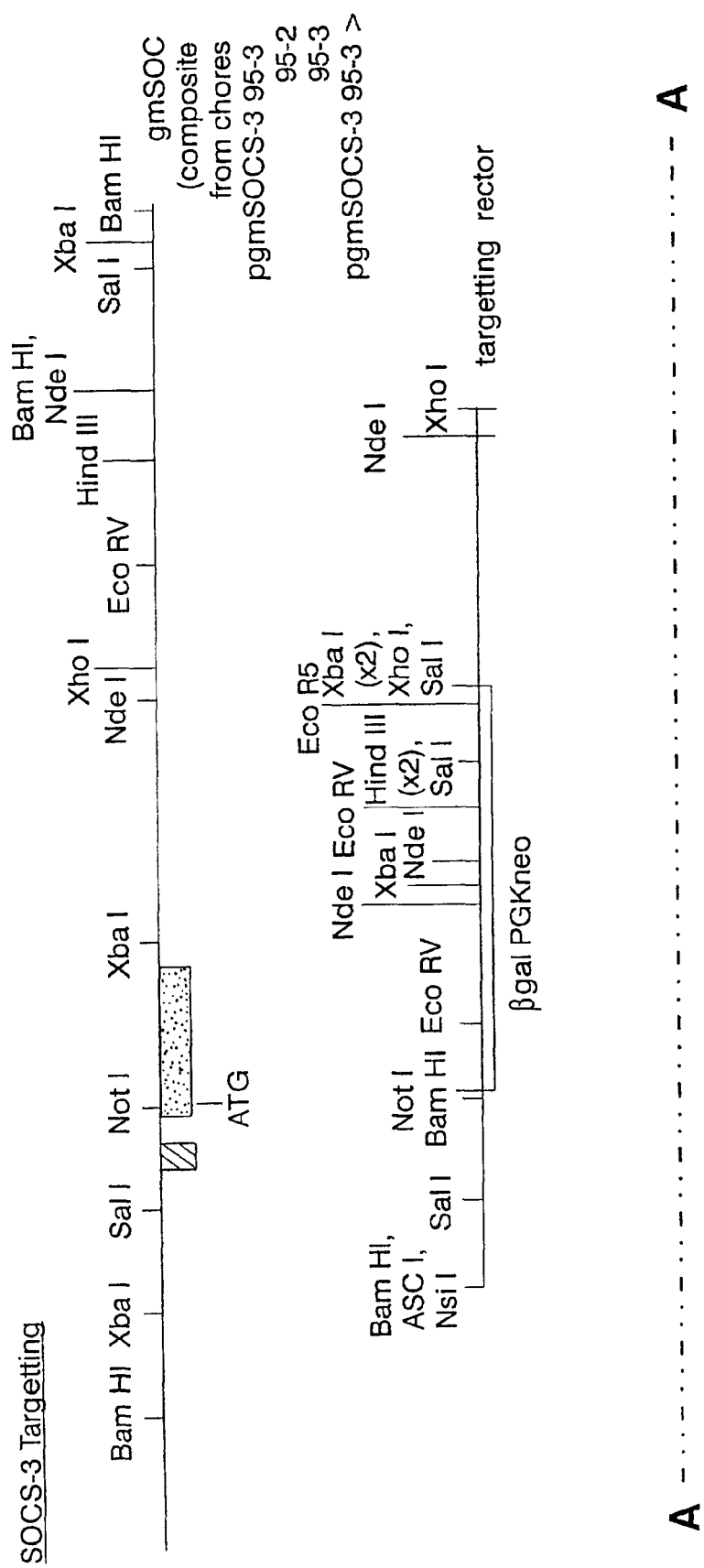
Figure 46B:
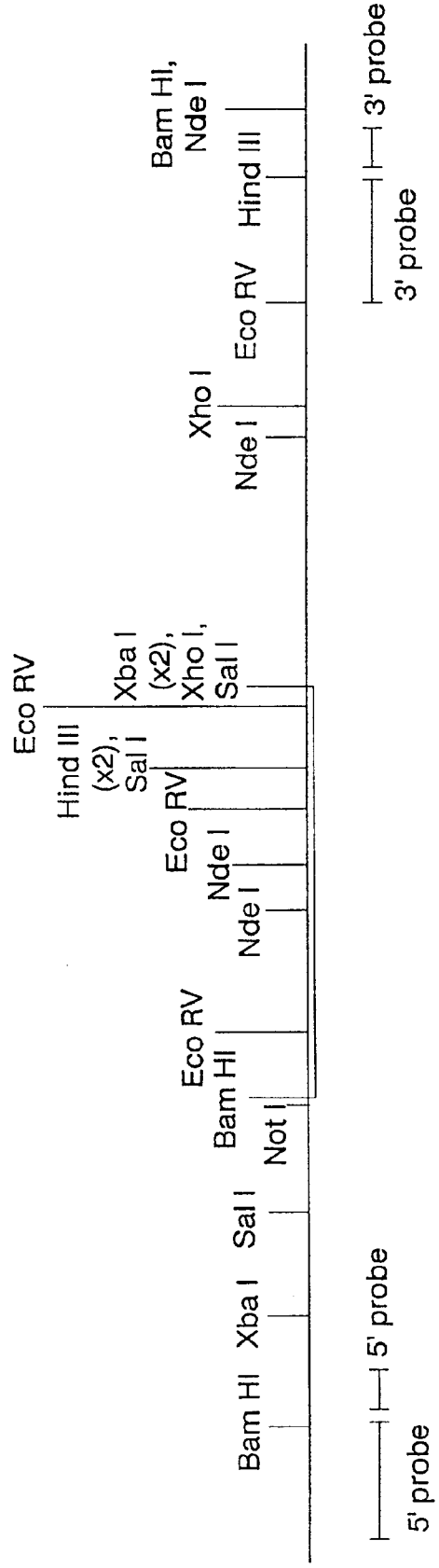

FIG. 46 is a diagrammatic representation of SOCS-3 targeting.

Figure 47A:
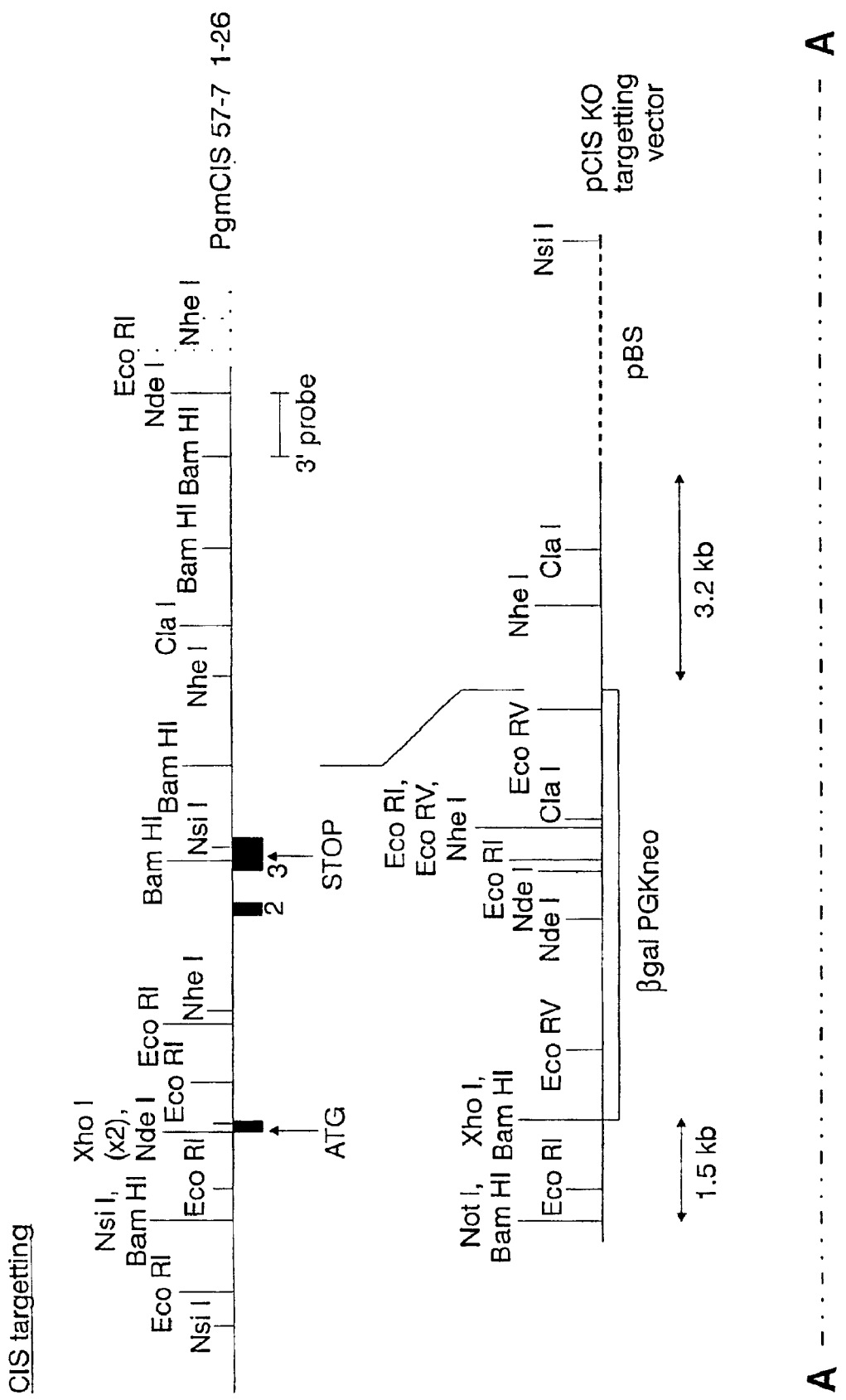
Figure 47B:

FIG. 47 is a diagrammatic representation of CIS targeting.

Figure 48:
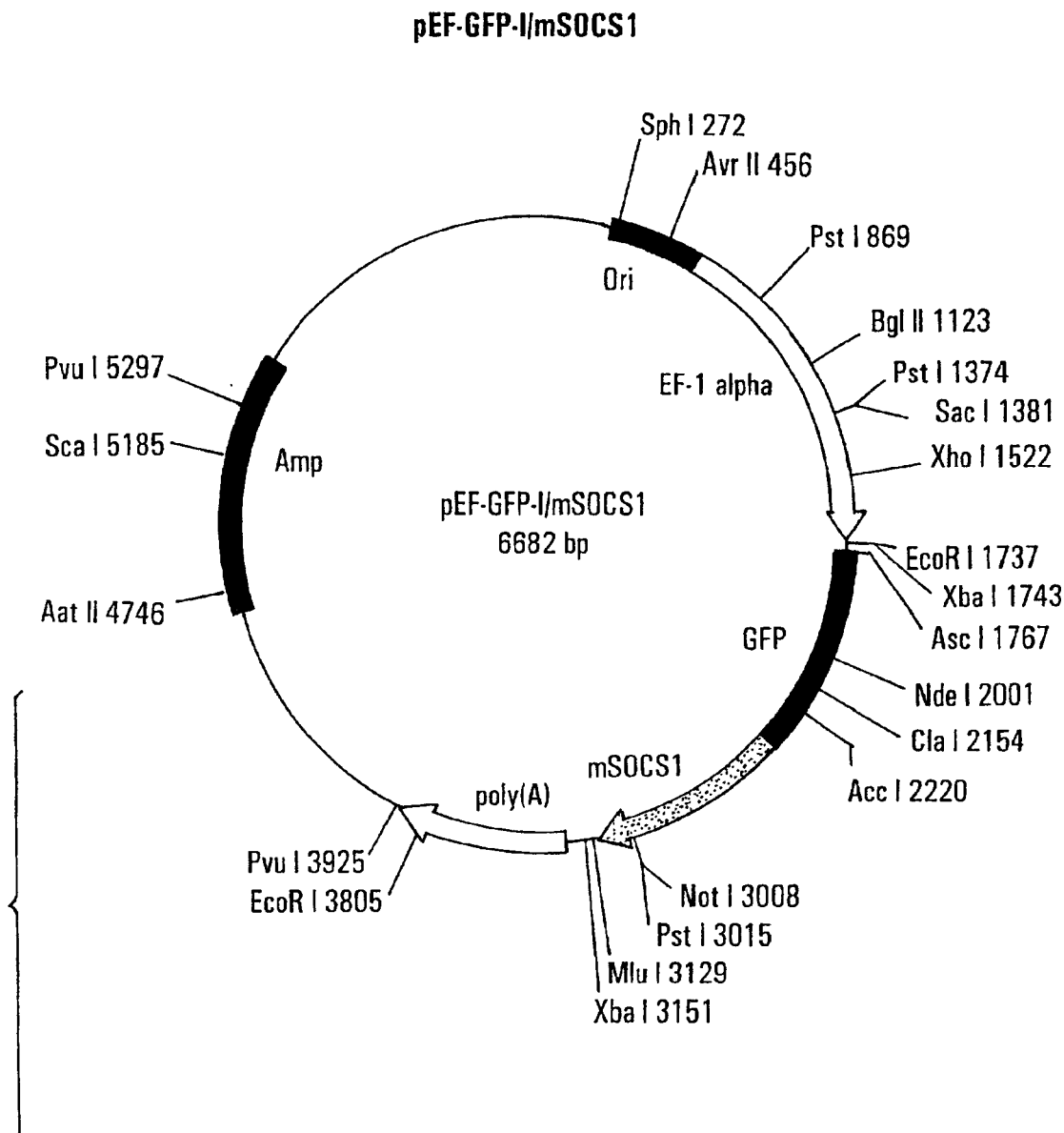

FIG. 48 is a diagrammatic representation of pEF-GFP-I/M SOCS-1.

FIG. 49 is a representation showing nucleotide sequences of oligonucleotides and full length coding sequence of SOCS-1.

FIG. 50 is a representation of amino acid sequence of SOCS-13.

FIG. 51 is a (A) nucleotide of mouse SOCS-5. The predicted translational start and stop sites underlined; (B) predicted amino acid sequence of mouse SOCS-5. The conventional three-letter code for amino acids is used.

FIG. 52 is a (A) nucleotide of mouse SOCS-9. The predicted translational start and stop sites underlined; (B)predicted amino acid sequence of mouse SOCS-9. The conventional three-letter code for amino acids is used.

DETAILED DESCRIPTION OF PREFERRED EMBODIMENTS

The present invention provides anew family of modulators of signal transduction. As the initial members of this family suppressed cytokine signalling, the family is referred to as the "suppressors of cytokine signalling" family of "SOCS". The SOCS family is defined by the presence of a C-terminal domain referred to as a "SOCS box". Different classes of SOCS molecules are defined by a motif generally but not exclusively located N-terminal to the SOCS box and which is involved by protein:molecule interaction such as protein:DNA or protein:protein interaction. Particularly preferred motifs are selected from an SH2 domain, WD-40 repeats and ankyrin repeats.

WD-40 repeats were originally recognised in the β-subunit of G-proteins. WD-40 repeats appear to form a β-propeller-like structure and may be involved in protein-protein interactions. Ankyrin repeats were originally recognised in the cytoskeletal protein ankyrin.

Members of the SOCS family may be identified by any number of means. For example, SOCS1 to SOCS3 were identified by their ability, to suppress cytokine-mediated signal transduction and hence, were identified based on activity. SOCS4 to SOCS15 were identified as nucleotide sequences exhibiting similarity at the level of the SOCS box.

The SOCS box is a conserved motif located in the C-terminal region of the SOCS molecule. In accordance with the present invention, the amino acid sequence of the SOCS box is:

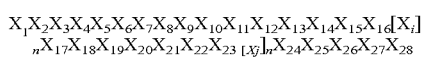

wherein
$X_1$ is L, I, V, M, A or P;
$X_2$ is any amino acid residue;
$X_3$ is P, T or S;

$X_4$ is L, I, V, M, A or P;
$X_5$ is any amino acid;
$X_6$ is any amino acid;
$X_7$ is L, I, V, M, A, F, Y or W;
$X_8$ is C, T or S;
$X_9$ is R, K or H;
$X_{10}$ is any amino acid;
$X_{11}$ is any amino acid;
$X_{12}$ is L, I, V, M, A or P;
$X_{13}$ is any amino acid;
$X_{14}$ is any amino acid;
$X_{15}$ is any amino acid;
$X_{16}$ is L, I, V, M, A, P, G, C, T or S;
$[X_i]_n$ is a sequence of n amino acids wherein n is from 1 to 50 amino acids and wherein the sequence $X_i$ may comprise the same or different amino acids selected from any amino acid residue;
$X_{17}$ is L, I, V, M, A or P;
$X_{18}$ is any amino acid;
$X_{19}$ is any amino acid;
$X_{20}$ L, I, V, M, A or P;
$X_{21}$ is P;
$X_{22}$ is L, I, V, M, A, P or G;
$X_{23}$ is P or N;
$[X_j]_n$ is a sequence of n amino acids wherein n is from 0 to 50 amino acids and wherein the sequence $X_j$ may comprise the same or different amino acids selected from any amino acid residue;
$X_{24}$ is L, I, V, M, A or P;
$X_{25}$ is any amino acid;
$X_{26}$ is any amino acid;
$X_{27}$ is Y or F;
$X_{28}$ is L, I, V, M, A or P;

As stated above and in accordance with the present invention, SOCS proteins are divided into separate classes based on the presence of a protein:molecule interacting region such as but not limited to an SH2 domain, WD-40 repeats and ankyrin repeats located N-terminal of the SOCS box. The latter three domains are protein:protein interacting domains.

Examples of SH2 containing SOCS proteins include SOCS1, SOCS2, SOCS3, SOCS5, SOCS9, SOCS11 and SOCS14. Examples of SOCS containing WD-40 repeats include SOCS4, SOCS6 and SOCS15. Examples of SOCS containing ankyrin repeats include SOCS7, SOCS10 and SOCS12.

The present invention provides inter alia nucleic acid molecules encoding SOCS proteins, purified naturally occurring SOCS proteins as well as recombinant forms of SOCS proteins and methods of modulating signal transduction by modulating activity of SOCS proteins or expression of SOCS genes. Preferably, signal transduction is mediated by a cytokine, examples of which include EPO, TPO, G-CSF, GM-CSF, IL-3, IL-2, IL-4, IL-7, IL-13, IL-6, LIF, IL-12, IFNγ, TNFα, IL-1 and/or M-CSF. Particularly preferred cytokines include IL-6, LIF, OSM, IFN-γ and/or thrombopoietin.

Accordingly, one aspect of the present invention provides an isolated nucleic acid molecule comprising a sequence of nucleotides encoding or complementary to a sequence encoding a protein or a derivative, homologue, analogue or mimetic thereof or comprises a nucleotide sequence capable of hybridizing thereto under low stringency conditions at 42° C. wherein said protein comprises a SOCS box in its C-terminal region and optionally a protein:molecule interacting domain N-terminal of the SOCS box.

Preferably, the protein:molecule interacting domain is a protein:DNA or protein:protein interacting domain. Most preferably, the protein:molecule interacting domain is one of an SH2 domain, WD-40 repeats and/or ankyrin repeats.

As stated above, preferably the subject SOCS modulate cytokine-mediated signal transduction. The present invention extends, however, to SOCS molecules modulating other effector-mediated signal transduction such as mediated by other endogenous or exogenous molecules, antigens, microbes and microbial products, viruses or components thereof, ions, hormones and parasites. Endogenous molecules in this context are molecules produced within the cell carrying the SOCS molecule. Exogenous molecules are produced by other cells or are introduced to the body.

Preferably, the nucleic acid molecule or SOCS protein is in isolated or purified form. The terms "isolated" and "purified" mean that a molecule has undergone at least one purification step away from other material.

Preferably, the nucleic acid molecule is in isolated form and is DNA such as cDNA or genomic DNA. The DNA may encode the same amino acid sequence as the naturally occurring SOCS or the SOCS may contain one or more amino acid substitutions, deletions and/or additions. The nucleotide sequence may correspond to the genomic coding sequence (including exons and introns) or to the nucleotide sequence in cDNA from mRNA transcribed from the genomic gene or it may carry one or more nucleotide substitutions, deletions and/or additions thereto.

In a preferred embodiment, the nucleic acid molecule comprises a sequence of nucleotide encoding or complementary to a sequence encoding a SOCS protein or a derivative, homologue, analogue or mimetic thereof wherein the amino acid sequence of said SOCS protein is selected from SEQ ID NO:4 (mSOCS1), SEQ ID NO:6 (mSOCS2), SEQ ID NO:8 (mSOCS3), SEQ ID NO:10 (hSOCS1), SEQ ID NO:12 (rSOCS1), SEQ ID NO:14 (mSOCS4), SEQ ID NO:18 (mSOCS5), SEQ ID NO:21 (mSOCS6), SEQ ID NO:25 (mSOCS27), SEQ ID NO:29 (mSOCS8), SEQ ID NO:36 (hSOCS11), SEQ ID NO:41 (mSOCS13), SEQ ID NO:44 (mSOCS14), SEQ ID NO:46 (mSOCS15) and SEQ ID NO:48 (mSOCS15) or encodes an amino acid sequence with a single or multiple amino acid substitution, deletion and/or addition to the listed sequences or is a nucleotide sequence capable of hybridizing to the nucleic acid molecule wider low stringency conditions at 42° C.

In an even more preferred embodiment, the present invention provides a nucleic acid molecule comprising a sequence of nucleotides encoding or complementary to a sequence encoding a SOCS protein or a derivative, homologue, analogue or mimetic thereof wherein the nucleotide sequence is selected from a nucleotide sequence substantially set forth in SEQ ID NO:3 (mSOCS1), SEQ ID NO:5 (mSOCS2), SEQ ID NO:7 (mSOCS3), SEQ ID NO:9 (hSOCS11), SEQ ID NO:11 (rSOCS1), SEQ ID NO:13 (mSOCS4), SEQ ID NO:15 and SEQ ID NO:16 (hSOCS4), SEQ ID NO:17 (mSOCS5), SEQ ID NO:19 (hSOCS5), SEQ ID NO:20 (mSOCS6), SEQ ID NO:22 and SEQ ID NO:23 (hSOCS6), SEQ ID NO:24 (mSOCS7), SEQ ID NO:26 and SEQ ID NO:27 (hSOCS7), SEQ ID NO:28 (mSOCS8), SEQ ID NO:30 (mSOCS9), SEQ ID NO:31 (hSOCS9), SEQ ID NO:32 (mSOCS10), SEQ ID NO:33 and SEQ ID NO:34 (hSOCS10), SEQ ID NO:35 (hSOCS11), SEQ ID NO:37 (mSOCS12), SEQ ID NO:38 and SEQ ID NO:39

(hSOCS12), SEQ ID NO:40 (mSOCS13), SEQ ID NO:42 (hSOCS13), SEQ ID NO:43 (mSOCS14), SEQ ID NO:45 (mSOCS15) and SEQ ID NO:47 (hSOCS15) or a nucleotide sequence having at least about 15% similarity to all or a region of any of the listed sequences or a nucleic acid molecule capable of hybridizing to any of the listed sequences under low stringency conditions at 42° C.

Reference herein to a low stringency at 42° C. includes and encompasses from at least about 1% v/v to at least about 15% v/v formamide and from at least about 1 M to at least about 2M salt for hybridisation, and at least about 1M to at least about 2M salt for washing conditions. Alternative stringency conditions may be applied where necessary, such as medium stringency, which includes and encompasses from at least about 16% v/v to at least about 30% v/v formamide and from at least about 0.5M to at least about 0.9M salt for hybridisation, and at least about 0.5M to at least about 0.9M salt for washing conditions, or high stringency, which includes and encompasses from at least about 31% v/v to at least about 50% v/v formamide and from at least about 0.01M to at least about 0.15M salt for hybridisation, and at least about 0.01M to at least about 0.15M salt for washing conditions.

In another embodiment, the present invention is directed to a SOCS protein or a derivative, homologue, analogue or mimetic thereof wherein said SOCS protein is identified as follows:

human SOCS4 characterised by EST81149EST180909, EST182619, ya99H09, ye70co4, yh53c09, yh77g11, yh87h05, yi45h07, yj04e06, yg12h06, yq56a06, yq60e02, yg92g03, yg97h06, yr90f01, yt69c03, yv30a08, yv55f07, yv57h09, yv87h02, yv98e11, yw68d10, yw82a03, yx08a07, yx72h06, yx76b09, yy37h08, yy66b02, za81f08, zb18f07, zc06e08, zd14g06, zd51h12, zd52b09, ze25g11, ze69f02, zf54f03, zh96e07, zv66h12, zs83a08 and zs83g08;

mouse SOCS-4 characterised by mc65f04, mf42e06, mp10c 10, mr81g09, and mt19h12;

human SOCS-5 characterised by EST15B103, EST15B105, EST27530 and zf50t01;

mouse SOCS-5 characterised by mc55a01, mh98f09, my26h12 and ve24e06;

human SOCS-6 characterised by yf61e08, yf93a09, yg05f12, yg41f04, yg45c02, yh11f10, yh13b05, zc35a12, ze02h08, z109a03, z169e10, zn39d08 and zo39e06;

mouse SOCS-6 characterised by mc04c05, md48a03, mf31d03, mh26b07, mh78e11, mh88h09, mh94h07, mi27h04 and mj29c05, mp66a04, mw75g03, va53b05, vb34h02, vc55d07, vc59e05, vc67d03, vc68d10, vc97h01, vc99c08, vd07h03, vd08c01, vd09b12, vd19b02, vd29a04 and vd46d06;

human SOCS-7 characterised by STS WI30171, EST00939, EST12913, yc29b05, yp49f10, zt10f03 and zx73g04;

mouse SOCS-7 characterised by mj39a01 and vi52h07;

mouse SOCS-8 characterised by mj6e09 and vj27a029;

human SOCS-9 characterised by CSRL-82f2-u, EST114054, yy06b07, yy06g06, zr40c09, zr72h01, yx92c08, yx93b08 and hfe0662;

mouse SOCS-9 characterised by me65d05;

human SOCS-10 characterised by aa48h10, zp35h01, zp97h12, zq08h01, zr34g05, EST73000 and HSDHI005;

mouse SOCS-10 characterised by mb14d12, mb40f06, mg89b11, mg89e12, mp03g12 and vh53c11;

human SOCS-11 characterised by zt24h06 and zr43b02;

human SOCS-13 characterised by EST59161;

mouse SOCS-13 characterised by ma39a09, me60c05, mi78g05, mk10, mo48g12, mp94a01, vb57c07 and vh07c11; and human SOCS-14 characterised by mi75e03, vd29h11 and vd53g07; or a derivative or homologue of the above ESTs characterised by a nucleic acid molecule being capable of hybridizing to any of the listed ESTs under low stringency conditions at 42° C.

In another embodiment, the nucleotide sequence encodes the following amino acid sequence:

$$X_1X_2X_3X_4X_5X_6X_7X_8X_9X_{10}X_{11}X_{12}X_{13}X_{14}X_{15}X_{16}[X_i]_nX_{17}X_{18}X_{19}X_{20}X_{21}X_{22}X_{23}[X_j]_nX_{24}X_{25}X_{26}X_{27}X_{28}$$

wherein $X_1$ is L, I, V, M, A or P;

$X_2$ is any amino acid residue;

$X_3$ is P, T or S;

$X_4$ is L, I, V, M, A or P;

$X_5$ is any amino acid;

$X_6$ is any amino acid;

$X_7$ is L, I, V, M, A, F, Y or W;

$X_8$ is C, T or S;

$X_9$ is R, K or H;

$X_{10}$ is any amino acid;

$X_{11}$ is any amino acid;

$X_{12}$ is L, I, V, M, A or P;

$X_{13}$ is any amino acid;

$X_{14}$ is any amino acid;

$X_{15}$ is any amino acid;

$X_{16}$ is L, I, V, M, A, P, G, C, T or S;

$[X_i]_n$ is a sequence of n amino acids wherein n is from 1 to 50 amino acids and wherein the sequence $X_i$ may comprise the same or different amino acids selected from any amino acid residue;

$X_{17}$ is L, I, V, M, A or P;

$X_{18}$ is any amino acid;

$X_{19}$ is any amino acid;

$X_{20}$ L, I, V, M, A or P;

$X_{21}$ is P;

$X_{22}$ is L, I, V, M, A, P or G;

$X_{23}$ is P or N;

$[X_j]_n$ is a sequence of n amino acids wherein n is from 0 to 50 amino acids and wherein the sequence $X_j$ may comprise the same or different amino acids selected from any amino acid residue;

$X_{24}$ is L, I, V, M, A or P;

$X_{25}$ is any amino acid;

$X_{26}$ is any amino acid;

$X_{27}$ is Y or F;

$X_{28}$ is L, I, V, M, A or P;

The above sequence comparisons are preferably to the whole molecule but may also be to part thereof Preferably, the comparisons are made to a contiguous series of at least about 21 nucleotides or at least about 5 amino acids. More preferably, the comparisons are made against at least about 21 contiguous nucleotides or at least 7 contiguous amino acids. Comparisons may also only be made to the SOCS box region or a region encompassing the protein:molecule interacting region such as the SH2 domain WD-00 repeats and/or ankyrin repeats.

Still another embodiment of the present invention contemplates an isolated polypeptide or a derivative, homologue, analogue or mimetic thereof comprising a SOCS box in its C-terminal region.

Preferably the polypeptide farther comprises a protein:molecule interacting domain such as a protein:DNA or protein:protein interacting domain. Preferably, this domain is located N-terminal of the SOCS box. It is particularly preferred for the protein:molecule interacting domain to be at least one of an SH2 domain, WD-40 repeats and/or ankyrin repeats.

Preferably, the signal transduction is mediated by a cytokine selected from EPO, TPO, G-CSF, GM-CSF, IL-3, IL-2, IL-4, IL7, IL-13, IL-6, LIF, IL-12, IFNγ, TNFα, IL-1 I and/or M-CSF. Preferred cytokines are IL-6, LIF, OSM, IFN-γ or thrombopoietin.

More preferably, the protein comprises a SOCS box having the amino acid sequence:

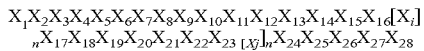

wherein $X_1$ is L, I, V, M, A or P;

$X_2$ is any amino acid residue;

$X_3$ is P, T or S;

$X_4$ is L, I, V, M, A or P;

$X_5$ is any amino acid;

$X_6$ is any amino acid;

$X_7$ is L, I, V, M, A, F, Y or W;

$X_8$ is C, T or S;

$X_9$ is R, K or H;

$X_{10}$ is any amino acid;

$X_{11}$ is any amino acid;

$X_{12}$ is L, I, V, M, A or P;

$X_{13}$ is any amino acid;

$X_{14}$ is any amino acid;

$X_{15}$ is any amino acid;

$X_{16}$ is L, I, V, M, A, P, G, C, T or S;

$[X_i]_n$ is a sequence of n amino acids wherein n is from 1 to 50 amino acids and wherein the sequence $X_i$ may comprise the same or different amino acids selected from any amino acid residue;

$X_{17}$ is L, I, V, M, A or P;

$X_{18}$ is any amino acid;

$X_{19}$ is any amino acid;

$X_{20}$ L, I, V, M, A or P;

$X_{21}$ is P;

$X_{22}$ is L, I, V, M, A, P or G;

$X_{23}$ is P or N;

$[X_j]_n$ is a sequence of n amino acids wherein n is from 0 to 50 amino acids and wherein the sequence $X_j$ may comprise the same or different amino acids selected from any amino acid residue;

$X_{24}$ is L, I, V, M, A or P;

$X_{25}$ is any amino acid;

$X_{26}$ is any amino acid;

$X_{27}$ is Y or F; and $X_{28}$ is L, I, V, M, A or P.

Still another embodiment provides an isolated polypeptide or a derivative, homologue, analogue or mimetic thereof comprising a sequence of amino acids substantially as set forth in SEQ ID NO:4 (mSOCS1), SEQ ID NO:6 (mSOCS2), SEQ ID NO:8 (mSOCS3), SEQ ID NO:10 (hSOCS1), SEQ ID NO:12 (rSOCS1), SEQ ID NO:14 (mSOCS4), SEQ ID NO:18 (mSOCS5), SEQ ID NO:21 (mSOCS6), SEQ ID NO:25 (mSOCS7), SEQ ID NO:29 (mSOCS8), SEQ ID NO:36 (hSOCS11), SEQ ID NO:41 (mSOCS13), SEQ ID NO:44 (mSOCS14), SEQ ID NO:46 (mSOCS15) and SEQ ID NO:48 (hSOCS15) or an amino acid sequence having at least 15% similarity to all or a part of the listed sequences.

Preferred nucleotide percentage similarities include at least about 20%, at least about 40%, at least about 50%, at least about 60%, at least about 70%, at least about 80%, at least about 90% or above such as 93%, 95%, 98% or 99%.

Preferred amino acid similarities include at least about 20%, at least about 30%, at least about 40%, at least about 50%, at least about 60%, at least about 80%, at least about 90%, at least about 95%, at least about 97% or 98% or above.

As stated above, similarity may be measured against an entire molecule or a region comprising at least 21 nucleotides or at least 7 amino acids. Preferably, similarity is measured in a conserved region such as SH2 domain, WD-40 repeats, ankyrin repeats or other protein:molecule interacting domains or a SOCS box.

The term "similarity" includes exact identity between sequences or, where the sequence differs, different amino acids are related to each other at the structural, functional, biochemical and/or conformational levels.

The nucleic acid molecule may be isolated from any animal such as humans, primates, livestock animals (e.g. horses, cows, sheep, donkeys, pigs), laboratory test animals (e.g. mice, rats, rabbits, hamsters, guinea pigs), companion animals (e.g. dogs, cats) or captive wild animals (e.g. deer, foxes, kangaroos).

The terms "derivatives" or its singular form "derivative" whether in relation to a nucleic acid molecule or a protein includes parts, mutants, fragments and analogues as well as hybrid or fusion molecules and glycosylation variants. Particularly useful derivatives comprise single or multiple amino acid substitutions, deletions and/or additions to the SOCS amino acid sequence.

Preferably, the derivatives have functional activity or alternatively act as antagonists or agonists. The present invention further extends to homologues of SOCS which include the functionally or structurally related molecule from different animal species. The present invention also encompasses analogues and mimetics. Mimetics include a class of molecule generally but not necessarily having a non-amino acid structure and which functionally are capable of acting in an analogous manner to the protein for which it is a mimic, in this case, a SOCS. Mimetics may comprise a carbohydrate, aromatic ring, lipid or other complex chemical structure or may also be proteinaceous in composition. Mimetics as well as agonists and antagonists contemplated herein are conveniently located through systematic searching of environments, such as coral, marine and freshwater river beds, flora and microorganisms. This is sometimes referred to as natural product screening. Alternatively, libraries of synthetic chemical compounds may be screened for potentially useful molecules.

The present invention further extends to a range of deletion mutants such as SOCS molecules carrying deletion in the carboxy terminal region, the amino terminal region and in both the carboxy and amino terminal regions. Molecules are also contemplated by the present invention which encompasses only the carboxy terminal region or amino terminal region or fused to another peptide, polypeptide or protein. Molecules comprising the amino terminal portion of the SOCS molecules are particularly useful as molecules capable of interacting with cytokines. For example, the N-terminal region of SOCS-1 is critical for inhibition of M1 macrophage differentiation and LIF and IL-6 signalling.

As stated above, the present invention contemplates agonists and antagonists of the SOCS. One example of an antagonist is an antisense oligonucleotide sequence. Useful oligonucleotides are those which have a nucleotide sequence complementary to at least a portion of the protein-coding or "sense" sequence of the nucleotide sequence. These antisense nucleotides can be used to effect the specific inhibition of gene expression. The antisense approach can cause inhibition of gene expression apparently by forming an anti-parallel duplex by complementary base pairing between the antisense construct and the targeted mRNA, presumably resulting in hybridisation arrest of translation. Ribozymes and co-suppression molecules may also be used. Antisense and other nucleic acid molecules may first need to be chemically modified to permit penetration of cell membranes and/or to increase their serum half life or otherwise make them more stable for in vivo administration. Antibodies may also act as either antagonists or agonists although are more useful in diagnostic applications or in the purification of SOCS proteins. Antagonists and agonists may also be identified following natural product screening or screening of libraries of chemical compounds or may be derivatives or analogues of the SOCS molecules. Agonists and antagonists of SOCS proteins contemplated by the present invention include carboxy-terminal and N-terminal portions of the SOCS molecule. For example, the N-terminal portion of SOCS-1 is useful in inhibiting LIF and IL-6 signalling.

Accordingly, the present invention extends to analogues of the SOCS proteins of the present invention. Analogues may be used, for example, in the treatment or prophylaxis of cytokine mediated dysfunction such as autoimmunity, immune suppression or hyperactive immunity or other condition including but not limited to dysfunctions in the haemopoietic, endocrine, hepatic and neural systems. Dysfunctions mediated by other signal transducing elements such as hormones or endogenous or exogenous molecules, antigens, microbes and microbial products, viruses or components thereof, ions, hormones and parasites are also contemplated by the present invention.

Analogues of the proteins contemplated herein include, but are not limited to, modification to side chains, incorporating of unnatural amino acids and/or their derivatives during peptide, polypeptide or protein synthesis and the use of crosslinkers and other methods which impose conformational constraints on the proteinaceous molecule or their analogues.

Examples of side chain modifications contemplated by the present invention include modifications of amino groups such as by reductive alkylation by reaction with an aldehyde followed by reduction with $NaBH_4$; amidination with methylacetimidate; acylation with acetic anhydride; carbamoylation of amino groups with cyanate; trinitrobenzylation of amino groups with 2, 4, 6-trinitrobenzene sulphonic acid (TNBS); acylation of amino groups with succinic anhydride and tetrahydrophthalic anhydride; and pyridoxylation of lysine with pyridoxal-5-phosphate followed by reduction with $NaBH_4$.

The guanidine group of arginine residues may be modified by the formation of heterocyclic condensation products with reagents such as 2,3-butanedione, phenylglyoxal and glyoxal.

The carboxyl group may be modified by carbodiimide activation via O-acylisourea formation followed by subsequent derivitisation, for example, to a corresponding amide.

Sulphydryl groups may be modified by methods such as carboxymethylation with iodoacetic acid or iodoacetamide; performic acid oxidation to cysteic acid; formation of a mixed disulphides with other thiol compounds; reaction with maleimide, maleic anhydride or other substituted maleimide; formation of mercurial derivatives using 4-chloromercuribenzoate, 4-chloromercuriphenylsulphonic acid, phenylmercury chloride, 2-chloromercuri-4-nitrophenol and other mercurials; carbamoylation with cyanate at alkaline pH.

Tryptophan residues may be modified by, for example, oxidation with N-bromosuccinimide or alkylation of the indole ring with 2-hydroxy-5-nitrobenzyl bromide or sulphenyl halides. Tyrosine residues on the other hand, may be altered by nitration with tetranitromethane to form a 3-nitrotyrosine derivative.

Modification of the imidazole ring of a histidine residue may be accomplished by alkylation with iodoacetic acid derivatives or N-carbethoxylation with diethylpyrocarbonate.

Examples of incorporating unnatural amino acids and derivatives during peptide synthesis include, but are not limited to, use of norleucine, 4-amino butyric acid, 4-amino-3-hydroxy-5-phenylpentanoic acid, 6-aminohexanoic acid, t-butylglycine, norvaline, phenylglycine, ornithine, sarcosine, 4-amino-3-hydroxy-6-methylheptanoic acid, 2-thienyl alanine and/or D-isomers of amino acids. A list of unnatural amino acid, contemplated herein is shown in Table 3.

TABLE 3

| Non-conventional amino acid | Code | Non-conventional amino acid | Code |
| --- | --- | --- | --- |
| α-aminobutyric acid | Abu | L-N-methylalanine | Nmala |
| α-amino-α-methylbutyrate | Mgabu | L-N-methylarginine | Nmarg |
| aminocyclopropane-carboxylate | Cpro | L-N-methylasparagine | Nmasn |
|  |  | L-N-methylaspartic acid | Nmasp |
| aminoisobutyric acid | Aib | L-N-methylcysteine | Nmcys |
| aminonorbornyl-carboxylate | Norb | L-N-methylglutamine | Nmgln |
|  |  | L-N-methylglutamic acid | Nmglu |
| cyclohexylalanine | Chexa | L-N-methylhistidine | Nmhis |
| cyclopentylalanine | Cpen | L-N-methylisolleucine | Nmile |
| D-alanine | Dal | L-N-methylleucine | Nmleu |
| D-arginine | Darg | L-N-methyllysine | Nmlys |
| D-aspartic acid | Dasp | L-N-methylmethionine | Nmmet |
| D-cysteine | Dcys | L-N-methylnorleucine | Nmnle |
| D-glutamine | Dgln | L-N-methylnorvaline | Nmnva |
| D-glutamic acid | Dglu | L-N-methylornithine | Nmorn |

TABLE 3-continued

| Non-conventional amino acid | Code | Non-conventional amino acid | Code |
|---|---|---|---|
| D-histidine | Dhis | L-N-methylphenylalanine | Nmphe |
| D-isoleucine | Dile | L-N-methylproline | Nmpro |
| D-leucine | Dleu | L-N-methylserine | Nmser |
| D-lysine | Dlys | L-N-methylthreonine | Nmthr |
| D-methionine | Dmet | L-N-methyltryptophan | Nmtrp |
| D-ornithine | Dorn | L-N-methyltyrosine | Nmtyr |
| D-phenylalanine | Dphe | L-N-methylvaline | Nmval |
| D-proline | Dpro | L-N-methylethylglycine | Nmetg |
| D-serine | Dser | L-N-methyl-t-butylglycine | Nmtbug |
| D-threonine | Dthr | L-norleucine | Nle |
| D-tryptophan | Dtrp | L-norvaline | Nva |
| D-tyrosine | Dtyr | α-methyl-aminoisobutyrate | Maib |
| D-valine | Dval | α-methyl-γ-aminobutyrate | Mgabu |
| D-α-methylalanine | Dmala | α-methylcyclohexylalanine | Mchexa |
| D-α-methylarginine | Dmarg | α-methylcylcopentylalanine | Mcpen |
| D-α-methylasparagine | Dmasn | α-methyl-α-napthylalanine | Manap |
| D-α-methylaspartate | Dmasp | α-methylpenicillamine | Mpen |
| D-α-methylcysteine | Dmcys | N-(4-aminobutyl)glycine | Nglu |
| D-α-methylglutamine | Dmgln | N-(2-aminoethyl)glycine | Naeg |
| D-α-methylhistidine | Dmhis | N-(3-aminopropyl)glycine | Norn |
| D-α-methylisoleucine | Dmile | N-amino-α-methylbutyrate | Nmaabu |
| D-α-methylleucine | Dmleu | α-napthylalanine | Anap |
| D-α-methyllysine | Dmlys | N-benzylglycine | Nphe |
| D-α-methylmethionine | Dmmet | N-(2-carbamylethyl)glycine | Ngln |
| D-α-methylornithine | Dmorn | N-(carbamylmethyl)glycine | Nasn |
| D-α-methylphenylalanine | Dmphe | N-(2-carboxyethyl)glycine | Nglu |
| D-α-methylproline | Dmpro | N-(carboxymethyl)glycine | Nasp |
| D-α-methylserine | Dmser | N-cyclobutylglycine | Ncbut |
| D-α-methylthreonine | Dmthr | N-cycloheptylglycine | Nchep |
| D-α-methyltryptophan | Dmtrp | N-cyclohexylglycine | Nchex |
| D-α-methyltyrosine | Dmty | N-cyclodecylglycine | Ncdec |
| D-α-methylvaline | Dmval | N-cylcododecylglycine | Ncdod |
| D-N-methylalanine | Dnmala | N-cyclooctylglycine | Ncoct |
| D-N-methylarginine | Dnmarg | N-cyclopropylglycine | Ncpro |
| D-N-methylasparagine | Dnmasn | N-cycloundecylglycine | Ncund |
| D-N-methylaspartate | Dnmasp | N-(2,2-diphenylethyl)glycine | Nbhm |
| D-N-methylcysteine | Dnmcys | N-(3,3-diphenylpropyl)glycine | Nbhe |
| D-N-methylglutamine | Dnmgln | N-(3-guanidinopropyl)glycine | Narg |
| D-N-methylglutamate | Dnmglu | N-(1-hydroxyethyl)glycine | Nthr |
| D-N-methylhistidine | Dnmhis | N-(hydroxyethyl))glycine | Nser |
| D-N-methylisoleucine | Dnmile | N-(imidazolylethyl))glycine | Nhis |
| D-N-methylleucine | Dnmleu | N-(3-indolylyethyl)glycine | Nhtrp |
| D-N-methyllysine | Dnmlys | N-methyl-γ-aminobutyrate | Nmgabu |
| N-methylcyclohexylalanine | Nmchexa | D-N-methylmethionine | Dnmmet |
| D-N-methylornithine | Dnmorn | N-methylcyclopentylalanine | Nmcpen |
| N-methylglycine | Nala | D-N-methylphenylalanine | Dnmphe |
| N-methylaminoisobutyrate | Nmaib | D-N-methylproline | Dnmpro |
| N-(1-methylpropyl)glycine | Nile | D-N-methylserine | Dnmser |
| N-(2-methylpropyl)glycine | Nleu | D-N-methylthreonine | Dnmthr |
| D-N-methyltryptophan | Dnmtrp | N-(1-methylethyl)glycine | Nval |
| D-N-methyltyrosine | Dnmtyr | N-methyla-napthylalanine | Nmanap |
| D-N-methylvaline | Dnmval | N-methylpenicillamine | Nmpen |
| γ-aminobutyric acid | Gabu | N-(p-hydroxyphenyl)glycine | Nhtyr |
| L-t-butylglycine | Tbug | N-(thiomethyl)glycine | Ncys |
| L-ethylglycine | Etg | penicillamine | Pen |
| L-homophenylalanine | Hphe | L-α-methylalanine | Mala |
| L-α-methylarginine | Marg | L-α-methylasparagine | Masn |
| L-α-methylaspartate | Masp | L-α-methyl-t-butylglycine | Mtbug |
| L-α-methylcysteine | Mcys | L-methylethylglycine | Metg |
| L-α-methylglutamine | Mgln | L-α-methylglutamate | Mglu |
| L-α-methylhistidine | Mhis | L-α-methylhomophenylalanine | Mhphe |
| L-α-methylisoleucine | Mile | N-(2-methylthioethyl)glycine | Nmet |
| L-α-methylleucine | Mleu | L-α-methyllysine | Mlys |
| L-α-methylmethionine | Mmet | L-α-methylnorleucine | Mnle |
| L-α-methylnorvaline | Mnva | L-α-methylornithine | Morn |
| L-α-methylphenylalanine | Mphe | L-α-methylproline | Mpro |
| L-α-methylserine | Mser | L-α-methylthreonine | Mthr |
| L-α-methyltryptophan | Mtrp | L-α-methyltyrosine | Mtyr |
| L-α-methylvaline | Mval | L-N-methylhomophenylalanine | Nmhphe |
| N-(N-(2,2-diphenylethyl) carbamylmethyl)glycine | Nnbhm | N-(N-(3,3-diphenylpropyl) carbamylmethyl)glycine | Nnbhe |
| 1-carboxy-1-(2,2-diphenyl-ethylamino)cyclopropane | Nmbc | | |

Crosslinkers can be used, for example, to stabilise 3D conformations, using homo-bifunctional crosslinkers such as the bifunctional imido esters having $(CH_2)_n$ spacer groups with n=1 to n=6, glutaraldehyde, N-hydroxysuccinimide esters and hetero-bifunctional reagents which usually contain an amino-reactive moiety such as N-hydroxysuccinimide and another group specific-reactive moiety such as maleimido or dithio moiety (SH) or carbodiimide (COOH). In addition, peptides can be conformationally constrained by, for example, incorporation of $C_\alpha$ and $N_\alpha$-methylamino acids, introduction of double bonds between $C_\alpha$ and $C_\beta$ atoms of amino acids and the formation of cyclic peptides or analogues by introducing covalent bonds such as forming an amide bond between the N and C termini, between two side chains or between a side chain and the N or C terminus.

These types of modifications may be important to stabilise the cytokines if administered to an individual or for use as a diagnostic reagent.

Other derivatives contemplated by the present invention include a range of glycosylation variants from a completely unglycosylated molecule to a modified glycosylated molecule. Altered glycosylation patterns may result from expression of recombinant molecules in different host cells.

Another embodiment of the present invention contemplates a method for modulating expression of a SOCS protein in a mammal, said method comprising contacting a gene encoding a SOCS or a factor/element involved in controlling expression of the SOCS gene with an effective amount of a modulator of SOCS expression for a time and under conditions sufficient to up-regulate or down-regulate or otherwise modulate expression of SOCS. An example of a modulator is a cytokine such as IL-6 or other transcription regulators of SOCS expression.

Expression includes transcription or translation or both.

Another aspect of the present invention contemplates a method of modulating activity of SOCS in a human, said method comprising administering to said mammal a modulating effective amount of a molecule for a time and under conditions sufficient to increase or decrease SOCS activity. The molecule may be a proteinaceous molecule or a chemical entity and may also be a derivative of SOCS or a chemical analogue or truncation mutant of SOCS.

A further aspect of the present invention provides a method of inducing synthesis of a SOCS or transcription/translation of a SOCS comprising contacting a cell containing a SOCS gene with an effective amount of a cytokine capable of inducing said SOCS for a time and under conditions sufficient for said SOCS to be produced. For example, SOCS1 may be induced by IL-6.

Still a further aspect of the present invention contemplates a method of modulating levels of a SOCS protein in a cell said method comprising contacting a cell containing a SOCS gene with an effective amount of a modulator of SOCS gene expression or SOCS protein activity for a time and under conditions sufficient to modulate levels of said SOCS protein.

Yet a further aspect of the present invention contemplates a method of modulating signal transduction in a cell containing a SOCS gene comprising contacting said cell with an effective amount of a modulator of SOCS gene expression or SOCS protein activity for a time sufficient to modulate signal transduction.

Even yet a further aspect of the present invention contemplates a method of influencing interaction between cells wherein at least one cell carries a SOCS gene, said method comprising contacting the cell carrying the SOCS gene with an effective amount of a modulator of SOCS gene expression or SOCS protein activity for a time sufficient to modulate signal transduction.

As stated above, of the present invention contemplates a range of mimetics or small molecules capable of acting as agonists or antagonists of the SOCS. Such molecules may be obtained from natural product screening such as from coral, soil, plants or the ocean or antarctic environments. Alternatively, peptide, polypeptide or protein libraries or chemical libraries may be readily screened. For example, M1 cells expressing a SOCS do not undergo differentiation in the presence of IL-6. This system can be used to screen molecules which permit differentiation in the presence of IL-6 and a SOCS. A range of test cells may be prepared to screen for antagonists and agonists for a range of cytokines. Such molecules are preferably small molecules and may be of amino acid origin or of chemical origin. SOCS molecules interacting with signalling proteins (eg. JAKS) provide molecular screens to detect molecules which interfere or promote this interaction. Once such screening protocol involves natural product screening.

Accordingly, the present invention contemplates a pharmaceutical composition comprising SOCS or a derivative thereof or a modulator of SOCS expression or SOCS activity and one or more pharmaceutically acceptable carriers and/or diluents. These components are referred to as the "active ingredients". These and other aspects of the present invention apply to any SOCS molecules such as but not limited to SOCS1 to SOCS15.

The pharmaceutical forms containing active ingredients suitable for injectable use include sterile aqueous solutions (where water soluble) sterile powders for the extemporaneous preparation of sterile injectable solutions. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol and liquid polyethylene glycol, and the like), suitable mixtures thereof, and vegetable oils. The proper fluidity can be maintained, for example, by the use of a coating such as licithin, by the maintenance of the required particle size in the case of dispersion and by the use of superfactants. The preventions of the action of microorganisms can be brought about by various antibacterial and antifungal agents, for example, parabens, chlorobutanol, phenol, sorbic acid, thimerosal and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

Sterile injectable solutions are prepared by incorporating the active compounds in the required amount in the appropriate solvent with various of the other ingredients enumerated above, as required, followed by filtered sterilization. In the case of sterile powders for the preparation of sterile injectable solutions, the preferred methods of preparation are vacuum drying and the freeze-drying technique which yield a powder of the active ingredient plus any additional desired ingredient from previously sterile-filtered solution thereof.

When the active ingredients are suitably protected they may be orally administered, for example, with an inert diluent or with an assimilable edible carrier, or it may be enclosed in hard or soft shell gelatin capsule, or it may be compressed into tablets. For oral therapeutic administration, the active compound may be incorporated with excipients and used in the form of ingestible tablets, buccal tablets, troches, capsules, elixirs, suspensions, syrups, wafers and the like. Such compositions and preparations should contain at least 1% by weight of active compound. The percentage of the compositions and preparations may, of course, be varied and may conveniently be between about 5 to about 80% of the weight of the unit. The amount of active compound in such therapeutically useful compositions in such that a suitable dosage will be obtained. Preferred compositions or preparations according to the present invention are prepared so that an oral dosage unit form contains between about 0.1 µg and 2000 mg of active compound.

The tablets, troches, pills, capsules and the like may also contain the components as listed hereafter. A binder such as gum, acacia, corn starch or gelatin; excipients such as dicalcium phosphate; a disintegrating agent such as corn starch, potato starch, alginic acid and the like; a lubricant such as magnesium stearate; and a sweetening agent such a sucrose, lactose or saccharin may be added or a flavouring agent such as peppermint, oil of wintergreen or cherry flavouring. When the dosage unit form is a capsule, it may contain, in addition to materials of the above type, a liquid carrier. Various other materials may be present as coatings or to otherwise modify the physical form of the dosage unit. For instance, tablets, pills, or capsules may be coated with shellac, sugar or both. A syrup of elixir may contain the active compound, sucrose as a sweetening agent, methyl and propylparabens as preservatives, a dye and flavouring such as cherry or orange flavour. Of course, any material used in preparing any dosage unit form should be pharmaceutically pure and substantially non-toxic in the amounts employed. In addition, the active compound(s) may be incorporated into sustained-release preparations and formulations.

The present invention also extends to forms suitable for topical application such as creams, lotions and gels.

Pharmaceutically acceptable carriers and/or diluents include any and all solvents, dispersion media, coatings, antibacterial and antifungal agents, isotonic and absorption delaying agents and the like. The use of such media and agents for pharmaceutical active substances is well known in the art. Except insofar as any conventional media or agent is incompatible with the active ingredient, use thereof in the therapeutic compositions is contemplated. Supplementary active ingredients can also be incorporated into the compositions.

It is especially advantageous to formulate parenteral compositions in dosage unit form for ease of administration and uniformity of dosage. Dosage unit form as used herein refers to physically discrete units suited as unitary dosages for the mammalian subjects to be treated; each unit containing a predetermined quantity of active material calculated to produce the desired therapeutic effect in association with the required pharmaceutical carrier. The specification for the novel dosage unit forms of the invention are dictated by and directly dependent on (a) the unique characteristics of the active material and the particular therapeutic effect to be achieved, and (b) the limitations inherent in the art of compounding such an active material for the treatment of disease in living subjects having a diseased condition in which bodily health is impaired as herein disclosed in detail.

The principal active ingredient is compounded for convenient and effective administration in effective amounts with a suitable pharmaceutically acceptable carrier in dosage unit form as hereinbefore disclosed. A unit dosage form can, for example, contain the principal active compound in amounts ranging from 0.5 µg to about 2000 mg. Expressed in proportions, the active compound is generally present in from about 0.5 µg to about 2000 mg/ml of carrier. In the case of compositions containing supplementary active ingredients, the dosages are determined by reference to the usual dose and manner of administration of the said ingredients. The effective amount may also be conveniently expressed in terms of an amount per kg of body weight. For example, from about 0.01 ng to about 10,000 mg/kg body weight may be administered.

The pharmaceutical composition may also comprise genetic molecules such as a vector capable of transfecting target cells where the vector carries a nucleic acid molecule capable of modulating SOCS expressions or SOCS activity. The vector may, for example, be a viral vector. In this regard, a range of gene therapies are contemplated by the present invention including isolating certain cells, genetically manipulating and returning the cell to the same subject or to a genetically related or similar subject.

Still another aspect of the present invention is directed to antibodies to SOCS and its derivatives. Such antibodies may be monoclonal or polyclonal and may be selected from naturally occurring antibodies to SOCS or may be specifically raised to SOCS or derivatives thereof. In the case of the latter, SOCS or its derivatives may first need to be associated with a carrier molecule. The antibodies and/or recombinant SOCS or its derivatives of the present invention are particularly useful as therapeutic or diagnostic agents.

For example, SOCS and its derivatives can be used to screen for naturally occurring antibodies to SOCS. These may occur, for example in some autoimmune diseases. Alternatively, specific antibodies can be used to screen for SOCS. Techniques for such assays are well known in the art and include, for example, sandwich assays and ELISA. Knowledge of SOCS levels may be important for diagnosis of certain cancers or a predisposition to cancers or monitoring cytokine mediated cellular responsiveness or for monitoring certain therapeutic protocols.

Antibodies to SOCS of the present invention may be monoclonal or polyclonal. Alternatively, fragments of antibodies may be used such as Fab fragments. Furthermore, the present invention extends to recombinant and synthetic antibodies and to antibody hybrids. A "synthetic antibody" is considered herein to include fragments and hybrids of antibodies. The antibodies of this aspect of the present invention are particularly useful for immunotherapy and may also be used as a diagnostic tool for assessing apoptosis or monitoring the program of a therapeutic regimin.

For example, specific antibodies can be used to screen for SOCS proteins. The latter would be important, for example, as a means for screening for levels of SOCS in a cell extract or other biological fluid or purifying SOCS made by recombinant means from culture supernatant fluid. Techniques for the assays contemplated herein are known in the art and include, for example, sandwich assays and ELISA.

It is within the scope of this invention to include any second antibodies (monoclonal, polyclonal or fragments of antibodies or synthetic antibodies) directed to the first mentioned antibodies discussed above. Both the first and second antibodies may be used in detection assays or a first antibody may be used with a commercially available anti-immunoglobulin antibody. An antibody as contemplated herein includes any antibody specific to any region of SOCS.

Both polyclonal and monoclonal antibodies are obtainable by immunization with the enzyme or protein and either type is utilizable for immunoassays. The methods of obtaining both types of sera are well known in the art. Polyclonal sera are less preferred but are relatively easily prepared by injection of a suitable laboratory animal with an effective amount of SOCS, or antigenic parts thereof, collecting serum from the animal, and isolating specific sera by any of the known immunoadsorbent techniques. Although antibodies produced by this method are utilizable in virtually any type of immunoassay, they are generally less favoured because of the potential heterogeneity of the product.

The use of monoclonal antibodies in an immunoassay is particularly preferred because of the ability to produce them in large quantities and the homogeneity of the product. The preparation of hybridoma cell lines for monoclonal antibody production derived by fusing an immortal cell line and lymphocytes sensitized against the immunogenic preparation can be done by techniques which are well known to those who are skilled in the art.

Another aspect of the present invention contemplates a method for detecting SOCS in a biological sample from a subject and method comprising contacting said biological sample with an antibody specific for SOCS or its derivatives or homologues for a time and under conditions sufficient for an antibody-SOCS complex to form and then detecting said complex.

The presence of SOCS may be accomplished in a number of ways such as by Western blotting and ELISA procedures. A wide range of immunoassay techniques are available as can be seen by reference to U.S. Pat. Nos. 4,016,043, 4,424,279 and 4,018,653. These, of course, include both single-site and two-site or "sandwich" assays of the non-competitive types, as well as in the traditional competitive binding assays. These assays also include direct binding of a labelled antibody to a target.

Sandwich assays are among the most useful and commonly used assays and are favoured for use in the present invention. A number of variations of the sandwich assay technique exist, and all are intended to be encompassed by the present invention. Briefly, in a typical forward assay, an unlabelled antibody is immobilized on a solid substrate and the sample to be tested brought into contact with the bound molecule. After a suitable period of incubation, for a period of time sufficient to allow formation of an antibody-antigen complex, a second antibody specific to the antigen, labelled with a reporter molecule capable of producing a detectable signal is then added and incubated, allowing time sufficient for the formation of another complex of antibody-antigen-labelled antibody. Any unreacted material is washed away, and the presence of the antigen is determined by observation of a signal produced by the reporter molecule. The results may either be qualitative, by simple observation of the visible signal, or may be quantitated by comparing with a control sample containing known amounts of hapten. Variations on the forward assay include a simultaneous assay, in which both sample and labelled antibody are added simultaneously to the bound antibody. These techniques are well known to those skilled in the art, including any minor variations as will be readily apparent. In accordance with the present invention the sample is one which might contain SOCS including cell extract, tissue biopsy or possibly serum, saliva, mucosal secretions, lymph, tissue fluid and respiratory fluid. The sample is, therefore, generally a biological sample comprising biological fluid but also extends to fermentation fluid and supernatant fluid such as from a cell culture.

In the typical forward sandwich assay, a first antibody having specificity for the SOCS or antigenic parts thereof, is either covalently or passively bound to a solid surface. The solid surface is typically glass or a polymer, the most commonly used polymers being cellulose, polyacrylamide, nylon, polystyrene, polyvinyl chloride or polypropylene. The solid supports may be in the form of tubes, beads, discs of microplates, or any other surface suitable for conducting an immunoassay. The binding processes are well-known in the art and generally consist of cross-linking covalently binding or physically adsorbing, the polymer-antibody complex is washed in preparation for the test sample. An aliquot of the sample to be tested is then added to the solid phase complex and incubated for a period of time sufficient (e.g. 2–40 minutes or overnight if more convenient) and under suitable conditions (e.g. room temperature to 37° C.) to allow binding of any subunit present in the antibody. Following the incubation period, the antibody subunit solid phase is washed and dried and incubated with a second antibody specific for a portion of the hapten. The second antibody is linked to a reporter molecule which is used to indicate the binding of the second antibody to the hapten.

An alternative method involves immobilizing the target molecules in the biological sample and then exposing the immobilized target to specific antibody which may or may not be labelled with a reporter molecule. Depending on the amount of target and the strength of the reporter molecule signal, a bound target may be detectable by direct labelling with the antibody. Alternatively, a second labelled antibody, specific to the first antibody is exposed to the target-first antibody complex to form a target-first antibody-second antibody tertiary complex. The complex is detected by the signal emitted by the reporter molecule.

By "reporter molecule" as used in the present specification, is meant a molecule which, by its chemical nature, provides an analytically identifiable signal which allows the detection of antigen-bound antibody. Detection may be either qualitative or quantitative. The most commonly used reporter molecules in this type of assay are either enzymes, fluorophores or radionuclide containing molecules (i.e. radioisotopes) and chemiluminescent molecules.

In the case of an enzyme immunoassay, an enzyme is conjugated to the second antibody, generally by means of glutaraldehyde or periodate. As will be readily recognized, however, a wide variety of different conjugation techniques exist, which are readily available to the skilled artisan. Commonly used enzymes include horseradish peroxidase, glucose oxidase, beta-galactosidase and alkaline phosphatase, amongst others. The substrates to be used with the specific enzymes are generally chosen for the production, upon hydrolysis by the corresponding enzyme, of a detectable colour change. Examples of suitable enzymes include alkaline phosphatase and peroxidase. It is also possible to employ fluorogenic substrates, which yield a fluorescent product rather than the chromogenic substrates noted above. In all cases, the enzyme-labelled antibody is added to the first antibody hapten complex, allowed to bind, and then the excess reagent is washed away. A solution containing the appropriate substrate is then added to the complex of antibody-antigen-antibody. The substrate will react with the enzyme linked to the second antibody, giving a qualitative visual signal, which may be further quantitated, usually spectrophotometrically, to give an indication of the amount of hapten which was present in the sample. "Reporter molecule" also extends to use of cell agglutination or inhibition of agglutination such as red blood cells on latex beads, and the like.

Alternately, fluorescent compounds, such as fluorescein and rhodamine, may be chemically coupled to antibodies without altering their binding capacity. When activated by illumination with light of a particular wavelength, the fluorochrome-labelled antibody adsorbs the light energy, inducing a state to excitability in the molecule, followed by emission of the light at a characteristic colour visually detectable with a light microscope. As in the EIA, the fluorescent labelled antibody is allowed to bind to the first antibody-hapten complex. After washing off the unbound reagent, the remaining tertiary complex is then exposed to the light of the appropriate wavelength the fluorescence observed indicates the presence of the hapten of interest. Immunofluorescence and EIA techniques are both very well established in the art and are particularly preferred for the present method. However, other reporter molecules, such as radioisotope, chemiluminescent or bioluminescent molecules, may also be employed.

The present invention also contemplates genetic assays such as involving PCR analysis to detect SOCS gene or its derivatives. Alternative methods or methods used in conjuction include direct nucleotide sequencing or mutation scanning such as single stranded conformation polymorphisms analysis (SSCP) as specific oligonucleotide hybridisation, as methods such as direct protein truncation tests.

Since cytokines are involved in transcription of some SOCS molecules, the detection of SOCS provides surrogate markers for cytokines or cytokine activity. This may be useful in assessing subjects with a range of conditions such as those will autoimmune diseases, for example, rheumatoid arthritis, diabetes and stiff man syndrome amongst others.

The nucleic acid molecules of the present invention may be DNA or RNA. When the nucleic acid molecule is in DNA form, it may be genomic DNA or cDNA. RNA forms of the nucleic acid molecules of the present invention are generally mRNA.

Although the nucleic acid molecules of the present invention are generally in isolated form, they may be integrated into or ligated to or otherwise fused or associated with other genetic molecules such as vector molecules and in particular expression vector molecules. Vectors and expression vectors are generally capable of replication and, if applicable, expression in one or both of a prokaryotic cell or a eukaryotic cell. Preferably, prokaryotic cells include *E. coli*, *Bacillus* sp and *Pseudomonas* sp. Preferred eukaryotic cells include yeast, fungal, mammalian and insect cells.

Accordingly, another aspect of the present invention contemplates a genetic construct comprising a vector portion and a mammalian and more particularly a human SOCS gene portion, which SOCS gene portion is capable of encoding a SOCS polypeptide or a functional or immunologically interactive derivative thereof.

Preferably, the SOCS gene portion of the genetic construct is operably linked to a promoter on the vector such that said promoter is capable of directing expression of said SOCS gene portion in an appropriate cell.

In addition, the SOCS gene portion of the genetic construct may comprise all or part of the gene fused to another genetic sequence such as a nucleotide sequence encoding glutathione-S-transferase or part thereof.

The present invention extends to such genetic constructs and to prokaryotic or eukaryotic cells comprising same.

The present invention also extends to any or all derivatives of SOCS including mutants, part, fragments, portions, homologues and analogues or their encoding genetic sequence including single or multiple nucleotide or amino acid substitutions, additions and/or deletions to the naturally occurring nucleotide or amino acid sequence. The present invention also extends to mimetics and agonists and antagonists of SOCS.

The SOCS and its genetic sequence of the present invention will be useful in the generation of a range of therapeutic and diagnostic reagents and will be especially useful in the detection of a cytokine involved in a particular cellular response or a receptor for that cytokine. For example, cells expressing SOCS gene such as M1 cells expressing the SOCS1 gene, will no longer be responsive to a particular cytokine such as, in the case of SOCS1, IL-6. Clearly, the present invention further contemplates cells such as M1 cells expressing any SOCS gene such as from SOCS1 to SOCS15. Furthermore, the present invention provides the use of molecules that regulate or potentiate the ability of therapeutic cytokines. For example, molecules which block some SOCS activity, may act to potential therapeutic cytokine activity (eg. G-CSF).

Soluble SOCS polypeptides are also contemplated to be particularly useful in the treatment of disease, injury or abnormality involving cytokine mediated cellular responsiveness such as hyperimmunity, immunosuppression, allergies, hypertension and the like.

A further aspect of the present invention contemplates the use of SOCS or its functional derivatives in the manufacture of a medicament for the treatment of conditions involving cytokine mediated cellular responsiveness.

The present invention further contemplates transgenic mammalian cells expressing a SOCS gene. Such cells are useful indicator cell lines for assaying for suppression of cytokine function. One example is M1 cells expressing a SOCS gene. Such cell lines may be useful for screening for cytokines or screening molecules such as naturally occurring molecules from plants, coral, microorganisms or bioorganically active soil or water capable of acting as cytokine antagonists or agonists. The present invention further contemplates transgenic animals such as mice, rats, sheep, pigs, rabbits and guinea pigs which are homozygous or heterozygous knockout animals for the SOCS genes or parts thereof.

The present invention further contemplates hybrids between different SOCS from the same or different animal species. For example, a hybrid may be formed between all or a functional part of mouse SOCS1 and human SOCS1. Alternatively, the hybrid may be between all or part of mouse SOCS1 and mouse SOCS2. All such hybrids are contemplated herein and are particularly useful in developing pleiotropic molecules.

The present invention further contemplates a range of genetic based diagnostic assays screening for individuals with defective SOCS genes. Such mutations may result in cell types not being responsive to a particular cytokine or resulting in over responsiveness leading to a range of conditions. The SOCS genetic sequence can be readily verified using a range of PCR or other techniques to determine whether a mutation is resident in the gene. Appropriate gene therapy or other interventionist therapy may then be adopted.

The present invention is further described by the following non-limiting Examples.

Examples 1–16 relate to SOCS1, SOCS2 and SOCS3 which were identified on the basis of activity. Examples 17–24 relate to various aspects of SOCS4 to SOCS15 which were cloned initially on the basis of sequence similarity. Examples 25–36 relate to specific aspects of SOCS4 to SOCS15, respectively.

EXAMPLE 1

Cell Culture and Cytokines

The M1 cell line was derived from a spontaneously arising leukaemia in SL mice [Ichikawa, 1969]. Parental M1 cells used in this study have been in passage at the Walter and Eliza Hall Institute for Medical Research, Melbourne, Victoria, Australia, for approximately 10 years. M1 cells were maintained by weekly passage in Dulbecco's modified Eagle's medium (DME) containing 10% (v/v) foetal bovine serum (FCS). Recombinant cytokines are generally available from commercial sources or were prepared by published methods. Recombinant murine LIF was produced in *Escherichia coli* and purified, as previously described [Gearing, 1989]. Purified human oncostatin M was purchased from Pepro Tech Inc (Rocky Hill, N.J., USA), and purified mouse IFN-γ was obtained from Genzyme Diagnostics (Cambridge, Mass., USA). Recombinant murine thrombopoietin was produced as a FLAG™-tagged fusion protein in CHO cells and then purified.

EXAMPLE 2

Agar Colony Assays

In order to assay the differentiation of M1 cells in response to cytokines, 300 cells were cultured in 35 mm Petri dishes containing 1 ml of DME supplemented with 20% (v/v) fƒtal calf serum (FCS), 0.3% (w/v) agar and 0.1 ml of serial dilutions of IL-6, LIF, OSM, IFN-γ, tpo or dexamethasone (Sigma Chemical Company, St Louis, Mo.). After 7 days culture at 37° C. in a fully humidified atmosphere, containing 10% (v/v) $CO_2$ in air, colonies of M1 cells were counted and classified as differentiated if they were composed of dispersed cells or had a corona of dispersed cells around a tightly packed centre.

EXAMPLE 3

Generation of Retroviral Library

A cDNA expression library was constructed from the factor-dependent haemopoietic cell line FDC-P1, essentially as described [Rayner, 1994]. Briefly, cDNA was cloned into the retroviral vector pRUFneo and then transfected into an amphotrophic packaging cell line (PA317). Transiently generated virus was harvested from the cell supernatant at 48 hr posttransfection, and used to infect Y2 ecotropic packaging cells, to generate a high titre virus-producing cell line.

EXAMPLE 4

Retroviral Infection of M1 Cells

Pools of $10^6$ infected Ψ2 cells were irradiated (3000 rad) and cocultivated with $10^6$ M1 cells in DME supplemented with 10% (v/v) FCS and 4 µg/ml Polybrene, for 2 days at 37° C. To select for IL-6-unresponsive clones, retrovirally-infected M1 cells were washed once in DME, and cultured at approximately $2 \times 10^4$ cells/ml in 1 ml agar cultures containing 400 µg/ml geneticin (GibcoBRL, Grand Island, N.Y.) and 100 ng/ml IL-6. The efficiency of infection of M1 cells was 1–2%, as estimated by agar plating the infected cells in the presence of geneticin only.

EXAMPLE 5

PCR

Genomic DNA from retrovirally-infected M1 cells was digested with Sac I and 1 µg of phenol/chloroform extracted DNA was then amplified by polymerase chain reaction (PCR). Primers used for amplification of cDNA inserts from the integrated retrovirus were GAG3 (5' CACGCCGC-CCACGTGAAGGC 3' [SEQ ID NO:1]), which corresponds to the vector gag sequence approximately 30 bp 5' of the multiple cloning site, and HSVTK (5' TTCGCCAATGA-CAAGACGCT 3' [SEQ ID NO:2]), which corresponds to the pMC1neo sequence approximately 200 bp 3' of the multiple cloning site. The PCR entailed an initial denaturation at 94° C. for 5 min, 35 cycles of denaturation at 94° C. for 1 min, annealing at 56° C. for 2 min, and extension at 72° C. for 3 min, followed by a final 10 min extension. PCR products were gel purified and then ligated into the pGEM-T plasmid (Promega, Madison, Wis.), and sequenced using an ABI PRISM Dye Terminator Cycle Sequencing Kit and a Model 373 Automated DNA Sequencer (Applied Biosystems Inc., Foster City, Calif.).

EXAMPLE 6

Cloning of cDNAs

Independent cDNA clones encoding mouse SOCS1 were isolated from a murine thymus cDNA library essentially as described (Hilton et al, 1994). The nucleotide and predicted amino acid sequences of mouse SOCS1 cDNA were compared to databases using the BLASTN and TFASTA algorithms (Pearson and Lipman, 1988; Pearson, 1990; Altshcul et al, 1990). Oligonucleotides were designed from the ESTs encoding human SOCS1 and mouse SOC-1 and SOCS3 and used to probe commercially available mouse thymus and spleen cDNA libraries. Sequencing was performed using an ABI automated sequencer according to the manufacturer's instructions.

EXAMPLE 7

Southern and Northern Blot Analyses and RT-PCR $^{32}$P-labelled probes were generated using a random decanucleotide labelling kit (Bresatec, Adelaide, South Australia) from a 600 bp Pst I fragment encoding neomycin phophotransfease from the plasmid pPGKneo, 1070 bp fragment of the SOCS1 gene obtained by digestion of the 1.4 kbp PCR product with Xho I, SOCS2, SOCS3, CIS and a 1.2 kbp fragment of the chicken glyceraldehyde 3-phosphate dehydrogenase gene [Dugaiczyk, 1983].

Genomic DNA was isolated from cells using a proteinase K-sodium dodecyl sulfate procedure essentially as described. Fifteen micrograms of DNA was digested with either BamH I or Sac I, fractionated on a 0.8% (w/v) agarose gel, transferred to GeneScreenPlus membrane (Du Pont NEN, Boston, Mass.), prehybridised, hybridised with random-primed $^{32}$P-labelled DNA fragments and washed essentially as described [Sambrook, 1989].

Total RNA was isolated from cells and tissues using Trizol Reagent, as recommended by the manufacturer (GibcoBRL, Grand Island, N.Y.). When required polyA+ mRNA was purified essentially as described [Alexander, 1995]. Northern blots were prehybridised, hybridized with random-primed 32P-labelled DNA fragments and washed as described [Alexander, 1995].

To assess the induction of SOCS genes by IL-6, mice (C57BL6) were injected intravenously with 5 µg IL-6 followed by harvest of the liver at the indicated timepoints after injection. M1 cells were cultured in the presence of 20 ng/ml IL-6 and harvested at the indicated times. For RT-PCR analysis, bone marrow cells were harvested as described (Metcalf et al, 1995) and stimulated for 1 hr at 37° C. with 100 ng/ml of a range of cytokines. RT-PCR was performed on total RNA as described (Metcalf et al, 1995). PCR products were resolved on an agarose gel and Southern blots were hybridised with probes specific for each SOCS family member. Expression of β-actin was assessed to ensure uniformity of amplification.

EXAMPLE 8

DNA Constructs and Transfection

A cDNA encoding epitope-tagged SOCS1 was generated by subcloning the entire SOCS1 coding region into the pEF-BOS expression vector [Mizushima, 1990], engineered to encode an inframe FLAG epitope downstream of an initiation methionine (pF-SOCS1). Using electroporation as described previously [Hilton, 1994], M1 cells expressing the thrombopoietin receptor (M1.mpl) were transfected with the 20 µg of Aat II-digested pF-SOCS1 expression plasmid and 2 µg of a Sca I-digested plasmid in which transcription of a cDNA encoding puromycin N-acetyl transferase was driven from the mouse phosphoglycerokinase promoter (pPGKPuropA). After 48 hours in culture, transfected cells were selected with 20 µg/ml puromycin (Sigma Chemical Company, St. Louis, Mo.), and screened for expression of SOCS1 by Western blotting, using the M2 anti-FLAG monoclonal antibody according to the manafacturer's instructions (Eastman Kodak, Rochester, N.Y.). In other experiments M1 cells were transfected with only the pF-SOCS1 plasmid or a control and selected by their ability to grow in agar in the presence of 100 ng/ml of IL-6.

EXAMPLE 9

Immunoprecipitation and Western Blotting

Prior to either immunoprecipitation or Western blotting, $10^7$ M1 cells or their derivatives were washed twice, resuspended in 1 ml of DME, and incubated at 37° C. for 30 min. The cells were then stimulated for 4 min at 37° C. with either saline or 100 ng/ml IL-6, after which sodium vanadate (Sigma Chemical Co., St Louis, Mo.) was added to a concentration of 1 mM. Cells were placed on ice, washed once with saline containing 1 mM sodium vanadate, and then solubilised for 5 min on ice with 300 µl 1% (v/v) Triton X-100, 150 mM NaCl, 2 mM EDTA, 50 mM Tris-HCl pH 7.4, containing Complete protease inhibitors (Boehringer Mannheim, Mannheim, Germany) and 1 mM sodium vanadate. Lysates were cleared by centrifugation and quantitated using a Coomassie Protein Assay Reagent (Pierce, Rockford, Ill.).

For immunoprecipitations, equal concentrations of protein extracts (1–2 mg) were incubated for 1 hr or overnight at 4° C. with either 4 µg of anti-gp130 antibody (M20; Santa Cruz Biotechnology Inc., Santa Cruz, Calif.) or 4 µg of anti-phosphotyrosine antibody (4G10; Upstate Biotechnology Inc., Lake Placid, N.Y.), and 15 µl packed volume of Protein G Sepharose (Pharmacia, Uppsala, Sweden) [Hilton et al, 1996]. Immunoprecipitates were washed twice in 1% (v/v) NP40, 150 mM NaCl, 50 mM Tris-HCl pH 8.0, containing Complete protease inhibitors (Boehringer Mannheim, Mannheim, Germany and 1 mM sodium vanadate. The samples were heated for 5 min at 95° C. in SDS sample buffer (625 mM Tris-HCl pH 6.8, 0.05% (w/v) SDS, 0.1% (v/v) glycerol, bromophenol blue, 0.125% (v/v) 2-mercaptoethanol), fractionated by SDS-PAGE and immunoblotted as described above.

For Western blotting, 10 µg of protein from a cellular extract or material from an immunoprecipitation reaction was loaded onto 4–15% Ready gels (Bio-Rad Laboratories, Hercules, Calif.), and resolved by sodium dodecyl sulfate polyacrylamide gel electrophoresis (SDS-PAGE). Proteins were transferred to PVDF membrane (Micron Separations Inc., Westborough, Mass.) for 1 hr at 100 V. The membranes were probed with the following primary antibodies; anti-tyrosine phosphorylated STAT3 (1:1000 dilution; New England Biolabs, Beverly, Mass.); anti-STAT3 (C-20; 1:100 dilution; Santa Cruz Biotechnology Inc., Santa Cruz, Calif.); anti-gp130 (M20, 1:100 dilution; Santa Cruz Biotechnology Inc., Santa Cruz, Calif.); anti-phosphotyrosine (horseradish peroxidase-conjugated RC20, 1:5000 dilution; Transduction Laboratories, Lexington, Ky.); anti-tyrosine phosphorylated MAP kinase and anti-MAP kinase antibodies (1:1000 dilution; New England Biolabs, Beverly, Mass.). Blots were visualised using peroxidase-conjugated secondary antibodies and Enhanced Chemiluminescence (ECL) reagents according to the manufacturer's instructions (Pierce, Rockford, Ill.).

EXAMPLE 10

Electrophoretic Mobility Shift Assays

Assays were performed as described [Novak, 1995], using the high affinity SIF (c-sis-inducible factor) binding site m67 [Wakao, 1994]. Protein extracts were prepared from M1 cells incubated for 4–10 min at 37° C. in 10 ml serum-free DME containing either saline, 100 ng/ml IL-6 or 100 ng/ml IFN-γ. The binding reactions contained 4–6 µg protein (constant within a given experiment), 5 ng $^{32}$P-labelled m67 oligonucleotide, and 800 ng sonicated salmon sperm DNA. For certain experiments, protein samples were preincubated with an excess of unlabelled m67 oligonucleotide, or antibodies specific for either STAT1 (Transduction Laboratories, Lexington, Ky.) or STAT3 (Santa Cruz Biotechnology Inc., Santa Cruz, Calif.), as described [Novak, 1995].

Western blots were performed using anti-tyrosine phosphorylated STAT3 or anti-STAT3 (New England Biolabs, Beverly, Mass.) or anti-gp130 (Santa Cruz Biotechnology Inc.) as described (Nicola et al, 1996). EMSA were performed using the m67 oligonucleotide probe, as described (Novak et al, 1995).

EXAMPLE 11

Expression Cloning of a Novel Suppressor of Cytokine Signal Transduction

Figure 1:
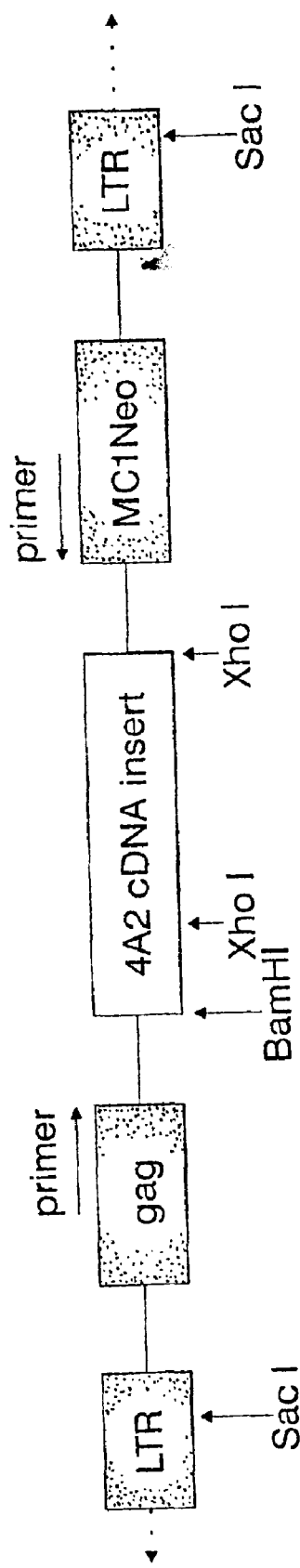
FIG. 1 is a diagrammatic representation showing generation of an IL-6-unresponsive M1 clone by retroviral infection. The RUFneo retrovirus, showing the position of landmark restriction endonuclease cleavage sites, the 4A2 cDNA insert and the position of PCR primer sequences.

In order to identify cDNAs capable of suppressing cytokine signal transduction, an expression cloning approach was adopted. This strategy centred on M1 cells, a monocytic leukaemia cell line that differentiates into mature macrophages and ceases proliferation in response to the cytokines IL-6, LIF, OSM and IFN-γ, and the steroid dexamethasone. Parental M1 cells were infected with the RUFneo retrovirus, into which cDNAs from the factor-dependent haemopoietic cell line FDC-P1 had been cloned. In this retrovirus, transcription of both the neomycin resistance gene and the cloned cDNA was driven off the powerful constitutive promoter present in the retroviral LTR (FIG. 1). When cultured in semi-slid agar, parental M1 cells form large tightly packed colonies. Upon stimulation with IL-6, M1 cells undergo rapid differentiation, resulting in the formation in agar of only single macrophages or small dispersed clusters of cells. Retrovirally-infected M1 cells that were unresponsive to IL-6 were selected in semi-solid agar culture by their ability to form large, tightly packed colonies in the presence of IL-6 and geneticin. A single stable IL-6 unresponsive clone, 4A2, was obtained after examining $10^4$ infected cells.

Figure 2A:
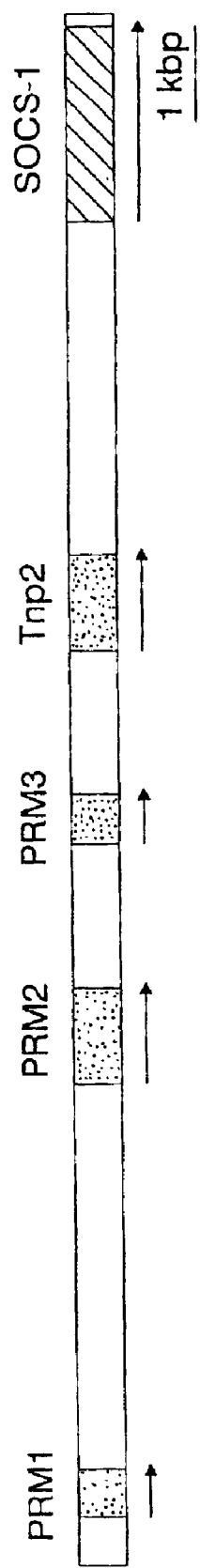

A fragment of the neomycin phosphotransferase (neo) gene was used to probe a Southern blot of genomic DNA from clone 4A2 and this revealed that the cell line was infected with a single retrovirus containing a cDNA approximately 1.4 kbp in length (FIG. 2). PCR amplification using primers from the retroviral vector which flanked the cDNA cloning site enabled recovery of a 1.4 kbp cDNA insert, which we have named suppressor of cytokine signalling-1, or SOCS1. This PCR product was used to probe a similar Southern blot of 4A2 genomic DNA and hybridised to two fragments, one which corresponded to the endogenous SOCS1 gene and the other, which matched the size of the band seen using the neo probe, corresponded to the SOCS1 cDNA cloned into the integrated retrovirus. The latter was not observed in an M1 cell clone infected with a retrovirus containing an irrelevant cDNA. Similarly, Northern blot analysis revealed that SOCS1 mRNA was abundant in the cell line 4A2, but not in the control infected M1 cell clone.

EXAMPLE 12

SOCS1, SOCS2, SOCS3 and CIS Define a New Family of SH2-Containing Proteins

The SOCS1 PCR product was used as a probe to isolate homologous cDNAs from a mouse thymus cDNA library. The sequence of the cDNAs proved to be identical to the PCR product, suggesting that constitutive or over expression, rather than mutation, of the SOCS1 protein was sufficient for generating an IL-6-unresponsive phenotype. Comparison of the sequence of SOCS1 cDNA with nucleotide sequence databases revealed that it was present on mouse and rat genomic DNA clones containing the protamine gene cluster found on mouse chromosome 16. Closer inspection revealed that the 1.4 kb SOCS1 sequence was not homologous to any of the protamine genes, but rather represented a previously unidentified open reading frame located at the extreme 3' end of these clones (FIG. 2). There were no regions of discontinuity between the sequences of the SOCS1 cDNA and genomic locus, suggesting that SOCS1 is encoded by a single exon. In addition to the genomic clone containing the protamine genes, a series of murine and human expressed sequenced tags (ESTs) also revealed large blocks of nucleotide sequence identity to mouse SOCS1. The sequence information provided by the human ESTs allowed the rapid cloning of cDNAs encoding human SOCS1.

The mouse and rat SOCS1 gene encodes a 212 amino acid protein whereas the human SOCS1 gene encodes a 211 amino acid protein. Mouse, rat and human SOCS1 proteins share 95–99% amino acid identity (FIG. 3). A search of translated nucleic acid databases with the predicted amino acid sequence of SOCS1 showed that it was most related to a recently cloned cytokine-inducible immediate early gene product, CIS, and two classes of ESTs. Full length cDNAs from the two classes of ESTs were isolated and found to encode proteins of similar length and overall structure to SOCS1 and CIS. These clones were given the names SOCS2 and SOCS3. Each of the four proteins contains a central SH2 domain and a C-terminal region termed the SOCS motif. The SOCS1 proteins exhibit an extremely high level of amino acid sequence similarity (95–99% identity) amongst different species. However, the forms of the SOCS1, SOCS2, SOCS3 and CIS from the same animal, while clearly defining a new family of SH2-containing proteins, exhibited a lower amino acid identity. SOCS2 and CIS exhibit approximately 38% amino acid identity, while the remaining members of the family share approximately 25% amino acid identity (FIG. 3). The coding region of the genes for SOCS1 and SOC3 appear to contain no introns while the coding region of the genes for SOCS2 and CIS contain one and two introns, respectively.

The Genbank Accession Numbers for the sequences referred to herein are mouse SOCS1 cDNA (U88325), human SOCS1 cDNA (U88326), mouse SOCS2 cDNA (U88327), mouse SOCS3 cDNA (U88328).

EXAMPLE 13

Constitutive Expression of SOCS1 Suppresses the Action of a Range of Cytokines To formally establish that the phenotype of the 4A2 cell line was directly related to expression of SOCS1, and not to unrelated genetic changes which may have occurred independently in these cells, a cDNA encoding an epitope-tagged version of SOCS1 under the control of the EF1α promoter was transfected into parental M1 cells, and M1 cells expressing the receptor for thrombopoietin, c-mpl (M1.mpl). Transfection of the SOCS1 expression vector into both cell lines resulted in an increase in the frequency of IL-6 unresponsive M1 cells.

Multiple independent clones of M1 cells expression SOCS1, as detected by Western blot, displayed a cytokine-unresponsive phenotype that was indistinguishable from 4A2. Further, if transfectants were not maintained in puromycin, expression of SOCS1 was lost over time and cells regained their cytokine responsiveness. In the absence of cytokine, colonies derived from 4A2 and other SOCS1 expressing clones characteristically grew to a smaller size than colones formed by control M1 cells.

The effect of constitutive SOCS1 expression on the response of M1 cells to a range of cytokines was investigated using the 4A2 cell line and a clone of M1.mpl cells expressing SOCS1 (M1.mpl.SOCS1). Unlike parental M1 cells and M1.mpl cells, the two cell lines expressing SOCS1 continued to proliferate and failed to form differentiated colonies in response to either IL-6, LIF, OSM, IFN-γ or, in the case of the M1.mpl.SOCS1 cell line, thrombopoietin. For both cell lines, however, a normal response to dexamethasone was observed, suggesting that SOCS1 specifically affected cytokine signal transduction rather than differentiation per se. Consistent with these data, while parental M1 cells and M1.mpl cells became large and vacuolated in response to IL-6, 4A2 and M1.mpl.SOCS1 cells showed no evidence of morphological differentiation in response to IL-6 or other cytokines.

EXAMPLE 14

SOCS1 Inhibits a Range of IL-6 Signal Transduction Processes, Including STAT3 Phosphorylation and Activation Phosphorylation of the cell surface receptor component gp130, the cytoplasmic tyrosine kinase JAK1 and the transcription factor STAT3 is thought to play a central role in IL-6 signal transduction. These events were compared in the parental M1 and M1.mpl cell lines and their SOCS1-expressing counterparts. As expected, gp130 was phosphorylated rapidly in response to IL-6 in both parental lines, however, this was reduced five- to ten-fold in the cell lines expressing SOCS1. Likewise, STAT3 phosphorylation was also reduced by approximately ten-fold in response to IL-6 in those cell lines expressing SOCS1. Consistent with a reduction in STAT3 phosphorylation, activation of specific STAT DNA binding complexes, as determined by electrophoretic mobility shift assay, was also reduced. Notably, there was a reduction in the formation of SIF-A (containing STAT3), SIF-B (STAT1/STAT3 heterodimer) and SIF-C (containing STAT1), the three STAT complexes induced in M1 cells stimulated with IL-6. Similarly, constitutive expression of SOCS1 also inhibited IFN-γ-stimulated formation of p91 homodimers. STAT phosphorylation and activation were not the only cytoplasmic processes to be effected by SOCS1 expression, as the phosphorylation of other proteins, including shc and MAP kinase, was reduced to a similar extent.

EXAMPLE 15

Transcription of the SOCS1 Gene is Stimulated by IL-6 In vitro and In vivo

Although SOCS1 can inhibit cytokine signal transduction when constitutively expressed in M1 cells, this does not necessarily indicate that SOCS1 normally functions to negatively regulate an IL-6 response. In order to investigate this possibility the inventors determined whether transcription of the SOCS1 gene is regulated in the response of M1 cells to IL-6 and, because of the critical role IL-6 plays in regulating the acute phase response to injury and infection, the response of the liver to intravenous injection of 5 mg IL-6. In the absence of IL-6, SOCS1 mRNA was undetectable in either M1 cells or in the liver. However, for both cell types, a 1.4 kb SOCS1 transcript was induced within 20 to 40 minutes by IL-6. For M1 cells, where the IL-6 was present throughout the experiment, the level of SOCS1 mRNA remained elevated. In contrast, IL-6 was administered in vivo by a single intravenous injection and was rapidly cleared from the circulation, resulting in a pulse of IL-6 stimulation to the liver. Consistent with this, transient expression of SOCS1 mRNA was detectable in the liver, peaking approximately 40 minutes after injection and declining to basal levels within 4 hours.

EXAMPLE 16

Regulation of SOCS Genes

Since CIS was cloned as a cytokine-inducible immediate early gene the inventors examined whether SOCS1, SOCS2 and SOCS3 were similarly regulated. The basal pattern of expression of the four SOCS genes was examined by Northern blot analysis of mRNA from a variety of tissues from male and female C57B1/6 mice. Constitutive expression of SOCS1 was observed in the thymus and to a lesser extend in the spleen and the lung. SOCS2 expression was restricted primarily to the testis and in some animals the liver and lung; for SOCS3 a low level of expression was observed in the lung, spleen and thymus, while CIS expression was more widespread, including the testis, heart, lung, kidney and, in some animals, the liver.

The inventors sought to determine whether expression of the four SOCS genes was regulated by IL-6. Northern blots of mRNA prepared from the livers of untreated and IL-6-injected mice, or from unstimulated and IL-6-stimulated M1 cells, were hybridised with labelled fragments of SOCS1, SOCS2, SOCS3 and CIS cDNAs. Expression of all four SOCS genes was increased in the liver following IL-6 injection, however the kinetics of induction appeared to differ. Expression of SOCS1 and SOCS3 was transient in the liver, with mRNA detectable after 20 minutes of IL-6 injection and declining to basal levels within 4 hours for SOCS and 8 hours for SOCS3. Induction of SOCS2 and CIS mRNA in the liver followed similar initial kinetics to that of SOCS1, but was maintained at an elevated level for at least 24 hours. A similar induction of SOCS gene mRNA was observed in other organs, notably the lung and the spleen. In contrast, in M1 cells, while SOCS1 and CIS mRNA were induced by IL-6, no induction of either SOCS2 or SOCS3 expression was detected. This result highlights cell type-specific differences in the expression of the genes of SOCS family members in response to the same cytokine.

In order to examine the spectrum of cytokines that was capable of inducing transcription of the various members of the SOCS gene family, bone marrow cells were stimulated for an hour with a range of cytokines, after which mRNA was extracted and cDNA was synthesised. PCR was then used to assess the expression of SOCS1, SOCS2, SOCS3 and CIS. In the absence of stimulation, little or no expression of any of the SOCS genes was detectable in bone marrow by PCR. Stimulation of bone marrow cells with a broad array of cytokines appeared capable of up regulating mRNA for one or more members of the SOCS family. IFNγ, for example, induced expression of all four SOCS genes, while erythropoietin, granulocyte colony-stimulating factor, granulocyte-macrophage colony stimulating factor and interleukin-3 induced expression of SOCS2, SOCS3 and CIS. Interestingly, tumor necrosis factor alpha, macrophage colony-stimulating factor and interleukin-1, which act through receptors that do not fall into the type I cytokine receptor class also appeared capable of inducing expression of SOCS3 and CIS, suggesting that SOCS proteins may play a broader role in regulating signal transduction.

As constitutive expression of SOCS1 inhibited the response of M1 cells to a range of cytokines, the inventors examined whether phosphorylation of the cell surface receptor component gp130 and the transcription factor STAT3, which are though to play a central role in IL-6 signal transduction, were affected. These events were compared in the parental M1 and M1.mpl cell lines and their SOCS1-expressing counterparts. As expected, gp130 was phyosphorylated rapidly in response to IL-6 in both parental lines, however, this was reduced in the cell lines expressing SOCS1. Likewise, STAT3 phosphorylation was also reduced in response to IL-6 in those cell lines expressing SOCS1. Consistent with a reduction in STAT3 phosphorylation, activation of specific STAT/DNA binding complexes, as determined by electrophoretic mobility shift assay, was also reduced. Notably, there was a failure to form SIF-A (containing STAT3) and SIF-B(STAT1/STAT3 heterodimer), the major STAT complexes induced in M1 cells stimulated with IL-6. Similarly, constitutive expression of SOCS1 also inhibited IFNγ-stimulating formation of SIF-C (STAT1 homodimer, FIG. 12B). These experiments are consistent with the proposal that SOCS1 inhibits signal transduction upstream of receptor and STAT phosphorylation, potentially at the level of the JAK kinases.

The ability of SOCS1 to inhibit signal transduction and ultimately the biological response to cytokines suggest that, like the SH2-containing phosphatase SHP-1 [Ihle et al, 1994; Yi et al, 1993], the SOCS proteins may play a central role in controlling the intensity and/or duration of a cell's response to a diverse range of extracellular stimuli by suppressing the signal transduction process. The evidence provided here indicates that the SOCS family acts in a classical negative feedback loop for cytokine signal transduction. Like other genes such as OSM, expression of genes encoding the SOCS proteins is induced by cytokines through the activation of STATs. Once expressed, it is proposed that the SOCS proteins inhibit the activity of JAKs and so reduce the phosphorylation of receptors and STATs, thereby suppressing signal transduction and any ensuing biological response. Importantly, inhibition of STAT activation will, over time, lead to a reduction in SOCS gene expression, allowing cells to regain responsiveness to cytokines.

EXAMPLE 17

Database Searches

The NCBI genetic sequence database (Genbank), which encompasses the major database of expressed sequence tags (ESTs) and TIGR database of human expressed sequence tags, were searched for sequences with similarity to a concensus SOCS box sequence using the TFASTA and MOTIF/PATTERN algorithms [Pearson, 1990; Cockwell and Giles, 1989]. Using the software package SRS [Etzold et al, 1996], ESTs that exhibited similarity to the SOCS box (and their partners derived from sequencing the other end of cDNAs) were retrieved and assembled into contigs using Autoassembler (Applied Biosystems, Foster City, Calif.). Consensus nucleotide sequences derived from overlapping ESTs were then used to search the various databases using BLASTN [Altschul et al, 1990]. Again, positive ESTs were retrieved and added to the contig. This process was repeated until no additional ESTs could be recovered. Final consensus nucleotide sequences were then translated using Sequence Navigator (Applied Biosystems, Foster City, Calif.).

The ESTs encoding the new SOCS proteins are as follows: human SOCS4 (EST81149, EST180909, EST182619, ya99H09, ye70co4, yh53c09, yh77g11, yh87h05, yi45h07, yj04c06, yq12h06, yq56a06, yq60e02, yq92g03, yq97h06, yr90f01, yt69c03, yv30a08, yv55f07, yv57h09, yv87h02, yv98e11, yw68d10, yw82a03, yx08a07, yx72h06, yx76b09, yy37h08, yy66b02, za81f08, zb18f07, zc06e08, zd14g06, zd51h12, zd52b09, ze25g11, ze69f02, zf54f03, zh96e07, zv66h12, zs83a08 and zs83g98). mouse SOCS-4 (mc65f04, mf42e06, mp10c10, mr81g09, and mt19h12). human SOCS-5 (EST15B103, EST15B105, EST27530 and zf50f01). mouse SOCS-5 (mc55a01, mh98f09, my26h12 and ve24e06). human SOCS-6 (yf61e08, yf93a09, yg05f12, yg41f04, yg45c02, yh11f10, yh13b05, zc35a12, ze02h08, zl09z03, zl69e10, zn39d08, and zo39e06). mouse SOCS-6 (mc04c05, md48a03, mf31d03, mh26b07, mh78e11, mh88h09, mh94h07, mi27h04 and mj29c05, mp66g04, mw75g03, va53b05, vb34h02, vc55d07, vc59e05, vc67d03, vc68d10, vc97h01, vc99c08, vd07h03, vd08c01, vd09b12, vd19b02, vd29a04 and vd46d06). human SOCS-7 (STS WI30171, EST00939, EST12913, yc29b05, yp49f10, zt10f03 and zx27g 04). mouse-SOCS-7 (mj39a01 and vi52h07). mouse SOCS-8 (mj6e09 and vj27a029). human SOCS-9 (CSRL-82f2-u, EST114054, yy06b07, yy06g06, zr40c09, zr72h01, yx92c08, yx93b08 and hfe0662). mouse SOCS-9 (me65d05). human SOCS-10 (aa48h10, zp35h01, zp97h12, zp08h01, zr34g05, EST73000 and HSDHE1005). mouse SOCS-10 (mb14d12, mb40f06, mg89b11, mq89e12, mp03g12 and vh53c11). human SOCS-11 (zt24h06 and zr43b02). human SOCS-13 (EST59161). mouse SOCS-13 (ma39a09, me60c05, mi78g05, mk10c11, mo48g12, mp94a01, vb57c07 and vh07c11). human SOCS-14 (mi75e03, vd29h11 and vd53g07).

EXAMPLE 18 cDNA Cloning

Based on the concensus sequences derived from overlapping ESTs, oligonucleotides were designed that were specific to various members of the SOCS family. As described above, oligonucleotides were labelled and used to screen commercially available genomic and cDNA libraries cloned with λ bacteriophage. Genomic and/or cDNA clones covering the entire coding region of mouse SOCS4, mouse SOCS5 and mouse SOCS6 were isolated. The entire gene for SOCS15 is on the human 12p13 BAC (Genbank Accession Number HSU47924) and the mouse chromosome 6 BAC (Genbank Accession Number AC002393). Partial cDNAs for mouse SOCS7, SOCS9, SOCS10, SOCS11, SOCS12, SOCS13 and SOCS14 were also isolated.

EXAMPLE 19

Northern Blots and rtPCR

Northern blots were performed as described above. The sources of hybridisation probes were as follows; (i) the entire coding region of the mouse SOCS1 cDNA, (ii) a 1059 bp PCR product derived from coding region of SOCS5 upstream of the SH2 domain, (iii) the entire coding region of the mouse SOCS6 cDNA, (iv) a 790 bp PCR product derived from the coding region of a partial SOCS7 cDNA and (v) a 1200 bp Pst I fragment of the chicken glyceraldehyde 3-phosphate dehydrogenase (GAPDH) cDNA.

EXAMPLE 20

Additional Members of SOCS Family

SOCS1, SOCS2 and SOCS3 are members of the SOCS protein family identified in Examples 1–16. Each contains a central SH2 domain and a conserved motif at the C-terminus, named the SOCS box. In order to isolate further members of this protein family, various DNA databases were searched with the amino acid sequence corresponding to conserved residues of the SOCS box. This search revealed the presence of human and mouse ESTs encoding twelve further members of the SOCS protein family (FIG. 4). Using this sequence information cDNAs encoding SOCS4, SOCS5, SOCS6, SOCS7, SOCS9, SOCS10, SOCS11, SOCS12, SOCS13, SOCS14 and SOCS15 have been isolated. Further analysis of contigs derived from ESTs and cDNAs revealed that the SOCS proteins could be placed into three groups according to their predicted structure N-terminal of the SOCS box. The three groups are those with (i) SH2 domains, (ii) WD-40 repeats and (iii) ankyrin repeats.

EXAMPLE 21

SOCS Protein with SH2 Domains

Eight SOCS proteins with SH2 domains have been identified. These include SOCS1, SOCS2 and SOCS3, SOCS5, SOCS9, SOCS11 and SOCS14 (FIG. 4). Full length cDNAs were isolated for mouse SOCS5 and SOCS14 and partial clones encoding mouse SOCS9 and SOCS14. Analysis of primary amino acid sequence and genomic structure suggest that pairs of these proteins (SOCS1 and SOCS3, SOCS2 and CIS, SOCS5 and SOCS14 and SOCS9 and SOCS11) are most closely related (FIG. 4). Indeed, the SH2 domains of SOCS5 and SOCS14 are almost identical (FIG. 4B), and unlike CIS, SOCS1, SOCS2 and SOCS3, SOCS5 and SOCS14 have an extensive, though less well conserved, N-terminal region preceding their SH2 domains (FIG. 4A).

EXAMPLE 22

SOCS Proteins with WD-40 Repeats

Four SOCS proteins with WD-40 repeats were identified. As with the SOCS proteins with SH2 domains, pairs of these proteins appeared to be closely related. Full length cDNAs of mouse SOCS4 and SOCS6 were isolated and shown to encode proteins containing eight WD-40 repeats N-terminal of the SOCS box (FIG. 4) and SOCS4 and SOCS6 share 65% amino acid similarity. SOCS15 was recognized as an open reading frame upon sequencing BACs from human chromosome 12p13 and the syntenic region of mouse chromosome 6 [Ansari-Lari et al, 1997]. In the human, chimp and mouse, SOCS15 is encoded by a gene with two coding exons that lies within a few hundred base pairs of the 3' end of the triose phosphate isomerase (TPI) gene, but which is encoded on the opposite strand to TPI (9). In addition to a C-terminal SOCS box, the SOCS15 protein contains four WD-40 repeats. Interestingly, within the EST databases, there is a sequence of a nematode, an insect and a fish relative of SOCS15. SOCS15 appears most closely related to SOCS13.

EXAMPLE 23

SOCS Proteins with Ankyrin Repeats

Three SOCS proteins with ankyrin repeats were identified. Analysis of partial cDNAs of mouse SOCS7, SOCS10 and SOCS12 demonstrated the presence of multiple ankyrin repeats.

EXAMPLE 24

Expression Pattern of SOCS Proteins

The expression of mRNA from representative members of each class of SOCS proteins—SOCS1 and SOCS5 from the SH2 domain group, SOCS6 from the WD-40 repeat group and SOCS7 from the ankyrin repeat group was examined. As shown above, SOCS1 mRNA is found in abundance in the thymus and at lower levels in other adult tissues.

Since transcription of the SOCS1 gene is induced by cytokines, the inventors sought to determine whether levels of SOCS5, SOCS6 and SOCS7 mRNA increased upon cytokine stimulation. In the livers of mice injected with IL-6, SOCS1 mRNA is detectable after 20 min and decreases to background levels within 2 hours. In contrast, the kinetics of SOCS5 mRNA expression are quite different, being only detectable 12 to 24 hours after IL-6 injection. SOCS6 mRNA appears to be expressed constitutively while SOCS7 mRNA was not detected in the liver either before injection of IL-6 or at any time after injection.

Expression of these genes was also examined after cytokine stimulation of the factor-dependent cell line FDCP-1 engineered to express bcl-w. Again, SOCS6 mRNA was expressed constitutively.

EXAMPLE 25

SOCS4

Mouse and human SOCS4 were recognized through searching EST databases using the SOCS box consensus (FIG. 13). Those ESTs derived from mouse and human SOCS4 cDNAs are tabulated below (Tables 4.1 and 4.2). Using sequence information derived from mouse ESTs several oligonucleotides were designed and used to screen, in the conventional manner, a mouse thymus cDNA library cloned into λ-bacteriophage. Two cDNAs encoding mouse SOCS4 were isolated and sequenced in their entirety (FIG. 5) and shown to overlap the mouse ESTs identified in the database (Table 4.1). These cDNAs include a region of 5' untranslated region, the entire mouse SOCS4 coding region and a region of 3' untranslated region (FIG. 7). Analysis of the sequence confirms that the SOCS4 cDNA encodes a SOCS Box at its C-terminus and a series of 8 WD-40 repeats before the SOCS Box (FIGS. 6 and 7). The relationship of the two sequence contigs of human SOCS4 (h4.1 and h4.2) to the experimentally determined mouse SOCS4 cDNA sequence is shown in FIG. 7. The nucleotide sequence of the two human contigs is listed in FIG. 8.

SEQ ID NOS:13 and 14 represent the nucleotide sequence of murine SOCS4 and the corresponding amino acid sequence. SEQ ID NOS:15 and 16 are SOCS4 cDNA human contigs h4.1 and h4.2, respectively.

EXAMPLE 26

SOCS5

Figure 8:
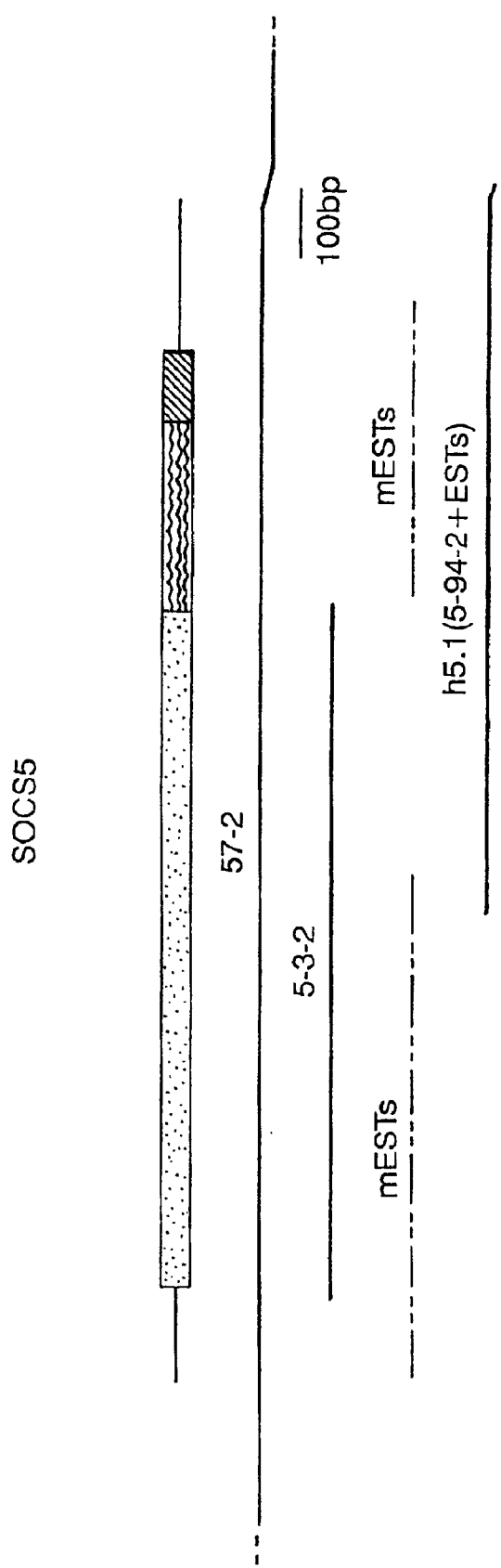
FIG. 8 is a diagrammatic representation showing the relationship of mouse SOCS5 genomic (57-2) and cDNA (5-3-2) clones to contigs derived from analysis of mouse ESTs (Table 5.1) and human cDNA clone (5-94-2) and ESTs (Table 5.2). The nucleotide sequence of the mouse SOCS5 contig is shown in FIG. 9A, with the sequence of human SOCS5 contig (h5.1) being shown in FIG. 10. The deduced amino acid sequence of mouse SOCS5 is shown in FIG. 9B. The structure of the protein is shown schematically, with the SH2 domain indicated by the open white wave box and the SOCS box by the open hatched box. The putative 5' and 3' translated regions are shown by the thin solid line.

Mouse and human SOCS5 were recognized through searching EST databases using the SOCS box consensus (FIG. 4). Those ESTs derived from mouse and human SOCS5 cDNAs are tabulated below (Tables 5.1 and 5.2). Using sequence information derived from mouse and human ESTs, several oligonucleotides were designed and used to screen, in the conventional manner, a mouse thymus cDNA library, a mouse genomic DNA library and a human thymus cDNA library cloned into λ-bacteriophage. A single genomic clone (57-2) and (5-3-2) cDNA clone encoding mouse SOCS5 were isolated and sequenced in their entirety and shown to overlap with the mouse ESTs identified in the database (FIGS. 8 and 9A). The entire coding region, in addition to a region of 5' and 3' untranslated regions of mouse SOCS5 appears to be encoded on a single exon (FIG. 8). Analysis of the sequence (FIG. 9) confirms that SOCS5 genomic and cDNA clones encode a protein with a SOCS box at its C-terminus in addition to an SH2 domain (FIGS. 8 and 9B). The relationship of the human SOCS5 contig (h5.1; FIG. 10) derived from analysis of cDNA clone 5-94-2 and the human SOCS5 ESTs (Table 5.2) to the mouse SOCS5 DNA sequence is shown in FIG. 8. The nucleotide sequence and corresponding amino acid sequence of murine SOCS5 are shown in SEQ ID NOS:17 and 18, respectively. The human SOCS5 nucleotide sequence is shown in SEQ ID NO:19.

EXAMPLE 27

SOCS6

Figure 11:
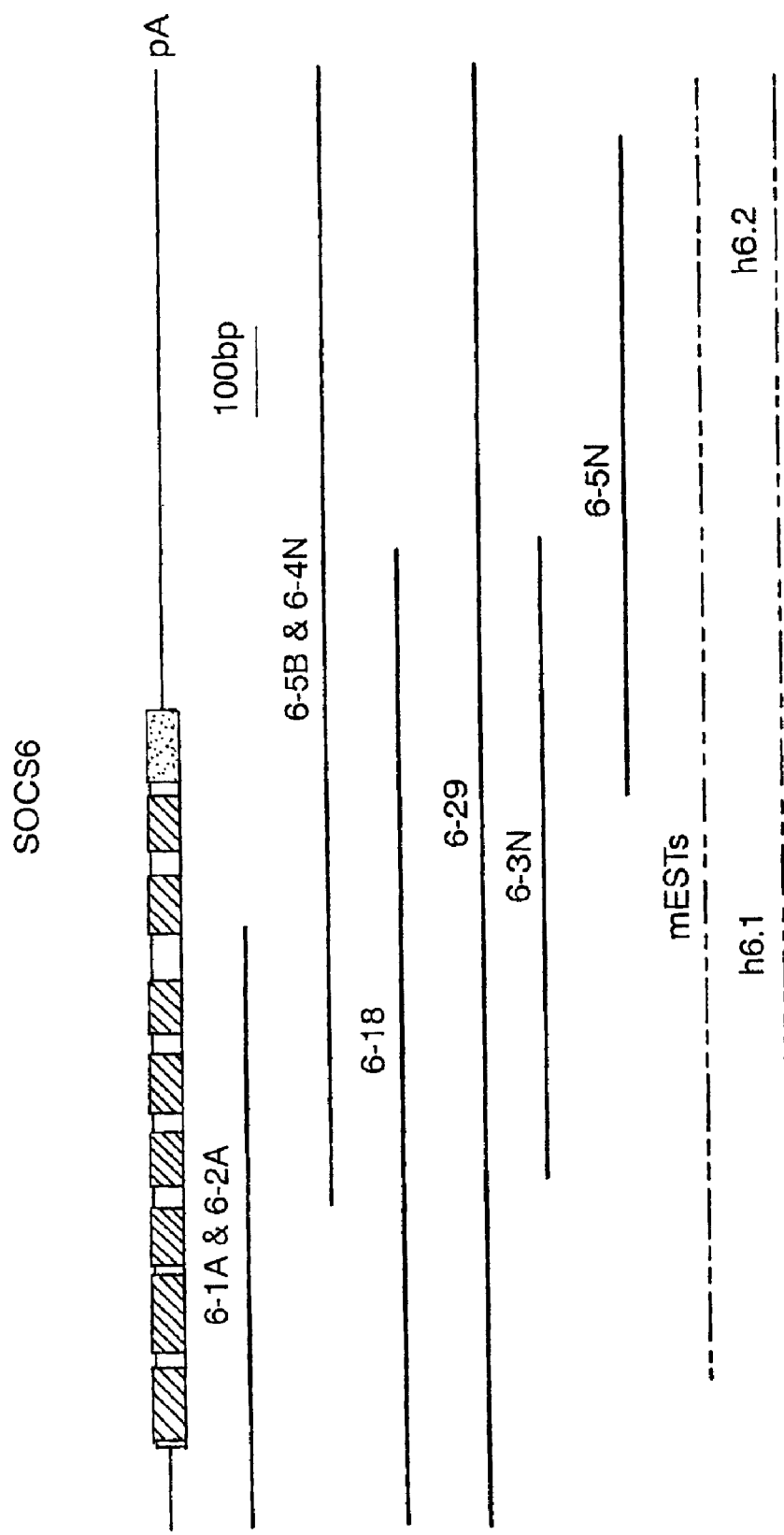
FIG. 11 is a diagrammatic representation showing the relationship of mouse SOCS6 cDNA clones (6-1A, 6-2A, 6-5B, 6-4N, 6-18, 6-29, 6-3N and 6-5N) to contigs derived from analysis of mouse ESTs (Table 6.1) and human ESTs (Table 6.2). The nucleotide sequence of the mouse SOCS-6 contig is shown in FIG. 12A, with the sequence of human SOCS2 contigs (h6.1 and h6.2) being shown in FIG. 13. The deduced amino acid sequence of mouse SOCS2 is shown in FIG. 12B. The structure of the protein is shown schematically, while the WD-40 repeats indicated by the open hatched boxes and the SOCS box by the open dotted box. The putative 5' and 3' untranslated regions are shown by the thin solid line.

Mouse and human SOCS6 were recognized through searching EST databases using the SOCS box consensus (FIG. 4). Those ESTs derived from mouse and human SOCS6 cDNAs are tabulated below (Tables 6.1 and 6.2). Using sequence information derived from mouse ESTs, several oligonucleotides were designed and use to screen, in the conventional manner, a mouse thymus cDNA library. Eight cDNA clones (6-1A, 6-2A, 6-5B, 6-4N, 6-18, 6-29, 6-3N, 6-5N) cDNA clone encoding mouse SOCS6 were isolated and sequenced in their entirety and shown to overlap with the mouse ESTs identified in the database (FIGS. 11 and 12A). Analysis of the sequence (FIG. 12) confirms that the mouse SOCS6 cDNA clones encode a protein with a SOCS box at its C-terminus in addition to a eight WD-40 repeats (FIGS. 11 and 12B). The relationship of the human SOCS-6 contigs (h6.1 and h6.2; FIG. 4) derived from analysis of human SOCS6 ESTs (Table 6.2) to the mouse SOCS6 DNA sequence is shown in FIG. 11. The nucleotide and corresponding amino acid sequences of murine SOCS6 are shown in SEQ ID NOS:20 and 21,

EXAMPLE 28

SOCS7

Figure 14:
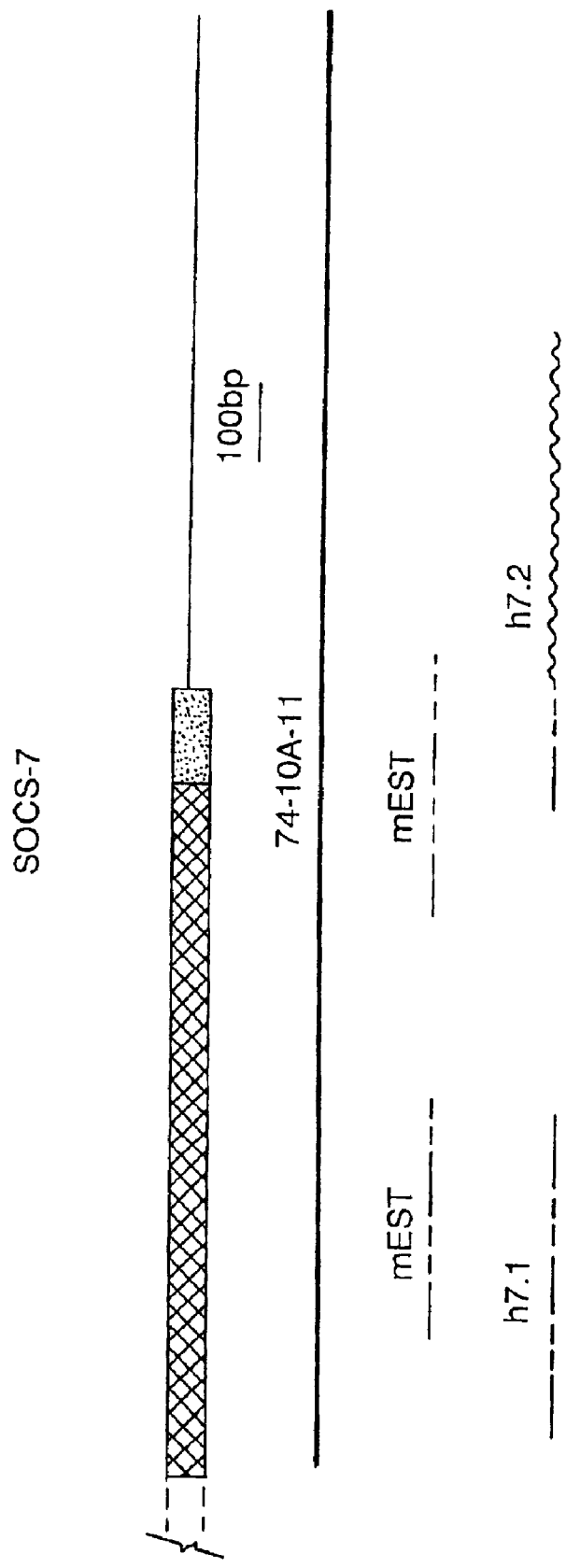
FIG. 14 is a diagrammatic representation showing the relationship of mouse SOCS7 cDNA clone (74-10A-11) to contigs derived from analysis of mouse ESTs (Table 7.1) and human ESTs (Table 7.2). The nucleotide sequence of the mouse SOCS7 contig is shown in FIG. 15A with the sequence of human SOCS7 contigs (h7.1 and h7.2) being shown in FIG. 16. The deduced amino acid sequence of mouse SOCS7 is shown in FIG. 15B. The structure of the protein is shown schematically, with the ankyrin repeats indicated by the cross hatched box and the SOCS box by the open dotted box. The putative 5' and 3' untranslated regions are shown by the thin solid line in the mouse and by the wavy line in h7.2. Based on analysis of clones isolated to date and ESTs the 3' untranslated regions of mSOCS2 and hSOCS7 share little similarity.

Mouse and human SOCS7 were recognized through searching EST databases using the SOCS box consensus (FIG. 4). Those ESTs derived from mouse and human SOCS-7 cDNAs are tabulated below (Tables 7.1 and 7.2). Using sequence information derived from mouse ESTs, several oligonucleotides were designed and use to screen, in the conventional manner, a mouse thymus cDNA library. One cDNA clone (74-10A-11) cDNA clone encoding mouse SOCS7 was isolated and sequenced in its entirety and shown to overlap with the mouse ESTs identified in the database (FIGS. 14 and 15A). Analysis of the sequence (FIG. 15) suggests that mouse SOCS7 encodes a protein with a SOCS box at its C-terminus, in addition to several ankyrin repeats (FIGS. 14 and 15B). The relationship of the human SOCS7 contigs (h7.1 and h7.2; FIG. 16) derived from analysis of human SOCS7 ESTs (Table 7.2) to the mouse SOCS7 DNA sequence is shown in FIG. 14. The nucleotide and corresponding amino acid sequences of murine SOCS7 are shown in SEQ ID NOS:24 and 25, respectively. The nucleotide sequence of SOCS7 human contigs h7.1 and h7.2 are shown in SEQ ID NOS:26 and 27, respectively.

EXAMPLE 29

SOCS8

Figure 17:
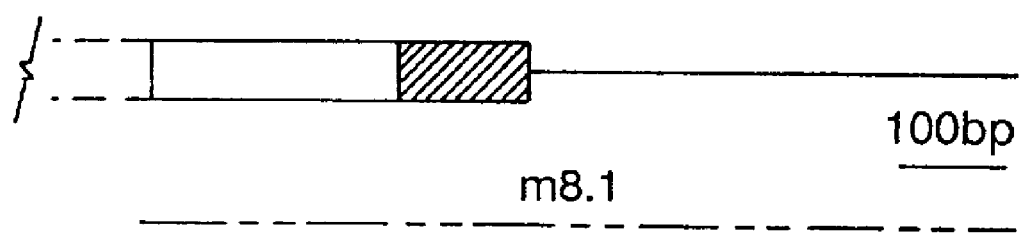
FIG. 17 is a diagrammatic representation of the relationship of sequence derived from analysis of mouse SOCS8 ESTs (Table 8.1) to the predicted protein structure of mouse SOCS8. The deduced partial amino acid sequence of mouse SOCS8 is shown in FIG. 18B. The structure of the protein is shown schematically with the SOCS box indicated by the cross hatched box . The predicted 3' untranslated region is shown by the thin line.

ESTs derived from mouse SOCS8 cDNAs are tabulated below (Table 8.1). As described for other members of the SOCS family, it is possible to isolate cDNAs for mouse SOCS8 using sequence information derived from mouse ESTs. The relationship of the ESTs to the predicted coding region of SOCS8 is shown in FIG. 17. With the nucleotide sequence obtained from the ESTs shown in FIG. 18A and the partial amino acid sequence of SOCS8 shown in FIG. 18B. The nucleotide sequence and corresponding amino acid sequences for murine SOCS8 are shown in SEQ ID NOS:28 and 29, respectively.

EXAMPLE 30

SOCS9

Mouse and human SOCS-9 were recognized through searching EST databases using the SOCS box consensus (FIG. 4). Those ESTs derived from mouse and human SOCS9 cDNAs are tabulated below (Tables 9.1 and 9.2). The relationship of the mouse SOCS9 contigs derived from analysis of the mouse SOCS9 EST (Table 9.1) to the human SOCS-9 DNA contig (h9.1; FIG. 21) derived from analysis of human SOCS9 ESTs (Table 9.2) is shown in FIG. 20. Analysis of the sequence (FIG. 22) indicates that the human SOCS9 cDNA encodes a protein with a SOCS box at C-terminus, in addition to an SH2 domain (FIG. 19). The nucleotide sequence of muring SOCS9 cDNA is shown in SEQ ID NO:30. The nucleotide sequence of human SOCS9 cDNA is shown in SEQ ID NO:31.

EXAMPLE 31

SOCS10

Mouse and human SOCS10 were recognized through searching EST databases using the SOCS box consensus (FIG. 4). Those ESTs derived from mouse and human SOCS10 cDNAs are tabulated below (Tables 10.1 and 10.2). Using sequence information derived from mouse ESTs, several oligonucleotides were designed and use to screen, in the conventional manner, a mouse thymus cDNA library. Four cDNA clones (10-9, 10-12, 10-23 and 10-24) encoding mouse SOCS10 were isolated, sequenced in their entirety and shown to overlap with the mouse and human ESTs identified in the database (FIGS. 22 and 23). Analysis of the sequence (FIG. 23) indicates that the mouse SOCS10 cDNA clone is not full length but that it does encode a protein with a SOCS box at its C-terminus, in addition to several ankyrin repeats (FIG. 22). The relationship of the human SOCS10 contigs (h10.1 and h10.2; FIG. 24) derived from analysis of human SOCS10 ESTs (Table 10.2) to the mouse SOCS10 DNA sequence is shown in FIG. 22. Comparison of mouse cDNA clones and ESTs with human ESTs suggests that the 3' untranslated regions of mouse and human SOCS10 differ significantly. The nucleotide sequence of murine SOCS10 is shown in SEQ ID NO:32 and the nucleotide sequence of SOCS10 human contigs h10.1 and h10.2 are shown in SEQ ID NOS:33 and 34, respectively.

EXAMPLE 32

SOCS11

Human SOCS11 were recognized through searching EST databases using the SOCS box consensus (FIG. 4). Those ESTs derived from human SOCS11 cDNAs are tabulated below (Table 11.1 and 11.2). The relationship of the human SOCS11 contigs (h11.1; FIG. 25A, B), derived from analysis ESTs (Table 11.2) to the predicted encoded protein, is shown in FIG. 26. Analysis of the sequence indicates that the human SOCS11 cDNA encodes a protein with a SOCS box at its C-terminus, in addition to an SH2 domain (FIGS. 26 and 25B). The nucleotide sequence and corresponding amino acid sequence of human SOCS11 are represented in SEQ ID NOS:35 and 36, respectively.

EXAMPLE 33

SOCS12

Mouse and human SOCS-12 were recognized through searching EST databases using the SOCS box consensus (FIG. 4). Those ESTs derived from mouse and human SOCS12 cDNAs are tabulated below (Tables 12.1 and 12.2). Using sequence information derived from mouse ESTs, several oligonucleotides were designed and use to screen, in the conventional manner, a mouse thymus cDNA library. Four cDNA clones (10-9, 10-12, 10-23 and 10-24) encoding mouse SOCS12 were isolated, sequenced in their entirety and shown to overlap with the mouse and human ESTs identified in the database (FIGS. 27 and 28). Analysis of the sequence (FIGS. 28 and 29) indicates that the SOCS12 cDNA clone encodes a protein with a SOCS box at its C-terminus, in addition to several ankyrin repeats (FIG. 27). The relationship of the human SOCS12 contigs (h12.1 and h12.2; FIG. 29) derived from analysis of human SOCS12 ESTs (Table 12.2) to the mouse SOCS12 DNA sequence is shown in FIG. 27. Comparison of mouse cDNA clones and ESTs with human ESTs suggests that the 3' untranslated regions of mouse and human SOCS12 differ significantly. The nucleotide sequence of SOCS12 is shown in SEQ ID NO:37. The nucleotide sequence of human SOCS12 contigs h12.1 and h12.2 are shown in SEQ ID NOS:38 and 39, respectively.

EXAMPLE 34

SOCS13

Mouse and human SOCS-13 were recognized through searching EST databases using the SOCS box consensus respectively. SOCS6 human contigs h6.1 and h6.2 are shown in SEQ ID NOS:22 and 23, respectively.

(FIG. 4). Those ESTs derived from mouse and human SOCS13 cDNAs are tabulated below (Tables 13.1 and 13.2). Using sequence information derived from mouse ESTs, several oligonucleotides were designed and use to screen, in the conventional manner, a mouse thymus and a mouse embryo cDNA library. Three cDNA clones (62-1, 62-6-7 and 62-14) encoding mouse SOCS13 were isolated, sequenced in their entirety and shown to overlap with the mouse ESTs identified in the database (FIGS. 30 and 31A). Analysis of the sequence (FIG. 31) indicates that the mouse SOCS13 cDNA encodes a protein with a SOCS box at its C-terminus, in addition to a potential WD-40 repeat (FIGS. 30 and 31B). The relationship of the human SOCS13 contigs (h13.1 and h13.2; FIG. 32) derived from analysis of human SOCS13 ESTs (Table 13.2) to the mouse SOCS13 DNA sequence is shown in FIG. 30. The nucleotide sequence and corresponding amino acid sequence of murine SOCS13 and shown in SEQ ID NOS:40 and 41, respectively. The nucleotide sequence of human SOCS13 contigs h13.1 is shown in SEQ ID NO:42.

Mice lacking SOCS-1 are born and appear outwardly normal. However, they fail to thrive and within two to three weeks are less than half the size of their normal littermates. All SOCS$^{-/-}$ mice die before weaning with profound fatty degeneration of the liver (FIG. 1). Consistent with the SOCS-1 expression pattern outlined above, significant deficiencies in haemopoietic populations, particularly lymphocytes (FIG. 2), are also evident. These experiments highlight the indispensable nature of SOCS-1 action, suggesting that negative regulation of cytokine signalling by this protein is critical in maintaining homeostasis in the liver, as well as in the proper control of the production of specific blood cells.

Analysis of β-galactosidase activity in mice in which one SOCS-1 allele has been replaced with β-gal has revealed expression in most thymocytes, as well as in the spleen and bone marrow, where it appears to be restricted largely to lymphoid populations.

EXAMPLE 34A

To explore the physiological role of SOCS-1, the inventors generated mice lacking this gene. SOCS-1 deficient (SOCS-1$^{-/-}$) mice are born at the expected Mendelian frequency, appear normal for the first week. Between 9 and 21 days of age the mice succumb to an illness characterised by fatty degeneration and monocytic infiltration of the liver, monocytic infiltration of the pancreas and heart and a severe lymphopaenia. While the molecular basis of this disease was unclear the most parsimonious hypothesis, given the role of SOCS proteins in negative regulation of signal transduction, is that the SOCS-1$^{-/-}$ mice are hyper-responsive to a cytokine known to have toxic side effects. Strikingly, the phenotype of the SOCS-1$^{-/-}$ mice was similar to that described for neonatal mice injected with interferon gamma from birth. SOCS-1 mRNA expression is induced by IFNα, IFNβ and IFNγ

In order to determine whether the cellular response to IFNα, IFNβ or IFNγ might be regulated by SOCS-1, the inventors examined whether these cytokines induced expression of SOCS-1 mRNA and whether expression of SOCS-1 inhibited the biological effect of interferon's. Northern blot analysis of mRNA from the fibroblast cell lines 2FTGH revealed that expression of SOCS-1, SOCS-2, SOCS-3 and CIS mRNA was low or undetectable in unstimulated cells. Within 15 to 30 minutes of stimulation by IFNα, IFNβ or IFNγ SOCS-1 and to a lesser extent SOCS-3 mRNA were detectable with expression peaking at about 60 minutes. Little or no expression of either SOCS-2 or CIS was observed in response to any of the interferons. A similar pattern of induction of SOCS mRNA was observed upon treatment of the J774 macrophage cell line with IFNγ and, in the liver, following intravenous injection of IFNγ into mice.

Expression of SOCS-1 and SOCS-3 but not SOCs-2 or CIS inhibits IFNα, IFNβ or IFNγ signalling 2FTGH cells were transfected with expression vectors encoding FLAG-tagged versions of SOCS-1, SOCS-2, SOCS-3 and CIS and clones stably expressing these proteins were selected. The capacity of these lines to respond to IFNα, IFNβ or IFNγ was compared with control 2FTGH cells. Cells were infected with virus and incubated with various concentrations of each IFN. Wild type cells and those expressing SOCS-2 and CIS were protected from the effects of virus infection of 300 IU/ml IFNα or IFNγ and 10 IU/ml IFNβ. In contrast, those expressing SOCS-1 and SOCS-3 exhibited reduced sensitivity to the protective effects of all three forms of IFN. In the case of IFNβ SOCS-1 expressing 2FTGH cells were at least 300-fold less sensitive and SOCS-3 expressing 2FTGH cells were 10 to 30-fold less sensitive than unmanipulated counterparts. A similar hyporesponsiveness was observed when the capacity of IFNβ to suppress cell proliferation was assessed.

Disease in SOCS-1$^{-/-}$ mice is predated by cellular responses to IFNγ

Three lines of evidence suggested that the pathology observed in SOCS-1 deficient mice might result from a hyper-responsiveness to IFNγ. These were (i) the capacity of IFNγ to stimulate SOCS-1 expression, (ii) the ability of SOCS-1 to inhibit IFNγ signalling when constitutively expressed and (iii) the similarity of the phenotype of SOCS-1 deficient mice and mice injected IFNγ. The inventors therefore examined whether SOCS-1 mice showed evidence of an ongoing response to IFNγ either during the first week of life prior to overt development of disease or during disease onset and progression in the second and third weeks of life.

Phosphorylation of the IFNγRα chain by JAK1 and JAK2 and the consequent activation of STAT1 are key elements in IFNγ signal transduction. In the livers of new born, six-day-old and 14-day-old SOCS-1–/– mice but not SOCS-1 +/– or wild type mice tyrosine phosphorylation of the IFNγRα was readily detectable. Likewise, activated STAT1, as measured by EMSA, was also detected in SOCS-1 –/– but not littermates, at the three time points examined.

Given the evidence of IFNγ signalling in SOCS-1 –/– mice examined the liver for expression of class I and II MHC, iNOS and IRF-1-hallmarks of a biological response to IFNγ. At birth and after 6 and 14 days of life wild type and SOCS-1 +/– mice showed a low level of expression of class I MHC and little or no expression of class II MHC, iNOS and IRF-1. In contrast, expression of each of these proteins was elevated in the livers of SOCS-1 –/– mice at each time point examined. Class I and II MHC expression was also found to be elevated in many cells of the haemopoietic system, notably thymic and splenic T cells, as well as bone marrow and splenic B cells and monocytes. Expression of markers of a response to IFNγ in the liver and the haemopoietic system occurred before the onset of the overt signs of disease in SOCS-1 –/– mice suggesting that it was not a secondary effect of the pathology observed.

Lack of IFNg completely ameliorates disease in SOCS-1 –/– mice

In order to determine whether a response to IFNγ was the basis of disease development in SOCS-1 –/– mice the inventors performed two experiments; (i) injection of mice with neutralising anti-IFNγ antibody and (ii) generation of mice lacking functional SOCS-1 and IFNγ genes.

Litters of mice born following the mating of SOCS-1–/+ mice were injected twice weekly from birth with either anti-IFNγ monoclonal antibody or an isotype control antibody. SOCS-1–/– mice injected with control antibody developed disease with the same onset as similar unmanipulated SOCS-1 –/–. The disease observed in unmanipulated and control antibody injected SOCS-1 –/– mice were also similar and was characterised by fatty degeneration of the liver, monocytic infiltration of several organs including the heart, liver, pancreas and skin, a generalised reduction in the size of the thymus and selective loss of pre-B and mature B cells.

EXAMPLE 35

SOCS14

Mouse and human SOCS-14 were recognized through searching EST databases using the SOCS box consensus (FIG. 4). Those ESTs derived from mouse and human SOCS14 cDNAs are tabulated below (Tables 14.1 and 14.2). Using sequence information derived from mouse and human ESTs, several oligonucleotides were designed and use to screen, in the conventional manner, a mouse thymus cDNA library, a mouse genomic DNA library and a human thymus cDNA library cloned into λ-bacteriophage. A single genomic DNA clone (57-2) and (5-3-2) cDNA clone encoding mouse SOCS14 were isolated and sequenced in their entirety and shown to overlap with the mouse ESTs identified in the database (FIGS. 33 and 34A). The entire coding region, in addition to a region of 5' and 3' untranslated regions, of mouse SOCS14 appears to be encoded on a single exon (FIG. 33). Analysis of the sequence (FIG. 34) confirms that SOCS14 genomic and cDNA clones encode a protein with a SOCS box at its C-terminus in addition to an SH2 domain (FIGS. 33 and 34B). The relationship of the human SOCS14 contigs (h14.1) derived from analysis of cDNA clone 5-94-2 and the human SOCS14 ESTs (Table 14.2) to the mouse SOCS14 DNA sequence is shown in FIG. 33.

The nucleotide sequence and corresponding amino acid sequence of murine SOCS14 are shown in SEQ ID NOS:43 and 44, respectively.

EXAMPLE 36

SOCS15

Mouse and human SOCS-15 were recognized through searching DNA databases using the SOCS box consensus (FIG. 4). Those ESTs derived from mouse and human SOCS15 cDNAs are tabulated below (Tables 15.1 and 15.2), as are a mouse and human BAC that contain the entire mouse and human SOCS-15 genes. Using sequence information derived from mouse ESTs and the BACs it is possible to predict the entire amino acid sequence of SOCS15 and as described for the other SOCS genes it is feasible to design specific oligonucleotide probes to allow cDNAs to be isolated. The relationship of the BACs to the ESTs is shown in FIG. 35 and the nucleotide and predicted amino acid sequence of the SOCS-15, derived from the mouse and human BACs is shown in FIGS. 36 and 37. The nucleotide sequence and corresponding amino acid sequence of murine SOCS15 are shown in SEQ ID NOS:46 and 47, respectively. The nucleotide and corresponding amino acid sequence of human SOCS15 are shown in SEQ ID NOS:48 and 49, respectively.

EXAMPLE 37

SOCS Interaction with JAK2 Kinase

These Examples show interaction between SOCS and JAK2 kinase. Interaction is mediated via the SH2 domain of SOCS1, 2, 3 and CIS. The interaction resulted in inhibition of JAK2 kinase activity by SOCS1.

The following methods are employed:

Immunoprecipitation: Cos6 cells were transiently transfected by electroporation and cultured for 48 hours. Cells were then lysed on ice in lysis buffer (50 mM Tris/HCL, pH 7.5, 150 mM NaCl, 1% v/v Triton-X-100, 1 mM EDTA, 1 mM Naf, 1 mM Na$_3$VO$_4$) with the addition of complete protease inhibitors (Boehringer Mannheim), centrifuged at 4° C. (14,000×g, 10 min) and the supernatant retained for immunoprecipitation. JAK2 proteins were immunoprecipitated using 5 μl anti-JAK2 antibody (UBI). Antigen-antibody complexes were recovered using protein A-Sepharose (30 μl of a 50% slurry).

Western blotting: Immunoprecipitates were analysed by sodium dodecyl sulphate (SDS)-polyacrylamide gel electrophoresis (PAGE) under reducing conditions. Protein was then electrophoretically transferred to nitrocellulose, blocked overnight in 10% w/v skim-milk and washed in PBS/0.1% v/v Tween-20 (Sigma) (wash buffer) prior to incubation with either anti-phosphotyrosine antibody (4G10) (1:5000, UBI), anti-FLAG antibody (1.6 μg/ml) or anti-JAK2 antibody (1:2000, UBI) diluted in wash buffer/1% w/v BSA for 2 hr. Nitrocellulose blots were washed and primary antibody detected with either peroxidase-conjugated sheep anti-rabbit immunoglobulin (1:5000, Silenus) or peroxidase-conjugated sheep anti-mouse immunoglobulin (1:5000, Silenus) diluted in wash buffer/1% w/v BSA. Blots were washed and antibody binding visualised using the enhanced chemiluminescence (ECL) system (Amersham, UK) according to the manufacturer's instructions.

In-vitro kinase assay: An in vitro kinase assy was performed to assess intrinsic JAK2 kinase catalytic activity. JAK2 protein were immunoprecipitated as described, washed twice in kinase assay buffer (50 mM NaCl, 5 mM MgCl$_2$, 5 mM MnCl2, 1 mM NaF, 1 mM Na$_3$VO$_4$, 10 mM HEPEs, pH 7.4) and suspended in an equal volume of kinase buffer containing 0.25 μCi/ml (γ-$^{32}$P)-ATP (30 min, room temperature). Excess (γ-$^{32}$P)-ATP was removed and the immunoprecipitates analysed by SDS/PAGE under reducing conditions. Gels were subjected to a mild alkaline hydrolysis by treatment with 1 M KOH (55° C., 2 hours) to remove phosphoserine and phosphothreonine. Radioactive bands were visualised with IMAGEQUANT software on a Phosphorimage system (Molecular Dynamics, Sunnyvale, Calif., USA).

EXAMPLE 38

Making SOCS-1 Knockout Constructs

Diagrams of plasmid constructs and knockout constructs are shown in FIGS. 51–53. The genomic SOCS-1 clone 95-11-10 was digested with the restriction enzymes BamH1 and EcoR1 to obtain a 3.6 Kb DNA fragment 3' of the coding region (SOCS-1 exon), which was used as the 3' arm in the SOCS-1 knockout vectors. The ends of this fragment were then blunted. This fragment was then ligated into the following vectors:

pBgalpAloxNeo and pBgalpAloxNeoTK which had been linearized at the unique Xho1 site and then blunted. This ligation resulted in the formation of the following vectors:

3'SOCS-1 arm in pBgalpAloxNeo and 3'SOCS-1 arm in pBgalpAloxNeoTK

The 5' arm of the SOCS-1 knockout vectors was constructed by using PCR to generate a 2.5 Kb PCR product from the genomic SOCS-1 clone 95-11-10 just 5' of the SOCS-1 coding region (SOCS-1 exon). The oligo's used to generate this product were:

5' oligo (sense) (2465)

AGCT AGA TCT GGA CCC TAC AAT GGC AGC [SEQ ID NO:49]

AGCT AG ATC TGC CAT CCT ACT CGA GGG GCC AGC TGG [SEQ ID NO:50]

The PCR product was then digested with the restriction enzyme BglII, to generate BglII ends to the PCR product. This 5'SOCS-1 PCR product, with BglII, ends was then ligated as follows: 3'SOCS-1 arm in pBgalpAloxNeo and 3'SOCS-1 arm in pBgalpAloxNeoTK, which had been linearized with the unique restriction enzyme BamH1. This resulted in the following vectors being formed:

5'&3'SOCS-1 arms in pBgalpAloxNeo and 5'&3'SOCS-1 arms in pBgalpAloxNeoTK

These were the final SOCS-1 knockout constructs. Both these constructs lacked the entire SOCS-1 coding region (SOCS-1 EXON), being replaced with portions of the Bgal, B globin polyA, PGK promoter, neomycin and PGK polyA sequences. The 5'&3'SOCS-1 arms in pBgalpAloxNeoTK vector also contained the tymidine kinase gene sequence, between the neomycin and PGK poly A sequences.

The vectors: 5'&3'SOCS-1 arms in pBgalpAloxNeo and 5'&3'SOCS-1 arms in pBgalpAloxNeoTK were linearized with the unique restriction enzyme Not1 and then transfected into Embryonic stem cells by electroporation. Clones which were resistant to neomycin were selected and analysed by southern blot to determine if they contained the correctly integrated SOCS-1 targeting sequence. In order to determine if correct integration had occurred, genomic DNA from the neomycin resistant clones was digested with the restriction enzyme EcoR1. The digested DNA was then blotted onto nylon filters and probed with a 1.5 Kb EcoR1 /Hind III DNA fragment, which was further 5' of the 5'arm sequence used in the knockout constructs. The band sizes expected for correct integration were:

Wild type SOCS-1 allele 5.4 Kb

SOCS-1 knockout allele 8.2 Kb in 5'&3'SOCS-1 arms in pBgalpAloxNeo or 11 Kb in 5'&3'SOCS-1 arms in pBgalpAloxNeoTK transformed cells.

EXAMPLE 39

Analysis of SOCS-1 Deletion Mutants

SOCS-1 deletion mutants were generated by PCR to give fragments with Asc 1/Mlu 1 linkers at the N- and C-terminus and subcloned into pEF-FLAG-I (found at http://www.wehi.edu.au/willson vectors) to give N-terminal Flagged proteins. SOCS-1 deletion mutants were therefore constructed in which the N-terminal domain was deleted, retaining amino acids 77–211 ($\Delta$N), the C-terminal domain encompassing the SOCS box was deleted, retaining amino acids 1–169 ($\Delta$C) and both the N-terminal region and the SOCS box were deleted, retaining amino acids 77–169, leaving an intact SH2 domain ($\Delta$N/C). In addition, a construct was created in which the SH2 domain and the SOCS box were both deleted, retaining the N-terminal 81 amino acids ($\Delta$SH2/C). These constructs were transfected into parental M1 cells and with the exception of $\Delta$SH2/C, several stable transfectants were obtained for each construct. Protein expression of the deletion mutants was confirmed by immunoprecipitation and Western blot analysis using anti-Flag antibodies.

These constructs were then assessed for their ability to inhibit IL-6 and LIF signalling in several different assay systems.

1. Colony assays in soft agar

Cultures were performed as previously described (Metcalf, 1984). M1 parental cells form large compact colonies in soft agar. When cells are incubated in the presence of IL-6 or LIF the colonies are dispersed with a halo of cells migrating out from the central core. At high concentrations of cytokine, the number of colonies observed is highly diminished, a phenomenon known as clonal suppression. M1 cells which constitutively express SOCS-1 are unable to respond to either IL-6 or LIF, as both macrophage differentiation and clonal suppression are inhibited (Starr et al. 1997).

To assess the ability of the SOCS-1 deletion mutants to suppress M1 cell differentiation, cells expressing the various constructs were plated in agar in the presence or absence of increasing concentrations of IL-6 or LIF. M1 cells expressing either SOCS-1 $\Delta$N or $\Delta$N/C protein at equivalent levels to cells expressing full-length SOCS-1 were unable to block IL-6 or LIF-induced differentiation, responding to growth factor in a similar manner to the parental M1 cells (M1-P). These results indicated that the N-terminal region of SOCS-1 was critical for inhibition of M1 macrophage differentiation.

2. Inhibition of LIF-induced luciferase activity in 293T cells 293T is a human fibroblast line expressing endogenous LIF receptors. Briefly, 293T cells were plated into either 24-well plates at 1×105 cells/well or 10 cm dishes at 2×106 cells/dish. The LIF responsive promoter-luciferase reporter gene (APRE-luc) and has been described previously (Masuhara et al. 1997). The positive control vector Sra-b-gal encoding the $\beta$-galactosidase gene has also been described (Ogilvy et al. 1998). Plasmids of reporter genes with either vector alone or pEF-FLAG-SOCS constructs were introduced into cells using FuGENE transfection reagent (Boehringer Mannheim) according to the Manufacturers' instructions and harvested after 48 hr. Cells were stimulated with or without 10 ng/ml hLIF overnight prior to lysis with 40 ml Reporter Lysis Buffer (Promega) containing protease inhibitors. Lysates were then assayed for luciferase and $\beta$-galactosidase activity.

293T cells were transiently transfected with the LIF-responsive reporter construct, APRE-luc and LIF induction of luciferase activity measured. A clear increase in luciferase activity is observed via JAK activation of Stat3 which dimerizes and in turn binds to the APRE (acute phase response element). The differential ability of the various SOCS proteins to modulate IL-6 and LIF signalling in M1 cells was confirmed by transient expression of the APRE-luc reporter gene with or without Flag-tagged SOCS-1, SOCS-2, SOCS-3, CIS, SOCS-5 and SOCS-6 in 293T cells. SOCS-1 and SOCS-3 completely abolished the LIF-induced activation of luciferase activity, whereas SOCS-2, CIS and SOCS-6 had no effect, and SOCS-5 partially inhibited the LIF response. Transfection efficiency was controlled for by co-expression of a b-galactosidase reporter construct under a constitutive promoter (Sra-b-gal) and luciferase activity normalized against the b-galactosidase results. Similarly, the ability of the SOCS-1 deletion mutants to inhibit M1 differentiation was parallelled by their ability to inhibit luciferase activity when transiently expressed in 293T cells. In addition, expression of SOCS1 ΔSH2/C did not inhibit LIF-induced luciferase activity, suggesting that the N-terminal region alone was insufficient to mediate SOCS-1 inhibition of LIF signalling.

3. Inhibition of JAK2 autophosphorylation in an in vitro kinase assay

To further investigate the function of the SOCS-1 deletion mutants, the inventors examined the ability of the different SOCS proteins to directly inhibit JAK kinase activity. The methods used are outlined below.

Briefly, cell lysates were prepared as previously described (Nicholson et al. 1995). Proteins were immunoprecipitated with either anti-JAK2 antibodies (UBI) or anti-Flag antibody conjugated to Sepharose (M2; Eastman Kodak Company) and proteins separated on 4–15% w/v gradient SDS-PAGE gels. Protein was then electrophoretically transferred to PVDF membranes. Membranes were blocked overnight in 10% w/v skim milk and incubated with primary antibody for 2 hr. Antibody binding was visualized with either peroxidase-conjugated anti-rabbit Ig (Silenus) or peroxidase conjugated anti-mouse IgFc, which specifically recognises the immunoglobulin heavy chain (Jackson Laboratories) and the enhanced chemiluminescence (ECL) system (Amersham). Anti-JAK2 immunoprecipitates were washed and incubated with g-ATP as previously described (Nicholson et al. 1995).

Flag-tagged-JAK2 was transiently expressed in Cos cells with or without the various SOCS-1 deletion mutants. Cells were lysed and JAK2 proteins immunoprecipitated, incubated in kinase buffer containing radiolabelled γ-ATP, and the proteins separated by SDS-PAGE gel (as described above). Incorporation of radiolabelled phosphate into the JAK2 protein (autophosphorylation) was then visualised using a phosphoimager. Co-expression of full length SOCS-1 dramatically inhibited JAK2 autophosphorylation. Three of the SOCS-1 deletion mutants were tested (ΔC, ΔN/C, ΔN) for their ability to functionally inhibit the JAK2 kinase activity. Co-expression of each of these constructs with JAK2 indicated that they were also able to inhibit JAK2 kinase activity to the same degree as full-length SOCS-1. Immunoprecipitation of equal amounts of JAK2 protein was demonstrated by Western blot with anti-Flag antibodies. Expression levels of the various SOCS-1 deletion mutants was determined by immunoprecipitation and Western blot with anti-Flag antibodies. These results indicate that at least in an over-expression system where JAK2 is constitutively active (ie. not a ligand-inducible system), the SH2 domain of SOCS-1 is sufficient to inhibit JAK kinase assay.

JAK2 was transiently expressed in Cos cells with or without the various SOCS-1 deletion mutants. Cells were lysed and JAK2 tyrosine phosphorylation assessed by Western blot with anti-phosphotyrosine antibodies. Inhibition of JAK2 tyrosine phosphorylation correlated with the ability of the various SOCS-1 deletion mutants to inhibit JAK2 kinase activity. In addition, all three of the SOCS-1 mutants tested (ΔC, ΔN/C, ΔN) appeared able to associate with JAK2.

The data obtained with the SOCS-1 deletion mutants indicate that the N-terminal region of SOCS-1 was required for its ability to inhibit LIF and IL-6 signalling, particularly with respect to induction of M1 cell differentiation. In addition, the in vitro kinase data indicates that inhibition of JAK kinase activity is mediated through the SOCS-1 SH2 domain.

EXAMPLE 40

SOCS Chimaeras

In order to further investigate the importance of the different SOCS domains, a series of chimeric proteins were created in which the N-terminal domain of SOCS-1 was replaced with the either the N-terminal domain of SOCS-2, SOCS-3, SOCS-4, SOCS-5 or SOCS-6. A series of chimeric proteins were also created in which the SH2 domain of SOCS-1 was replaced with either the SH2 domain of SOCS-2, SOCS-3, CIS, SOCS-5 or SOCS-6.

To facilitate the synthesis of chimeric mouse SOCS1 cDNAs as Xho I site was introduced at the boundary between the N-terminal region and SH2 domain of the SOCS1 cDNA (see FIG. 42). Two nucleotide changes were introduced using a PCR-based technique known as splicing by overlap extension (Horton et al. 1989). The PCR fragment, designated mSOCS1 mutXho, was then cloned into the Kpn I and Sac I sites of pBLUESCRIPT SK II(+) [Stratagene]. In order to facilitate cloning of the DNA fragments into the mammalian expression vector pEF-FLAG-I (found at http://www.wehi.edu.au./willson vectors), an in-frame Asc I restriction enzyme site was introduced one amino acid after the predicted translational start site and an Mlu I site was inserted immediately before the stop codon of the mouse SOCS1 cDNA. Since the C>G nucleotide alteration leads to a Δ> E amino acid substitution at position 76, the SOCS1 mutXho cDNA was cloned into the Mlu I site of pEF-FLAG-I and shown to have similar activity to wild-type SOCS-1 in the luciferase assay (FIG. 42).

Hybrid cDNAs, in which the N-terminal region or the SH2 domain of the SOCS1 sequence were replaced with homologous regions of mouse CIS, SOCS2, SOCS3, SOCS5 or SOCS6, were synthesized from PCR generated restriction fragments (N-terminal regions were cloned in as Asc I-Xho I fragments and SH2 domain fragments were clone in as Xho I-Not I fragments). All the hybrid cDNAs were then cloned into the Mlu I site of pEF-FLAG-I in order to express mouse SOCS1 domain swap mutant proteins with an N-terminal FLAG epitope tag. Constructs were sequenced in their entirety before use. The exact specification of sequences present in each SOCS1 domain swap mutant is listed in Table 16.

TABLE 16

CONSTRUCTION OF MOUSE SOCS1 DOMAIN SWAP MUTANT PROTEINS

| Hybrid | Amino Acid Sequence Specifications |
|---|---|
| SOCS1-CNT | CIS(2–80): SOCS1(75–212) |
| SOCS1-2NT | SOCS2(2–46): SOCS1(75–212) |
| SOCS1-3NT | SOCS3(2–44): SOCS1(75–212) |
| SOCS1-5NT | SOCS5(2–379): SOCS1(75–212) |
| SOCS1-6(9)NT | SOCS6(2–380): SOCS1(75–212) |
| SOCS1-CSH2 | SOCS1(2–78): CIS(81–218): SOCS1(172–212) |
| SOCS1-2SH2 | SOCS1(2–78): SOCS2(47–159): SOCS1(172–212) |
| SOCS1-3SH2 | SOCS1(2–78): SOCS3(45–185): SOCS1(172–212) |
| SOCS1-5SH2 | SOCS1(2–78): SOCS5(380–480): SOCS1(172–212) |
| SOCS1-6(9)SH2 | SOCS1(2–78): SOCS6(381–494): SOCS1(172–212) |

Amino acid sequences are designated according to the following example. CIS(2–80):SOCS1(75–212) (hybrid SOCS1-CNT) denotes that amino acid residues 2 to 80 are derived from N-terminal region of the mCIS sequence and amino acid residues 75 to 212 are derived from mouse SOCS1 sequence.

These chimeric constructs were Flag-tagged, transiently expressed in 293T cells and LIF-induction of luciferase activity assayed. In contrast to wild-type SOCS-1, none of the chimeric proteins were able to inhibit LIF-induction of luciferase activity. Therefore, the N-terminal region of SOCS-1 cannot be functionally replaced by any of the SOCS-2, SOCS-3, CIS, SOCS-4, SOCS-5 and SOCS-6 N-terminal domains. Likewise, Although none of the introduced SH2 domains is able to fully replace the SOCS-1 SH2, partial inhibition of LIF-induced luciferase activity was observed with chimeric SOCs proteins, SOCS-1-3SH2, SOCS-1CSH2, and SOCS-1-5SH2.

The data in both M1 cells and 293T cells indicated that whilst the N-terminal region was critical for SOCS-1 function, the SH2 domains of several SOCS proteins was sufficient for some, though not normal, level of activity.

Previous work has shown that mutation of a conserved arginine residue to lysine within SH2 domains results in a non-functional domain. Mouse SOCS1, SOCS2, SOCS3 and CIS cDNAs, in which an R>K amino acid substitution in the SH2 domain was introduced (see FIG. 42), were generated using the PCR-based technique, splicing by overlap extension. To facilitate cloning of the PCR-generated fragments into pEF-FLAG-I, an in-frame Asc I restriction enzyme site was introduced immediately after the predicted translation start site and an Mlu I site was inserted immediately before the translation stop site. Expression construct pEF-FLAG-I/mSOCS1-R105K encodes a mSOCS1 protein with an R>K amino acid substitution at position 105 in the SH2 domain. pEF-FLAG-I/mSOCS2-R73K, pEF-FLAG-I/mSOCS3-R71K, pEF-FLAG-I/mCIS-R107K encode mSOCS2, SOCS3 and CIS proteins with R>K amino acid substitutions at the equivalent position in the SH2 domain, respectively.

To further confirm that the SH2 domain of SOCS-1 was required for activity, point mutations were made in each of the SOCS protein SH2 domains (SOCS-1 to SOCS-3, CIS; FIG. 42) changing the conserved arginine residue to a lysine. These constructs were then transiently expressed in the 293T reporter gene system. SOCS-1 containing a non-functional SH2 domain (SOCS-1-R105K) was unable to inhibit LIF-induced luciferase activity, providing further evidence that the SH2 domain has a critical role in SOCS-1 function. Further, a mutation of the SOCS-3-SH2 domain (SOCS-3-R71K) did not abrogate the ability of SOCS-1 to inhibit LIF signalling. This not only confirms a critical role for the SOCS-1-SH2 domain in LIF signalling, but is the first evidence to suggest that although both SOCS-1 and SOCS-3 are able to inhibit LIF and IL-6 signal transduction, they may do so through entirely different mechanisms.

EXAMPLE 41

Biochemical Analysis of SOCS Action

The inventors sought further evidence as to the molecular site of action of the various SOCS proteins.

M1 parental cells (M1-P) and M1 cells constitutively expressing a Flag-tagged SOCS-1 protein were serum-starved for 2 hrs and stimulated for 0, 5, 10 minutes with 104 U/ml mLIF. Cells were lysed and JAK proteins immunoprecipitated with 5 ml anti-JAK1 antibodies (UBI) and protein-A-Sepharose. Precipitates were washed and proteins separated by SDS-PAGE on a 4–15% w/v gradient gel, prior to analysis by Western blot with anti-phsophotyrosine antibodies. In parental M1 cells JAK1 was clearly phosphorylated in response in LIF. In contrast, constitutive expression of SOCS-1 inhibited JAK1 tyrosine phosphorylation.

High level expression of JAK2 protein in Cos cells results in a constitutively active JAK protein, presumably due to dimerisation and cross-phosphorylation. Flag-tagged JAK2 was, therefore, transiently expressed by electroporation in Cos cells with and without co-expression of Flag-tagged SOCS-1. After 48 hours cells were lysed on ice and JAK2 proteins immunoprecipitated using 5 ml anti-JAK2 antibody (UBI). Immunoprecipitates were washed, divided in two and half the proteins subjected to an in vitro kinase assay as previously described. Proteins were then separated by SDS-PAGE on a 4–15% w/v gradient gel and the gel treated with KOH to remove phosphoserine and phosphothreonine. Incorporation of radiolabelled phosphate was detected using a phosphoimager. The remaining half of the immunoprecipitation was run on a 4–15% w/v gradient gel and analysed by Western blot with anti-JAK2 antibodies (UBI) to demonstrate equal immunoprecipitation.

Lysates from Cos cells expressing either JAK2 or both JAK2 and SOCS-1, were run on a 4–15% w/v gel, electrophoretically transferred to PVDF and analysed with anti-phosphotyrosine antibodies at a 1:5000 dilution (4G10; UBI). A single phosphorylated band corresponding to JAK2 was observed in parental M1 cells, which was not evident in cells expressing SOCS-1. Lysates were re-probed with anti-Flag antibodies to demonstrate equal loading of JAK2 protein. Expression of SOCS-1 was therefore able to inhibit both JAK2 kinase activity or autophosphorylation and tyrosine phosphorylation.

The ability of SOCS family members, SOCS-2, SOCS-3 and CIS to inhibit JAK2 kinase activity was further investigated. Flag-tagged JAK2 was transiently expressed by electroporation, with were lysed on ice and JAK2 proteins immunoprecipitated using 5 ml anti-JAK2 antibody (UBI). Immunoprecipitates were washed and subjected to an in vitro kinase assay as previously described. Proteins were then separated by SDS-PAGE on a 4–15% w/v gradient gel and the gel treated with KOH to remove phosphoserine and phosphothreonine. Incorporation of radiolabelled phosphate was detected using a phosphoimager (FIG. 62*b*). As had been demonstrated previously, co-expression of SOCS-1 inhibited JAK2 kinase activity. Co-expression of SOCS-2 and CIS also appeared to inhibit JAK2 kinase activity, whilst co-expression of SOCS-3 did not inhibit kinase activity. These results suggests that SOCS-1 and SOCS-3 may have a differential ability to inhibit JAK2 kinase activity.

M1 cell lines stably expressing Flag-tagged SOCS-1, SOCS-2, SOCS-3 or CIS proteins, were lysed and the SOCS proteins immunoprecipitated using anti-Flag antibodies conjugated to sepharose. Immunoprecipitates were washed and the proteins were separated by SDS-PAGE on a 4–15% w/v gradient gel. Proteins were then electrophoretically transferred to PVDF membrane and analysed using anti-Flag antibodies. Expression levels of SOCS-2 (S2) were considerably higher than the other SOCS proteins with the expression levels of SOCS-1 (S1) being the lowest.

Stat3 tyrosine phosphorylation has previously been implicated in IL-6 induced differentiation, both by the use of dominant negative Stat3 constructs and by specific tyrosine mutations within the IL-6 signalling chain, gp130, which block recruitment of Stat3 to the receptor complex. The inventors examined, therefore, LIF-induced Stat3 tyrosine phosphorylation in M1 cells expressing the various SOCS-1, SOCS-2, SOCS-3 and CIS. M1 cell lines stably expressing the various SOCS proteins, were serum-starved for 1.5 hours prior to stimulation with 104 U/ml mLIF for 0, 5 and 10 minutes. Cells were then lysed, Stat3 proteins immunoprecipitated and analyzed by Western blot with antibodies specific to phosphorylated Stat3 (BioLabs). Stat3 was rapidly tyrosine phosphorylated in parental M1 cells in response to LIF. In contrast, Stat3 tyrosine phosphorylation was inhibited in M1 cells expressing SOCS-1 and SOCS-3. In each instance, Stat3 tyrosine phosphorylation correlated inversely with the ability of the expressed SOCS protein to inhibit M1 cell differentiation. This indicates that Stat3 has a critical role in IL-6-induced M1 cell differentiation and further suggests that the ability of SOCS-1 and SOCS-3 to inhibit M1 differentiation may be mediated through inhibition of the JAK-STAT pathway. Western blots were stripped and re-probed with anti-Stat3 antibodies to demonstrate equal loading of Stat3 protein.

EXAMPLE 42

Expression of SOCS-2, SOCS-3 and CIS in M1 Cells cDNAs encoding epitope-tagged SOCS-2, SOCS-3 or CIS were generated by subcloning the entire coding region of each gene into the pEF-BOS expression vector, engineered to encode an in-frame FLAG epitope downstream of an initiation methionine. Using electroporation, M1 cells were transfected with 20 mg of linearised expression plasmid and 2 mg of a linearised plasmid in which transcription of a cDNA encoding puromycin N-acetyl transferase was driven from the mouse phosphoglycerokinase promoter. After 48 hours in culture, transfected cells were selected with 20 µg/ml puromycin. Puromycin-resistant cells were screened for the expression of SOCS-2, SOCS-3 or CIS by immunoprecipitation and Western blotting of cell extractors with the M2 anti-FLAG monoclonal antibody.

In order to assay the differentiation of M1 cells in response to cytokines, 300 cells were cultured in 35 mm Petri dishes containing 1 ml of DME supplemented with 20% v/v foetal calf serum (FCS), 0.3% w/v agar and 0.1 ml of serial dilutions of interleukin 6 (IL-6). After 7 days culture at 37° C. in a fully humidified atmosphere, containing 10% v/v $CO_2$ in air, colonies of M1 cells were counted and classified as differentiated if they were composed of dispersed cells or had a corona of dispersed cells around a tightly packed centre. The total number of colonies in each dish were counted to determine the degree of clonal suppression induced by IL-6.

M1 cells expressing SOCS-2 were slightly hyporesponsive to differentiation induced by IL-6. However, IL-6 was unable to induce clonal suppression in these cells. The level of SOCS-2 expression in M1 cells was 10-fold higher than that for the other SOCS proteins. SOCS-3 expression in M1 cells completely inhibited the ability of IL-6 to induce either clonal suppression or differentiation in agar in response to IL-6, similar to the action of SOCS-1. M1 cells expressing CIS responded to IL-6 in a similar manner to parental M1 cells.

EXAMPLE 43

Knockout of SOCS Genes

In vitro studies have clearly identified the SOCS protein as key negative regulators of signal transduction. Moreover, injection of cytokines into mice has been shown to result in increased transcription of SOCS genes, implicating these proteins in regulation of cytokine responses in vivo. In order to determine the physiological processes regulated by each SOCS gene the inventors carry out experiments to "knockout" individual SOCS genes in mice. The first step in doing this is to clone genomic DNA encoding each of the SOCS genes. The maps of the genes for mouse SOCS-1, SOCS-2, SOCS-3, SOCS-5, SOCS-9 and SOCS-11 are shown in FIG. 43 A–F).

Generation and analysis of SOCS-1 knockout mice

To construct the SOCS1 targeting vector, a 5' arm extending approximately 2.5 kb from the protein initiation ATG was generated by PCR using specific SOCS1 oligonucleotides and genomic clone pgmSOCS1 95-11-10 as template. This fragment was fused to the ATG of β-galactosidase via the BamHI site in the plasmid vector pβgalpAloxneo (FIG. 38). The 3' arm, a 3.2 kb BamHI-EcoRV fragment from pgmSOCS1 95-11-10 (FIG. 44) was blunted and ligated into the XhoI (blunted) site of pβgalpAloxneo that already contained the 5' arm. This targeting vector was linearised with NotI and electroporated into W9.5 embryonic stem cells. After 48 hours, transfected cells were selected in 175 µg/ml G418 and resistant clones picked and expanded after a further 8 days. Clones in which the targeting vector had recombined with the endogenous SOCS1 gene were identified by hybridising EcoRI-digested genomic DNA with 1.5 kb EcoRI-HindIII fragment from pgmSOCS1 95-11-10. This probe (probe A, FIG. 44), which is located 5' to the SOCS1 sequences in the targeting vector, distinguished between the endogenous (5.3 kb) and targeted (8.0 kb) SOCS1 loci (FIG. 44). The appropriate homologous recombination event was confirmed in ES clones with probe B, a 0.7 kb BamHI-NheI fragment from pgmSOCS1 95-11-10 (FIG. 44) situated 3' to the SOCS1 gene. Genomic DNA was digested with EcoRI for 16 hrs at 37° C., electrophoresed through 0.8% w/v agarose, transferred to nylon membranes and hybridised to $^{32}$P-labelled probe in a solution containing 0.5M sodium phosphate, 7% w/v SDS, 1 mM EDTA and washed in a solution containing 40 mM sodium phosphate, 1% w/v SDS at 65° C. Hybridising bands were visualised by autoradiography for 16 hours at −70° C. using Kodak XAR-5 film and intensifying screens. A targeted ES cell clones, W9.5SOCS1 1.4-A8 was injected into C57B1/6 blastocysts to generate chimeric mice. Male chimeras were mated with C57B1/6 females to yield SOCS1 heterozygotes which are currently being interbred to produce wild-type (SOCS-1/+/+), heterozygous (SOCS +/−) and mutant (SOCS −/−) mice. The genotypes of offspring were determined by Southern Blot analysis of genomic DNA extracted from tail biopsies.

Mice lacking expression of SOCS-1 have been generated by replacing the entire coding region of SOCS-1 with bgal. In both heterozygous mice (SOCS-1+/−) and homozygous knockout mice (SOCS-1−/−), bgal expression should accurately reflect the normal tissue expression of SOCS-1. This experiment was a trial to determine whether βgal expression could be detected in SOCS-1+/− mice. The thymus was specifically chosen for analysis as Northern blots have previously shown high levels of constitutive SOCS-1 expression in this tissue. The procedure for FACSgal involves laoding cells with a bgal substrate, fluorescein di-β-D-galactopyranoside (FDG), and allowing time for the bgal to convert this substrate to fluorescein, which can be detected by FACS analysis.

The steps in this procedure are:
1) Tissues (thymus, spleen femur harvested from:
   a) SOCS-1+/− mice
   b) SOCS-1+/− littermates (negative control)
   c) ROSA mice (positive control)
2) Single cell suspension of each tissue obtained by flushing through KDS buffer containing 5% v/v FCS.
3) RBC lysis.
4) Cell pellet resuspended in 150 ml KDS/5% v/v FCS.
5) Hypotonic loading: Warmed cells diluted 1:1 with 2 mM FDG. Incubated at 37° C. for 120 secs.
6) Cells incubated on ice for ~3 hr to allow hydrolysis of FDG to fluorescein. 1 mg/ml propidium iodide added to cells prior to FACSCAN analysis.

From this analysis we have shown bgal expression is high (92% of cells) in the thymus of SOCS-1+/−mice, as expected. A smaller percentage of cells from spleen (12%) and bone marrow (22%) were also expressing βgal. The high level expression of SOCS-1 in the thymus accurately reflects the expression of SOCS-1 observed by Northern analysis showing that bgal expression in SOCS-1+/− mice can be used as a marker for SOCS-1 expression. Moreover, since β-galactosidase expression, and indeed any other marker in which is inserted into the SOCS-1 locus, like green fluorescent protein, will be transcribed in response to cytokines these mice are extremely useful reagents for monitoring responses to cytokines in vivo, in addition to being bred to yield mice which lack SOCS-1.

Generation of SOCS2 knockout mice:

To construct the SOCS2 targeting vector, a 5' arm extending approximately 2.0 kb from the protein initiation ATG was generated by PCR using specific SOCS2 oligonucleotides and genomic clone pgmSOCS2 57-60-1-45 as template. This fragment was fused to the ATG of β-galactosidase via the BamHI site in the plasmid vector pβgalpAloxneo (FIG. 38). The 3' arm, a 3.7 kb EcoRI fragment from pgmSOCS2 57-60-1-45 (FIG. 45) was blunted and ligated into the XhoI (blunted) site of pβgalpAloxneo that already contained the 5' arm. This targeting vector was linearised with NotI and electroporated into BRUCE 4 embryonic stem cells. Transfected cells were selected in G418 and resistant clones picked and expanded. Clones in which the targeting vector had recombined with the endogenous SOCS2 gene were identified by hybridising EcoRV-digested genomic DNA with a 1.8 kb EcoRI-EcoRV fragment from pgmSOCS2 57-60-1-45. This probe (probe A, FIG. 45), which is located 3' to the SOCS2 sequences in the targeting vector, distinguished between the endogenous (greater than 14 kb) and targeted (7.5 kb) SOCS2 loci (FIG. 45). Several targeted ES cell clones have been identified and are currently being injected into blastocysts to generate chimeric mice.

Generation of SOCS3 knockout mice:

To construct the SOCS3 targeting vector, a 5' arm extending approximately 3.0 kb from the protein initiation ATG was generated by PCR using specific SOCS3 oligonucleotides and genomic clone pgmSOCS3 95-3 Xba as template. This fragment was fused to the ATG of β-galactosidase via the BamHI site in the plasmid vector pβgalpAloxneo. The 3' arm is a 4.2 kb XbaI-XhoI fragment from pgmSOCS3 95-3 (FIG. 46). Initially, a 7.4 kb XbaI-HindII fragment from this genomic clone was ligated into pBluescript, from which the 3' arm was excised as a XhoI fragment and ligated into the XhoI site of pβgalpAloxneo that already contained the 5' arm. This targeting vector was linearised with AscI and is currently being electroporated into BRUCE 4 embryonic stem cells.

Generation of CIS knockout mice:

To construct the CIS targeting vector, a 5' arm extending approximately 1.5 kb from the protein initiation ATG was generated by PCR using specific CIS oligonucleotides and genomic clone pgmCIS 57-7-1-26 as template. This fragment was fused to the ATG of β-galactosidase via the BamHI site in the plasmid vector pβgalpAloxneo (see FIG. 38) into which the 3' arm, a 3.2 kb BamHI fragment from pgmCIS 57-7-1-26 had already been inserted. The 3' arm fragment was blunted and ligated into the XhoI (blunted) site of pβgalpAloxneo. The final targeting vector was linearised with NotI and electroporated into BRUCE 4 embryonic stem cells. After selection in G418, resistant clones were picked and expanded. Clones in which the targeting vector have recombined with the endogenous CIS gene are currently being identified by hybridising EcoRI-digested genomic DNA with a 0.8 kb BamHI-NdeI fragment from pgmCIS 57-7-1-26. This probe (probe A, FIG. 47), which is located 3' to the CIS sequences in the targeting vector, will distinguish between the endogenous (10 kb) and targeted (8 kb) CIS loci (FIG. 47).

EXAMPLE 44

SOCS-1 Fusion Proteins with Green Fluorescent Protein

The inventors consider that if the SOCS-1 protein is active as a fusion protein with an easily visualized marker, then this would be a valuable reagent for both monitoring expression and intracellular location of SOCS-1, as well as an extremely useful reagent for monitoring a cells response to cytokines (since production of SOCS-1 is tightly regulated by cytokine). In order to test whether SOCS-1 is active as a fusion protein, the inventors have made certain vectors. Briefly, using the PCR, a derivative of the mouse SOCS1 cDNA was generated that encoded an N-terminal GFP tag (MARQSKGEELFT . . . ELYKTR [SEQ ID NO:51]) preceding the coding region (minus ATG) of mSOCS1 (see FIG. 48A), designated pEF-GRP-I/mSOCS1. Details of mammalian expression vector pEF-GFP-I can be found at http://www.wehi.edu.au./willson vectors.

The activity of these constructs was then tested as follows.

A. Fluorescence detection:

Single cell suspensions of M1 cells transfected with EFBOS SOCS1/GFP fusion constructs were washed in balanced salts solution (BSS) supplemented with 2% v/v fetal calf serum (FCS) and resuspended in 50 µl of BSS containing 2% v/v FCS and 1 µg/ml propidium iodide. Analyses were performed on a FACScan cell sorter (Becton-Dickinson) with dead cells excluded by propidium iodide (1 mg/ml) staining. The results showed that M1 cells expressing wild type GFP (M1 GFP 7.1.12), M1 cells expressing SOCS-1 as an N-terminal fusion with GFP (M1 SOCS-1 GFP 5.15) and a C-terminal fusion with GTP (M1 GFP-SOCS-1 6.46) were fluorescent, in contrast to a negative control clone.

B. Inhibition of M1 differentiation:

The capacity of M1 cells expressing SOCS1/GFP fusion proteins to differentiate in response to IL-6 was assessed in agar cultures. 200 cells in DMEM containing 20% v/v FCS and 0.3% w/v agar were plated in 1 ml cultures in 35 mm Petri dishes stimulated serially diluted concentrations of IL-6. Colony numbers and morphology were scored after 7 days incubation at 37° C. in a fully humidified atmosphere of 10% v/v $CO_2$ in air. Undifferentiated colonies were compact while colonies composed of dispersed cells or which had a halo of migrating cells around a central core, were scored as differentiated. Importantly, as well as being fluorescent, both SOCS-1/GFP fusion proteins were also able to inhibit IL-6 induced differentiation of M1 cells when stably expressed.

SOCS-1 has previously been shown to inhibit the in vitro kinase activity of JAK2. This experiment examined the ability of SOCS-1-GFP and GFP-SOCS-1 proteins to inhibit the in vitro kinase activity of JAK2. Flag-tagged JAK2 was, therefore, transiently expressed by electroporation in Cos cells with and without co-expression of SOCS-1-GFP and GFP-SOCS-1. After 48 hours cells were lysed on ice and JAK2 proteins immunoprecipitated using 5 ml anti-JAK2 antibody (UBI). Immunoprecipitates were washed, and subjected to an in vitro kinase assay as previously described. Proteins were then separated by SDS-PAGE on a 4–15% w/v gradient gel and the gel treated with KOH to remove phosphoserine and phosphothreonine. Incorporation of radiolabelled phosphate was detected using a phosphoimager. The SOCS-1-GFP and GFP-SOCS-1 chimeric proteins were able to inhibit JAK2 kinase activity to the same extent as wild-type SOCS-1.

EXAMPLE 45

Control of SOCS Gene Transcription by Cytokine

The inventors have shown that socs gene transcription is regulated by a range of cytokines. These studies have been extended by the Northern blot analysis of mRNA from organs of mice injected with a range of cytokine and cells treated with cytokines. SOCS-1 and SOCS-3 expression in ES cells is strictly controlled by LIF, whereas LIF does not appear to tightly regulate either expression of SOCS-2 or CIS. The expression of the SOCS-1, SOCS-2, SOCS-3 and CIS genes in bone marrow, spleen and lung occurs in response to a range of cytokines such as IL-2, IL-4, IL-5, IL-7, IL-9, IL-13, M-CSF, SCF, FL, EPO, TPO, anti-μ and LGH. Furthermore, the regulation of SOCS genes in vivo by clinically important cytokines is highlighted by the injection of GM-CSF into mice and analysis of the bonemarrow, spleen and lung at various times afterward. For SOCS-1, SOCS-2, SOCS-3 and CIS there is evidence of transcriptional control by GM-CSF.

EXAMPLE 46

Cloning of SOCS cDNAs

DNA encoding the entire coding region of SOCS-13 has been constructed from cDNA and genomic DNA clones. Briefly, screening pulled out partial clones from both cDNA and genomic libraries, a full length coding region was generated by overlap PCR using a 5' genomic fragment and a 3' cDNA fragment. 5' oligo to the genomic fragment was made with an Asc1 site and the 3' oligo to the cDNa fragment was made with an Mlu1 site so that the stitched together coding region could be ligated straight into pEF Bos flag construct. 5' genomic SSB-1 Oligo No 3342

```
AGCT G GCG CGC C AG GGT CAG AAG GTC ACG GGA GGG [SEQ ID
NO: 58]

Asc 1          G   Q   K   V   T   G   G

3' genomic oligo No 3243
AAG TCC GTT CAA GTA GCG CAT GCG GAT CTC [SEQ ID NO: 52]

5' cDNA Oligo No 3244
GAG ATC CGC ATG CGC TAC TTG AAC GGA CTT [SEQ ID NO: 53]

E   I   R   M   R   Y   L   N   G   L (SEQ ID NO: 54)

3' cDNa Oligo No 3245
AGCT ACG CGT CTG GTA GAG GAG GTA GGC TTT GAG [SEQ ID NO:
55]

Mlu1
```

The resulting nucleotide and predicted amino acid sequences are shown in FIGS. 49 and 50.

Similarly complete DNA and predicted amino acid sequences of SOCS-5 and SOCS-9 are shown in FIGS. 51 A&B and 52 A&B.

Those skilled in the art will appreciate that the invention described herein is susceptible to variations and modifications other than those specifically described. It is to be understood that the invention includes all such variations and modifications. The invention also includes all of the steps, features, compositions and compounds referred to or indicated in this specification, individually or collectively, and any and all combinations of any two or more of said steps or features.

TABLE 4.1

Summary or ESTs derived from mouse SOCS-4 cDNAs

| SOCS | Species | EST name | End | EST no | Library source | Contig |
|---|---|---|---|---|---|---|
| SOCS-4 | Mouse | mc65f04 | 5' | EST0549700 | d13.5–14.5 mouse embryo | m4.1 |
|  |  | mf42e06 | 5' | EST0593477 | d13.5–14.5 mouse embryo | m4.1 |
|  |  | mp10c10 | 5' | EST0747905 | d8.5 mouse embryo | m4.1 |
|  |  | mr81g09 | 5' | EST0783081 | d13 embryo | m4.1 |
|  |  | mt19h12 | 5' | EST0816531 | spleen | m4.1 |

TABLE 4.2

Summary of ESTs derived from human SOCS-4 cDNAs

| SOCS | Species | EST name | End | EST no | Library source | Contig |
|---|---|---|---|---|---|---|
| SOCS-4 | Human | 27b5 | 5' | EST0534081 | retina | h4.2 |
| | | 30d2 | 5' | E5T0534315 | retina | h4.2 |
| | | J0159F | 5' | EST0461188 | foetal heart | h4.2 |
| | | J3802F | 5' | EST0461428 | foetal heart | h4.2 |
| | | EST19523 | 5' | EST0958884 | retina | h4.2 |
| | | EST81149 | 5' | EST1011015 | placenta | h4.2 |
| | | EST180909 | 5' | EST0951375 | Jurkat T-lymphocyte | h4.2 |
| | | EST182619 | 5' | EST0953220 | Jurkat T-lymphocyte | h4.1 |
| | | ya99h09 | 3' | EST0103262 | placenta | h4.2 |
| | | ye70c04 | 5' | EST0172673 | foetal liver/spleen | h4.2 |
| | | yh53c09 | 5' | EST0197390 | placenta | h4.2 |
| | | | 3' | EST0197391 | | h4.2 |
| | | yh77g11 | 5' | EST0203418 | placenta | h4.2 |
| | | | 3' | EST0203419 | | h4.1 |
| | | yh87h05 | 5' | EST0204888 | placenta | h4.1 |
| | | | 3' | EST0204773 | | h4.1 |
| | | yi45h07 | 5' | EST0246604 | placenta | h4.2 |
| | | yj04e06 | 5' | EST0258541 | placenta | h4.1 |
| | | | 3' | EST0258285 | | h4.1 |
| | | yq12h06 | 5' | EST0309968 | foetal liver spleen | h4.2 |
| | | yq56a06 | 3' | ES70346924 | foetal liver spleen | h4.2 |
| | | yq60e02 | 5' | EST0347259 | foetal liver spleen | h4.2 |
| | | | 3' | EST0347209 | | h4.2 |
| | | yq92g03 | 5' | EST0355932 | foetal liver spleen | h4.2 |
| | | | 3' | EST0355884 | | h4.2 |
| | | yq97h06 | 5' | EST0357618 | foetal liver spleen | h4.2 |
| | | | 3' | EST0357416 | | h4.2 |
| | | yr90f01 | 5' | EST0372402 | foetal liver spleen | h4.2 |
| | | yt69c03 | 5' | EST0338395 | foetal liver spleen | h4.2 |
| | | | 3' | EST0338303 | | h4.2 |
| | | yv30a08 | 3' | EST0458506 | foetal liver spleen | h4.2 |
| | | yv55f07 | 5' | EST0465391 | foetal liver spleen | h4.2 |
| | | | 3' | EST0463331 | | h4.2 |
| | | yv57h09 | 5' | EST0464336 | foetal liver spleen | h4.2 |
| | | | 3' | EST0458765 | | h4.2 |
| | | yv87h02 | 5' | EST0388085 | melanocyte | h4.2 |
| | | yv98e11 | 5' | EST0400679 | melanocyte | h4.2 |
| | | | 3' | EST0400680 | | h4.2 |
| | | yw68d10 | 5' | EST0441370 | placenta (8–9 wk) | h4.2 |
| | | yw82a03 | 5' | EST0463005 | placenta (8–9 wk) | h4.2 |
| | | | 3' | EST0433678 | | h4.1 |
| | | yx08a07 | 3' | EST0407016 | melanoocyte | h4.1 |
| | | yx72h06 | 5' | EST0435158 | melanocyte | h4.2 |
| | | | | EST0422871 | melanocyte | h4.1 |
| | | yx76b09 | 5' | EST0434011 | melanoocyte | h4.2 |
| | | yy37h08 | 5' | EST0451704 | melanocyte | h4.2 |
| | | yy66b02 | 5' | EST0505446 | multiple sclerosis lesion | h4.2 |
| | | za81f08 | 5' | EST0511777 | foetal lung | h4.2 |
| | | zbl8f07 | 3' | EST0485315 | foetal lung | h4.1 |
| | | zc06e08 | 5' | EST0540473 | parathyroid tumor | h4.1 |
| | | | 3' | EST0540354 | | h4.1 |
| | | zd14g06 | 3' | EST0564666 | foetal heart | h4.1 |
| | | zd51h12 | 3' | EST0578099 | foetal heart | h4.1 |
| | | zd52b09 | 5' | EST0582012 | foetal heart | h4.1 |
| | | | 3' | EST0581958 | | h4.1 |
| | | ze25g11 | 3' | EST0679543 | foetal heart | h4.1 |
| | | ze69f02 | 5' | EST0635563 | retina | h4.2 |
| | | | 3' | EST0635472 | | h4.1 |
| | | zf54f03 | 5' | EST0680111 | retina | h4.2 |
| | | zh96e07 | 5' | EST0616241 | foetal liver spleen | h4.2 |
| | | | 3' | EST0615745 | | h4.2 |
| | | zv66h12 | 5' | EST1043265 | 8–9w foetus | h4.2 |
| | | zs83a08 | 5' | EST0920072 | germinal centre B cell | h4.1 |
| | | | 3' | EST0920016 | | h4.1 |
| | | zs83g08 | 5' | EST0920121 | germinal centre B cell | h4.1 |
| | | | 3' | EST0920122 | | h4.1 |

TABLE 5.1

Summary of ESTs derived from mouse SOCS-5 cDNAs

| SOCS | Species | EST name | End | EST no | Library source | Contig |
|---|---|---|---|---|---|---|
| SOCS-5 | Mouse | mc55a01 | 5' | EST0541556 | d13.5–14.5 mouse embryo | m5.1 |
| | | mh98f09 | 5' | EST0638237 | placenta | m5.1 |
| | | my26h12 | 5' | EST0859939 | mixed organs | m5.1 |
| | | ve24e06 | 5' | EST0819106 | heart | m5.1 |

TABLE 5.2

Summary of ESTs derived from human SOCS-5 cDNAs

| SOCS | Species | EST name | End | EST no | Library source | Contig |
|---|---|---|---|---|---|---|
| SOCS-5 | Human | EST15B103 | ? | EST0258029 | adipose tissue | h5.1 |
| | | EST15B105 | ? | EST0258028 | adipose tissue | h5.1 |
| | | EST27530 | 5' | EST0965892 | cerebellum | h5.1 |
| | | zf50f01 | 5' | EST0679820 | retina | h5.1 |

TABLE 6.1

Summary of ESTs derived from mouse SOCS-6 cDNAs

| SOCS | Species | EST name | End | EST no | Library source | Contig |
|---|---|---|---|---|---|---|
| SOCS-6 | Mouse | mco4c05 | 5' | EST0525832 | d19.5 embryo | m6.1 |
| | | md48a03 | 5' | EST0566730 | d13.5–14.5 embryo | m6.1 |
| | | mf31d03 | 5' | EST0675970 | d13.5–14.5 embryo | m6.1 |
| | | mh26b07 | 5' | EST0628752 | d13 5–14.5 placenta | m6.1 |
| | | mh78e11 | 5' | EST0637608 | d13.5–14.5 placenta | m6.1 |
| | | mh88h09 | 5' | EST0644383 | d13.5–14.5 placenta | m6.1 |
| | | mh94h07 | 5' | EST0638078 | d13.5–14.5 placenta | m6.1 |
| | | mi27h04 | 5' | EST0644252 | d13.5–14.5 embryo | m6.1 |
| | | mj29c05 | 5' | EST0664093 | d13.5–14.5 embryo | m6.1 |
| | | mp66g04 | 5' | EST0757905 | thymus | m6.1 |
| | | mw75g03 | 5' | EST0847938 | liver | m6.1 |
| | | va53b05 | 5' | EST0901540 | d12.5 embryo | m6.1 |
| | | vb34h02 | 5' | EST0930132 | lymph node | m6.1 |
| | | vc55d07 | 3' | EST1057735 | 2 cell embryo | m6.1 |
| | | vc59e05 | 3' | EST1058201 | 2 cell embryo | m6 1 |
| | | vc67d03 | 3' | EST1057849 | 2 cell embryo | m6.1 |
| | | vc68d10 | 3' | EST1058663 | 2 cell embryo | m6.1 |
| | | vc97h01 | 3' | EST1059343 | 2 cell embryo | m6.1 |
| | | vc99c08 | 3' | EST1059410 | 2 cell embryo | m6.1 |
| | | vd07h03 | 3' | EST1058173 | 2 cell embryo | m6.1 |
| | | vd08c01 | 3' | EST1058275 | 2 cell embryo | m6.1 |
| | | vd09b12 | 3' | EST1058632 | 2 cell embryo | m6.1 |
| | | vd19b02 | 3' | EST1059723 | 2 cell embryo | m6.1 |
| | | vd29a04 | 3' | ? none found | | m6.1 |
| | | vd46d06 | 3' | ? none found | | m6.1 |

TABLE 6.2

Summary of ESTs derived from human SOCS-5 cDNAs

| SOCS | Species | EST name | End | EST no | Library source | Contig |
|---|---|---|---|---|---|---|
| SOCS-6 | Human | yf61e08 | 5' | EST0184387 | d73 infant brain | h6.1 |
| | | yf93a09 | 5' | EST0186084 | d73 infant brain | h6.1 |
| | | yg05f12 | 5' | EST0191486 | d73 infant brain | h6.1 |
| | | yg41f04 | 5' | EST0195017 | d73 infant brain | h6.1 |
| | | yg45c02 | 5' | EST0185308 | d73 infant brain | h6.1 |
| | | yh11f10 | 5' | EST0236705 | d73 infant brain | h6.1 |
| | | yh13b05 | 5' | EST0237191 | d73 infant brain | h6.1 |
| | | | 3' | EST0236958 | | h6.2 |
| | | zc35a12 | 5' | EST0555518 | senescent fibroblasts | h6.1 |
| | | ze02h08 | 5' | EST0603826 | foetal heart | h6.1 |
| | | | 3' | EST0603718 | | h6.2 |
| | | zl09a03 | 5' | EST0773936 | pregnant uterus | h6.1 |

TABLE 6.2-continued

Summary of ESTs derived from human SOCS-5 cDNAs

| SOCS | Species | EST name | End | EST no | Library source | Contig |
|---|---|---|---|---|---|---|
| | | | 3' | EST0773892 | | h6.1 |
| | | zl69e10 | 5' | EST0683363 | colon | h6.1 |
| | | zn39d08 | 5' | EST0718885 | endothelial cell | h6.1 |
| | | zo39e06 | 5' | EST0785947 | endothelial cell | h6.1 |

TABLE 7.1

Summary of ESTs derived from mouse SOCS-7 cDNAs

| SOCS | Species | EST name | End | EST no | Library source | Contig |
|---|---|---|---|---|---|---|
| SOCS-7 | Mouse | mj39a01 | 5' | EST0665627 | d13.5/14.5 embryo | m7.1 |
| | | vi52h07 | 5' | EST1267404 | d7.5 embryo | m7.1 |

TABLE 7.2

Summary of ESTs derived from human SOCS-5 cDNAs

| SOCS | Species | EST name | End | EST no | Library source | Contig |
|---|---|---|---|---|---|---|
| SOCS-7 | HUMAN | STS WI-30171 | | (G21563) | Chromosome 2 | h7.2 |
| | | EST00939 | 5' | EST0000906 | hippocampus | h7.1 |
| | | EST12913 | 3' | EST0944382 | uterus | h7.2 |
| | | yc29b05 | 3' | EST0128727 | liver | h7.2 |
| | | yp49f10 | 3' | EST0301914 | retina | h7.2 |
| | | zt10f03 | 5' | EST0922932 | germinal centre B cell | h7.2 |
| | | | 3' | EST0921231 | | h7.1 |
| | | zx73g04 | 3' | EST1102975 | ovarian tumour | h7.1 |

TABLE 8.1

Summary of ESTs derived from mouse SOCS-8 cDNAs

| SOCS | Species | EST name | End | EST no | Library source | Contig |
|---|---|---|---|---|---|---|
| SOCS-8 | Mouse | mj16e09 | r1 | EST0666240 | d13.5/14.5 embryo | m8.1 |
| | | vj27a029 | r1 | EST1155973 | heart | m8.1 |

TABLE 9.1

Summary of ESTs derived from mouse SOCS-9 cDNAs

| SOCS | Species | EST name | End | EST no | Library source | Contig |
|---|---|---|---|---|---|---|
| | Mouse | me65d05 | 5' | EST0585211 | d 13.5/14.5 embryo | m9.1 |

TABLE 9.2

Summary of ESTs derived from human SOCS-5 cDNAs

| SOCS | Species | EST name | End | EST no | Library source | Contig |
|---|---|---|---|---|---|---|
| SOCS-9 | Human | CSRL-83f2-u | | (B06659) | chromosome 11 | h9.1 |
| | | EST114054 | 5' | EST0939759 | placenta | h9.1 |
| | | yy06b07 | 3' | EST0434504 | melanocyte | h9.1 |
| | | yy06g06 | 5' | EST0443783 | melanocyte | h9.1 |
| | | zr40c09 | 5' | EST0832461 | melanocyte, heart, uterus | h9.1 |
| | | zr72h01 | 5' | EST0892025 | melanocyte, heart, uterus | h9.1 |
| | | | 3' | EST0892026 | | h9.1 |
| | | yx92c08 | 5' | EST0441160 | melanocyte | h9.1 |

TABLE 9.2-continued

Summary of ESTs derived from human SOCS-5 cDNAs

| SOCS | Species | EST name | End | EST no | Library source | Contig |
|------|---------|----------|-----|--------|----------------|--------|
|      |         | yx93b08  | 5'  | EST0441260 | melanocyte | h9.1 |
|      |         | hfe0662  | 5'  | EST0889611 | foetal heart | h9.1 |

TABLE 10.1

Summary of ESTs derived from mouse SOCS-10 cDNAs

| SOCS | Species | EST name | End | EST no | Library source | Contig |
|------|---------|----------|-----|--------|----------------|--------|
|      | Mouse   | mb14d12  | 5'  | EST0549887 | d19.5 embryo | m10.1 |
|      |         | mb40f06  | 5'  | EST0515064 | d19.5 embryo | m10.1 |
|      |         | mg89b11  | 5'  | EST0630631 | d13.5–14.5 embryo | m10.1 |
|      |         | mq89e12  | 5'  | EST0776015 | heart | m10.1 |
|      |         | mp03g12  | 5'  | EST0741991 | heart | m10.1 |
|      |         | vh53c11  | 5'  | EST1154634 | mammary gland | m10.1 |

TABLE 10.2

Summary of ESTs derived from human SOCS-5 cDNAs

| SOCS | Species | EST name | End | EST no | Library source | Contig |
|------|---------|----------|-----|--------|----------------|--------|
| SOCS-10 | Human | aa48h10 | 3' | EST1135220 | germinal centre B cell | h10.2 |
|         |       | zp35h01 | 3' | EST0819137 | muscle | h10.2 |
|         |       | zp97h12 | 5' | EST0835442 | muscle | h10.2 |
|         |       |         | 3' | EST0831211 |        | h10.2 |
|         |       | zq08h01 | 5' | EST0835907 | muscle | h10.1 |
|         |       | zr34g05 | 5' | EST0834251 | melanocyte, heart, uterus | h10.2 |
|         |       |         | 3' | EST0834440 |        | h10.2 |
|         |       | EST73000 | 5' | EST1004491 | ovary | h10.2 |
|         |       | HSDHE1005 | ? | EST0013906 | heart | h10.2 |

TABLE 11.1

5/28 Summary of ESTs derived from human SOCS-5 cDNAs

| SOCS | Species | EST name | End | EST no | Library source | Contig |
|------|---------|----------|-----|--------|----------------|--------|
| SOCS-11 | Human | zt24h06 | r1 | EST0926023 | ovarian tumor | 11.2 |
|         |       | zr43b02 | r1 | EST0873006 | melanocyte, heart, uterus | 11.1 |
|         |       |         | s1 | EST0872954 |        | 11.1 |

TABLE 12.1

Summary of ESTs derived from mouse SOCS-12 cDNAs

| SOCS | Species | EST name | End | EST no | Library source | Contig |
|------|---------|----------|-----|--------|----------------|--------|
| SOCS-12 | Mouse | EST03803 | 5' | EST1054173 | day 7.5 emb ecto- placental cone | m12.1 |
|         |       | mt18f02  | 5' | EST0817652 | 3NbMS spleen | m12.1 |
|         |       | mz60g10  | 5' | EST0890872 | lymph node | m12.1 |
|         |       | va05c11  | 5' | EST0909449 | lymph node | m12.1 |

TABLE 12.2

Summary of ESTs derived from human SOCS-5 cDNAs

| SOCS | Species | EST name | End | EST no | Library source | Contig |
|---|---|---|---|---|---|---|
| SOCS-12 | Human | STS-SHGC-13867 | | | Chromosome 2 | h12.2 |
| | | EST177695 | 5' | EST0948071 | Jurkat cells | h12.1 |
| | | EST64550 | 5' | EST0997367 | Jurkat cells | h12.1 |
| | | EST76868 | 5' | EST1007291 | pineal body | h12.2 |
| | | PMY2369 | 5' | EST1115998 | KG-1 | h12.1 |
| | | yb38f04 | 5' | EST0108807 | foetal spleen | h12.1 |
| | | | 3' | | | h12.2 |
| | | yg74e12 | 5' | EST0224407 | d73 brain | h12.1 |
| | | yh13g04 | 5' | EST0237226 | d73 brain | h12.1 |
| | | | 3' | EST0236992 | | h12.2 |
| | | yh48b06 | 5' | yh48b06 | placenta | h12.2 |
| | | yh53a05 | 5' | EST0197282 | placenta | h12.2 |
| | | | 3' | EST0197486 | | h12.2 |
| | | yn48h09 | 5' | EST0278258 | brain | h12.2 |
| | | | 3' | EST0278259 | | h12.2 |
| | | yn90a09 | 3' | EST0302557 | brain | h12.2 |
| | | yo08f03 | 5' | EST0301790 | brain | h12.2 |
| | | | 3' | EST0302059 | | h12.2 |
| | | yo11e01 | 3' | ? none found | | h12.2 |
| | | yo63b12 | 5' | EST0303606 | breast | h12.2 |
| | | | 3' | EST0304085 | | h12.2 |
| | | yq56g02 | 3' | EST0346935 | foetal liver spleen | h12.1 |
| | | zh57c04 | 3' | EST0594201 | foetal liver spleen | h12.2 |
| | | zh79h01 | 3' | EST0598945 | foetal liver spleen | h12.2 |
| | | zh99a11 | 3' | EST0618570 | foetal liver spleen | h12.2 |
| | | zo92h12 | 5' | EST0803392 | ovarian cancer | h12.1 |
| | | | 3' | EST0803393 | | h12.2 |
| | | zs48c01 | 5' | EST0925714 | germinal centre B cell | h12.1 |
| | | | 3' | EST0925530 | | h12.2 |
| | | zs45h02 | 3' | EST0932296 | germinal centre B cell | h12.2 |

TABLE 13.1

Summary of ESTs derived from mouse SOCS-13 cDNAs

| SOCS | Species | EST name | End | EST no | Library source | Contig |
|---|---|---|---|---|---|---|
| SOCS-13 | Mouse | ma39c09 | 5' | EST0517875 | day 19.5 embryo | m13.1 |
| | | me60c05 | 5' | EST0584950 | day 13.5/14.5 embryo | m13.1 |
| | | mi78g05 | 5' | EST0653834 | day 19.5 embryo | m13.1 |
| | | mk10c11 | 5' | EST0735158 | day 19.5 embryo | m13.1 |
| | | mo48g12 | 5' | EST0745111 | day 10.5 embryo | m13.1 |
| | | mp94a01 | 5' | EST0762827 | thymus | m13.1 |
| | | vb57c07 | 5' | EST1028976 | day 11.5 embryo | m13.1 |
| | | vh07c11 | 5' | EST1117269 | mammary gland | m13.1 |

TABLE 13.2

Summary of ESTs derived from human SOCS-13 cDNAs

| SOCS | Species | EST name | End | EST no | Library source | Contig |
|---|---|---|---|---|---|---|
| SOCS-13 | Human | EST59161 | 5' | EST0992726 | infant brain | h13.1 |

TABLE 14.1

Summary of ESTs derived from mouse SOCS-14 cDNAs

| SOCS | Species | EST name | End | EST no | Library source | Contig |
|---|---|---|---|---|---|---|
| SOCS-14 | mouse | mi75e03 | 5' | EST0651892 | d19.5 embryo | m14.1 |
| | | vd29h11 | 5' | EST1067080 | 2 cell embryo | m14.1 |
| | | vd53g07 | 5' | EST1119627 | 2 cell embryo | m14.1 |

TABLE 15.1

Summary of ESTs derived from mouse SOCS-15 cDNAs

| SOCS | Species | EST name | End | EST no | Library source | Contig |
|---|---|---|---|---|---|---|
| SOCS-15 | Mouse | mh29b05 | 5' | EST0628834 | placenta | m15.1 |
| | | mh98h09 | 5' | EST0638243 | placenta | m15.1 |
| | | ml45a02 | 5' | EST0687171 | testis | m15.1 |
| | | mu43a10 | 5' | EST851588 | thymus | m15.1 |
| | | my38c09 | 5' | EST878461 | pooled organs | m15.1 |
| | | vj37h07 | 5' | EST1174791 | diaphragm | m15.1 |
| | | AC002393 | | | Chromosome 6 BAC | m15.1 |

TABLE 15.2

Summary of ESTs derived from human SOCS-15 cDNAs

| SOCS | Species | EST name | End | EST no | Library source | Contig |
|---|---|---|---|---|---|---|
| SOCS-15 | Human | EST98889 | 5' | EST1026568 | thyroid | h15.1 |
| | | ne48bo5 | 3' | EST1138057 | colon tumour | h15.1 |
| | | yb12h12 | 5' | EST0098885 | placenta | h15.1 |
| | | | 3' | EST0098886 | | h15 1 |
| | | HSU47924 | | | Chromosome 12 BAC | h15 1 |

BIBLIOGRAPHY

Alexander W S, Metcalf D and Dunn A R (1995). *Embo Journal* 14, 5569–78.

Altschul, S. F. Gish, W. Miller, W. Myers, E. W. & Lipman, D. J. (1990) *J. Mol. Biol.* 215, 403–10.

Ansari-Lari, M. A., Shen, Y., Munzy, D. M., Lee, W. and Gibbs, R. A. (1997) *Genome. Res.* 7, 268–280.

Bazan J F (1990). [Review]. *Immunology Today* 11, 350–4.

Bork, P. (1993) *Proteins: Struct. Funct. Genet.* 17, 363–374.

Cockwell, L. Y. and Giles, I. G. (1989) *Comp. Appl. Biosci* 5, 227–232.

Cutler R L, Liu L, Damen J E and Krystal G (1993). *Journal of Biological Chemistry* 268, 21463–5.

Darnell J Jr., Kerr I M and Stark G R (1994). *Science* 264, 1415–21.

David M, Petricoin E3, Benjamin C, Pine R, Weber M J and Larner A C (1995). *Science* 269, 1721–3.

David M, Wong L, Flavell R, Thompson S A, Wells A, Larner A C and Johnson G R (1996). *Journal of Biological Chemistry* 271, 9185–8.

Dugaiczyk A, Haron J A, Stone E M, Dennison O E, Rothblum K N and Schwartz R J (1983). *Biochemistry* 22, 1605–13.

Durbin J E, Hackenmiller R, Simon M C and Levy D E (1996). *Cell* 84, 443–50.

Etzold, T., Ulyanov, A. and Argos, P. (1996) *Methods Enzymol.* 266, 114–28.

Gearing D P, Nicola N A, Metcalf D, Foote S, Willson T A, Gough N M and Williams L (1989). *BioTechnology* 7, 1157–1161.

Gupta S, Yan H, Wong L H, Ralph S, Krolewski J and Schindler C (1996). *Embo Journal* 15, 1075–84.

Hilton D J (1994). An introduction to cytokine receptors, p8–16 in *Guidebook to Cytokines and Their Receptors*, Eds: N. A. Nicola. Oxford University Press: Oxford.

Hilton D J, Hilton A A, Raicevic A, Rakar S, Harrison-Smith M, Gough N M, Begley C G, Metcalf D, Nicola N A and Willson T A (1994). *Embo Journal* 13, 4765–75.

Hilton D J, Watowich S S, Katz L and Lodish H F (1996). *J. Biol. Chem.* 271, 4699–4708.

Horton et al. 1989, *Gene,* 77: 61–68.

Ichikawa Y (1969). *Journal of Cellular Physiology* 74, 223–34.

Ihle J N, Witthuhn B A, Quelle F W, Yamamoto K and Silvennoinen O (1995). *Annual Review of Immunology* 13, 369–98.

Ihle J N (1995). *Nature* 377, 591–4.

Kaplan M H, Sun Y L, Hoey T and Grusby M J (1996b). *Nature* 382, 174–179.

Kaplan M H, Schindler U, Smiley S T and Grusby M J (1996a). *Immunity* 4, 313–9.

Levy D E and Stark G R (1996). *Molecular & Cellular Biology* 16, 369–75.

Masuhara, M., Sakamoto, H., Matsumoto, A., Suzuki, R., Yasukawa, H., Mitsui, K., Wakioka, T., Tanimura, S., Sasaki, A., Misawa, H.., Yokouchi, M., Ohtsubo, M. & Yoshimura, A. Cloning and characterization of novel CIS family genes (1997) Biochem. Biophys. Res. Comm., 239, 439–446.

Masuhara et al. 1997, *Biochem. Biophys. Res. Comm.,* 239: 439–446.

Meraz M A, White J M, Sheehan K C, Bach E A, Rodig S J, Dighe A S, Kaplan D H, Riley J K, Greenlund A C, Campbell D, Carver-Moore K, DuBois R N, Clark R, Aguet M and Schreiber R D (1996). *Cell* 84, 431–42.

Metcalf D, Wilson T A, Hilton D J, DiRago L and Mifsud S. (1995) *Leukaemia* 9, 1556–1564.

Metcalf, D. (1984) Clonal culture of hemopoietic cells: Techniques and applications, pp. 19–72, Elsevier, Amsterdam, The Netherlands.

Mizushima S and Nagata S (1990). *Nucleic Acids Research* 18, 5322.

Murakami M, Narazaki M, Hibi M, Yawata H, Yasukawa K, Hamaguchi M, Taga T and Kishimoto T (1991). *Proc. Natl. Acad. Sci. USA* 88, 11349–11353.

Neer, E. J., Schmidt, C. J., Nambudripad, R. and Smith, T. F. (1994) *Nature* 371, 297–300.

Nicholson et al. 1995, *Blood;* 86: 3698–3704.

Nicholson, S. E., Novak, U., Ziegler, S. F. & Layton, J. E. Distinct regions of the granulocyte colony-stimulating factor receptor are required for tyrosine phosphorylation of the signaling molecules JAK2, Stat3, and p42, p44MAPK (1995) Blood, 86,3698–3704.

Nicola, N V, Viney E, Hilton D J, Roberts B and Wilson T. (1996) *Growth Factors* 13, 141–149.

Nicola N A ((1994). *Guidebook to Cytokines and Their Receptors.* Oxford University Press: Oxford.

Novak U, Harpur A G, Paradiso L, Kanagasundaram V, Jaworowski A, Wilks A F and Hamilton J A (1995). *Blood* 86, 2948–56.

Ogilvy, S., Elefanty, A. G., Visvader, J., Bath, M. L., Harris, A. W. and Adams, J. M. (1998) Transcriptional regulation of vav, a gene expressed throughout the hematopoietic compartment. Blood, 91(2), 419–430.

Pearson W R and Lipman D J. (1988) *Proc. Natl. Acad. Sci. USA* 85, 2444–8.

Pearson W R. (1990) *Methods Enzymol.* 183, 63–98.

Rayner J R and Gonda T J (1994). *Molecular & Cellular Biology* 14, 880–7.

Sambrook J, Fritsch E F and Maniatis T (1989). *Molecular Cloning, A Laboratory Manual.* Cold Spring Harbour Laboratory Press, Cold Spring Harbour USA.

Sato N, Sakamaki K, Terada N, Arai K and Miyajima A (1993). *Embo Journal* 12, 4181–9.

Shimoda K, van Deursen J, Sangster M Y, Sarawar S R, Carson R T, Tripp R A, Chu C, Quelle F W, Nosaka T, Vignali D A, Doherty P C, Grosveld G, Paul W E and Ihle J N (1996). *Nature* 380, 630–3.

Shual K, Ziemiecki A, Wilks A F, Harpur A G, Sadowski H B, Gilman M Z and Darnell J E (1993). *Nature* 366, 580–3.

Sprang S R and Bazan J F (1993). *Curr. Opin. Structural Biol.* 3, 815–827.

Starr, R., Willson, T. A., Viney, E. M., Murray, L. J. L., Rayner, J. R., Jenkins, B. J., Gonda, T. J., Alexander, W. S., Metcalf, D., Nicola, N. A. & Hilton, D. J. A family of cytokine-inducible inhibitors of signalling (1997) Nature, 386, 917–921.

Starr et al. 1997, *Nature,* 386: 917–921.

Takeda K, Tanaka T, Shi W, Matsumoto M, Minami M, Kashiwamura S, Nakanishi K, Yoshida N, Kishimoto T and Akira S (1996). *Nature* 380, 627–30.

Thierfelder W E, Vandeursen J M, Yamamoto K, Tripp R A, Sarawar S R, Carson R T, Sangster M Y, Vignali D D A, Doherty P C, Grosveld G C and Ihle J N (1996). *Nature* 382, 171–174.

Wakao H, Gouilleux F and Groner B (1994). *Embo Journal* 13, 2182–91.

Wen Z, Zhong Z and Darnell J Jr. (1995). *Cell* 82, 241–50.

Yi T, Mui A L, Krystal G and Ihle J N (1993). *Molecular & Cellular Biology* 13, 7577–86.

Yoshimura A, Ohkubo T, Kiguchi T, Jenkins N A, Gilbert D J, Copeland N G, Hara T and Miyajima A (1995). *Embo Journal* 14, 2816–26.

---

SEQUENCE LISTING

```
<160> NUMBER OF SEQ ID NOS: 81

<210> SEQ ID NO 1
<211> LENGTH: 20
<212> TYPE: DNA
<213> ORGANISM: Artificial Sequence
<220> FEATURE:
<223> OTHER INFORMATION: Description of Artificial Sequence:Synthetic

<400> SEQUENCE: 1
cacgccgccc acgtgaaggc                                                   20

<210> SEQ ID NO 2
<211> LENGTH: 20
<212> TYPE: DNA
<213> ORGANISM: Artificial Sequence
<220> FEATURE:
<223> OTHER INFORMATION: Description of Artificial Sequence:Synthetic

<400> SEQUENCE: 2
ttcgccaatg acaagacgct                                                   20

<210> SEQ ID NO 3
<211> LENGTH: 1235
<212> TYPE: DNA
<213> ORGANISM: Mouse
<220> FEATURE:
<221> NAME/KEY: CDS
<222> LOCATION: (161)..(796)

<400> SEQUENCE: 3
cgaggctcaa gctccgggcg gattctgcgt gccgctctcg ctccttgggg tctgttggcc      60 yggcctgtgcc acccggacgc ccggctcact gcctctgtct cccccatcag cgcagccccg    120
gacgctatgg cccacccctc cagctggccc ctcgagtagg atg gta gca cgc aac       175
                                             Met Val Ala Arg Asn
                                              1               5 cag gtg gca gcc gac aat gcg atc tcc ccg gca gca gag ccc cga cgg       223
Gln Val Ala Ala Asp Asn Ala Ile Ser Pro Ala Ala Glu Pro Arg Arg
             10                  15                  20 cgg tca gag ccc tcc tcg tcc tcg tct tcg tcc tcg cca gcg gcc ccc       271
Arg Ser Glu Pro Ser Ser Ser Ser Ser Ser Ser Pro Ala Ala Pro
         25                  30                  35 gtg cgt ccc cgg ccc tgc ccg gcg gtc cca gcc cca gcc cct ggc gac       319
Val Arg Pro Arg Pro Cys Pro Ala Val Pro Ala Pro Ala Pro Gly Asp
     40                  45                  50 act cac ttc cgc acc ttc cgc tcc cac tcc gat tac cgg cgc atc acg       367
Thr His Phe Arg Thr Phe Arg Ser His Ser Asp Tyr Arg Arg Ile Thr
 55                  60                  65 cgg acc agc gcg ctc ctg gac gcc tgc ggc ttc tat tgg gga ccc ctg       415
Arg Thr Ser Ala Leu Leu Asp Ala Cys Gly Phe Tyr Trp Gly Pro Leu
 70                  75                  80                  85 agc gtg cac ggg gcg cac gag cgg ctg cgt gcc gag ccc gtg ggc acc       463
```

| | | | | | | | | | | | | | | | |
|---|---|---|---|---|---|---|---|---|---|---|---|---|---|---|---|
| Ser | Val | His | Gly | Ala | His | Glu | Arg | Leu | Arg | Ala | Glu | Pro | Val | Gly | Thr |
| | | | | 90 | | | | 95 | | | | | 100 | | |

```
ttc ttg gtg cgc gac agt cgt caa cgg aac tgc ttc ttc gcg ctc agc      511
Phe Leu Val Arg Asp Ser Arg Gln Arg Asn Cys Phe Phe Ala Leu Ser
            105                 110                 115 gtg aag atg gct tcg ggc ccc acg agc atc cgc gtg cac ttc cag gcc      559
Val Lys Met Ala Ser Gly Pro Thr Ser Ile Arg Val His Phe Gln Ala
        120                 125                 130 ggc cgc ttc cac ttg gac ggc agc cgc gag acc ttc gac tgc ctt ttc      607
Gly Arg Phe His Leu Asp Gly Ser Arg Glu Thr Phe Asp Cys Leu Phe
    135                 140                 145 gag ctg ctg gag cac tac gtg gcg gcg ccg cgc cgc atg ttg ggg gcc      655
Glu Leu Leu Glu His Tyr Val Ala Ala Pro Arg Arg Met Leu Gly Ala
150                 155                 160                 165 ccg ctg cgc cag cgc cgc gtg cgg ccg ctg cag gag ctg tgt cgc cag      703
Pro Leu Arg Gln Arg Arg Val Arg Pro Leu Gln Glu Leu Cys Arg Gln
                170                 175                 180 cgc atc gtg gcc gcc gtg ggt cgc gag aac ctg gcg cgc atc cct ctt      751
Arg Ile Val Ala Ala Val Gly Arg Glu Asn Leu Ala Arg Ile Pro Leu
            185                 190                 195 aac ccg gta ctc cgt gac tac ctg agt tcc ttc ccc ttc cag atc          796
Asn Pro Val Leu Arg Asp Tyr Leu Ser Ser Phe Pro Phe Gln Ile
        200                 205                 210 tgaccggctg ccgctgtgcc gcagcattaa gtgggggcgc cttattattt cttattatta    856
attattatta tttttctgga accacgtggg agccctcccc gcctgggtcg gagggagtgg    916
ttgtggaggg tgagatgcct cccacttctg gctggagacc tcatcccacc tctcagggggt   976
gggggtgctc ccctcctggt gctccctccg ggtccccccct ggttgtagca gcttgtgtct   1036
ggggccagga cctgaattcc actcctacct ctccatgttt acatattccc agtatctttg    1096
cacaaaccag gggtcgggga gggtctctgg cttcattttt ctgctgtgca gaatatccta    1156
ttttatattt ttacagccag tttaggtaat aaactttatt atgaaagttt tttttttaaaa   1216
gaaaaaaaaa aaaaaaaaa                                                 1235
```

<210> SEQ ID NO 4
<211> LENGTH: 212
<212> TYPE: PRT
<213> ORGANISM: Mouse

<400> SEQUENCE: 4

| | | | | | | | | | | | | | | | |
|---|---|---|---|---|---|---|---|---|---|---|---|---|---|---|---|
| Met | Val | Ala | Arg | Asn | Gln | Val | Ala | Ala | Asp | Asn | Ala | Ile | Ser | Pro | Ala |
| 1 | | | | 5 | | | | | 10 | | | | | 15 | |
| Ala | Glu | Pro | Arg | Arg | Arg | Ser | Glu | Pro | Ser | Ser | Ser | Ser | Ser | Ser | Ser |
| | | | 20 | | | | | 25 | | | | | 30 | | |
| Ser | Pro | Ala | Ala | Pro | Val | Arg | Pro | Arg | Pro | Cys | Pro | Ala | Val | Pro | Ala |
| | | | 35 | | | | | 40 | | | | | 45 | | |
| Pro | Ala | Pro | Gly | Asp | Thr | His | Phe | Arg | Thr | Phe | Arg | Ser | His | Ser | Asp |
| | | 50 | | | | | 55 | | | | | 60 | | | |
| Tyr | Arg | Arg | Ile | Thr | Arg | Thr | Ser | Ala | Leu | Leu | Asp | Ala | Cys | Gly | Phe |
| 65 | | | | | 70 | | | | | 75 | | | | | 80 |
| Tyr | Trp | Gly | Pro | Leu | Ser | Val | His | Gly | Ala | His | Glu | Arg | Leu | Arg | Ala |
| | | | | 85 | | | | | 90 | | | | | 95 | |
| Glu | Pro | Val | Gly | Thr | Phe | Leu | Val | Arg | Asp | Ser | Arg | Gln | Arg | Asn | Cys |
| | | | 100 | | | | | 105 | | | | | 110 | | |
| Phe | Phe | Ala | Leu | Ser | Val | Lys | Met | Ala | Ser | Gly | Pro | Thr | Ser | Ile | Arg |
| | | | 115 | | | | | 120 | | | | | 125 | | |

-continued

```
Val His Phe Gln Ala Gly Arg Phe His Leu Asp Gly Ser Arg Glu Thr
    130                 135                 140
Phe Asp Cys Leu Phe Glu Leu Leu Glu His Tyr Val Ala Ala Pro Arg
145                 150                 155                 160
Arg Met Leu Gly Ala Pro Leu Arg Gln Arg Val Arg Pro Leu Gln
                165                 170                 175
Glu Leu Cys Arg Gln Arg Ile Val Ala Ala Val Gly Arg Glu Asn Leu
            180                 185                 190
Ala Arg Ile Pro Leu Asn Pro Val Leu Arg Asp Tyr Leu Ser Ser Phe
        195                 200                 205
Pro Phe Gln Ile
    210
```

<210> SEQ ID NO 5
<211> LENGTH: 1121
<212> TYPE: DNA
<213> ORGANISM: Mouse
<220> FEATURE:
<221> NAME/KEY: CDS
<222> LOCATION: (223)..(816)

<400> SEQUENCE: 5

```
gcgatctgtg ggtgacagtg tctgcgagag actttgccac accattctgc cggaatttgg    60
agaaaaagaa ccagccgctt ccagtcccct ccccctccgc caccatttcg dacaccctgc   120
acactctcgt tttggggtac cctgtgactt ccaggcagca cgcgaggtcc actggcccca   180
gctcgggcga ccagctgtct gggacgtgtt gactcatctc cc atg acc ctg cgg      234
                                                  Met Thr Leu Arg
                                                    1 tgc ctg gag ccc tcc ggg aat gga gcg gac agg acg cgg agc cag tgg    282
Cys Leu Glu Pro Ser Gly Asn Gly Ala Asp Arg Thr Arg Ser Gln Trp
  5                  10                  15                  20 ggg acc gcg ggg ttg ccg gag gaa cag tcc ccc gag gcg gcg cgt ctg    330
Gly Thr Ala Gly Leu Pro Glu Glu Gln Ser Pro Glu Ala Ala Arg Leu
                 25                  30                  35 gcg aaa gcc ctg cgc gag ctc agt caa aca gga tgg tac tgg gga agt    378
Ala Lys Ala Leu Arg Glu Leu Ser Gln Thr Gly Trp Tyr Trp Gly Ser
             40                  45                  50 atg act gtt aat gaa gcc aaa gag aaa tta aaa gag gct cca gaa gga    426
Met Thr Val Asn Glu Ala Lys Glu Lys Leu Lys Glu Ala Pro Glu Gly
         55                  60                  65 act ttc ttg att aga gat agt tcg cat tca gac tac cta cta act ata    474
Thr Phe Leu Ile Arg Asp Ser Ser His Ser Asp Tyr Leu Leu Thr Ile
     70                  75                  80 tcc gtt aag acg tca gct gga ccg act aac ctg cgg att gag tac caa    522
Ser Val Lys Thr Ser Ala Gly Pro Thr Asn Leu Arg Ile Glu Tyr Gln
 85                  90                  95                 100 gat ggg aaa ttc aga ttg gat tct atc ata tgt gtc aag tcc aag ctt    570
Asp Gly Lys Phe Arg Leu Asp Ser Ile Ile Cys Val Lys Ser Lys Leu
                105                 110                 115 aaa cag ttt gac agt gtg gtt cat ctg att gac tac tat gtc cag atg    618
Lys Gln Phe Asp Ser Val Val His Leu Ile Asp Tyr Tyr Val Gln Met
            120                 125                 130 tgc aag gat aaa cgg aca ggc cca gaa gcc cca cgg aat ggg act gtt    666
Cys Lys Asp Lys Arg Thr Gly Pro Glu Ala Pro Arg Asn Gly Thr Val
        135                 140                 145 cac ctg tac ctg acc aaa cct ctg tat aca tca gca ccc act ctg cag    714
His Leu Tyr Leu Thr Lys Pro Leu Tyr Thr Ser Ala Pro Thr Leu Gln
    150                 155                 160
```

```
cat ttc tgt cga ctc gcc att aac aaa tgt acc ggt acg atc tgg gga      762
His Phe Cys Arg Leu Ala Ile Asn Lys Cys Thr Gly Thr Ile Trp Gly
165                 170                 175                 180 ctg cct tta cca aca aga cta aaa gat tac ttg gaa gaa tat aaa ttc      810
Leu Pro Leu Pro Thr Arg Leu Lys Asp Tyr Leu Glu Glu Tyr Lys Phe
                185                 190                 195 cag gta taagtatttc tctctctttt tcgtttttt ttaaaaaaaa aaaaacacat        866
Gln Val gcctcatata gactatctcc gaatgcagct atgtgaaaga gaacccagag gccctcctct    926
ggataactgc gcagaattct ctcttaagga cagttgggct cagtctaact taaaggtgtg    986
aagatgtagc taggtatttt aaagttcccc ttaggtagtt ttagctgaat gatgctttct   1046
ttcctatggc tgctcaagat caaatggccc ttttaaatga aacaaacaa aacaaaacaa    1106 aaaaaaaaaa aaaaa                                                    1121

<210> SEQ ID NO 6
<211> LENGTH: 198
<212> TYPE: PRT
<213> ORGANISM: Mouse

<400> SEQUENCE: 6

Met Thr Leu Arg Cys Leu Glu Pro Ser Gly Asn Gly Ala Asp Arg Thr
1               5                   10                  15

Arg Ser Gln Trp Gly Thr Ala Gly Leu Pro Glu Glu Gln Ser Pro Glu
            20                  25                  30

Ala Ala Arg Leu Ala Lys Ala Leu Arg Glu Leu Ser Gln Thr Gly Trp
        35                  40                  45

Tyr Trp Gly Ser Met Thr Val Asn Glu Ala Lys Glu Lys Leu Lys Glu
    50                  55                  60

Ala Pro Glu Gly Thr Phe Leu Ile Arg Asp Ser Ser His Ser Asp Tyr
65                  70                  75                  80

Leu Leu Thr Ile Ser Val Lys Thr Ser Ala Gly Pro Thr Asn Leu Arg
                85                  90                  95

Ile Glu Tyr Gln Asp Gly Lys Phe Arg Leu Asp Ser Ile Ile Cys Val
            100                 105                 110

Lys Ser Lys Leu Lys Gln Phe Asp Ser Val Val His Leu Ile Asp Tyr
        115                 120                 125

Tyr Val Gln Met Cys Lys Asp Lys Arg Thr Gly Pro Glu Ala Pro Arg
    130                 135                 140

Asn Gly Thr Val His Leu Tyr Leu Thr Lys Pro Leu Tyr Thr Ser Ala
145                 150                 155                 160

Pro Thr Leu Gln His Phe Cys Arg Leu Ala Ile Asn Lys Cys Thr Gly
                165                 170                 175

Thr Ile Trp Gly Leu Pro Leu Pro Thr Arg Leu Lys Asp Tyr Leu Glu
            180                 185                 190

Glu Tyr Lys Phe Gln Val
        195

<210> SEQ ID NO 7
<211> LENGTH: 2187
<212> TYPE: DNA
<213> ORGANISM: Mouse
<220> FEATURE:
<221> NAME/KEY: CDS
<222> LOCATION: (18)..(692)

<400> SEQUENCE: 7
```

```
cgctggctcc gtgcgcc atg gtc acc cac agc aag ttt ccc gcc gcc ggg              50
                   Met Val Thr His Ser Lys Phe Pro Ala Ala Gly
                    1               5                  10 atg agc cgc ccc ctg gac acc agc ctg cgc ctc aag acc ttc agc tcc             98
Met Ser Arg Pro Leu Asp Thr Ser Leu Arg Leu Lys Thr Phe Ser Ser
            15                  20                  25 aaa agc gag tac cag ctg gtg gtg aac gcc gtg cgc aag ctg cag gag            146
Lys Ser Glu Tyr Gln Leu Val Val Asn Ala Val Arg Lys Leu Gln Glu
        30                  35                  40 agc gga ttc tac tgg agc gcc gtg acc ggc ggc gag gcg aac ctg ctg            194
Ser Gly Phe Tyr Trp Ser Ala Val Thr Gly Gly Glu Ala Asn Leu Leu
    45                  50                  55 ctc agc gcc gag ccc gcg ggc acc ttt ctt atc cgc gac agc tcg gac            242
Leu Ser Ala Glu Pro Ala Gly Thr Phe Leu Ile Arg Asp Ser Ser Asp
60                  65                  70                  75 cag cgc cac ttc ttc acg ttg agc gtc aag acc cag tcg ggg acc aag            290
Gln Arg His Phe Phe Thr Leu Ser Val Lys Thr Gln Ser Gly Thr Lys
                80                  85                  90 aac cta cgc atc cag tgt gag ggg ggc agc ttt tcg ctg cag agt gac            338
Asn Leu Arg Ile Gln Cys Glu Gly Gly Ser Phe Ser Leu Gln Ser Asp
            95                  100                 105 ccc cga agc acg cag cca gtt ccc cgc ttc gac tgt gta ctc aag ctg            386
Pro Arg Ser Thr Gln Pro Val Pro Arg Phe Asp Cys Val Leu Lys Leu
        110                 115                 120 gtg cac cac tac atg ccg cct cca ggg acc ccc tcc ttt tct ttg cca            434
Val His His Tyr Met Pro Pro Pro Gly Thr Pro Ser Phe Ser Leu Pro
    125                 130                 135 ccc acg gaa ccc tcg tcc gaa gtt ccg gag cag cca cct gcc cag gca            482
Pro Thr Glu Pro Ser Ser Glu Val Pro Glu Gln Pro Pro Ala Gln Ala
140                 145                 150                 155 ctc ccc ggg agt acc ccc aag aga gct tac tac atc tat tct ggg ggc            530
Leu Pro Gly Ser Thr Pro Lys Arg Ala Tyr Tyr Ile Tyr Ser Gly Gly
                160                 165                 170 gag aag att ccg ctg gta ctg agc cga cct ctc tcc tcc aac gtg gcc            578
Glu Lys Ile Pro Leu Val Leu Ser Arg Pro Leu Ser Ser Asn Val Ala
            175                 180                 185 acc ctc cag cat ctt tgt cgg aag act gtc aac ggc cac ctg gac tcc            626
Thr Leu Gln His Leu Cys Arg Lys Thr Val Asn Gly His Leu Asp Ser
        190                 195                 200 tat gag aaa gtg acc cag ctg cct gga ccc att cgg gag ttc ctg gat            674
Tyr Glu Lys Val Thr Gln Leu Pro Gly Pro Ile Arg Glu Phe Leu Asp
    205                 210                 215 cag tat gat gct cca ctt taaggagcaa aagggtcaga gggggcctg                    722
Gln Tyr Asp Ala Pro Leu
220                 225 ggtcggtcgg tcgcctctcc tccgaggcac atggcacaag cacaaaaatc cagccccaac          782
ggtcggtagc tcccagtgag ccaggggcag attggcttct tcctcaggcc ctccactccc          842
gcagagtaga gctggcagga cctggaattc gtctgagggg aggggagct gccacctgct           902 ttcccccctc ccccagctcc agcttctttc aagtggagcc agccggcctg gctggtggg           962 acaatacctt tgacaagcgg actctcccct cccttcctc cacacccct ctgcttccca           1022 agggaggtgg ggacacctcc aagtgttgaa cttagaactg caaggggaat cttcaaactt         1082
tcccgctgga acttgtttgc gctttgattt ggtttgatca agagcaggca cctgggggaa         1142
ggatggaaga gaaagggtg tgtgaagggt ttttatgctg gccaaagaaa taaccactcc          1202
cactgcccaa cctaggtgag gagtggtggc tcctggctct ggggagagtg gcaagggtg          1262 acctgaagag agctatactg gtgccaggct cctctccatg gggcagctaa tgaaacctcg         1322
```

-continued

```
cagatccctt gcaccccaga accctccccg ttgtgaagag gcagtagcat ttagaaggga    1382
gacagatgag gctggtgagc tggccgcctt ttccaacacc gaagggaggc agatcaacag    1442
atgagccatc ttggagccca ggtttcccct ggagcagatg gagggttctg ctttgtctct    1502
cctatgtggg gctaggagac tcgccttaaa tgccctctgt cccagggatg gggattggca    1562
cacaaggagc caaacacagc caataggcag agagttgagg gattcaccca ggtggctaca    1622
ggccagggga agtggctgca ggggagagac ccagtcactc caggagactc ctgagttaac    1682
actgggaaga cattggccag tcctagtcat ctctcggtca gtaggtccga gagcttccag    1742
gccctgcaca gccctccttt ctcacctggg gggaggcagg aggtgatgga gaagccttcc    1802
catgccgctc acaggggcct cacgggaatg cagcagccat gcaattacct ggaactggtc    1862
ctgtgttggg gagaaacaag ttttctgaag tcaggtatgg ggctgggtgg ggcagctgtg    1922
tgttggggtg gcttttttct ctctgttttg aataatgttt acaatttgcc tcaatcactt    1982
ttataaaaat ccacctccag cccgcccctc tccccactca ggccttcgag gctgtctgaa    2042
gatgcttgaa aaactcaacc aaatcccagt tcaactcaga ctttgcacat atatttatat    2102
ttatactcag aaaagaaaca tttcagtaat ttataataaa agagcactat tttttaatga    2162
aaaaaaaaaa aaaaaaaaaa aaaaa                                         2187
```

<210> SEQ ID NO 8
<211> LENGTH: 225
<212> TYPE: PRT
<213> ORGANISM: Mouse

<400> SEQUENCE: 8

```
Met Val Thr His Ser Lys Phe Pro Ala Ala Gly Met Ser Arg Pro Leu
  1               5                  10                  15

Asp Thr Ser Leu Arg Leu Lys Thr Phe Ser Ser Lys Ser Glu Tyr Gln
                 20                  25                  30

Leu Val Val Asn Ala Val Arg Lys Leu Gln Glu Ser Gly Phe Tyr Trp
             35                  40                  45

Ser Ala Val Thr Gly Gly Glu Ala Asn Leu Leu Leu Ser Ala Glu Pro
         50                  55                  60

Ala Gly Thr Phe Leu Ile Arg Asp Ser Ser Asp Gln Arg His Phe Phe
     65                  70                  75                  80

Thr Leu Ser Val Lys Thr Gln Ser Gly Thr Lys Asn Leu Arg Ile Gln
                 85                  90                  95

Cys Glu Gly Gly Ser Phe Ser Leu Gln Ser Asp Pro Arg Ser Thr Gln
                100                 105                 110

Pro Val Pro Arg Phe Asp Cys Val Leu Lys Leu Val His His Tyr Met
            115                 120                 125

Pro Pro Pro Gly Thr Pro Ser Phe Ser Leu Pro Pro Thr Glu Pro Ser
        130                 135                 140

Ser Glu Val Pro Glu Gln Pro Ala Gln Ala Leu Pro Gly Ser Thr
145                 150                 155                 160

Pro Lys Arg Ala Tyr Tyr Ile Tyr Ser Gly Gly Glu Lys Ile Pro Leu
                165                 170                 175

Val Leu Ser Arg Pro Leu Ser Ser Asn Val Ala Thr Leu Gln His Leu
            180                 185                 190

Cys Arg Lys Thr Val Asn Gly His Leu Asp Ser Tyr Glu Lys Val Thr
        195                 200                 205

Gln Leu Pro Gly Pro Ile Arg Glu Phe Leu Asp Gln Tyr Asp Ala Pro
```

```
                   210                 215                 220

Leu
225

<210> SEQ ID NO 9
<211> LENGTH: 1094
<212> TYPE: DNA
<213> ORGANISM: Human

<400> SEQUENCE: 9
ctccggctgg cccttctgt aggatggtag cacacaacca ggtggcagcc gacaatgcag      60
tctccacagc agcagagccc cgacggcggc cagaaccttc ctcctcttcc tcctcctcgc     120
ccgcggcccc cgcgcgcccg cggccgtgcc ccgcggtccc ggccccggcc ccggcgaca     180 cgcacttccg cacattccgt tcgcacgccg attaccggcg catcacgcgc gccagcgcgc     240
tcctggacgc ctgcggattc tactgggggc ccctgagcgt gcacggggcg cacgagcggc     300
tgcgcgccga gcccgtgggc accttcctgg tgcgcgacag ccgccagcgg aactgctttt     360
tcgcccttag cgtgaagatg gcctcgggac ccacgagcat ccgcgtgcac tttcaggccg     420
gccgctttca cctggatggc agccgcgaga gcttcgactg cctcttcgag ctgctggagc     480
actacgtggc ggcgccgcgc cgcatgctgg gggccccgct gcgccagcgc cgcgtgcggc     540
cgctgcagga gctgtgccgc cagcgcatcg tggccaccgt gggccgcgag aacctggctc     600 gcatcccccct caaccccgtc ctccgcgact acctgagctc cttccccttc cagatttgac     660
cggcagcgcc cgccgtgcac gcagcattaa ctgggatgcc gtgttatttt gttattactt     720
gcctggaacc atgtgggtac cctccccggc ctgggttgga gggagcggat gggtgtaggg     780
gcgaggcgcc tcccgccctc ggctggagac gaggccgcag accccttctc acctcttgag     840
ggggtcctcc ccctcctggt gctccctctg ggtccccctg gttgttgtag cagcttaact     900
gtatctggag ccaggacctg aactcgcacc tcctacctct tcatgtttac atatacccag     960
tatctttgca caaaccaggg gttggggag ggtctctggc tttatttttc tgctgtgcag    1020
aatcctattt tatattttt aaagtcagtt taggtaataa actttattat gaaagttttt    1080
ttttttaaaa aaaa                                                     1094

<210> SEQ ID NO 10
<211> LENGTH: 211
<212> TYPE: PRT
<213> ORGANISM: Human

<400> SEQUENCE: 10

Met Val Ala His Asn Gln Val Ala Ala Asp Asn Ala Val Ser Thr Ala
 1               5                   10                  15

Ala Glu Pro Arg Arg Pro Glu Pro Ser Ser Ser Ser Ser Ser
                20                  25                  30

Pro Ala Ala Pro Ala Arg Pro Arg Pro Cys Pro Ala Val Pro Ala Pro
            35                  40                  45

Ala Pro Gly Asp Thr His Phe Arg Thr Phe Arg Ser His Ala Asp Tyr
        50                  55                  60

Arg Arg Ile Thr Arg Ala Ser Ala Leu Leu Asp Ala Cys Gly Phe Tyr
65                  70                  75                  80

Trp Gly Pro Leu Ser Val His Gly Ala His Glu Arg Leu Arg Ala Glu
                85                  90                  95

Pro Val Gly Thr Phe Leu Val Arg Asp Ser Arg Gln Arg Asn Cys Phe
                100                 105                 110
```

```
Phe Ala Leu Ser Val Lys Met Ala Ser Gly Pro Thr Ser Ile Arg Val
            115                 120                 125
His Phe Gln Ala Gly Arg Phe His Leu Asp Gly Ser Arg Glu Ser Phe
        130                 135                 140
Asp Cys Leu Phe Glu Leu Leu Glu His Tyr Val Ala Ala Pro Arg Arg
145                 150                 155                 160
Met Leu Gly Ala Pro Leu Arg Gln Arg Arg Val Arg Pro Leu Gln Glu
                165                 170                 175
Leu Cys Arg Gln Arg Ile Val Ala Thr Val Gly Arg Glu Asn Leu Ala
            180                 185                 190
Arg Ile Pro Leu Asn Pro Val Leu Arg Asp Tyr Leu Ser Ser Phe Pro
        195                 200                 205
Phe Gln Ile
    210

<210> SEQ ID NO 11
<211> LENGTH: 2807
<212> TYPE: DNA
<213> ORGANISM: Rat

<400> SEQUENCE: 11
ggaaaccgag gcggggagac caggaggcct tggcctcaga gcttcagagt cgcgtggcag      60
caaacagaga aacctgtaga gggcagtgtg cgtcacttag ctcagggaag ctgcacgcga     120
aactcacccg ccttcattca taaacatcgt cagctaggca cctactcctg ggctttcagg     180
acaaactgaa tcacgaaacc acagtgtcct taaaataggt ctgaccgcct gaatccctgg     240
ccaaggtgtg tacggggcat gggagccctt gtgcagagat gcttgcagga gccttgaggg     300
gctctgtaag acagaggcta ggaagacaaa gttgggggct acagcttctt gtcctgcccg     360
gggcctcagt ttcttcggtt gcccacgtag gagtgcagag agtccagccc ctggggaccc     420
aacccaaccc cgcccagttt ccgaggaact cgtccgggag cggggcgcc  cctcccgcac     480
cgccttaggc ttcctttgaa gcctctgcgg tcaggccacc gcttcctggg aagcccaagc     540
caaggccagg ccgagtggcc aacgggaggg gcccgcgcgc gattctggag gagggcggcg     600
gccccacagg tctccagggc tggctagccg ggctcctaga gcggagactg ccaaggcctt     660
cgggtcctgg gcaggaagga tcctggcagg gaggagttgc ttgggggtg  ggggggaaag     720
gctccaggcg cggtggagct ctgaccagga gaatgcacac actcggaggg gaggaggcgt     780
gtcagcccca agctagcatc ccacccgggg agcagcgatg tggggcgaag gtagccagag     840
caaaagagca ggcaccaggt gacacgaaac agaagattcc gggtagagcc agaaccccag     900
aagtcccatt cagggaaggt gcgaggcgag aacgagttag tggaccctc  tccagggca      960
gccaaagaaa tctaaagaga acccgaagga cttgccggaa agagaaaccg aaagcggcgg    1020
tgggcgggat cggtgggcgg ggcctccctg gtttaagagc ttgatgcagg ggcgggcagc    1080
agcagagaga actgcggccg tggcagcggc acggctcccg gccccggagc atgcgcgaca    1140
gcagccccgg aaccccagc  cgcggcgccc cgcgtcccgc cgccaggtga ccgaggcag     1200
ctgcgaagga gcaggcggga ggggatggga ggaagggag  cagagcctgg caggactatc    1260
ctcgcagact gcatggcggg gtcgtggatg ctatgcctct ggcgcccgcc ccaccggctg    1320
gcccaggcgg cccctcgcgc gcgcggggcg ccgtcagccc ctcctctccg gccctgagcc    1380
cggatcgtcc gccggggttc cagttccggg cgtggccagt aggcggcaac cgcgaggcgg    1440
caagccaccc agcggggacg gcctggagtc gggcccctct ccacgccccc ttctccacgc    1500
```

```
gcgcggggag gcagggctcc accgccagtc tggaagggtt ccacatacag gaacggccta   1560
cttcgcagat gagcccaccg aggctcaggc tccgggcgga ttctgcgtgt caccctcgct   1620
ccttggggtc cgctggccgg cctgtgccac ccggacgccc ggttcactgc ctctgtctcc   1680
cccatcagcg cagccccgga cgctatggcc caccccctcca gctggcccct cgagtaggat   1740
ggtagcacgt aaccaggtgg aagccgacaa tgcgatctcc ccggcatcag agccccgacg   1800
gcggccagag ccatcctcgt cctcgtcttc gtcctcgccg gcggccccgg cgcgtccccg   1860
gccctgcccg gtggtcccgg ccccggctcc gggcgacact cacttccgca ccttccgctc   1920
ccactctgat taccggcgca tcacgcggac cagcgctctc ctggacgcct gcggcttcta   1980
ctggggaccc ctgagcgtgc atggggcgca cgaacggctg cgttccgaac ccgtgggcac   2040
cttcttggtg cgcgacagtc gccagcggaa ctgcttcttc gcgctcagcg tgaagatggc   2100
ttcgggcccc acgagcattc gtgtgcactt ccaggccggc cgcttccacc tggacggcaa   2160
ccgcgagacc ttcgactgcc tcttcgagct gctggagcac tacgtggcgg cgccgcgccg   2220
catgttgggg gccccactgc gccagcgccg cgtgcgcccg ctgcaggagc tgtgtcgcca   2280
gcgcatcgtg gccgccgtgg gtcgcgagaa cctggcacgc atccctctta acccggtact   2340
ccgtgactac ctgagttcct tccccttcca gatctgaccg gctgccgccg tgcccgcaga   2400
attaagtggg agcgccttat tatttcttat tattaattat tattattttt ctggaaccac   2460
gtgggagccc tccccgccta ggtcggaggg agtgggtgtg gagggtgaga tccctcccac   2520
ttctggctgg agaccttatc ccgcctctcg ggggcctcc cctcctggtg ctccctcccg   2580
gtccccctgg ttgtagcagc ttgtgtctgg ggccaggacc tgaactccac gcctacctct   2640
ccatgtttac atgttcccag tatctttgca caaaccaggg gtgggggagg gtctctggct   2700
tcatttttct gctgtgcaga atattctatt ttatattttt acatccagtt tagataataa   2760
actttattat gaaagttttt ttttttaaag aaacaaagat ttctaga              2807
```

<210> SEQ ID NO 12
<211> LENGTH: 212
<212> TYPE: PRT
<213> ORGANISM: Rat

<400> SEQUENCE: 12

```
Met Val Ala Arg Asn Gln Val Glu Ala Asp Asn Ala Ile Ser Pro Ala
 1               5                  10                  15

Ser Glu Pro Arg Arg Pro Glu Pro Ser Ser Ser Ser Ser Ser Ser Ser
                20                  25                  30

Ser Pro Ala Ala Pro Ala Arg Pro Arg Pro Cys Pro Val Val Pro Ala
            35                  40                  45

Pro Ala Pro Gly Asp Thr His Phe Arg Thr Phe Arg Ser His Ser Asp
        50                  55                  60

Tyr Arg Arg Ile Thr Arg Thr Ser Ala Leu Leu Asp Ala Cys Gly Phe
 65                  70                  75                  80

Tyr Trp Gly Pro Leu Ser Val His Gly Ala His Glu Arg Leu Arg Ser
                85                  90                  95

Glu Pro Val Gly Thr Phe Leu Val Arg Asp Ser Arg Gln Arg Asn Cys
               100                 105                 110

Phe Phe Ala Leu Ser Val Lys Met Ala Ser Gly Pro Thr Ser Ile Arg
           115                 120                 125

Val His Phe Gln Ala Gly Arg Phe His Leu Asp Gly Asn Arg Glu Thr
       130                 135                 140
```

```
Phe Asp Cys Leu Phe Glu Leu Leu Glu His Tyr Val Ala Ala Pro Arg
145                 150                 155                 160

Arg Met Leu Gly Ala Pro Leu Arg Gln Arg Val Arg Pro Leu Gln
            165                 170                 175

Glu Leu Cys Arg Gln Arg Ile Val Ala Ala Val Gly Arg Glu Asn Leu
            180                 185                 190

Ala Arg Ile Pro Leu Asn Pro Val Leu Arg Asp Tyr Leu Ser Ser Phe
            195                 200                 205

Pro Phe Gln Ile
    210
```

<210> SEQ ID NO 13
<211> LENGTH: 1611
<212> TYPE: DNA
<213> ORGANISM: Mouse
<220> FEATURE:
<221> NAME/KEY: CDS
<222> LOCATION: (263)..(1525)

<400> SEQUENCE: 13

```
cgaattccgg gcgggctgtg tgagtctgtg agtggaaggc gcgccggctc ttttgtctga      60
gtgtgacccg gtggctttgt tccaggcatt ccggtgattt cctccgggca gtccgcagaa     120
gccgcagcgg ccgcccgcgc tctctctgca gtctccacac ccgggagagc ctgagcccgc     180
gtcacgcccc tcagccccccg ctgagtcccct tctctgttgt cgcgtccgaa tcgagttccc     240
ggaatcagac ggtgccccat ag atg gcc agc ttt ccc ccg agg gtt aac gag        292
                         Met Ala Ser Phe Pro Pro Arg Val Asn Glu
                           1               5                  10 aaa gag atc gtg aga tca cgt act ata ggg gaa ctc ttg gct cca gca        340
Lys Glu Ile Val Arg Ser Arg Thr Ile Gly Glu Leu Leu Ala Pro Ala
             15                  20                  25 gct cct ttt gac aag aaa tgt ggt ggt gag aac tgg acg gtt gct ttt        388
Ala Pro Phe Asp Lys Lys Cys Gly Gly Glu Asn Trp Thr Val Ala Phe
         30                  35                  40 gct cct gat ggt tcc tac ttt gcg tgg tca caa gga tat cgc ata gtg        436
Ala Pro Asp Gly Ser Tyr Phe Ala Trp Ser Gln Gly Tyr Arg Ile Val
     45                  50                  55 aag ctt gtc ccg tgg tcc cag tgc cgt aag aac ttt ctt ttg cat ggt        484
Lys Leu Val Pro Trp Ser Gln Cys Arg Lys Asn Phe Leu Leu His Gly
 60                  65                  70 tcc aaa aat gtt acc aat tca agc tgt cta aaa ttg gca aga caa aac        532
Ser Lys Asn Val Thr Asn Ser Ser Cys Leu Lys Leu Ala Arg Gln Asn
 75                  80                  85                  90 agt aat ggt ggt cag aaa aac aag cct cct gag cac gtt ata gac tgt        580
Ser Asn Gly Gly Gln Lys Asn Lys Pro Pro Glu His Val Ile Asp Cys
             95                 100                 105 gga gac ata gtc tgg agt ctt gct ttt ggg tct tca gtt cca gaa aaa        628
Gly Asp Ile Val Trp Ser Leu Ala Phe Gly Ser Ser Val Pro Glu Lys
         110                 115                 120 cag agt cgt tgc gtt aat ata gaa tgg cat cgg ttc cga ttt gga cag        676
Gln Ser Arg Cys Val Asn Ile Glu Trp His Arg Phe Arg Phe Gly Gln
     125                 130                 135 gat cag cta ctc ctt gcc aca gga tta aac aat ggt cgc atc aaa atc        724
Asp Gln Leu Leu Leu Ala Thr Gly Leu Asn Asn Gly Arg Ile Lys Ile
 140                 145                 150 tgg gat gta tat aca gga aaa ctc ctc ctt aat ttg gta gac cac att        772
Trp Asp Val Tyr Thr Gly Lys Leu Leu Leu Asn Leu Val Asp His Ile
155                 160                 165                 170
```

```
gaa atg gtt aga gat tta act ttt gct cca gat ggg agc tta ctc ctt    820
Glu Met Val Arg Asp Leu Thr Phe Ala Pro Asp Gly Ser Leu Leu Leu
            175                 180                 185 gta tca gct tca aga gac aaa act cta aga gtg tgg gac ctg aaa gat    868
Val Ser Ala Ser Arg Asp Lys Thr Leu Arg Val Trp Asp Leu Lys Asp
        190                 195                 200 gat gga aac atg gtg aaa gta ttg cgg gca cat cag aat tgg gtg tac    916
Asp Gly Asn Met Val Lys Val Leu Arg Ala His Gln Asn Trp Val Tyr
    205                 210                 215 agt tgt gca ttc tct ccc gac tgt tct atg ctg tgt tca gtg ggc gcc    964
Ser Cys Ala Phe Ser Pro Asp Cys Ser Met Leu Cys Ser Val Gly Ala
220                 225                 230 agt aaa gca gtt ttc ctt tgg aat atg gat aaa tac acc atg att agg    1012
Ser Lys Ala Val Phe Leu Trp Asn Met Asp Lys Tyr Thr Met Ile Arg
235                 240                 245                 250 aag ctg gaa ggt cat cac cat gat gtt gta gct tgt gac ttt tct cct    1060
Lys Leu Glu Gly His His His Asp Val Val Ala Cys Asp Phe Ser Pro
                255                 260                 265 gat gga gca ttg cta gct act gca tcc tat gac act cgt gtg tat gtc    1108
Asp Gly Ala Leu Leu Ala Thr Ala Ser Tyr Asp Thr Arg Val Tyr Val
            270                 275                 280 tgg gat cca cac aat gga gac ctt ctg atg gag ttt ggg cac ctg ttt    1156
Trp Asp Pro His Asn Gly Asp Leu Leu Met Glu Phe Gly His Leu Phe
        285                 290                 295 ccc tcg ccc act cca ata ttt gct gga gga gca aat gac cga tgg gtg    1204
Pro Ser Pro Thr Pro Ile Phe Ala Gly Gly Ala Asn Asp Arg Trp Val
    300                 305                 310 aga gct gtg tct ttc agt cat gat gga ctg cat gtt gcc agc ctt gct    1252
Arg Ala Val Ser Phe Ser His Asp Gly Leu His Val Ala Ser Leu Ala
315                 320                 325                 330 gat gat aaa atg gtg agg ttc tgg aga atc gat gag gat tgt ccg gta    1300
Asp Asp Lys Met Val Arg Phe Trp Arg Ile Asp Glu Asp Cys Pro Val
                335                 340                 345 caa gtt gca cct ttg agc aat ggt ctt tgc tgt gcc ttt tct act gat    1348
Gln Val Ala Pro Leu Ser Asn Gly Leu Cys Cys Ala Phe Ser Thr Asp
            350                 355                 360 ggc agt gtt tta gct gct ggg aca cat gat gga agt gtg tat ttt tgg    1396
Gly Ser Val Leu Ala Ala Gly Thr His Asp Gly Ser Val Tyr Phe Trp
        365                 370                 375 gcc act cca agg caa gtc cct agc ctt caa cat ata tgt cgc atg tca    1444
Ala Thr Pro Arg Gln Val Pro Ser Leu Gln His Ile Cys Arg Met Ser
    380                 385                 390 atc cga aga gtg atg tcc acc caa gaa gtc caa aaa ctg cct gtt cct    1492
Ile Arg Arg Val Met Ser Thr Gln Glu Val Gln Lys Leu Pro Val Pro
395                 400                 405                 410 tcc aaa ata ttg gcg ttt ctc tcc tac cgc ggt tagactgaag actgcctttc  1545
Ser Lys Ile Leu Ala Phe Leu Ser Tyr Arg Gly
                415                 420 ctggtaggcc tgccagacag agcgcccttt acaagacaca cctcaagctt tacctcgtgc  1605
cgaatt                                                             1611

<210> SEQ ID NO 14
<211> LENGTH: 421
<212> TYPE: PRT
<213> ORGANISM: Mouse

<400> SEQUENCE: 14

Met Ala Ser Phe Pro Pro Arg Val Asn Glu Lys Glu Ile Val Arg Ser
1               5                   10                  15
```

```
Arg Thr Ile Gly Glu Leu Leu Ala Pro Ala Ala Pro Phe Asp Lys Lys
            20                  25                  30

Cys Gly Gly Glu Asn Trp Thr Val Ala Phe Ala Pro Asp Gly Ser Tyr
        35                  40                  45

Phe Ala Trp Ser Gln Gly Tyr Arg Ile Val Lys Leu Val Pro Trp Ser
    50                  55                  60

Gln Cys Arg Lys Asn Phe Leu Leu His Gly Ser Lys Asn Val Thr Asn
65                  70                  75                  80

Ser Ser Cys Leu Lys Leu Ala Arg Gln Asn Ser Asn Gly Gly Gln Lys
            85                  90                  95

Asn Lys Pro Pro Glu His Val Ile Asp Cys Gly Asp Ile Val Trp Ser
            100                 105                 110

Leu Ala Phe Gly Ser Ser Val Pro Glu Lys Gln Ser Arg Cys Val Asn
            115                 120                 125

Ile Glu Trp His Arg Phe Arg Phe Gly Gln Asp Gln Leu Leu Leu Ala
            130                 135                 140

Thr Gly Leu Asn Asn Gly Arg Ile Lys Ile Trp Asp Val Tyr Thr Gly
145                 150                 155                 160

Lys Leu Leu Leu Asn Leu Val Asp His Ile Glu Met Val Arg Asp Leu
            165                 170                 175

Thr Phe Ala Pro Asp Gly Ser Leu Leu Leu Val Ser Ala Ser Arg Asp
            180                 185                 190

Lys Thr Leu Arg Val Trp Asp Leu Lys Asp Asp Gly Asn Met Val Lys
            195                 200                 205

Val Leu Arg Ala His Gln Asn Trp Val Tyr Ser Cys Ala Phe Ser Pro
            210                 215                 220

Asp Cys Ser Met Leu Cys Ser Val Gly Ala Ser Lys Ala Val Phe Leu
225                 230                 235                 240

Trp Asn Met Asp Lys Tyr Thr Met Ile Arg Lys Leu Glu Gly His His
            245                 250                 255

His Asp Val Val Ala Cys Asp Phe Ser Pro Asp Gly Ala Leu Leu Ala
            260                 265                 270

Thr Ala Ser Tyr Asp Thr Arg Val Tyr Val Trp Asp Pro His Asn Gly
            275                 280                 285

Asp Leu Leu Met Glu Phe Gly His Leu Phe Pro Ser Pro Thr Pro Ile
            290                 295                 300

Phe Ala Gly Gly Ala Asn Asp Arg Trp Val Arg Ala Val Ser Phe Ser
305                 310                 315                 320

His Asp Gly Leu His Val Ala Ser Leu Ala Asp Asp Lys Met Val Arg
            325                 330                 335

Phe Trp Arg Ile Asp Glu Asp Cys Pro Val Gln Val Ala Pro Leu Ser
            340                 345                 350

Asn Gly Leu Cys Cys Ala Phe Ser Thr Asp Gly Ser Val Leu Ala Ala
            355                 360                 365

Gly Thr His Asp Gly Ser Val Tyr Phe Trp Ala Thr Pro Arg Gln Val
            370                 375                 380

Pro Ser Leu Gln His Ile Cys Arg Met Ser Ile Arg Arg Val Met Ser
385                 390                 395                 400

Thr Gln Glu Val Gln Lys Leu Pro Val Pro Ser Lys Ile Leu Ala Phe
            405                 410                 415

Leu Ser Tyr Arg Gly
            420
```

<210> SEQ ID NO 15
<211> LENGTH: 783
<212> TYPE: DNA
<213> ORGANISM: Human

<400> SEQUENCE: 15

| | | | | | | |
|---|---|---|---|---|---|---|
| ctgtcttcct | ccgcagcgcg | aggctgggta | caggtctat | tgtctgtggt | tgactccgta | 60 |
| ctttggtctg | aggccttcgg | gagctttccc | gaggcagtta | gcagaagccg | cagcgaccgc | 120 |
| ccccgcccgt | ctcctctgtc | cctgggcccg | ggagacaaac | ttggcgtcac | gccctcagcg | 180 |
| gtcgccactc | tcttctctgt | tgttgggtcc | gcatcgtatt | cccggaatca | gacggtgccc | 240 |
| catagatggc | cagctttccc | ccgagggtca | acgagaaaga | gatcgtgaga | tcacgtacta | 300 |
| taggtgaact | tttagctcct | gcagctcctt | ttgacaagaa | atgtggtcgt | gaaaattgga | 360 |
| ctgttgcttt | tgctccagat | ggttcatact | ttgcttggtc | acaaggacat | cgcacagtaa | 420 |
| agcttgttcc | gtggtcccag | tgccttcaga | actttctctt | gcatggcacc | aagaatgtta | 480 |
| ccaattcaag | cagtttaaga | ttgccaagac | aaaatagtga | tggtggtcag | aaaaataagc | 540 |
| ctcgtgacat | attatagact | gtggagatat | agtctggagt | cttgcttttg | ggtcatcagt | 600 |
| tccagaaaaa | cagagtcgct | gtgtaaatat | agaatggcat | cgcttcagat | ttggacaaga | 660 |
| tcagctactt | cttgctacag | ggttgaacaa | tgggcgtatc | aaaatatggg | atgtatatca | 720 |
| ggaaactcct | ccttaacttg | gtagatcata | ctgaagtggt | cagagattta | acttttgctc | 780 |
| cag | | | | | | 783 |

<210> SEQ ID NO 16
<211> LENGTH: 1122
<212> TYPE: DNA
<213> ORGANISM: Human

<400> SEQUENCE: 16

| | | | | | | |
|---|---|---|---|---|---|---|
| ctctgtatgt | ctgaatgaag | ctataacatt | tgccttttta | ttgcaggttt | tcctttggaa | 60 |
| tatggataaa | tacaccatga | tacggaaact | agaaggacat | caccatgatg | tggtagcttg | 120 |
| tgactttttct | cctgatggag | cattactggc | tactgcatct | tatgatactc | gagtatatat | 180 |
| ctgggatcca | cataatggag | acattctgat | ggaatttggg | cacctgtttc | ccccacctac | 240 |
| tccaatatttt | gctggaggag | caaatgaccg | gtgggtacga | tctgtatctt | ttagccatga | 300 |
| tggactgcat | gttgcaagcc | ttgctgatga | taaaatggtg | aggttctgga | gaattgatga | 360 |
| ggattatcca | gtgcaagttg | cacctttgag | caatggtctt | tgctgtgcct | tctctactga | 420 |
| tggcagtgtt | ttagctgctg | ggacacatga | cggaagtgtg | tattttttggg | ccactccacg | 480 |
| gcaggtccct | agcctgcaac | atttatgtcg | catgtcaatc | cgaagagtga | tgcccaccca | 540 |
| agaagttcag | gagctgccga | ttccttccaa | gcttttggag | tttctctcgt | atcgtattta | 600 |
| gaagattctg | ccttccctag | tagtagggac | tgacagaata | cacttaacac | aaacctcaag | 660 |
| ctttactgac | ttcaattatc | tgtttttaaa | gacgtagaag | atttatttaa | tttgatatgt | 720 |
| tcttgtactg | catttttgatc | agttgagctt | ttaaaatatt | atttatagac | aatagaagta | 780 |
| tttctgaaca | tatcaaatat | aaatttttt | aaagatctaa | ctgtgaaaac | atacatacct | 840 |
| gtacatattt | agatataagc | tgctatatgt | tgaatggacc | ctttttgcttt | tctgatttt | 900 |
| agttctgaca | tgtatatatt | gcttcagtag | agccacaata | tgtatctttg | ctgtaaagtg | 960 |
| caaggaaatt | ttaaattctg | ggacactgag | ttagatggta | aatactgact | tacgaaagtg | 1020 |
| gaattgggtg | aggcgggcaa | atcacctgag | gtcagcagtt | tgagactagc | ctggcaaaca | 1080 |

-continued

```
tgatgaaacc ctgtctctac taaaaataca aaaaaaaaaa aa        1122
```

<210> SEQ ID NO 17
<211> LENGTH: 2544
<212> TYPE: DNA
<213> ORGANISM: Mouse
<220> FEATURE:
<221> NAME/KEY: CDS
<222> LOCATION: (423)..(2030)
<221> NAME/KEY: UNSURE
<222> LOCATION: (320)
<223> OTHER INFORMATION: Xaa is unsure
<221> NAME/KEY: UNSURE
<222> LOCATION: (451)
<223> OTHER INFORMATION: Xaa is unsure
<221> NAME/KEY: UNSURE
<222> LOCATION: (531)
<223> OTHER INFORMATION: Xaa is unsure

<400> SEQUENCE: 17

```
cggcacgagc cgggctccgt ccggaggaag cgaggctgcg ccgccggccc ggcaggagcg    60
gaggacggga mgcgcgggcg gtcgcgctcg ccctgtcgct gactgcgctg ccccggccca   120
tccttgcctg gccgcaggtg ccctggatga ggccgccgcg cgtgtcccgg ccgctgagtg   180 tccccgcgg tcgcccggcg cctgccctca gcggccgcc tctccttgcc cgggtccccg    240
ttttcccccg cgcagtcct cctccggtgg gcgcctccgc acctcggcgc aggcggcacg    300
gccctcgggc cggatggat ccgccgggaa gaggaagaca agccggggcg ttgagcccct    360
gcgcacggtg ccgccgcgcg tagtgggagc ttactcgcag taggctctcg ctcttctaat    420 ca atg gat aaa gtg ggg aaa atg tgg aac aac tta aaa tac aga tgc       467
   Met Asp Lys Val Gly Lys Met Trp Asn Asn Leu Lys Tyr Arg Cys
    1               5                  10                  15 cag aat ctc ttc agc cac gag gga gga agc cgt aat gag aac gtg gag    515
Gln Asn Leu Phe Ser His Glu Gly Gly Ser Arg Asn Glu Asn Val Glu
                20                  25                  30 atg aac ccc aac aga tgt ccg tct gtc aaa gag aaa agc atc agt ctg    563
Met Asn Pro Asn Arg Cys Pro Ser Val Lys Glu Lys Ser Ile Ser Leu
            35                  40                  45 gga gag gca gct ccc cag caa gag agc agt ccc tta aga gaa aat gtt    611
Gly Glu Ala Ala Pro Gln Gln Glu Ser Ser Pro Leu Arg Glu Asn Val
        50                  55                  60 gcc tta cag ctg gga ctg agc cct tcc aag acc ttt tcc agg cgg aac    659
Ala Leu Gln Leu Gly Leu Ser Pro Ser Lys Thr Phe Ser Arg Arg Asn
    65                  70                  75 caa aac tgt gcc gca gag atc cct caa gtg gtt gaa atc agc atc gag    707
Gln Asn Cys Ala Ala Glu Ile Pro Gln Val Val Glu Ile Ser Ile Glu
80                  85                  90                  95 aaa gac agt gac tcg ggt gcc acc cca gga acg agg ctt gca cgg aga    755
Lys Asp Ser Asp Ser Gly Ala Thr Pro Gly Thr Arg Leu Ala Arg Arg
                100                 105                 110 gac tcc tac tcg cgg cac gcc ccg tgg gga gga aag aag aaa cat tcc    803
Asp Ser Tyr Ser Arg His Ala Pro Trp Gly Gly Lys Lys Lys His Ser
            115                 120                 125 tgt tcc aca aag acc cag agt tca ttg gat acc gag aaa aag ttt ggt    851
Cys Ser Thr Lys Thr Gln Ser Ser Leu Asp Thr Glu Lys Lys Phe Gly
        130                 135                 140 aga act cga agc ggc ctt cag agg cga gag cgg cgc tat gga gtc agc    899
Arg Thr Arg Ser Gly Leu Gln Arg Arg Glu Arg Arg Tyr Gly Val Ser
    145                 150                 155 tcc atg cag gac atg gac agc gtt tct agc cgc gcg gtc ggg agc cgc    947
Ser Met Gln Asp Met Asp Ser Val Ser Ser Arg Ala Val Gly Ser Arg
160                 165                 170                 175
```

```
tcc ctg agg cag agg ctc cag gac acg gtg ggt ttg tgt ttt ccc atg      995
Ser Leu Arg Gln Arg Leu Gln Asp Thr Val Gly Leu Cys Phe Pro Met
            180                 185                 190 aga act tac agc aag cag tca aag cca ctc ttt tcc aat aaa aga aaa     1043
Arg Thr Tyr Ser Lys Gln Ser Lys Pro Leu Phe Ser Asn Lys Arg Lys
        195                 200                 205 ata cat ctt tct gaa tta atg ctg gag aaa tgc cct ttt cct gct ggc     1091
Ile His Leu Ser Glu Leu Met Leu Glu Lys Cys Pro Phe Pro Ala Gly
    210                 215                 220 tcg gat tta gca caa aag tgg cat ttg att aaa cag cat acc gcc cct     1139
Ser Asp Leu Ala Gln Lys Trp His Leu Ile Lys Gln His Thr Ala Pro
225                 230                 235 gtg agc cca cac tca aca ttt ttt gat aca ttt gat cca tca ctg gtg     1187
Val Ser Pro His Ser Thr Phe Phe Asp Thr Phe Asp Pro Ser Leu Val
240                 245                 250                 255 tct aca gaa gat gaa gaa gat agg ctt cgc gag aga aga cgg ctt agt     1235
Ser Thr Glu Asp Glu Glu Asp Arg Leu Arg Glu Arg Arg Arg Leu Ser
            260                 265                 270 atc gaa gaa ggg gtg gat ccc cct ccc aac gca caa ata cac acc ttt     1283
Ile Glu Glu Gly Val Asp Pro Pro Pro Asn Ala Gln Ile His Thr Phe
        275                 280                 285 gaa gct act gca cag gtc aac cca ttg tat aag ctg gga cca aag tta     1331
Glu Ala Thr Ala Gln Val Asn Pro Leu Tyr Lys Leu Gly Pro Lys Leu
    290                 295                 300 gct cct ggg atg aca gag ata agt gga gat ggt tct gca att cca caa     1379
Ala Pro Gly Met Thr Glu Ile Ser Gly Asp Gly Ser Ala Ile Pro Gln
305                 310                 315 gcs aat tgt gac tca gaa gag gat tca acc acc cta tgt ctg cag tca     1427
Xaa Asn Cys Asp Ser Glu Glu Asp Ser Thr Thr Leu Cys Leu Gln Ser
320                 325                 330                 335 cgg agg cag aag cag cgc cag gtg tcc ggg gac agc cac gcg cac gtt     1475
Arg Arg Gln Lys Gln Arg Gln Val Ser Gly Asp Ser His Ala His Val
            340                 345                 350 agc aga cag gga gct tgg aaa gtt cat acg cag atc gat tac ata cac     1523
Ser Arg Gln Gly Ala Trp Lys Val His Thr Gln Ile Asp Tyr Ile His
        355                 360                 365 tgc ctc gtg cca gat ttg ctt cag atc aca ggg aat ccc tgt tac tgg     1571
Cys Leu Val Pro Asp Leu Leu Gln Ile Thr Gly Asn Pro Cys Tyr Trp
    370                 375                 380 ggc gtg atg gac cga tac gag gcc gaa gcc ctt cta gaa ggg aaa ccg     1619
Gly Val Met Asp Arg Tyr Glu Ala Glu Ala Leu Leu Glu Gly Lys Pro
385                 390                 395 gaa ggc acg ttc ttg ctc agg gac tct gca cag gag gac tac ctc ttc     1667
Glu Gly Thr Phe Leu Leu Arg Asp Ser Ala Gln Glu Asp Tyr Leu Phe
400                 405                 410                 415 tct gtg agc ttc cgc cgc tac aac agg tct ctg cac gcc cgg atc gag     1715
Ser Val Ser Phe Arg Arg Tyr Asn Arg Ser Leu His Ala Arg Ile Glu
            420                 425                 430 cag tgg aac cac aac ttc agc ttc gat gcc cat gac ccc tgc gtg ttt     1763
Gln Trp Asn His Asn Phe Ser Phe Asp Ala His Asp Pro Cys Val Phe
        435                 440                 445 cac tcc tcc acw gtc acg ggg ctt ctc gaa cac tat aaa gac ccc agc     1811
His Ser Ser Xaa Val Thr Gly Leu Leu Glu His Tyr Lys Asp Pro Ser
    450                 455                 460 tct tgc atg ttt ttt gaa ccg ttg cta acg ata tca ctg aat aga act     1859
Ser Cys Met Phe Phe Glu Pro Leu Leu Thr Ile Ser Leu Asn Arg Thr
465                 470                 475 ttc cct ttc agc ctg cag tat atc tgc cgc gca gtg atc tgc aga tgc     1907
Phe Pro Phe Ser Leu Gln Tyr Ile Cys Arg Ala Val Ile Cys Arg Cys
```

|     |     |     |     |     |     |     |     |     |     |     |     |     |     |     |     |      |
| --- | --- | --- | --- | --- | --- | --- | --- | --- | --- | --- | --- | --- | --- | --- | --- | ---- |
|     | 480 |     |     |     | 485 |     |     |     | 490 |     |     |     | 495 |     |     |      |
| act | acg | tat | gat | ggg | att | gac | ggg | ctc | ccg | cta | ccg | tcg | atg | tta | cag | 1955 |
| Thr | Thr | Tyr | Asp | Gly | Ile | Asp | Gly | Leu | Pro | Leu | Pro | Ser | Met | Leu | Gln |      |
|     |     |     | 500 |     |     |     |     | 505 |     |     |     |     | 510 |     |     |      |
| gat | ttt | tta | aaa | gag | tat | cat | tat | aaa | caa | aaa | gtt | agg | gtt | cgc | tgg | 2003 |
| Asp | Phe | Leu | Lys | Glu | Tyr | His | Tyr | Lys | Gln | Lys | Val | Arg | Val | Arg | Trp |      |
|     |     |     | 515 |     |     |     |     | 520 |     |     |     |     | 525 |     |     |      |
| tta | gaa | cga | gar | cca | gtc | aaa | gca | aag | taactcctgt | | | ccccaaggg | | | | 2050 |
| Leu | Glu | Arg | Xaa | Pro | Val | Lys | Ala | Lys |     |     |     |     |     |     |     |      |
|     |     |     | 530 |     |     |     |     | 535 |     |     |     |     |     |     |     |      |

```
cactaactaa gtctgctcct cccgtgcatc mgaactgcac ccataggrag gcagtcagct    2110
gctaggattt cccacccaga atgggagctt agtcattagc ctctgcccta tggggtccgc    2170
tgttcctcag acaaaggtgc ctagggacag caagatggct tgcaggtgtt cggtgggctg    2230
tgacaactga gggaggcaac tctggggcat ttgctatgaa gaattctatt tcttaccgaa    2290
gaacaaatta ttaatattgg atgggtattt caatagtgtg actaatgttt gaaattattt    2350
tttctaagaa tttttctata accttcagaa aaagtagtga tgtttgtagt tactataaat    2410
caagctttga aagttcaaaa caaacaagtt aaataaaaga ctaccttcct tttagagaaa    2470
acaaatgcaa gttttcccag ccacaggcat tgtgcactgt taatgttagc ttgttatcag    2530
ctcctttctc ctcc                                                     2544

<210> SEQ ID NO 18
<211> LENGTH: 536
<212> TYPE: PRT
<213> ORGANISM: Mouse
<220> FEATURE:
<221> NAME/KEY: UNSURE
<222> LOCATION: (320)
<223> OTHER INFORMATION: Xaa is unsure
<221> NAME/KEY: UNSURE
<222> LOCATION: (451)
<223> OTHER INFORMATION: Xaa is unsure
<221> NAME/KEY: UNSURE
<222> LOCATION: (531)
<223> OTHER INFORMATION: Xaa is unsure

<400> SEQUENCE: 18
```

| Met | Asp | Lys | Val | Gly | Lys | Met | Trp | Asn | Asn | Leu | Lys | Tyr | Arg | Cys | Gln |
| --- | --- | --- | --- | --- | --- | --- | --- | --- | --- | --- | --- | --- | --- | --- | --- |
| 1   |     |     |     | 5   |     |     |     |     | 10  |     |     |     |     | 15  |     |
| Asn | Leu | Phe | Ser | His | Glu | Gly | Gly | Ser | Arg | Asn | Glu | Asn | Val | Glu | Met |
|     |     |     |     | 20  |     |     |     |     | 25  |     |     |     |     | 30  |     |
| Asn | Pro | Asn | Arg | Cys | Pro | Ser | Val | Lys | Glu | Lys | Ser | Ile | Ser | Leu | Gly |
|     |     |     | 35  |     |     |     |     | 40  |     |     |     |     | 45  |     |     |
| Glu | Ala | Ala | Pro | Gln | Gln | Glu | Ser | Ser | Pro | Leu | Arg | Glu | Asn | Val | Ala |
|     | 50  |     |     |     |     | 55  |     |     |     |     | 60  |     |     |     |     |
| Leu | Gln | Leu | Gly | Leu | Ser | Pro | Ser | Lys | Thr | Phe | Ser | Arg | Arg | Asn | Gln |
| 65  |     |     |     |     | 70  |     |     |     |     | 75  |     |     |     |     | 80  |
| Asn | Cys | Ala | Ala | Glu | Ile | Pro | Gln | Val | Val | Glu | Ile | Ser | Ile | Glu | Lys |
|     |     |     |     | 85  |     |     |     |     | 90  |     |     |     |     | 95  |     |
| Asp | Ser | Asp | Ser | Gly | Ala | Thr | Pro | Gly | Thr | Arg | Leu | Ala | Arg | Arg | Asp |
|     |     |     || 100|     |     |     |     | 105 |     |     |     |     | 110 |     |     |
| Ser | Tyr | Ser | Arg | His | Ala | Pro | Trp | Gly | Gly | Lys | Lys | Lys | His | Ser | Cys |
|     |     |     | 115 |     |     |     |     | 120 |     |     |     |     | 125 |     |     |
| Ser | Thr | Lys | Thr | Gln | Ser | Ser | Leu | Asp | Thr | Glu | Lys | Lys | Phe | Gly | Arg |
|     |     |     | 130 |     |     |     |     | 135 |     |     |     |     | 140 |     |     |
| Thr | Arg | Ser | Gly | Leu | Gln | Arg | Arg | Glu | Arg | Arg | Tyr | Gly | Val | Ser | Ser |
| 145 |     |     |     |     | 150 |     |     |     |     | 155 |     |     |     |     | 160 |

```
Met Gln Asp Met Asp Ser Val Ser Ser Arg Ala Val Gly Ser Arg Ser
                165                 170                 175
Leu Arg Gln Arg Leu Gln Asp Thr Val Gly Leu Cys Phe Pro Met Arg
            180                 185                 190
Thr Tyr Ser Lys Gln Ser Lys Pro Leu Phe Ser Asn Lys Arg Lys Ile
        195                 200                 205
His Leu Ser Glu Leu Met Leu Glu Lys Cys Pro Phe Pro Ala Gly Ser
    210                 215                 220
Asp Leu Ala Gln Lys Trp His Leu Ile Lys Gln His Thr Ala Pro Val
225                 230                 235                 240
Ser Pro His Ser Thr Phe Phe Asp Thr Phe Asp Pro Ser Leu Val Ser
                245                 250                 255
Thr Glu Asp Glu Glu Asp Arg Leu Arg Glu Arg Arg Leu Ser Ile
            260                 265                 270
Glu Glu Gly Val Asp Pro Pro Asn Ala Gln Ile His Thr Phe Glu
        275                 280                 285
Ala Thr Ala Gln Val Asn Pro Leu Tyr Lys Leu Gly Pro Lys Leu Ala
    290                 295                 300
Pro Gly Met Thr Glu Ile Ser Gly Asp Gly Ser Ala Ile Pro Gln Xaa
305                 310                 315                 320
Asn Cys Asp Ser Glu Glu Asp Ser Thr Thr Leu Cys Leu Gln Ser Arg
                325                 330                 335
Arg Gln Lys Gln Arg Gln Val Ser Gly Asp Ser His Ala His Val Ser
            340                 345                 350
Arg Gln Gly Ala Trp Lys Val His Thr Gln Ile Asp Tyr Ile His Cys
        355                 360                 365
Leu Val Pro Asp Leu Leu Gln Ile Thr Gly Asn Pro Cys Tyr Trp Gly
    370                 375                 380
Val Met Asp Arg Tyr Glu Ala Glu Ala Leu Leu Glu Gly Lys Pro Glu
385                 390                 395                 400
Gly Thr Phe Leu Leu Arg Asp Ser Ala Gln Glu Asp Tyr Leu Phe Ser
                405                 410                 415
Val Ser Phe Arg Arg Tyr Asn Arg Ser Leu His Ala Arg Ile Glu Gln
            420                 425                 430
Trp Asn His Asn Phe Ser Phe Asp Ala His Asp Pro Cys Val Phe His
        435                 440                 445
Ser Ser Xaa Val Thr Gly Leu Leu Glu His Tyr Lys Asp Pro Ser Ser
    450                 455                 460
Cys Met Phe Phe Glu Pro Leu Leu Thr Ile Ser Leu Asn Arg Thr Phe
465                 470                 475                 480
Pro Phe Ser Leu Gln Tyr Ile Cys Arg Ala Val Ile Cys Arg Cys Thr
                485                 490                 495
Thr Tyr Asp Gly Ile Asp Gly Leu Pro Leu Pro Ser Met Leu Gln Asp
            500                 505                 510
Phe Leu Lys Glu Tyr His Tyr Lys Gln Lys Val Arg Val Arg Trp Leu
        515                 520                 525
Glu Arg Xaa Pro Val Lys Ala Lys
530                 535
```

<210> SEQ ID NO 19
<211> LENGTH: 1221
<212> TYPE: DNA
<213> ORGANISM: Human

<400> SEQUENCE: 19

| | |
|---|---|
| gattaaacag catacagctc ctgtgagccc acattcaaca ttttttgata ctttgatcca | 60 |
| tctttggttt ctacagaaga tgaagaagat aggcttagag agagaaggcg gcttagtatt | 120 |
| gaagaagggg ttgatccccc tcccaatgca caaatacata catttgaagc tactgcacag | 180 |
| gttaatccat tattaaactg ggaccaaaat tagctcctgg aatgactgaa ataagtgggg | 240 |
| acagttctgc aattccacaa gctaattgtg actcggaaga ggatacaacc accctgtgtt | 300 |
| gcagtcacgg aggcagaagc agcgtcagat atctggagac agccataccc atgttagcag | 360 |
| acagggagct tggaaagtcc acacacagat tgattacata cactgcttcg tgcctgattt | 420 |
| gcttcaaatt acagggaatc cctgttactg gggagtgatg gaccgttatg aagcagaagc | 480 |
| ccttctcgaa gggaaacctg aaggcacgtt tttgctcagg gactctgcgc aagaggacta | 540 |
| cttcttctct gtgagcttcc gccgatacaa cagatccctg catgcccgaa ttgagcagtg | 600 |
| gaatcacaac tttagtttcg cgcccatga ccgtgtgta tttcactcct ccactgtaac | 660 |
| gggactttta gaacattata aagatcccag ttcgtgcatg ttttttgaac cattgcttac | 720 |
| tatatcacta aataggactt tccctttag cctgcagtat atctgtcgcg cggtaatctg | 780 |
| caggtgcact acgtatgatg gaattgatgg gctccctcta ccctcaatgt tacaggattt | 840 |
| tttaaaagag tatcattata aacaaaaagt tagagttcgc tggttggaac gagaaccagt | 900 |
| caaggcaaag taaactctcc ggtccccaaa gggtgttaac taggtccgct tcatgtgca | 960 |
| tcagacagta cacctatagc aagcacacgt agcagtgtta ggcttttca tacagtatgt | 1020 |
| aagcttagtg ttagtatctg tcagatgcta cctgctgtta cttattcaga taaacatggt | 1080 |
| gcctattgga acaatagcgg atagagctac aggtgttcag taagactaca aaacatttt | 1140 |
| gcctatttcg ctaacagttt ggtttttaat ggctgtggta tttgagtgag caactctgg | 1200 |
| ggcatttgtt atgaagaaat g | 1221 |

<210> SEQ ID NO 20
<211> LENGTH: 2369
<212> TYPE: DNA
<213> ORGANISM: Murine
<220> FEATURE:
<221> NAME/KEY: CDS
<222> LOCATION: (116)..(1327)

<400> SEQUENCE: 20

| | |
|---|---|
| ggcacgaggc ggtggtggcg gcggcgggcg cggccgcggc ggggcgggcg cggaatgaag | 60 |
| gcccacggcc ctgggggctg aggcgcccgc cgcctgggc gggccgcgcg tcctc atg<br>                                                 Met<br>                                                  1 | 118 |
| gag gcc gga gag gag ccg ctg ctg ctg gct gaa ctc aag cct ggg cgc<br>Glu Ala Gly Glu Glu Pro Leu Leu Leu Ala Glu Leu Lys Pro Gly Arg<br>     5          10          15 | 166 |
| ccc cac cag ttc gac tgg aag tca agc tgc gag acc tgg agc gtg gcc<br>Pro His Gln Phe Asp Trp Lys Ser Ser Cys Glu Thr Trp Ser Val Ala<br>    20          25          30 | 214 |
| ttc tcg cca gac ggt tcc tgg ttc gcc tgg tct caa gga cac tgc gtg<br>Phe Ser Pro Asp Gly Ser Trp Phe Ala Trp Ser Gln Gly His Cys Val<br>35          40          45 | 262 |
| gtc aag ctg gtc ccc tgg ccc tta gag gaa cag ttc atc cct aaa gga<br>Val Lys Leu Val Pro Trp Pro Leu Glu Glu Gln Phe Ile Pro Lys Gly<br> 50         55          60          65 | 310 |
| ttc gaa gcc aag agc cga agc agc aag aat gac cca aaa gga cgg ggc<br>Phe Glu Ala Lys Ser Arg Ser Ser Lys Asn Asp Pro Lys Gly Arg Gly | 358 |

-continued

```
                    70                  75                  80
agt ctg aag gag aag acg ctg gac tgt ggc cag att gtg tgg ggg ctg    406
Ser Leu Lys Glu Lys Thr Leu Asp Cys Gly Gln Ile Val Trp Gly Leu
             85                  90                  95 gcc ttc agc ccg tgg ccc tct cca ccc agc agg aaa ctc tgg gca cgt    454
Ala Phe Ser Pro Trp Pro Ser Pro Pro Ser Arg Lys Leu Trp Ala Arg
        100                 105                 110 cac cat ccc cag gcg cct gat gtt tct tgc ctg atc ctg gcc aca ggt    502
His His Pro Gln Ala Pro Asp Val Ser Cys Leu Ile Leu Ala Thr Gly
    115                 120                 125 ctc aac gat ggg cag atc aag att tgg gag gta cag aca ggc ctc ctg    550
Leu Asn Asp Gly Gln Ile Lys Ile Trp Glu Val Gln Thr Gly Leu Leu
130                 135                 140                 145 ctt ctg aat ctt tct ggc cac caa gac gtc gtg aga gat ctg agc ttc    598
Leu Leu Asn Leu Ser Gly His Gln Asp Val Val Arg Asp Leu Ser Phe
                150                 155                 160 acg ccc agc ggc agt ttg att ttg gtc tct gca tcc cgg gat aag aca    646
Thr Pro Ser Gly Ser Leu Ile Leu Val Ser Ala Ser Arg Asp Lys Thr
            165                 170                 175 ctt cga att tgg gac ctg aat aaa cac ggt aag cag atc cag gtg tta    694
Leu Arg Ile Trp Asp Leu Asn Lys His Gly Lys Gln Ile Gln Val Leu
        180                 185                 190 tcc ggc cat ctg cag tgg gtt tac tgc tgc tcc atc tcc cct gac tgt    742
Ser Gly His Leu Gln Trp Val Tyr Cys Cys Ser Ile Ser Pro Asp Cys
    195                 200                 205 agc atg ctg tgc tct gca gct ggg gag aag tcg gtc ttt ctg tgg agc    790
Ser Met Leu Cys Ser Ala Ala Gly Glu Lys Ser Val Phe Leu Trp Ser
210                 215                 220                 225 atg cgg tcc tac aca cta atc cgg aaa cta gaa ggc cac caa agc agt    838
Met Arg Ser Tyr Thr Leu Ile Arg Lys Leu Glu Gly His Gln Ser Ser
                230                 235                 240 gtt gtc tcc tgt gat ttc tct cct gat tca gcc ttg ctt gtc aca gct    886
Val Val Ser Cys Asp Phe Ser Pro Asp Ser Ala Leu Leu Val Thr Ala
            245                 250                 255 tcg tat gac acc agt gtg att atg tgg gac ccc tac acc ggc gcg agg    934
Ser Tyr Asp Thr Ser Val Ile Met Trp Asp Pro Tyr Thr Gly Ala Arg
        260                 265                 270 ctg agg tca ctt cat cac aca caa ctt gaa ccc acc atg gat gac agt    982
Leu Arg Ser Leu His His Thr Gln Leu Glu Pro Thr Met Asp Asp Ser
    275                 280                 285 gac gtc cac atg agc tcc ctg agg tcc gtg tgc ttc tca cct gaa ggc    1030
Asp Val His Met Ser Ser Leu Arg Ser Val Cys Phe Ser Pro Glu Gly
290                 295                 300                 305 ttg tat ctc gct acg gtg gca gat gac agg ctg ctc agg atc tgg gct    1078
Leu Tyr Leu Ala Thr Val Ala Asp Asp Arg Leu Leu Arg Ile Trp Ala
                310                 315                 320 ctg gaa ctg aag gct ccg gtt gcc ttt gct ccg atg acc aat ggt ctt    1126
Leu Glu Leu Lys Ala Pro Val Ala Phe Ala Pro Met Thr Asn Gly Leu
            325                 330                 335 tgc tgc acg ttc ttc cca cac ggt gga att att gcc aca ggg acg aga    1174
Cys Cys Thr Phe Phe Pro His Gly Gly Ile Ile Ala Thr Gly Thr Arg
        340                 345                 350 gat ggc cat gtc cag ttc tgg aca gct ccc cgg gtc ctg tcc tca ctg    1222
Asp Gly His Val Gln Phe Trp Thr Ala Pro Arg Val Leu Ser Ser Leu
    355                 360                 365 aag cac tta tgc agg aaa gcc ctc cga agt ttc ctg aca acg tat caa    1270
Lys His Leu Cys Arg Lys Ala Leu Arg Ser Phe Leu Thr Thr Tyr Gln
370                 375                 380                 385 gtc cta gca ctg cca atc ccc aag aag atg aaa gag ttc ctc aca tac    1318
```

-continued

```
Val Leu Ala Leu Pro Ile Pro Lys Lys Met Lys Glu Phe Leu Thr Tyr
            390                 395                 400
```

| | |
|---|---:|
| agg act ttc tagcagtgcc ggctccccca cctcctgcag cagcagcagt | 1367 |
| Arg Thr Phe | |
| acaagggact ggctaggatg gagtcaggca gctcacactg gaccagtgtg gaccttcctt | 1427 |
| cctcccatgg catgtgcaag taggtctgcg tgaccccact tctgtggtgc cggccttacc | 1487 |
| tcgtcttcat ccgtggtgag cagccttcgt cagtctagtt gtgttgaagc caagtgcagt | 1547 |
| tgtggatgtt gctggggtaa taaaggcaag cgggctccag agcctctctg gtggcggcca | 1607 |
| agccacactc ccttaactgg gaagtacctg ccacgtaggg catttctgct gcctatttcc | 1667 |
| agccagcggc tgcatggttt gaagttcctc cgttgtggtc agaagaactc tggtgtttgg | 1727 |
| ttccctgctc agctgcgcgt ggactgggct gagctcctca ccatacacta gtgccggctt | 1787 |
| ttgtttcctg taaacagtgg ttgcatgtgt agagaagtaa caagcgagta ttcagatcat | 1847 |
| acgaggaggc gttcctcggt gcatgacggt cagatggcca tttatcagca tatttatttg | 1907 |
| tattttctca gcacatagta aggtacaact gtgttttctc aattgtctcg aaaaaacaga | 1967 |
| gttcttaagt ggcccagttg tggagccaag tctaagtcgt gtggagtcag tgctgacatc | 2027 |
| actggcttgt gctgtctgtc acatgtgttt gtctctgctg cttgacctca tgggatgtac | 2087 |
| cctccagttc aactgcccaa acagacagc cccttccaag caccgttctt tgacagcggt | 2147 |
| agcagctacc tattcaagac gcctcacaca aaatctgcct tagaaagtta atatatttta | 2207 |
| aattattta aaagaaactc aacatcttat tctttggcct ttcttaattg atgctttatg | 2267 |
| gaggcagtgt taacattgta cagtgtatgc atagaggagt ctcctctatt tgaagaacaa | 2327 |
| tgcaaaatga ggctttcatt gaagggaaaa aaaaaaaaaa aa | 2369 |

<210> SEQ ID NO 21
<211> LENGTH: 404
<212> TYPE: PRT
<213> ORGANISM: Murine

<400> SEQUENCE: 21

```
Met Glu Ala Gly Glu Glu Pro Leu Leu Leu Ala Glu Leu Lys Pro Gly
 1               5                  10                  15

Arg Pro His Gln Phe Asp Trp Lys Ser Ser Cys Glu Thr Trp Ser Val
            20                  25                  30

Ala Phe Ser Pro Asp Gly Ser Trp Phe Ala Trp Ser Gln Gly His Cys
        35                  40                  45

Val Val Lys Leu Val Pro Trp Pro Leu Glu Glu Gln Phe Ile Pro Lys
    50                  55                  60

Gly Phe Glu Ala Lys Ser Arg Ser Lys Asn Asp Pro Lys Gly Arg
 65                  70                  75                  80

Gly Ser Leu Lys Glu Lys Thr Leu Asp Cys Gly Gln Ile Val Trp Gly
                85                  90                  95

Leu Ala Phe Ser Pro Trp Ser Pro Pro Ser Arg Lys Leu Trp Ala
            100                 105                 110

Arg His His Pro Gln Ala Pro Asp Val Ser Cys Leu Ile Leu Ala Thr
        115                 120                 125

Gly Leu Asn Asp Gly Gln Ile Lys Ile Trp Glu Val Gln Thr Gly Leu
    130                 135                 140

Leu Leu Leu Asn Leu Ser Gly His Gln Asp Val Val Arg Asp Leu Ser
145                 150                 155                 160

Phe Thr Pro Ser Gly Ser Leu Ile Leu Val Ser Ala Ser Arg Asp Lys
```

```
                        165                 170                 175
Thr Leu Arg Ile Trp Asp Leu Asn Lys His Gly Lys Gln Ile Gln Val
            180                 185                 190
Leu Ser Gly His Leu Gln Trp Val Tyr Cys Ser Ile Ser Pro Asp
            195                 200                 205
Cys Ser Met Leu Cys Ser Ala Ala Gly Glu Lys Ser Val Phe Leu Trp
            210                 215                 220
Ser Met Arg Ser Tyr Thr Leu Ile Arg Lys Leu Glu Gly His Gln Ser
225                 230                 235                 240
Ser Val Val Ser Cys Asp Phe Ser Pro Asp Ser Ala Leu Leu Val Thr
                245                 250                 255
Ala Ser Tyr Asp Thr Ser Val Ile Met Trp Asp Pro Tyr Thr Gly Ala
            260                 265                 270
Arg Leu Arg Ser Leu His His Thr Gln Leu Glu Pro Thr Met Asp Asp
            275                 280                 285
Ser Asp Val His Met Ser Ser Leu Arg Ser Val Cys Phe Ser Pro Glu
            290                 295                 300
Gly Leu Tyr Leu Ala Thr Val Ala Asp Asp Arg Leu Leu Arg Ile Trp
305                 310                 315                 320
Ala Leu Glu Leu Lys Ala Pro Val Ala Phe Ala Pro Met Thr Asn Gly
                325                 330                 335
Leu Cys Cys Thr Phe Phe Pro His Gly Ile Ile Ala Thr Gly Thr
            340                 345                 350
Arg Asp Gly His Val Gln Phe Trp Thr Ala Pro Arg Val Leu Ser Ser
            355                 360                 365
Leu Lys His Leu Cys Arg Lys Ala Leu Arg Ser Phe Leu Thr Thr Tyr
            370                 375                 380
Gln Val Leu Ala Leu Pro Ile Pro Lys Lys Met Lys Glu Phe Leu Thr
385                 390                 395                 400
Tyr Arg Thr Phe

<210> SEQ ID NO 22
<211> LENGTH: 1246
<212> TYPE: DNA
<213> ORGANISM: Human

<400> SEQUENCE: 22
gacactgcat cgtcaaactg atcccctggc cgttggagga gcagttcatc cctaaagggt      60
ttgaagccaa aagccgaagt agcaaaaatg agacgaaagg gcggggcagc ccaaaagaga     120
agacgctgga ctgtggtcag attgtctggg ggctggcctt cagcctgtgc tttccccacc     180
cagcaggaag ctctgggcac gccaccaccc caagtgccc gatgtctctt gcctggttct      240
tgctacggga ctcaacgatg ggcagatcaa gatctggag gtgcagacag gctcctgct      300
tttgaatctt tccggccacc aagatgtcgt gagagatctg agcttacac ccagtggcag     360
tttgattttg gtctccgcgt cacgggataa gactcttcgc atctgggacc tgaataaaca     420
cggtaaacag attcaagtgt tatcgggcca cctgcagtgg gtttactgct gttccatctc     480
cccagactgc agcatgctgt gctctgcagc tggagagaag tcggtctttc tatggagcat     540
gaggtcctac acgttaattc ggaagctaga gggccatcaa gcagtgttg tctcttgtga     600
cttctccccc gactctgccc tgcttgtcac ggcttcttac gataccaatg tgattatgtg     660
ggaccoctac accggcgaaa ggctgaggtc actccaccac acccaggttg acccogccat     720
ggatgacagt gacgtccaca ttagctcact gagatctgtg tgcttctctc cagaaggctt     780
```

```
gtaccttgcc acggtggcag atgacagact cctcaggatc tgggccctgg aactgaaaac      840
tcccattgca tttgctccta tgaccaatgg gctttgctgg cacattttt ccacatggtg      900 gagtcattgc cacagggaca agagatggcc acgtccagtt ctggacagct cctagggtcc      960
tgtcctcact gaagcactta tgccggaaag cccttcgaag tttcctaaca acttaccaag     1020
tcctagcact gccaatcccc aagaaaatga aagagttcct cacatacagg actttttaag     1080
caacaccaca tcttgtgctt ctttgtagca gggtaaatcg tcctgtcaaa gggagttgct     1140
ggaataatgg gccaaacatc tggtcttgca ttgaaatagc atttctttgg gattgtgaat     1200
agaatgtagc aaaaccagat tccagtgtac tagtcatgga tttttc                    1246

<210> SEQ ID NO 23
<211> LENGTH: 422
<212> TYPE: DNA
<213> ORGANISM: Human

<400> SEQUENCE: 23
accatggttc caagtcctct cccctgtggt caagttgccc gaatgttggg cccaagtgcc       60
ttttcctcct tgggcctccc cttctgacct gcaggacagt tttccggagc ccatttggta      120
tgaggtatta attagcctta actaaattac aggggactca gaggccgtgc tcctgaccga      180
tccagacact attttttttt tttttttta acaatggtgt gcatgtgcag gaaatgacaa       240
atttgtatgt cagattatac aaggatgtat tcttaaaccg catgactatt cagatggcta      300
ctgagttatc agtggccatt tattagcatc atatttattt gtattttctc aacagatgtt      360
aaggtacaac tgtgttttc tcgattatct aaaaaccata gtacttaaat tgaaaaaaaa      420
aa                                                                    422

<210> SEQ ID NO 24
<211> LENGTH: 2019
<212> TYPE: DNA
<213> ORGANISM: Mouse
<220> FEATURE:
<221> NAME/KEY: UNSURE
<222> LOCATION: (2000)
<223> OTHER INFORMATION: n is unsure

<400> SEQUENCE: 24
ggcacgaggc ggggtcaggg cggaggctga ggaccaagta ggcatggcgg agggcgggac       60 cggcccccgat ggacgggccg gcccgggacc cgcaggtcct aatctgaagg agtggctgag    120
ggagcagttc tgtgaccatc cactggagca ctgtgacgat acaagactcc atgatgcagc     180
ctatgtaggg gacctccaga ccctcaggaa cctactgcaa gaggagagct accggagccg     240
catcaatgag aagtctgtct ggtgctgcgg ctggcttccc tgcacaccac tgaggatcgc     300
agccactgca ggccatggga actgtgtgga cttcctcata cgcaaagggg ccgaggtgga     360
cctggtggat gtcaagggc agactgccct gtatgtggct gtagtgaacg ggcacttgga      420
gagcactgag atcctttggg aagctggtgc tgatcccaac ggcagccggc accaccgcag     480
cactcctgtg taccatgcct ytcgtgtggg tagggacgac atcctgaagg ctcttatcag     540
gtatggggca gatgttgatg tcaaccatca tctgaattct gacacccggc cccttttttc     600
acggcggcta acctccttgg tggtctgtcc tctatacatc agtgctgcct accataacct     660
tcagtgcttc aggctgctct tgcaggctgg ggcaaatcct gacttcaatt gcaatggccc     720
tgtcaacacc caggagttct acaggggatc ccctgggtgt gtcatggatg ctgtcctgcg     780
```

-continued

```
ccatggctgt gaagcagcct tcgtgagtct gttggtagag tttggagcca acctgaacct    840
ggtgaagtgg gaatccctgg gcccagaggc aagaggcaga agaaagatgg atcctgaggc    900
cttgcaggtc tttaaagagg ccagaagtat tcccaggacc ttgctgagtt tgtgccgggt    960
ggctgtgaga agagctcttg gcaaataccg actgcatctg gttccctcgc tgccgctgcc   1020
agacccata aagaagtttt tgctttatga gtagcattca catgcagtgc tgactgcaat   1080
gtggaagccg atcacctgca gtgaaaactg acacagactc tggcatcctg ggaaccatgg   1140
cctgtgctgc cagcttgatc cttggctgtc agtgaagaaa aaacggctgt gttctcttgg   1200
actgtgattc tatctcaggt gcttgggcca tcgaacgctc cttgagtcat tgtcaactga   1260
gaggcacata caaacttaat tttgttcctc ttcagtctct ctgttttgga ttcttcctgg   1320
caatgtgtgc agcatgggct gagcctggtg attgccctag tggggaaggc ttttttctcc   1380
aggctatgca tctatttatg ttcctacttt gcaatttatt gttcttttaa ggcttgatat   1440
caaaacagaa agaggtttgt taagaaaaga tatagggaga aaggaattcc ggttccgtgc   1500
acttgctagc ctgctttcct tgcctgggtt tgtctgtcta tgctgcctgg tgcacatccc   1560
ttctctttgc tgccactgtt ctattttggg agttgtcttc cgtctaagat ggcttctggg   1620
gttctatctt attgcacaga ggtcccagaa cagtgttcat agggcaccat ctgctctgcc   1680
aagggttttc tgatgtctta ccctggggat cttcagacag tggttacctt taggagaccc   1740
acctggaact aaccattaag tgactgccca cattcagatc agggaccatc ttaatagtac   1800
tcactgccag tcctcacaag agaagatgac acgggtgctc tcttcagaca ctcccataca   1860
ggaagttgga aaatgtcttg gtcacctggg ttgttcccag gctacaactt cttggtgttc   1920
cactaaracc agratatcct agtttttttgg gttgactgtt ccctccccac tttccttgaa   1980
ncccaatgcc cntttgtktn ggttgcttcc ctaaaaktt                          2019
```

<210> SEQ ID NO 25
<211> LENGTH: 350
<212> TYPE: PRT
<213> ORGANISM: Mouse
<220> FEATURE:
<221> NAME/KEY: UNSURE
<222> LOCATION: (167)
<223> OTHER INFORMATION: Xaa is unsure

<400> SEQUENCE: 25

```
Ala Arg Gly Gly Val Arg Ala Glu Ala Glu Asp Gln Val Gly Met Ala
 1               5                  10                  15

Glu Gly Gly Thr Gly Pro Asp Gly Arg Ala Gly Pro Gly Pro Ala Gly
             20                  25                  30

Pro Asn Leu Lys Glu Trp Leu Arg Glu Gln Phe Cys Asp His Pro Leu
         35                  40                  45

Glu His Cys Asp Asp Thr Arg Leu His Asp Ala Tyr Val Gly Asp
     50                  55                  60

Leu Gln Thr Leu Arg Asn Leu Leu Gln Glu Glu Ser Tyr Arg Ser Arg
 65                  70                  75                  80

Ile Asn Glu Lys Ser Val Trp Cys Cys Gly Trp Leu Pro Cys Thr Pro
                 85                  90                  95

Leu Arg Ile Ala Ala Thr Ala Gly His Gly Asn Cys Val Asp Phe Leu
            100                 105                 110

Ile Arg Lys Gly Ala Glu Val Asp Leu Val Asp Val Lys Gly Gln Thr
        115                 120                 125

Ala Leu Tyr Val Ala Val Val Asn Gly His Leu Glu Ser Thr Glu Ile
```

```
            130                 135                 140
Leu Leu Glu Ala Gly Ala Asp Pro Asn Gly Ser Arg His His Arg Ser
145                 150                 155                 160

Thr Pro Val Tyr His Ala Xaa Arg Val Gly Arg Asp Asp Ile Leu Lys
                165                 170                 175

Ala Leu Ile Arg Tyr Gly Ala Asp Val Asp Val Asn His His Leu Asn
            180                 185                 190

Ser Asp Thr Arg Pro Pro Phe Ser Arg Arg Leu Thr Ser Leu Val Val
        195                 200                 205

Cys Pro Leu Tyr Ile Ser Ala Ala Tyr His Asn Leu Gln Cys Phe Arg
210                 215                 220

Leu Leu Leu Gln Ala Gly Ala Asn Pro Asp Phe Asn Cys Asn Gly Pro
225                 230                 235                 240

Val Asn Thr Gln Glu Phe Tyr Arg Gly Ser Pro Gly Cys Val Met Asp
                245                 250                 255

Ala Val Leu Arg His Gly Cys Glu Ala Ala Phe Val Ser Leu Leu Val
            260                 265                 270

Glu Phe Gly Ala Asn Leu Asn Leu Val Lys Trp Glu Ser Leu Gly Pro
        275                 280                 285

Glu Ala Arg Gly Arg Arg Lys Met Asp Pro Glu Ala Leu Gln Val Phe
290                 295                 300

Lys Glu Ala Arg Ser Ile Pro Arg Thr Leu Leu Ser Leu Cys Arg Val
305                 310                 315                 320

Ala Val Arg Arg Ala Leu Gly Lys Tyr Arg Leu His Leu Val Pro Ser
                325                 330                 335

Leu Pro Leu Pro Asp Pro Ile Lys Lys Phe Leu Leu Tyr Glu
            340                 345                 350

<210> SEQ ID NO 26
<211> LENGTH: 419
<212> TYPE: DNA
<213> ORGANISM: Human

<400> SEQUENCE: 26
gcatccatgg cggagggcgg cagcacgacg ggcgggcagg ccgggctcc gcaggtcgta      60 atctgaagga gtggctgagg gagcaattt gtgatcatcc gctggagcac tgtgaggaca     120
cgaggctcca tgatgcagct acgtcgggg acctccagac cctcaggagc ctattgcaag     180
aggagagcta ccggagccgc atcaacgaga agtctgtctg gtgctgtggc tggctcccct    240
gcacaccgtt gcgaatcgcg ccactgcag gccatggag ctgtgtggac ttcctcatcc      300 ggaaggggc cgaggtggat ctggtggacg taaaaggaca gacggccctg tatgtggctg     360
tggtgaacgg gcacctagag agtacccaga tccttctcga agctggcgcg gaccccaac    419

<210> SEQ ID NO 27
<211> LENGTH: 595
<212> TYPE: DNA
<213> ORGANISM: Human

<400> SEQUENCE: 27
gaggaagaag aaaagtggac cctgaggcct tgcaggtctt taagaggcc agaagtgttc      60 ccagaacctt gctgtgtctg tgccgtgtgg ctgtgagaag agctcttggc aaaaccggct    120
tcatctgatt ccttcgctgc ctctgccaga ccccataaag aagtttctac tccatgagta    180
gactccaagt gctgcggttg attccagtga gggagaaagt gatctgcagg gaggtggaca    240
```

-continued

```
ccgagccctg agtgctgtgc tgctgctggt ctcctgatgg ctgttgctgc agaagatgtc      300
ctcgtagact gtcattgctc ctcaggtgcc tgggccgctg aacagtcctt gggtcattgt      360
cagctgagag gcttatacta aagttattat tgtttttccc aagttctctg ttctggattt      420
tcagttgcat attaatgtaa cgggccatgg ggtatgtaca tgtaggggct gaggttggag      480
gcctactaat ttcctgtagg gaagactccc agcacttctg gaactgtgct tctctttatt      540
tttctacttc tcaatttgat ggttcgatta aagccttcta gtatctcaat gaaaa           595
```

<210> SEQ ID NO 28
<211> LENGTH: 896
<212> TYPE: DNA
<213> ORGANISM: Mouse
<220> FEATURE:
<221> NAME/KEY: CDS
<222> LOCATION: (4)..(393)
<221> NAME/KEY: UNSURE
<222> LOCATION: (551)
<223> OTHER INFORMATION: n is unsure
<221> NAME/KEY: UNSURE
<222> LOCATION: (651)
<223> OTHER INFORMATION: n is unsure

<400> SEQUENCE: 28

```
ctg atg tcc gca att ctg aag gtt gga cac cac tgc tgg ctg cct gtg        48
    Met Ser Ala Ile Leu Lys Val Gly His His Cys Trp Leu Pro Val
    1               5                   10                  15 aca tcc gct gtc aat ccc caa agg atg ctg agg cca cca acc gct            96
Thr Ser Ala Val Asn Pro Gln Arg Met Leu Arg Pro Pro Thr Ala
                20                  25                  30 gtt ttc aac tgt gcc gct tgc tgc tgt ctg tgg ggg cag atg ctg atg        144
Val Phe Asn Cys Ala Ala Cys Cys Cys Leu Trp Gly Gln Met Leu Met
            35                  40                  45 aat aca tac cgt gta gtt cag ctt cct gag gag gcc aag ggc ttg gtg        192
Asn Thr Tyr Arg Val Val Gln Leu Pro Glu Glu Ala Lys Gly Leu Val
        50                  55                  60 cca cca gag att cta cag aag tac cat gga ttc tac tct tcc ctc ttt        240
Pro Pro Glu Ile Leu Gln Lys Tyr His Gly Phe Tyr Ser Ser Leu Phe
65                  70                  75 gcc ttg gtg agg cag ccc agg tcg ctg cag cat ctc tgc cgt tgt gcg        288
Ala Leu Val Arg Gln Pro Arg Ser Leu Gln His Leu Cys Arg Cys Ala
80                  85                  90                  95 ctc cgc agt cac ctg gag ggc tgt ctg ccc cat gca cta ccg cgc ctt        336
Leu Arg Ser His Leu Glu Gly Cys Leu Pro His Ala Leu Pro Arg Leu
                100                 105                 110 ccc ctg cca ccg cgc atg ctc cgc ttt ctg cag ctg gac ttt gag gat        384
Pro Leu Pro Pro Arg Met Leu Arg Phe Leu Gln Leu Asp Phe Glu Asp
            115                 120                 125 ctg ctc tac taggcttgct gccctgtgaa caaagcagac ccacccccca               433
Leu Leu Tyr
        130 ccccaagggc atctctcagc aatgaatgat gcaaggcggt ctgtcttcaa gtcaggagtg     493 gacgccttga tccacacttg agagaagagg ccagatcagc accyggctgg tagtgatngc     553 agagggcacc tgtgcagatc tgtgtgcgca ctggaaatct ctaggctgaa ggcyagagca     613 aatggtgcar gtgttagtcc ttgggangag agacagangg tgagaaagca agacagaggt     673 gagagtgcac atgtcaagtg gtagattgcc ttaaaagaaa gctaaaaaaa gaaaaagatt     733 cgggcgaact tctttagggg taatgctgca gcgtgttaaa ctgactgacc agcgtccata     793 tctttggacc cttcccgggt gaaaaagccc cttcatcctc cagcgctccc caagggtgct     853
```

```
tagcaatacc gggtgctttt ctgccgcaaa gtgagttacc aaa         896
```

<210> SEQ ID NO 29
<211> LENGTH: 130
<212> TYPE: PRT
<213> ORGANISM: Mouse

<400> SEQUENCE: 29

| Met | Ser | Ala | Ile | Leu | Lys | Val | Gly | His | His | Cys | Trp | Leu | Pro | Val | Thr |
|---|---|---|---|---|---|---|---|---|---|---|---|---|---|---|---|
| 1 | | | | 5 | | | | | 10 | | | | | 15 | |

| Ser | Ala | Val | Asn | Pro | Gln | Arg | Met | Leu | Arg | Pro | Pro | Thr | Ala | Val |
|---|---|---|---|---|---|---|---|---|---|---|---|---|---|---|
| | | | 20 | | | | | 25 | | | | | 30 | |

| Phe | Asn | Cys | Ala | Ala | Cys | Cys | Cys | Leu | Trp | Gly | Gln | Met | Leu | Met | Asn |
|---|---|---|---|---|---|---|---|---|---|---|---|---|---|---|---|
| | | 35 | | | | | 40 | | | | | 45 | | | |

| Thr | Tyr | Arg | Val | Val | Gln | Leu | Pro | Glu | Glu | Ala | Lys | Gly | Leu | Val | Pro |
|---|---|---|---|---|---|---|---|---|---|---|---|---|---|---|---|
| 50 | | | | | 55 | | | | | 60 | | | | | |

| Pro | Glu | Ile | Leu | Gln | Lys | Tyr | His | Gly | Phe | Tyr | Ser | Ser | Leu | Phe | Ala |
|---|---|---|---|---|---|---|---|---|---|---|---|---|---|---|---|
| 65 | | | | | 70 | | | | | 75 | | | | | 80 |

| Leu | Val | Arg | Gln | Pro | Arg | Ser | Leu | Gln | His | Leu | Cys | Arg | Cys | Ala | Leu |
|---|---|---|---|---|---|---|---|---|---|---|---|---|---|---|---|
| | | | | 85 | | | | | 90 | | | | | 95 | |

| Arg | Ser | His | Leu | Glu | Gly | Cys | Leu | Pro | His | Ala | Leu | Pro | Arg | Leu | Pro |
|---|---|---|---|---|---|---|---|---|---|---|---|---|---|---|---|
| | | | 100 | | | | | 105 | | | | | 110 | | |

| Leu | Pro | Pro | Arg | Met | Leu | Arg | Phe | Leu | Gln | Leu | Asp | Phe | Glu | Asp | Leu |
|---|---|---|---|---|---|---|---|---|---|---|---|---|---|---|---|
| | | | 115 | | | | | 120 | | | | | 125 | | |

| Leu | Tyr |
|---|---|
| | 130 |

<210> SEQ ID NO 30
<211> LENGTH: 436
<212> TYPE: DNA
<213> ORGANISM: Mouse

<400> SEQUENCE: 30

```
gtgggggcgt catcatgacc tcctctaggg ctctgcaaca tgactcctgt ggtgcaaatc   60
aacaaattgt tcactgatga atccacaagg atctctgggc ctacaaccag gtcctggtcc  120
acatgactgt cgtcttcgga gaaggcacca ctcgcccccg gcaggtacgg ctgacacctc  180
catgggagaa gacgtatcca ggcagcagct gcgcggccct tcaagagggc acatcccgtc  240
atctaaaggc acggtgtact gaaggtagtc ctgagacatg agtccgatta ctacaggcac  300
gtgttcctcc aggtggaggc tcaggtcccc gggtgagctg gggctgcagc gggactcagg  360
gcgcggctct ggctgcaggt ctcgcagctc cctgggctgt agctcccgca gatccttgcg  420
cacaccgttg actggt                                                   436
```

<210> SEQ ID NO 31
<211> LENGTH: 2180
<212> TYPE: DNA
<213> ORGANISM: Human

<400> SEQUENCE: 31

```
ttaatagtac ctacatagta gaaaattata actccacttt aaaacaatgt tttctttcta   60
ttcaaatcaa tttaaaactt tttataaaca ttaatgttgc aagagaatcc agtccattta  120
tgaaaattag ttgacaatca agttcaccca agaaaatgtt gactaagcta aagaaatcac  180
agataaaaca ttttaccaaa aggataggta acacacaaaa aaatgctatc acaggaagct  240
atgatcatct aatatttctt taataataat tctagttcca taggttttca tgttatgcca  300
```

```
atttgtaccc gagtttaatt acagaaaagg caacaatttc taaattggtg gtatacatttt    360 cttttacaatt ttttaatgta aggccattta ttaaaataga caaactagaa gatgaaaacg    420
aaggcaacag aaaaattcaa cttttcacaa ccaaaagaat tagcacaacc ttagaaataa    480
tttagaaaaa agtgttgtta aagatatgt tgcagatctc cgttccatta cccaagatta    540
tgtcaattca cgattctaaa taaatctttt taaagtaaga gattaaaaac tcatcttcag    600
tgtatatgta aattccgtgg ttttatcaca caggtatgtt tattcaacac tgctttggaa    660
atggaccatt taaaggaca tggcaatttc cattctgtta agtttcattc aacctttact    720 tagggggttga ttaccacatg aaatgtgctt ttaatgcata aaaatcacag tggattagcc    780
agcaaaaggg actgggcggg gggggcattg aggagaattt gataattcac attgtgatta    840
ttctgcacat tgatgaaaca taattcacac ctctaaaacc tcaagacttc ccttttttaa    900
agaaccaaaa taaacccaag acaccttgct gacacttccc caccctaaa caaactgatg    960 actcttttac acataaaact gaaatagtta tggcagcaaa agattttgat ggcaatgaaa   1020
gtttgtaaac tgtatttcaa tctcttgttc ttattcccaa agtgcaagat gcagggttct   1080 caatcttca gtagtgcttc tcctgtaaat aatccttcat tttgtttggc aaaggcagtt   1140
tctgaattaa gtctattctg gtatactgac gtataacaaa acgacacagg tactgcaacg   1200
agcgcaccta tgaaccccgg aacactggtt ggcaagttct gacggaagtg cagattccag   1260
gcagcgagac cttgaataac aaaaagctcc cattttcaga gtccctgatt gaatgctcca   1320
attagatcaa ctatggacgt atgtccttcc acatcggctg ttcataaaag ctaaacctac   1380
catttgagtg ctcaattcta gtgtgaagtg ttttaccatg ggagcgaaag tcacagctta   1440
aaaggtaacg gtcgtcagaa ctgtcccgaa caagaaaaga accatctggc acgtttgcta   1500
gcttcccttc tgcctcccaa cgtgtgattg gtccccagta ccatccttgc tttgcaagtt   1560
ttttcagctc ctctgtaagg cttgtcacaa ccatgggacc actactttgc actgagtcat   1620
aaactcttgc aaccccagga gcagagttcg gatcaaaatt caaatgacag cgcataactt   1680
tcagccacgt ggggctttct gtccagtgag tccactgaaa gttccccttt gggatttgga   1740
ttattcctgc attggagtaa ccaatggtga agattggagg gacatccatc gtgaacccgc   1800
tctccggggt tctgcaacat gactcccgtg gtgccaatca acaagccatt caccggactg   1860
atccacgaag atctctgggg cgacaactag gtcctggtct acctgactct catcctcggg   1920
gaaagcgcgc cctcccactt gaggaggaac cgcagagact tccatgggag aagagctgtc   1980
cagacaatag ctccgtgatc cttccaaagg atacatcccc tcatctaaag gcacagtata   2040
ctgaatgtag tcctgaggca taagtccaat aacgacaggc acatgttcat ccaggtgaag   2100
atgcaggtct ccattatgag aagccgagct cttcagtgaa ttggcttgct cctggcacgt   2160
ggtctcagac tggaggtcgt                                                2180
```

<210> SEQ ID NO 32
<211> LENGTH: 2649
<212> TYPE: DNA
<213> ORGANISM: Mouse

<400> SEQUENCE: 32

```
ggcacgaggc tgtgtccagc acacagagag ggcccggcca tctgctttgg ttcagagccc     60
tgtgtctgtc tgtcacttag actcttcctc ccggctcgca gctcaccctc catcctcctt    120
actggctcca gcatgactcg cttctcttat gcagagtact tgctctgtt tcactctggc    180 tctgcacctt ccaggtcccc ttcgtctccc gagaacccac cggcccgcgc acccctgggt    240
```

-continued

```
ctgttccaag gggtcatgca gaagtatagc agcaacctgt tcaagacctc ccagatggcg      300
gctatggacc ccgtgctgaa ggccatcaag gaagggatg aagaggcctt gaagatcatg       360
atccaggatg ggaagaatct tgcagagccc aacaaggagg ctggctgcc gctccacgag       420
gctgcctact atggccagct gggctgcctg aaagtcctgc agcaagccta cccagggacc      480
attgaccaac gcacactgca ggaagagaca gcattatacc tggccacatg cagagaacac     540
ctggattgcc tcctgtcgct gctccaggcg ggggcagagc ctgacatctc taacaaatcc     600
agggagactc cactttacaa agcctgtgag cgcaagaacg cggaggcggt gaggatattg     660
gtgcgataca acgcagacgc caaccaccgc tgtaacaggg gctggaccgc actgcacgag    720
tctgtctccc gcaatgacct ggaggtcatg gagatcctag tgagtggcgg ggccaaggtg    780
gaggccaaga atgtctacag catcacccct ttgtttgtgg ctgcccagag tgggcagctg     840
gaggccctga ggttcctggc caagcatggt gcagacatca acacgcaggc cagtgacagt    900
gcatcagccc tctacgaggc cagcaagaat gagcatgaag acgtggtaga gtttcttctc     960
tctcagggcg ccgatgctaa caaagccaac aaggacggcc tgctcccct gcatgttgcc    1020
tccaagaagg gcaactatag aatagtgcag atgctgctgc ctgtgaccag ccgcacgcgc    1080
gtgcgccgta gcggcatcag cccgctgcac ctagcggccg agcgcaacca cgacgcggtg     1140
ctggaggcgc tgctggccgc gcgcttcgac gtgaacgcac ctctggctcc cgagcgcgcc    1200
cgcctctacg aggaccgccg cagttctgcg ctctacttcg ctgtggtcaa caacaatgtg    1260
tacgccaccg agctgttgct gctggcgggc gcggaccccg accgcgatgt catcagccct     1320
ctgctcgtgg ccatccgcca cggctgcctg cgcaccatgc agctgctgtt ggaccatggc    1380
gccaacatcg acgcctacat cgccactcac cccaccgcct ttccagccac catcatgttt    1440
gccatgaagt gcctgtcgtt actcaagttc cttatggacc tcggctgcga tggcgagccc    1500
tgcttctcct gcctgtacgg caacgggccg caccacccgc cccgcgacct ggccgcttcc    1560
acgacgcacc cgtggacgac aaggcaccta gcgtggtgca gttctgtgag ttcctgtcgg    1620
ccccggaagt gagccgctgg gcgggaccca tcatcgatgt cctcctggac tatgtgggca    1680
acgtgcagct gtgctcccgg ctgaaggagc acatcgacag ctttgaggac tgggctgtca    1740
tcaaggagaa ggcagaacct ccgagacctc tggctcacct ctgccggctg cgggttcgga    1800
aggccatagg aaaataccgg ataaaactcc tggacacact gccgcttccc ggcaggctaa    1860
tcagatactt gaaatatgag aatacacagt aaccagcctg gagaggagat gtggccttca    1920
gactgttccc gggacgcccc aggtggcctg catccaggac ccctgggggt cagaacaggt    1980
gtgaccttgc tggttctttg ctggagcttc acccaaagtg agaacctgat gtggggagtg    2040
gacgtggaac ctctgctttc acactgtcag cggatcgcag acccgctctg cttctggcca    2100
tagccagaga ccttcaacct ggggccaggg gagagctggc tgggcaaggg tggcccaggc    2160
aggaatcctg gccttaagct ggagaacttg taggaatccc tcactggacc ctcagctttc    2220
aggctgcgag ggagacgccc agcccaagta ttttatttcc gtgacacaat aacgttgtat    2280
cagaaaaaaa aaaaaacatg ggcgcagctt attccttagt agggtattta cttgcatgcg    2340
cgcttaaagc tactgaaaac atgcgttcca ctatgcttga gaatcccctt gcactggtaa    2400
acgagagccg acgtgcttca aggttggatt tttggttgcc cctttggcgt tccgcgggtt    2460
tgtccgacgt aattgacccc gtgttttgtc actttcgagt gttccgacta ttgggggct    2520
tttggttgtc cccaaaattg tgggtggtgt gcggacgcca cgagaagtgg ttcatgggcg    2580
```

| | |
|---|---:|
| ataatcatta ctggagaatg tagagcggcg gttttacgaa taaatatttt ttaagccgcc | 2640 |
| ttcccaaaa | 2649 |

<210> SEQ ID NO 33
<211> LENGTH: 495
<212> TYPE: DNA
<213> ORGANISM: Human

<400> SEQUENCE: 33

| | |
|---|---:|
| cctcctgaga gttcgccggc ccgggcccaa tgggttgttc caagggtgtca tgcagaaata | 60 |
| cagcagcagc ttgttcaaga cctcccagct ggcgcctgcg gacccttga taaaggccat | 120 |
| caaggatgcg atgaagaggc cttgaagacc atgatcaagg aagggaagaa tctcgcagag | 180 |
| cccaacaagg agggctggct gccgctgcac gaggccgcat actatggcca ggtgggctgc | 240 |
| ctgaaagtcc tgcagcgagc gtacccaggg accatcgacc agcgcaccct gcaggaggaa | 300 |
| acagccgttt acttggcaac gtgcaggggc cacctggact gtctcctgtc actgctccaa | 360 |
| gcagggcag agcgggacat ctccaacaaa tcccgagaga accgctctac aaagcctgtg | 420 |
| agcgcaagaa cgcggaagcc gtgaagattc ttggtgcagc acaacgcaga caccaacaac | 480 |
| gctgcaaccg ggctg | 495 |

<210> SEQ ID NO 34
<211> LENGTH: 709
<212> TYPE: DNA
<213> ORGANISM: Human

<400> SEQUENCE: 34

| | |
|---|---:|
| gtgcagctct gctcgcggct gaaggaacac atcgacagct ttgaggactg ggccgtcatc | 60 |
| aaggagaagg cagaacctcc aagacctctg gctcaccttt gccgactgcg ggttcgaaag | 120 |
| gccattggga ataccgtat aaaactccta gacaccttgc cgctcccagg caggctgatt | 180 |
| agatacctga atacgagaa cacccagtaa ctggggccac ggggagagag gagtagcccc | 240 |
| tcagactctt cttactaagt ctcaggacgt cggtgttccc aactccaagg ggacctggtg | 300 |
| acagacgagg ctgcaggctg cctccctctc agcctggaca gctaccagga tctcactggg | 360 |
| tctcagggcc cagagctttg gccagagcag agaacagaat gtgtcaagga gaagaatcat | 420 |
| ttgtttacaa actgatgagc agatcccaga ccttctctac cttcaggaat ggcagaaacc | 480 |
| tctattcctg gggccagggc agagcttgag gtgttctggg gaaggtggtg ctcagagcct | 540 |
| tccctgtgcc cctccacttg ttctggaaaa ctcaccactt gacttcagag ctttctctcc | 600 |
| aaagactaag atgaagacgt ggcccaaggt aggggtagg gggagcctgg gtcttggagg | 660 |
| gctttgttaa gtattaatat aataaatgtt acacatgtga aaaaaaaa | 709 |

<210> SEQ ID NO 35
<211> LENGTH: 848
<212> TYPE: DNA
<213> ORGANISM: Human
<220> FEATURE:
<221> NAME/KEY: CDS
<222> LOCATION: (1)..(621)

<400> SEQUENCE: 35

| | |
|---|---:|
| ttg gag aag tgt ggt tgg tat tgg ggg cca atg aat tgg gaa gat gca<br>Leu Glu Lys Cys Gly Trp Tyr Trp Gly Pro Met Asn Trp Glu Asp Ala<br>1                  5                  10                  15 | 48 |
| gag atg aag ctg aaa ggg aaa cca gat ggt tct ttc ctg gta cga gac<br>Glu Met Lys Leu Lys Gly Lys Pro Asp Gly Ser Phe Leu Val Arg Asp | 96 |

-continued

```
              20                  25                  30
agt tct gat cct cgt tac atc ctg agc ctc agt ttc cga tca cag ggt     144
Ser Ser Asp Pro Arg Tyr Ile Leu Ser Leu Ser Phe Arg Ser Gln Gly
         35                  40                  45 atc acc cac cac act aga atg gag cac tac aga gga acc ttc agc ctg     192
Ile Thr His His Thr Arg Met Glu His Tyr Arg Gly Thr Phe Ser Leu
 50                  55                  60 tgg tgt cat ccc aag ttt gag gac cgc tgt caa tct gtt gta gag ttt     240
Trp Cys His Pro Lys Phe Glu Asp Arg Cys Gln Ser Val Val Glu Phe
 65                  70                  75                  80 att aag aga gcc att atg cac tcc aag aat gga aag ttt ctc tat ttc     288
Ile Lys Arg Ala Ile Met His Ser Lys Asn Gly Lys Phe Leu Tyr Phe
                 85                  90                  95 tta aga tcc agg gtt cca gga ctg cca cca act cct gtc cag ctg ctc     336
Leu Arg Ser Arg Val Pro Gly Leu Pro Pro Thr Pro Val Gln Leu Leu
            100                 105                 110 tat cca gtg tcc cga ttc agc aat gtc aaa tcc ctc cag cac ctt tgc     384
Tyr Pro Val Ser Arg Phe Ser Asn Val Lys Ser Leu Gln His Leu Cys
        115                 120                 125 aga ttc cgg ata cga cag ctc gtc agg ata gat cac atc cca gat ctc     432
Arg Phe Arg Ile Arg Gln Leu Val Arg Ile Asp His Ile Pro Asp Leu
130                 135                 140 cca ctg cct aaa cct ctg atc tct tat atc cga aag ttc tac tac tat     480
Pro Leu Pro Lys Pro Leu Ile Ser Tyr Ile Arg Lys Phe Tyr Tyr Tyr
145                 150                 155                 160 gat cct cag gaa gag gta tac ctg tct cta aag gaa gcg cag cgt cag     528
Asp Pro Gln Glu Glu Val Tyr Leu Ser Leu Lys Glu Ala Gln Arg Gln
                165                 170                 175 ttt cca aac aga agc aag agg tgg aac cct cca cgt agc gag ggg ctc     576
Phe Pro Asn Arg Ser Lys Arg Trp Asn Pro Pro Arg Ser Glu Gly Leu
            180                 185                 190 cct gct ggt cac cac caa ggg cat ttg gtt gcc aag ctc cag ctt         621
Pro Ala Gly His His Gln Gly His Leu Val Ala Lys Leu Gln Leu
        195                 200                 205 tgaagaacca aattaagcta ccatgaaaag aagaggaaaa gtgagggaac aggaaggttg    681
ggattctctg tgcagagact tggttcccc acgcaagccc tggggcttgg aagaagcaca    741
tgaccgtact ctgcgtgggg ctccacctca cacccacccc tgggcatctt aggactggag   801
gggctccttg gaaaactgga agaagtctca acactgtttc tttttca                 848
```

<210> SEQ ID NO 36
<211> LENGTH: 207
<212> TYPE: PRT
<213> ORGANISM: Human

<400> SEQUENCE: 36

```
Leu Glu Lys Cys Gly Trp Tyr Trp Gly Pro Met Asn Trp Glu Asp Ala
 1               5                  10                  15

Glu Met Lys Leu Lys Gly Lys Pro Asp Gly Ser Phe Leu Val Arg Asp
                20                  25                  30

Ser Ser Asp Pro Arg Tyr Ile Leu Ser Leu Ser Phe Arg Ser Gln Gly
         35                  40                  45

Ile Thr His His Thr Arg Met Glu His Tyr Arg Gly Thr Phe Ser Leu
 50                  55                  60

Trp Cys His Pro Lys Phe Glu Asp Arg Cys Gln Ser Val Val Glu Phe
 65                  70                  75                  80

Ile Lys Arg Ala Ile Met His Ser Lys Asn Gly Lys Phe Leu Tyr Phe
                 85                  90                  95
```

```
Leu Arg Ser Arg Val Pro Gly Leu Pro Pro Thr Pro Val Gln Leu Leu
            100                 105                 110
Tyr Pro Val Ser Arg Phe Ser Asn Val Lys Ser Leu Gln His Leu Cys
        115                 120                 125
Arg Phe Arg Ile Arg Gln Leu Val Arg Ile Asp His Ile Pro Asp Leu
    130                 135                 140
Pro Leu Pro Lys Pro Leu Ile Ser Tyr Ile Arg Lys Phe Tyr Tyr Tyr
145                 150                 155                 160
Asp Pro Gln Glu Glu Val Tyr Leu Ser Leu Lys Glu Ala Gln Arg Gln
                165                 170                 175
Phe Pro Asn Arg Ser Lys Arg Trp Asn Pro Pro Arg Ser Glu Gly Leu
            180                 185                 190
Pro Ala Gly His His Gln Gly His Leu Val Ala Lys Leu Gln Leu
        195                 200                 205

<210> SEQ ID NO 37
<211> LENGTH: 464
<212> TYPE: DNA
<213> ORGANISM: Mouse

<400> SEQUENCE: 37
gttccaagcc taacccatct ttgtcgtttg gaaattcggg ccagtctaaa agcagagcac    60
cttcactctg acattttcat ccatcagttg ccacttccca gaagtctgca gaactatttg   120
ctctatgaag aggttttaag aatgaatgag attctagaac cagcagctaa tcaggatgga   180
gaaaccagca aggccaccct gacacaggtc tttaattctg tttagtcaca aaagacggct   240
tgtgtgactg tttggatttg gtgatcaaat gtccatgttt acagttgctt ttcccagttt   300
gtgtctttcc caatattgtg aaccttatcc atcttgcctt actcagtttt atttctagtg   360
cactttgttg tgtattattt gtttacctga ccatttccta ctttattctg ctaataaact   420
gtaattctga aaaaaaaaaa aaaaaaaaa aaaaaaaaa aaaa                      464

<210> SEQ ID NO 38
<211> LENGTH: 747
<212> TYPE: DNA
<213> ORGANISM: Human

<400> SEQUENCE: 38
ggggatcgaa agcgggggct tctgggacgc agctctggag acgcggcctc ggaccagcca    60
tttcggtgta gaagtggcag cacggcagac tggtcaaaca aatggatttt acagaggctt   120
acgcggacac gtgctctaca gttggacttg ctgccaggga aggcaatgtt aaagtcttaa   180
ggaaactgct caaaaagggc cgaagtgtcg atgttgctga taacagggga tggatgccaa   240
ttcatgaagc agcttatcac aactctgtag aatgtttgca aatgttaatt aatgcagatt   300
catctgaaaa ctacattaag atgaagacct tgaaggtttt ctgtgctttg catctcgctg   360
caagtcaagg acattggaaa atcgtacaga ttcttttaga agctggggca gatcctaatg   420
caactacttt agaagaaacg acaccattgt ttttagctgt tgaaaatgga cagatagatg   480
tgttaaggct gttgcttcaa cacggagcaa atgttaatgg atcccattct atgtgtggat   540
ggaactcctt gcaccaggct tcttttcagg aaaatgctga gatcataaaa ttgcttctta   600
gaaaaggagc aaacaaggaa tgccaggatg actttggaat cacacctta tttgtggctg   660
ctcagtatgg ccaagctaga aagctttgaa gcatacttat ttcatccggg tgcaaatgtc   720
aattgtcaag ccttggacaa agctacc                                       747
```

<210> SEQ ID NO 39
<211> LENGTH: 1018
<212> TYPE: DNA
<213> ORGANISM: Human

<400> SEQUENCE: 39

| | | | | | |
|---|---|---|---|---|---|
| cacaaatggg | accatacaaa | aatcttggac | ttgttaataa | ccacttacta | accgggacct | 60 |
| gtgacactgg | gctaaacaaa | gtaagtccct | gtttactcag | cagtgtttgg | gggacatgaa | 120 |
| ggattgccta | gaaatattac | tccggaatgg | tctacagccc | agacgcccag | gcgtgccttg | 180 |
| tttttggatt | cagttctcct | gtgtgcatgg | cttttccaaaa | ggaggtggag | ctgtagttct | 240 |
| ttggaattgt | gaacattctt | ttgaaatatg | gagcccagat | aaatgaactt | catttggcat | 300 |
| actgcctgaa | gtacgagaag | ttttcgatat | ttcgctactt | tttgaggaaa | ggttgctcat | 360 |
| tgggaccatg | gaaccatata | tatgaatttg | taaatcatgc | aattaaagca | caagcaaaat | 420 |
| ataaggagtg | gttgccacat | cttctggttg | ctggatttga | cccactgatt | ctactgtgca | 480 |
| attcttggat | tgactcagtc | agcattgaca | cccttatctt | cactttggag | tttactaatt | 540 |
| ggaagacact | tgcaccagct | gttgaaagga | tgctctctgc | tcgtgcctca | aacgcttgga | 600 |
| ttctacagca | acatattgcc | cactgttcca | tccctgaccc | atctttgtcg | tttggaaatt | 660 |
| cggtccagtc | taaaatcaga | acgtctacgg | tctgacagtt | atattagtca | gctgccactt | 720 |
| cccagaagcc | tacataatta | tttgctctat | gaagacgttc | tgaggatgta | tgaagttcca | 780 |
| gaactggcag | ctattcaaga | tggataaatc | agtgaaacta | cttaacacag | ctaatttttt | 840 |
| tctctgaaaa | atcatcgaga | caaaagagcc | acagagtaca | agttttttatg | attttatagt | 900 |
| caaaagatga | ttattgattg | tcagataggt | taggttttgg | ggggccagta | gttcagtgag | 960 |
| aatgttttatg | tttacaacta | gccttcccag | taaaaaaaaa | aaaaaaaaaa | aaaaaaaa | 1018 |

<210> SEQ ID NO 40
<211> LENGTH: 1897
<212> TYPE: DNA
<213> ORGANISM: Mouse

<400> SEQUENCE: 40

| | | | | | |
|---|---|---|---|---|---|
| cgggggggctg | ggacctgggg | cgtaaccgtc | tctaccacga | cggcaagaac | cagccaagta | 60 |
| aaacataccc | agcctttctg | gagccggacg | agacattcat | tgtccctgac | tccttttttcg | 120 |
| tggccctgga | catgratgat | gggaccttaa | gtttcatcgt | ggatggacag | tacatgggag | 180 |
| tggctttccg | gggactcaag | ggtaaaaagc | tgtatcctgt | agtgagtgcc | gtctggggcc | 240 |
| actgtgagat | ccgcatgcgc | tacttgaacg | gacttgatcc | tgagcccctg | ccactcatgg | 300 |
| acctgtgccg | gcgttcggtg | cgcctagcgc | tgggaaaaga | gcgcctgggt | gccatccccg | 360 |
| ctctgccgct | acctgcctcc | ctcaaagcct | acctcctcta | ccagtgatcc | acatcccagg | 420 |
| accgccatac | gacagccatc | tggtgccaar | tcactgagcc | cgttgggggtc | cgccgacccc | 480 |
| tgcgcctggg | atggaagccc | acctcagcca | tgggcagacg | tgcccctca | tcctaccggc | 540 |
| tgcctctgct | gggggaacct | atgccaacgg | acttctccct | tcccaacact | ggctgaagca | 600 |
| gcagcaccca | ggcccttccc | tgaaccgat | gcagagaata | aactatgaaa | acctctctca | 660 |
| ggcgccttct | gctctcaggt | ggagtgggct | gcccccccact | ctctgcagag | agaggctaca | 720 |
| cccacctggg | gggtcctggg | aggtaagact | agtaggaggt | gccagggctg | artccaaaag | 780 |
| caggaatggc | caggamcagg | ccatacagat | gaagctcagg | atgtcacata | ccatggacam | 840 |

```
tgagacagaa ccccaggttg gamttccctt gggccaacga gtgccagctt taatgtcagc      900
tgcmggtgct ctgtggcctg tatttattct ttaaacagta gcaaaggcca tttatttatt      960
ccacttagaa aggaaacctt ggtgggtggy ttccctcgat gtgctttccc ccacctccct     1020
ggaatgtgtg tgccacacct gtccttgtcc caggccagga ctgtgcaca tgagctggtg      1080 tgcacagata cacgtatgtc gtcgtgcatg acccctgact agttcctaag tagccctgca     1140
ccaagcacca gagcagaccc caagagaggc ccgtgcaagt ccccatgtcc ccaggtcctt     1200
gcttctgttg ccttgggact catacaccgg cacacgtgtt tcagcctctt gacttccatg     1260
agcttcgaat tttgccccccg attcttctga tatttcccat tggcatcctc caaagctctg     1320
ggcctggagg gcattaggac acatggaatg agtggggtct ccagcccctg ggaaagccac     1380
tggcaaggca ggattagaaa gaccaagagc agggtggggc gccatgaagc ctgtatgcct     1440
ctcaggctca agaccccgcc acacacccac tcaagcctca gaagtggtgt gtagggcagc     1500
cccaggagag gaatgcctgt cctagcagca cgtacatgga gcaccccaca tgtgctccag     1560
ccctctggct gtttctcttg ctctagaatc aactccctac attgggaatg tagccatttg     1620
gtagaggact tgcctagcct gcaggaagct cacgttccat cccctgcacc aaggagaatc     1680
aaagctcagg aggctgaggc aggaggattg ctgtcagtgg tgtacagagg tcatggccat     1740
cctgggctat attaaaacctt gtcctttaag aaaaagaaaa gaaatcaact tccattgaat     1800
ctgagttctg ctcatttctg cacaggtaca atagatgact tkatttgttg aaaaatgktt     1860
aatatattta cmtatatata tatttgtaag aagcatt                              1897
```

<210> SEQ ID NO 41
<211> LENGTH: 134
<212> TYPE: PRT
<213> ORGANISM: Mouse
<220> FEATURE:
<221> NAME/KEY: UNSURE
<222> LOCATION: (45)
<223> OTHER INFORMATION: Xaa is unsure

<400> SEQUENCE: 41

```
Gly Gly Trp Asp Leu Gly Arg Asn Arg Leu Tyr His Asp Gly Lys Asn
 1               5                  10                  15

Gln Pro Ser Lys Thr Tyr Pro Ala Phe Leu Glu Pro Asp Glu Thr Phe
            20                  25                  30

Ile Val Pro Asp Ser Phe Phe Val Ala Leu Asp Met Xaa Asp Gly Thr
        35                  40                  45

Leu Ser Phe Ile Val Asp Gly Gln Tyr Met Gly Val Ala Phe Arg Gly
    50                  55                  60

Leu Lys Gly Lys Leu Tyr Pro Val Val Ser Ala Val Trp Gly His
65                  70                  75                  80

Cys Glu Ile Arg Met Arg Tyr Leu Asn Gly Leu Asp Pro Glu Pro Leu
                85                  90                  95

Pro Leu Met Asp Leu Cys Arg Arg Ser Val Arg Leu Ala Leu Gly Lys
            100                 105                 110

Glu Arg Leu Gly Ala Ile Pro Ala Leu Pro Leu Pro Ala Ser Leu Lys
        115                 120                 125

Ala Tyr Leu Leu Tyr Gln
    130
```

<210> SEQ ID NO 42
<211> LENGTH: 265
<212> TYPE: DNA

<213> ORGANISM: Human

<400> SEQUENCE: 42

| | | | | | |
|---|---|---|---|---|---|
| aagggtaaaa | aactgtatcc | tgtagtgagt | gccgtctggg | gccactgtag | atccgaatgc | 60 |
| gctacttgaa | cggactcgat | cccgagactg | ccgctcatgg | atttgtgccg | tcgctcggtg | 120 |
| cgcctggccc | tggggaggga | gcgcctgggg | gagaaccaca | cctgccgctg | ccggcttccc | 180 |
| tcaaggccta | cctcctctac | cagtgacgtt | cgccatcata | ccgccagcgc | gacagccacc | 240 |
| tggtgccaac | tcactgagcc | gcctg | | | | 265 |

<210> SEQ ID NO 43
<211> LENGTH: 2438
<212> TYPE: DNA
<213> ORGANISM: Mouse

<400> SEQUENCE: 43

| | | | | | |
|---|---|---|---|---|---|
| aagtggcggc | ggtccctgga | gagcaggcgg | aggcagcggc | aagtctgact | ctgggctgac | 60 |
| cgtggagccg | gggcggggc | tgacagccag | gcctccgcct | ggcgggagcc | gcacgaggag | 120 |
| cgggagtggc | cgggcctctc | ttccgcgctt | gagcgagcgc | cgggtgatgg | cggtggtgat | 180 |
| ggcggcaggc | gctcggacag | ctccgcttga | gctgagctcg | gagagatccg | tccagaaagt | 240 |
| gcccagaaga | aacttcctct | tagaaaagct | gaaaaacaca | rtatttataa | cactggaaat | 300 |
| tgtaaagaat | ttgtttaaaa | tggctgaaaa | caatagtaaa | aatgtagatg | tacggcctaa | 360 |
| aacaagtcgg | agtcgaagtg | ctgacaggaa | ggatggttat | gtgtggagtg | gaaagaagtt | 420 |
| gtcttggtcc | aaaaagagtg | agagttgttc | tgaatctgaa | gccataggta | ctgttgagaa | 480 |
| tgttgaaatt | cctctaagaa | gccaagaaag | gcagcttagc | tgttcgtcca | ttgagttgga | 540 |
| cttagatcat | tcctgtgggc | atagattttt | aggccgatcc | cttaaacaga | aactgcaaga | 600 |
| tgcggtgggg | cagtgttttc | caataaagaa | ttgtagtggc | cgacactctc | cagggcttcc | 660 |
| atctaaaaga | aagattcata | tcagtgaact | catgttagat | aagtgccctt | tcccacctcg | 720 |
| ctcagattta | gcctttaggt | ggcattttat | taaacgacac | actgttccta | tgagtcccaa | 780 |
| ctcagatgaa | tgggtgagtg | cagacctgtc | tgagaggaaa | ctgagagatg | ctcagctgaa | 840 |
| acgaagaaac | acagaagatg | acatacccctg | tttctcacat | accaatggcc | agccttgtgt | 900 |
| cataactgcc | aacagtgctt | cgtgtacagg | tggtcacata | actggttcta | tgatgaactt | 960 |
| ggtcacaaac | aacagcatag | aagacagtga | catggattca | gaggatgaaa | ttataacgct | 1020 |
| gtgcacaagc | tccagaaaaa | ggaataagcc | caggtgggaa | atggaagagg | agatcctgca | 1080 |
| gttggaggca | cctcctaagt | tccacaccca | gatcgactac | gtccactgcc | ttgttccaga | 1140 |
| cctccttcag | atcagtaaca | atccgtgcta | ctggggtgtc | atggacaaat | atgcagccga | 1200 |
| agctctgctg | gaaggaaagc | cagagggcac | cttttttactt | cgagattcag | cgcaggaaga | 1260 |
| ttatttattc | tctgttagtt | ttagacgcta | cagtcgttct | cttcatgcta | gaattgagca | 1320 |
| gtggaatcat | aactttagct | ttgatgccca | tgatccttgt | gtcttccatt | ctcctgatat | 1380 |
| tactgggctc | ctggaacact | ataaggaccc | cagtgcctgt | atgttctttg | agccgctctt | 1440 |
| gtccactccc | ttaatccgga | cgttcccctt | ttccttgcag | catatttgca | gaacggttat | 1500 |
| ttgtaattgt | acgacttacg | atggcatcga | tgcccttccc | attccttcgc | ctatgaaatt | 1560 |
| gtatctgaag | gaataccatt | ataaatcaaa | agttaggtta | ctcaggattg | atgtgccaga | 1620 |
| gcagcagtga | tgcggagagg | ttagaatgtc | gacctgcata | catattttca | tttaatattt | 1680 |
| tatttttctt | atgcctcttt | gaattttttgt | acaaaggcag | ttgaatcaaa | taaaactgtg | 1740 |

```
ccctaagttt taattccaga tcaatttatt ttttttatga tacacttgtt atatatttt    1800 aagcaggtgt ttggttttgt ttttaccata taaatttaca tatggtccag gcatatttac    1860
aatttcaagg cattgcatat acatttgaat attctgtatt ttttaaataa tcttttgttc    1920
tttcctatgt gtgaaatatt ttgctaatct atgctatcag tattcttgta tgaccgaata    1980
gttacctatt ctcttttcat cttgaagatt ttcagtaaag agtgttgtaa tcaatccatt    2040
ataatgtaat tgacttttgt aatttgccaa taggagtgtt aaacaacaaa atgatttaaa    2100
atgaaactta atgtattttc atttttaaata ttaactaaac caagtttgtt tgttagttat    2160
tctagccaat aagaaaagag aatgtagcat cctagaggtg tatttgttct gcagtttggc    2220
aggaccgtca gttagtccaa ataaacatcc cctcagcgtg gaggcgaatg gaacctgtgc    2280
tcctttctta cgggaagctt tgcaaagcaa aatagcaggg ttacaagctt ggagttgtta    2340
aggcaactag agttttctct attaatttat agactgttgt tgcacctact tagctctttt    2400
ttgggaactc tagttcccag gggaaaatac ctcgtgcc                            2438
```

<210> SEQ ID NO 44
<211> LENGTH: 542
<212> TYPE: PRT
<213> ORGANISM: Mouse
<220> FEATURE:
<221> NAME/KEY: UNSURE
<222> LOCATION: (94)
<223> OTHER INFORMATION: Xaa is unsure

<400> SEQUENCE: 44

```
Ser Gly Gly Gly Pro Trp Arg Ala Gly Gly Ser Gly Lys Ser Asp
 1               5                  10                  15

Ser Gly Leu Thr Val Glu Pro Gly Arg Gly Leu Thr Ala Arg Pro Pro
             20                  25                  30

Pro Gly Gly Ser Arg Thr Arg Ser Gly Ser Gly Arg Ala Ser Leu Pro
         35                  40                  45

Arg Leu Ser Glu Arg Arg Val Met Ala Val Val Met Ala Ala Gly Ala
     50                  55                  60

Arg Thr Ala Pro Leu Glu Leu Ser Ser Glu Arg Ser Val Gln Lys Val
 65                  70                  75                  80

Pro Arg Arg Asn Phe Leu Leu Glu Lys Leu Lys Asn Thr Xaa Phe Ile
                 85                  90                  95

Thr Leu Glu Ile Val Lys Asn Leu Phe Lys Met Ala Glu Asn Asn Ser
            100                 105                 110

Lys Asn Val Asp Val Arg Pro Lys Thr Ser Arg Ser Arg Ser Ala Asp
        115                 120                 125

Arg Lys Asp Gly Tyr Val Trp Ser Gly Lys Lys Leu Ser Trp Ser Lys
    130                 135                 140

Lys Ser Glu Ser Cys Ser Glu Ser Glu Ala Ile Gly Thr Val Glu Asn
145                 150                 155                 160

Val Glu Ile Pro Leu Arg Ser Gln Glu Arg Gln Leu Ser Cys Ser Ser
                165                 170                 175

Ile Glu Leu Asp Leu Asp His Ser Cys Gly His Arg Phe Leu Gly Arg
            180                 185                 190

Ser Leu Lys Gln Lys Leu Gln Asp Ala Val Gly Gln Cys Phe Pro Ile
        195                 200                 205

Lys Asn Cys Ser Gly Arg His Ser Pro Gly Leu Pro Ser Lys Arg Lys
    210                 215                 220
```

```
Ile His Ile Ser Glu Leu Met Leu Asp Lys Cys Pro Phe Pro Pro Arg
225                 230                 235                 240

Ser Asp Leu Ala Phe Arg Trp His Phe Ile Lys Arg His Thr Val Pro
            245                 250                 255

Met Ser Pro Asn Ser Asp Glu Trp Val Ser Ala Asp Leu Ser Glu Arg
        260                 265                 270

Lys Leu Arg Asp Ala Gln Leu Lys Arg Arg Asn Thr Glu Asp Asp Ile
    275                 280                 285

Pro Cys Phe Ser His Thr Asn Gly Gln Pro Cys Val Ile Thr Ala Asn
290                 295                 300

Ser Ala Ser Cys Thr Gly Gly His Ile Thr Gly Ser Met Met Asn Leu
305                 310                 315                 320

Val Thr Asn Asn Ser Ile Glu Asp Ser Asp Met Asp Ser Glu Asp Glu
                325                 330                 335

Ile Ile Thr Leu Cys Thr Ser Ser Arg Lys Arg Asn Lys Pro Arg Trp
            340                 345                 350

Glu Met Glu Glu Ile Leu Gln Leu Glu Ala Pro Pro Lys Phe His
        355                 360                 365

Thr Gln Ile Asp Tyr Val His Cys Leu Val Pro Asp Leu Leu Gln Ile
    370                 375                 380

Ser Asn Pro Cys Tyr Trp Gly Val Met Asp Lys Tyr Ala Ala Glu
385                 390                 395                 400

Ala Leu Leu Glu Gly Lys Pro Glu Gly Thr Phe Leu Leu Arg Asp Ser
                405                 410                 415

Ala Gln Glu Asp Tyr Leu Phe Ser Val Ser Phe Arg Arg Tyr Ser Arg
            420                 425                 430

Ser Leu His Ala Arg Ile Glu Gln Trp Asn His Asn Phe Ser Phe Asp
        435                 440                 445

Ala His Asp Pro Cys Val Phe His Ser Pro Asp Ile Thr Gly Leu Leu
    450                 455                 460

Glu His Tyr Lys Asp Pro Ser Ala Cys Met Phe Phe Glu Pro Leu Leu
465                 470                 475                 480

Ser Thr Pro Leu Ile Arg Thr Phe Pro Phe Ser Leu Gln His Ile Cys
                485                 490                 495

Arg Thr Val Ile Cys Asn Cys Thr Thr Tyr Asp Gly Ile Asp Ala Leu
            500                 505                 510

Pro Ile Pro Ser Pro Met Lys Leu Tyr Leu Lys Glu Tyr His Tyr Lys
        515                 520                 525

Ser Lys Val Arg Leu Leu Arg Ile Asp Val Pro Glu Gln Gln
    530                 535                 540
```

<210> SEQ ID NO 45
<211> LENGTH: 5000
<212> TYPE: DNA
<213> ORGANISM: Mouse

<400> SEQUENCE: 45

```
ccctctgggc aagccgcccc ccccccaccc atctaccaca cacacacaca cacacacaca      60
cacacattca gaccttgggg caaaacaaa gcaaataac aacaacaaaa acactgcctg       120
tggaaagtcc ttacttcagg aaggttggca gatgaggagc aagggaacat ttatcagga      180
ctgccacaaa ggagtctttt tttttaatgg ttttttcaaga cagggtttct ctgtatagcc    240
ctggctgtcc tggagctcac tttgtagacc aggctggcct cgaactcaga aattcgcctg    300
cctctgcctc ctgagtgctg ggattaaagg cgtgcagcac catgtccaac tggcattttc    360
```

-continued

| | |
|---|---|
| tcaattaagg ttcgttcctt tcagataact ctaggttctg ggtcaagctg acacaaggct | 420 |
| acacagcaca gtttgtatgc cacattcagt tcagaagaca cccaacctcc ctggaactgg | 480 |
| aacttatgca catttgtgag cttccacttg ggagtgggaa cctgaactgg gtcctctgca | 540 |
| agagcagccg tgctcttaac tgctgagcca tttcagcagc ctcacatcag aattaagtta | 600 |
| gaaattagcc gggtatgaat catacccttc gaatcctagc atctgaaagc agagctaaga | 660 |
| gaaacaggga ttcaagacca gctcttggct acagagcccg tcctgtccta ggatgggcta | 720 |
| caagagacta tttcaaagcc atccaaacaa caataactac aacaacaaca aggttaaaat | 780 |
| taggctgggc acagggtaca cacctttaat gccaacactc aggaggcaga ggcaggctga | 840 |
| tcagtgtgag tttgagttca acgtggtcta catagggagt tctaggccag cagaggttac | 900 |
| agtctctctc tctctctctc tctctctctc tctctcacac acacacacac acacacacac | 960 |
| acacacacac acacacacgg tggcattatg ggattttttt gggataaggt ttctctgtct | 1020 |
| agccctggca tagattcact ctgtagacta ggctagcctt gaactcagag atccgcctgc | 1080 |
| ctctgcctcc caagtgctgg gattataggt gttgcaccac cactgcccag ccactttggg | 1140 |
| attttttgaac tgttatcaag aggctttcga ggaggtcaaa cttcaacagc aacctctcca | 1200 |
| tgataatgta gctaatgatc aaacgacact caaaacttaa cccttaaagc acacatccac | 1260 |
| cagacagcgt gcccactcgt agttccatta ctcaggaggc tgaagcagga ggatgaagga | 1320 |
| ctaaggcttc agcaacctag ggagccgcag gggacagtag tctcaatccc tacattctcc | 1380 |
| tgaacacagg agcaggagtt caggaagggt gtcaaggccg cttactgatc ttagggcctc | 1440 |
| aggaatgact agctcaggca gagagagcaa aggtctccag tggagaagtc tacacacaca | 1500 |
| cacacacaca cacacacaca cacacacaca cagaatccaa ggcgatgacg tcatcaaagg | 1560 |
| gttaattcta gtctgggatg gggggaggg tggggcacgc agctgtcagg tggctttgga | 1620 |
| aaaataaact gctgaagagt ctgacgccag ggagtcctgg gagggacaag aggttaccca | 1680 |
| ctcaaagagt gtgctccaca aagcatgcgc gcttgtccac gtctggagtc gtcacttatt | 1740 |
| ttttgcctgg attctttgta gccggtgggt tctcaaggcg gtaagtggtg tggccgccgt | 1800 |
| ggtctgggag gtgacgatag ggttaatcgt ccacagagcc caggggcgga gcgcgggcgg | 1860 |
| gcgtccgcag ccccgctgga gccggaagca gtggctggtc aggggcgctt ctagccttcc | 1920 |
| ctatctgtac ttccacagag gtctctgcga gctaggggga cagtgaggtg cggggtaggg | 1980 |
| gcccggcgtt agagccagca aggggacggt tcacggtaag gtctgaggga gagagagctc | 2040 |
| ctgagaaact tggggggcgc gacacagata gggtgaaagc agagtgatag acctgggatg | 2100 |
| gttaggggac caagggaaga ccaggctggt tggcatacac cggtaacgg atgggagtcc | 2160 |
| tagggaaaga tgatgcgcct aacagtcctt tctgtctcca caccactcca ggggacgatc | 2220 |
| cggagctcaa ctttcaaaag cgagacgccc cagcaagcct gttttgagaa gttcttcagc | 2280 |
| ggctctcctc atgggccaga cggccctggc aaggggcagc agcagcaccc ctacctcgca | 2340 |
| ggctctgtac tcggacttct ctcctcccga gggcttggag gagctcctgt ctgctccccc | 2400 |
| tcctgacctg gttgcccaac ggcaccacgg ctggaacccc aaggattgct ccgagaacat | 2460 |
| cgatgtcaag gaaggggtc tgtgctttga gcggcgccct gtgcccaga gcactgatgg | 2520 |
| agtccggggg aaacgggct attcgagagg tctgcacgcc tggagatca gctggcccct | 2580 |
| ggagcaaagg ggcacacacg ccgtggtggg cgtggccacc gccctcgccc cgctgcaggc | 2640 |
| tgaccactat gcggcgcttt tgggcagcaa cagcgagtcc tggggctggg atattgggcg | 2700 |

-continued

```
gggaaaattg tatcatcaga gtaagggcct cgaggccccc cagtatccag ctggacctca    2760
gggtgagcag ctagtggtgc cagagagact gctggtggtt ctggacatgg aggaggggac    2820
tcttggctac tctattgggg gcacgtacct gggaccagcc ttccgtggac tgaaggggag    2880
gaccctctat ccctctgtaa gtgctgtttg gggccagtgc caggtccgca tccgctacat    2940
gggcgaaaga agaggtgaga tacgactag gtgtggggag atcactactc ttggcaatgg    3000
tttgggctgg aaactcatgg ttggagcaca ggaagtaggc ttcttgtcac tttggcctgt    3060
cacttagatg gccttggatc tagcttcact cccaatccct attggatgtg atgcacaaat    3120
tcagagcctt tgggtctccc tcagctgagg tggcggtgga aatggaggaa gaggaagggg    3180
tgcctgagca ggatctcaag ttcaaggatg cctggagttg cttacttacc ttgtcttcct    3240
tctctctccg cagtggagga accacaatcc cttctgcacc tgagccgcct gtgtgtgcgc    3300
catgctctgg gggacacccg gctgggtcaa atatccactc tgcctttgcc ccctgccatg    3360
aagcgctatc tgctctacaa atgacccagt agtacaggt gtgctggcac cctaccgtgg    3420
ggacaggtgg agaggcaccc gctggcctag acaactttaa aaagctggtg aagctggggg    3480
gggggggctg gaccccttca cctccccttc tcacaggagc aagacatata gaaatgatat    3540
taaacaccat ggcagcctgg gacaaagagg ttttgaagt aaaaaatgag atgtattgtc    3600
acaacctgtt tcattattgt tttttgtttt gttttacact ccccccaccccc aggctagagc    3660
cccatcactg tcttaaggaa ttatgacaac ccacaaagct caggcccagg tgtttatttc    3720
ccttacatgt aggatggttc acaaacacaa tacagggggc ttggcaccgt ggggagggg    3780
actatcccag gcctcttagg gtctcatgta taccgaattc agacccgaaa gctctgaatt    3840
tctgcatcag acatccagta gaacttggga gtgaagctag agccaaggcc atctaagtga    3900
caggccaaag tgacacgaag cccacttcct gtgctccaac catgagtttc cagcccaaac    3960
caatggaagg tgatttcact tgtcagggcc caaagggaca gtcagttcta ctccctcccc    4020
tcactaggag ccaccttggt gacagttgat tctacccact gtaagtggta aagggattgg    4080
cctggtccca accataatag ggcggtggaa acggctcagg agggtacagc gtggattagg    4140
ccacaagatg gggcagatga tgtcatcaga agcatgtgac cggtgggagc agttactaaa    4200
cttctgggca acctagtcca tgctatgcag gcaggtagag ggatgggcag tgctcattgt    4260
ttggcattga tgatgtccac aaattcaggc ttgagagatg cgccacccac aaggaagccg    4320
tccacgtcag gctggcttgc cagctctttg caggttgctc cagtcacaga acctgtacca    4380
ggaacaagaa gacagtttgg tcaggtctat gatcagaaca cttaagcccc acctctctgt    4440
gcaaggcagc ctcagtctgt cttagcccat ttccgtctta gctagagcca aagccactca    4500
cctccataaa tgatccgggt gctctgagcc acccatcat tgacattgga tttcagccat    4560
cccccggagct tctcgtgtac ttcctgtgcc tagaaggagg aggcagagct actaagtaag    4620
ctccttccta tctatcattc aaggagtaaa accactggt tctcacatag agttgagttt    4680
ccagaaaagc cccgggacca gagagtggca aggctccaat cccaccaggc ttggaatgaa    4740
cattttggc aaagtcactc tccttggtga gtttgggggc cctctgtctc taaagggggct    4800
tggatgggct ccatagctgt gtgagtctgt taaagccgga caggctgagg agctctgggt    4860
agttacctgc tgagggttg ccgtcttgcc agtcccaatg gccacacag gttcataggc    4920
caggaccacc ttgctccagt cttttcacatt atctgtgggg cagagaggag agtgagtagg    4980
aaggagctga cccgccaagc                                                  5000
```

-continued

<210> SEQ ID NO 46
<211> LENGTH: 264
<212> TYPE: PRT
<213> ORGANISM: Mouse

<400> SEQUENCE: 46

```
Met Gly Gln Thr Ala Leu Ala Arg Gly Ser Ser Thr Pro Thr Ser
 1               5                  10                  15

Gln Ala Leu Tyr Ser Asp Phe Ser Pro Glu Gly Leu Glu Leu
             20                  25                  30

Leu Ser Ala Pro Pro Asp Leu Val Ala Gln Arg His His Gly Trp
         35                  40                  45

Asn Pro Lys Asp Cys Ser Glu Asn Ile Asp Val Lys Glu Gly Gly Leu
     50                  55                  60

Cys Phe Glu Arg Arg Pro Val Ala Gln Ser Thr Asp Gly Val Arg Gly
 65                  70                  75                  80

Lys Arg Gly Tyr Ser Arg Gly Leu His Ala Trp Glu Ile Ser Trp Pro
                 85                  90                  95

Leu Glu Gln Arg Gly Thr His Ala Val Val Gly Val Ala Thr Ala Leu
            100                 105                 110

Ala Pro Leu Gln Ala Asp His Tyr Ala Ala Leu Leu Gly Ser Asn Ser
        115                 120                 125

Glu Ser Trp Gly Trp Asp Ile Gly Arg Gly Lys Leu Tyr His Gln Ser
130                 135                 140

Lys Gly Leu Glu Ala Pro Gln Tyr Pro Ala Gly Pro Gln Gly Glu Gln
145                 150                 155                 160

Leu Val Val Pro Glu Arg Leu Val Val Leu Asp Met Glu Glu Gly
                165                 170                 175

Thr Leu Gly Tyr Ser Ile Gly Gly Thr Tyr Leu Gly Pro Ala Phe Arg
            180                 185                 190

Gly Leu Lys Gly Arg Thr Leu Tyr Pro Ser Val Ser Ala Val Trp Gly
        195                 200                 205

Gln Cys Gln Val Arg Ile Arg Tyr Met Gly Glu Arg Val Glu Glu
    210                 215                 220

Pro Gln Ser Leu Leu His Leu Ser Arg Leu Cys Val Arg His Ala Leu
225                 230                 235                 240

Gly Asp Thr Arg Leu Gly Gln Ile Ser Thr Leu Pro Leu Pro Pro Ala
                245                 250                 255

Met Lys Arg Tyr Leu Leu Tyr Lys
            260
```

<210> SEQ ID NO 47
<211> LENGTH: 5615
<212> TYPE: DNA
<213> ORGANISM: Human

<400> SEQUENCE: 47

```
gtactttctt tatatctcca taattttatt tactattact acatgataca ttatttata     60
aaagtctttg taacctcctt aaggattcac tgcttaatct ccagtgctta gcacaaatca   120
ttaaatgcga accagaaact cttccaaatg tgttacatct ataacctcat tggattctca   180
ctaccaaccc catgcaatag atactaatgt gatctctgtc ttacagagga agaaacaggc   240
acagggaggt tcagtaattt gcccaaggtc atacacacac tggccttcag gtattcatgc   300
ccggggagtc tggtcccaca gctggcatgt ttgccattat attatattgc ctccttatag   360
tgtcggcact cattaagcac attgacagct atgcttggtg agtgactact atgtacccag   420
```

```
ctctgtgcta catgctttac ctggattatt tcaactgcac aacaaccctg tgaggtaact      480
accatcattg ctcctatttt acataacaga aaactacaga aatctggggc tgggcgtagt      540
ggctcatgcc tgaaatccca gcactttggg agaccctgtc tctaaaaaaa attttttttt      600
ggccggacgt ggtggctcac acctgtaatc tcagcacttt gggaggctaa ggcaggcaga      660
tcacaaggtc aggagttcta gaccagcctg ccaacatgg caaaaccctg tgtctactaa       720
aaatacaaaa aatagctagg cgtggtggca ggtgcctgta atcccagcta ctcaggaggc      780
tgaggcagga gaatcccctg aacctgggag atggaggtta cagagagccg agatcgtgcc      840
gctgcactcc agcctgggca acaagagcaa gactctgtct cgaaaaaaat aaaaataaaa      900
ataaaaatat ttttttaaaa attagctggg tgtggtagca catgcctgta gtcccagcta      960
cttgggaggc tgaggtagga ggatcacttg agcccaggag gtcaaggctg cagtgggctg     1020
tgatggcgcc actgcactct agccttggtg acagcaagac cctgtctcaa aaaaaaaaa      1080 aagagaaatc gggcaacttc cccaagatcg cgcagttaac tagtggcata gcttcactca     1140
aactcgaagt cttaatcagg acactctacc aaatgagatc aacggctcag taatggattg     1200
gcatccagta tgaagactgg accagcaggg agaactatga tgcgtacagc ctagagcctg     1260
aagcagattt cacagcctca gaggtggcac aggctgactc acaacccggg gcagaaaggg     1320
accagcccag aaacagtgac ccagaatcac agggaagtag aaatgggatt cggcacaatg     1380
aagcccctcc ttgaccccat gctccttacc ctcaggggcg caggagttag tcgctcaggc     1440
ggctcaaagg tcttgacggt ggagaacacc atccccaggg attcccgacg cggtgatgcc     1500
atcaaagcgt taattctgag atgggcctgc ccgggtgcgg actctgccgc agcaagagaa     1560
gggttaactg ccccgggcct tcgccgtggg ggcggggcct cggggagggt cacagcccgg     1620
gactgagacc cgaggttaac cgcccggggt gggctccacg gggcggggc atgctctccg      1680 cggctgctgc cggtatagag cggtaactgc ccaggagggg gcgggccccc acaggggcgt     1740
ggcctcggag ctgcacggcc gtgggcggcg atgagagggt taagcccag agggccctgg      1800 aggggcgggg ccgcgggacg ggctcggccc aaggaggag ctgggggcgg aagcggccgg      1860
cggtctgcgc cctgcgcgcc tcggcttctt ccgcccggc tccttcagag gcccggcgac      1920
ctccagggct gggaagtcaa ccgaggttcg ggggcagcgg cgagggctcc gggcgagtaa     1980
gggggatggt ccatgctgag gcccaaatgg ggcgaactcg cgagagtctc tggcgacctg     2040
gatcagatgg ggcgagggca gatgaagggc ccaggagctt tggggcagcg aggagggagg     2100
agcgggcccg ttggcaaact tgggtgaaag gatggggtac ctgggtgacg agccccgcc      2160 aggattctgc tcttcacgcc ccttttctcc cagctccctt ccaggtcaat ccaaactgga     2220
gctcaacttt cagaagagaa agacgcccca gcaagcctct ttcgggagt cctctagctc      2280 ctcacctcca tgggccagac agctctggca gggggcagca gcagcacccc cacgccacag     2340
gccctgtacc ctgacctctc ctgtcccgag ggcttggaag agctgctgtc tgcacccct      2400 cctgacctgg gggcccagcg gcgccacggt tggaacccca agactgttc agagaacatc      2460 gaggtcaagg aaggagggtt gtactttgag cggcggcccg tgcccagag cactgatggg      2520 gcccggggta agaggggcta ttcaaggggc ctgcacgcct gggagatcag ctggcccta      2580 gagcagaggg gcacgcatgc cgtggtgggc gtggccacgg ccctcgcccc gctgcagact     2640
gaccactacg cggcgctgct gggcagcaac agcgagtcgt ggggctggga catcgggcgg     2700
gggaagctgt accatcagag caaggggccc ggagccccc agtatccagc gggaactcag      2760
```

-continued

```
ggtgagcagc tggaggtgcc agagagactg ctggtggttc tggacatgga ggagggaact    2820
ctgggctacg ctattggggg cacctacctg gggccagcat tccgcggact gaagggcagg    2880
accctctatc cggcagtaag cgctgtctgg ggccagtgcc aggtccgcat ccgctacctg    2940
ggcgaaagga gaggtgaggc ctggggcaga cgtggggaga actttctgtc cctggtggca    3000
gtggtttggg atggaaactc ttctgacaag agcagagggg atggaccttc atccagcctg    3060
cctcaacctc tgttcagtgc tgggaaaggc tagggtctt cacagctgtt atttaattta    3120
acccaacagc aatagaggtg aaacaggctt gagaaagcaa ctttctcaag ttctcttggc    3180
cagtaaatgg tgaaccttca gaatggaggg aggaactgca gggatgagag aattcaggag    3240
atatcaaccc ctgagcaaga ggtgcaaagc gttaggtact gggtttgatg tacaggtcca    3300
aaagaaggat gggcagagcc aggtacccag gctgtatacc ggattccctg ggctctaacc    3360
tgtctctgtg ccacatacct acttccttcc tcagccacac ctctggatgg agacactggg    3420
gccctgggca ccaggagga gagcagtgga ggaggcaggg ccttagggtg gggcagcagg    3480
ggaggagcct ccccaggaac tgactgggtc cagggcttgg agctgctctc tgcagttgtg    3540
tgggctgtag agtggagggc catccctcct cacctcagcc ccagctccca agcctctgga    3600
gtcaaagcct gggccagctc caccactgtc agagccacct tggcctgttg tttagagggc    3660
cttagccagc tcttcacccc cagctctgac tagggatgtg tgaaatctta tctgggaggc    3720
agaacttccg ggtatctcaa attccccttt cagccaggtg ggcacactcg aagcaggaaa    3780
gcagaaaggc atctgagtag gaccccgtag tttgaggaca tctggctggt ggctgcaccc    3840
atacttacat tcccctcctt ctctctccca gcggagccac actcccttct gcacctgagc    3900
cgcctgtgtg tgcgccacaa cctgggggat acccggctcg gccaggtgtc tgccctgccc    3960 ttgcccctg ccatgaagcg ctacctgctc taccagtgag ccctgtgata ccacagactg    4020
tgctgaggtc ttgccaccac ccctcccctt ggggaggtgg ggaggcactg ctggcctaga    4080
ccagctgctg aaagctggtg aggctgagcc cctaccccaa cccaagctct gcggaaatca    4140
acagccccag agccacttgg agggaggaag aaagggagcc ggcgttcaag gctatgacag    4200
tctgctacgc aaaacatttt ttcaagtaaa aatagtaaga gatgttgtta tagaaacctg    4260
ttcttgtttt tttttttttc ttgcacaaat gatcatttat atagctgcct caaaaaggaa    4320
gattatctgg gcaagtccag tgaaggcaga caaaccacaa gacctagtgc caggtttatt    4380
ccctcacatg ggtggttcac atacacagca cagaggcacg ggcaccatgg gagagggcag    4440
cactcctgcc ttctgagggg atcttggcct cacggtgtaa gaagggagag gatggtttct    4500
cttctgccct cactagggcc tagggaaccc aggagcaaat cccaccacgc cttccatctc    4560
tcagccaagg agaagccacc ttggtgacgt ttagttccaa ccattatagt aagtggagaa    4620
gggattggcc tggtcccaac cattacaggg tgaagatata aacagtaaag gaagatacag    4680 tttgatgag gccacaggaa ggagcagatg acaccatcag aagcatatgc agggaagggg    4740
cagttactgg gcttctgggc tgcttagtcc ctggcttggc aggaagggta gggaagatgg    4800
atggggctca ttgtttggca ttgatgatgt ccacgaattc gggcttgagg gaagcaccac    4860
ccacaaggaa gccatccaca tcaggctggc tggccagctc cttgcaggtt gccccagtca    4920
cagagcctgg gaagggagca gaacaaggc ttggtcaaga atgggatgag tctgcccca    4980 ccccacctcc atgtccgagg gctcagtcta gtcctcagcc cactccacct cagccgggaa    5040
ccaaagccac tcacctccat aaatgatacg ggtgctctga gccaccgcat cagagacgtt    5100
ggacttcagc catcctcgga gcttctcgtg tacttcctgg gcctagaaca agaagctggc    5160
```

-continued

```
ctaagtaaga cctttctgc ctctctaaga ggaaaaatca ctggcaccag tggacactta    5220
gtgtggtttc tgactgagtc agagtaccag ggctctgatc aagccaggc cctggactgg    5280 atgcccttgg acaagtcact gtctctgggt tcaaggtctc tgtgtctttg aaataagggg    5340
ttgccccatg tgggctgtgt ctgtccaaac ctattgaggc aggctgggat gagggcaggg    5400
ctcctgggcc cggttacctg ttggggtgtt gcagtcttgc cagtaccaat ggcccacaca    5460
ggctcatagg ccaggacgac cttgctccag tccttcacgt tatctgcagg gcagagatac    5520
agatggaggg aagggtgaac aagaaagagc tctccagcca ggttctccgg agtacgaaga    5580
acggtggcct actgccccct agtggacatt ggggg                              5615
```

<210> SEQ ID NO 48
<211> LENGTH: 263
<212> TYPE: PRT
<213> ORGANISM: Human

<400> SEQUENCE: 48

Met Gly Gln Thr Ala Leu Ala Gly Gly Ser Ser Thr Pro Thr Pro
1               5                   10                  15

Gln Ala Leu Tyr Pro Asp Leu Ser Cys Pro Glu Gly Leu Glu Leu
            20                  25                  30

Leu Ser Ala Pro Pro Asp Leu Gly Ala Gln Arg Arg His Gly Trp
        35                  40                  45

Asn Pro Lys Asp Cys Ser Glu Asn Ile Glu Val Lys Glu Gly Gly Leu
    50                  55                  60

Tyr Phe Glu Arg Arg Pro Val Ala Gln Ser Thr Asp Gly Ala Arg Gly
65                  70                  75                  80

Lys Arg Gly Tyr Ser Arg Gly Leu His Ala Trp Glu Ile Ser Trp Pro
                85                  90                  95

Leu Glu Gln Arg Gly Thr His Ala Val Val Gly Val Ala Thr Ala Leu
            100                 105                 110

Ala Pro Leu Gln Thr Asp His Tyr Ala Ala Leu Leu Gly Ser Asn Ser
        115                 120                 125

Glu Ser Trp Gly Trp Asp Ile Gly Arg Gly Lys Leu Tyr His Gln Ser
    130                 135                 140

Lys Gly Pro Gly Ala Pro Gln Tyr Pro Ala Gly Thr Gln Gly Glu Gln
145                 150                 155                 160

Leu Glu Val Pro Glu Arg Leu Leu Val Val Leu Asp Met Glu Glu Gly
                165                 170                 175

Thr Leu Gly Tyr Ala Ile Gly Gly Thr Tyr Leu Gly Pro Ala Phe Arg
            180                 185                 190

Gly Leu Lys Gly Arg Thr Leu Tyr Pro Ala Val Ser Ala Val Trp Gly
        195                 200                 205

Gln Cys Gln Val Arg Ile Arg Tyr Leu Gly Glu Arg Ala Glu Pro
    210                 215                 220

His Ser Leu Leu His Leu Ser Arg Leu Cys Val Arg His Asn Leu Gly
225                 230                 235                 240

Asp Thr Arg Leu Gly Gln Val Ser Ala Leu Pro Leu Pro Pro Ala Met
                245                 250                 255

Lys Arg Tyr Leu Leu Tyr Gln
            260

<210> SEQ ID NO 49
<211> LENGTH: 28

```
<212> TYPE: DNA
<213> ORGANISM: Artificial Sequence
<220> FEATURE:
<223> OTHER INFORMATION: Description of Artificial Sequence:Synthetic

<400> SEQUENCE: 49
agctagatct ggaccctaca atggcagc                                          28

<210> SEQ ID NO 50
<211> LENGTH: 36
<212> TYPE: DNA
<213> ORGANISM: Artificial Sequence
<220> FEATURE:
<223> OTHER INFORMATION: Description of Artificial Sequence:Synthetic

<400> SEQUENCE: 50
agctagatct gccatcctac tcgaggggcc agctgg                                 36

<210> SEQ ID NO 51
<211> LENGTH: 18
<212> TYPE: PRT
<213> ORGANISM: Artificial Sequence
<220> FEATURE:
<223> OTHER INFORMATION: Description of Artificial Sequence:N-terminal GFP
      tag

<400> SEQUENCE: 51

Met Ala Arg Gln Ser Lys Gly Glu Glu Leu Phe Thr Glu Leu Tyr Lys
                 5                  10                  15

Thr Arg

<210> SEQ ID NO 52
<211> LENGTH: 30
<212> TYPE: DNA
<213> ORGANISM: Artificial Sequence
<220> FEATURE:
<223> OTHER INFORMATION: Description of Artificial Sequence:3' genomic
      oligonucleotide no.3243

<400> SEQUENCE: 52
aagtccgttc aagtagcgca tgcggatctc                                        30

<210> SEQ ID NO 53
<211> LENGTH: 30
<212> TYPE: DNA
<213> ORGANISM: Artificial Sequence
<220> FEATURE:
<223> OTHER INFORMATION: Description of Artificial Sequence:5' genomic
      oligonucleotide no.3244

<400> SEQUENCE: 53
gagatccgca tgcgctactt gaacggactt                                        30

<210> SEQ ID NO 54
<211> LENGTH: 10
<212> TYPE: PRT
<213> ORGANISM: Artificial Sequence
<220> FEATURE:
<223> OTHER INFORMATION: Description of Artificial Sequence: Amino acid
      sequence encoded by SEQ ID NO:53

<400> SEQUENCE: 54

Glu Ile Arg Met Arg Tyr Leu Asn Gly Leu
                 5                  10

<210> SEQ ID NO 55
```

-continued

```
<211> LENGTH: 34
<212> TYPE: DNA
<213> ORGANISM: Artificial Sequence
<220> FEATURE:
<223> OTHER INFORMATION: Description of Artificial Sequence:3' cDNA
      oligonucleotide no.3245

<400> SEQUENCE: 55
agctacgcgt ctggtagagg aggtaggctt tgag                               34

<210> SEQ ID NO 56
<211> LENGTH: 822
<212> TYPE: DNA
<213> ORGANISM: Mouse
<220> FEATURE:
<221> NAME/KEY: CDS
<222> LOCATION: (1)..(822)

<400> SEQUENCE: 56
```

| | | | | | | | | | | | | | | | | |
|---|---|---|---|---|---|---|---|---|---|---|---|---|---|---|---|---|
| atg | ggt | cag | aag | gtc | acg | gga | ggg | atc | aag | act | gtg | gac | atg | cgg | gac | 48 |
| Met | Gly | Gln | Lys | Val | Thr | Gly | Gly | Ile | Lys | Thr | Val | Asp | Met | Arg | Asp | |
| 1 | | | | 5 | | | | | 10 | | | | | 15 | | |
| ccc | aca | tac | cga | cct | ctg | aag | cag | gaa | ctc | cag | ggg | ctg | gat | tac | tgc | 96 |
| Pro | Thr | Tyr | Arg | Pro | Leu | Lys | Gln | Glu | Leu | Gln | Gly | Leu | Asp | Tyr | Cys | |
| | | | 20 | | | | | 25 | | | | | 30 | | | |
| aag | ccc | acc | cgg | ctg | gac | ctg | ctg | ctc | gac | atg | ccc | ccc | gtg | tcc | tac | 144 |
| Lys | Pro | Thr | Arg | Leu | Asp | Leu | Leu | Leu | Asp | Met | Pro | Pro | Val | Ser | Tyr | |
| | | 35 | | | | | 40 | | | | | 45 | | | | |
| gat | gtg | cag | ctg | ctc | cac | tcc | tgg | aac | aat | aac | gac | cgt | tcg | ctc | aac | 192 |
| Asp | Val | Gln | Leu | Leu | His | Ser | Trp | Asn | Asn | Asn | Asp | Arg | Ser | Leu | Asn | |
| | 50 | | | | | 55 | | | | | 60 | | | | | |
| gtc | ttc | gtg | aag | gaa | gat | gac | aag | ttg | atc | ttt | cac | cgg | cat | ccg | gtg | 240 |
| Val | Phe | Val | Lys | Glu | Asp | Asp | Lys | Leu | Ile | Phe | His | Arg | His | Pro | Val | |
| 65 | | | | | 70 | | | | | 75 | | | | | 80 | |
| gcc | cag | agc | acg | gac | gcc | atc | agg | ggc | aaa | gtt | ggg | tac | aca | cgt | gga | 288 |
| Ala | Gln | Ser | Thr | Asp | Ala | Ile | Arg | Gly | Lys | Val | Gly | Tyr | Thr | Arg | Gly | |
| | | | | 85 | | | | | 90 | | | | | 95 | | |
| ctg | cac | gta | tgg | cag | atc | aca | tgg | gcc | atg | agg | cag | cga | ggc | acg | cat | 336 |
| Leu | His | Val | Trp | Gln | Ile | Thr | Trp | Ala | Met | Arg | Gln | Arg | Gly | Thr | His | |
| | | | | 100 | | | | | 105 | | | | | 110 | | |
| gcc | gtg | gtg | ggg | gtg | gcc | aca | gca | gat | gcc | cct | ttg | cac | tcc | gtt | ggg | 384 |
| Ala | Val | Val | Gly | Val | Ala | Thr | Ala | Asp | Ala | Pro | Leu | His | Ser | Val | Gly | |
| | | | 115 | | | | | 120 | | | | | 125 | | | |
| gac | aca | acc | ctt | gta | gga | aat | aac | cat | gaa | tcc | tgg | ggc | tgg | gac | ctg | 432 |
| Tyr | Thr | Thr | Leu | Val | Gly | Asn | Asn | His | Glu | Ser | Trp | Gly | Trp | Asp | Leu | |
| | 130 | | | | | 135 | | | | | 140 | | | | | |
| ggg | cgt | aac | cgt | ctc | tac | cac | gac | ggc | aag | aac | cag | cca | agt | aaa | aca | 480 |
| Gly | Arg | Asn | Arg | Leu | Tyr | His | Asp | Gly | Lys | Asn | Gln | Pro | Ser | Lys | Thr | |
| 145 | | | | | 150 | | | | | 155 | | | | | 160 | |
| tac | cca | gcc | ttt | ctg | gag | ccg | gac | gag | aca | ttc | att | gtc | cct | gac | tcc | 528 |
| Tyr | Pro | Ala | Phe | Leu | Glu | Pro | Asp | Glu | Thr | Phe | Ile | Val | Pro | Asp | Ser | |
| | | | | 165 | | | | | 170 | | | | | 175 | | |
| ttt | ctc | gtg | gcc | ctg | gac | atg | gat | gat | ggg | acc | tta | agt | ttc | atc | gtg | 576 |
| Phe | Leu | Val | Ala | Leu | Asp | Met | Asp | Asp | Gly | Thr | Leu | Ser | Phe | Ile | Val | |
| | | | | 180 | | | | | 185 | | | | | 190 | | |
| gat | gga | cag | tac | atg | gga | gtg | gct | ttc | cgg | gga | ctc | aag | ggt | aaa | aag | 624 |
| Asp | Gly | Gln | Tyr | Met | Gly | Val | Ala | Phe | Arg | Gly | Leu | Lys | Gly | Lys | Lys | |
| | | | | 195 | | | | | 200 | | | | | 205 | | |
| ctg | tat | cct | gta | gtg | agt | gcc | gtc | tgg | ggc | cac | tgt | gag | atc | cgc | atg | 672 |
| Leu | Tyr | Pro | Val | Val | Ser | Ala | Val | Trp | Gly | His | Cys | Glu | Ile | Arg | Met | |
| | 210 | | | | | 215 | | | | | 220 | | | | | |
| cgc | tac | ttg | aac | gga | ctt | gat | cct | gag | ccc | ctg | cca | ctc | atg | gac | ctg | 720 |

```
Arg Tyr Leu Asn Gly Leu Asp Pro Glu Pro Leu Pro Leu Met Asp Leu
225                 230                 235                 240 tgc cgg cgt tcg gtg cgc cta gcg ctg gga aag gag cgc ctg ggt gcc        768
Cys Arg Arg Ser Val Arg Leu Ala Leu Gly Lys Glu Arg Leu Gly Ala
                245                 250                 255 atc ccc gct ctg ccg cta cct gcc tcc ctc aaa gcc tac ctc ctc tac        816
Ile Pro Ala Leu Pro Leu Pro Ala Ser Leu Lys Ala Tyr Leu Leu Tyr
                260                 265                 270 cag tga                                                                822
Gln
```

<210> SEQ ID NO 57
<211> LENGTH: 273
<212> TYPE: PRT
<213> ORGANISM: Mouse

<400> SEQUENCE: 57

```
Met Gly Gln Lys Val Thr Gly Gly Ile Lys Thr Val Asp Met Arg Asp
1               5                   10                  15

Pro Thr Tyr Arg Pro Leu Lys Gln Glu Leu Gln Gly Leu Asp Tyr Cys
                20                  25                  30

Lys Pro Thr Arg Leu Asp Leu Leu Asp Met Pro Pro Val Ser Tyr
            35                  40                  45

Asp Val Gln Leu Leu His Ser Trp Asn Asn Asn Asp Arg Ser Leu Asn
    50                  55                  60

Val Phe Val Lys Glu Asp Asp Lys Leu Ile Phe His Arg His Pro Val
65                  70                  75                  80

Ala Gln Ser Thr Asp Ala Ile Arg Gly Lys Val Gly Tyr Thr Arg Gly
                85                  90                  95

Leu His Val Trp Gln Ile Thr Trp Ala Met Arg Gln Arg Gly Thr His
                100                 105                 110

Ala Val Val Gly Val Ala Thr Ala Asp Ala Pro Leu His Ser Val Gly
            115                 120                 125

Tyr Thr Thr Leu Val Gly Asn Asn His Glu Ser Trp Gly Trp Asp Leu
    130                 135                 140

Gly Arg Asn Arg Leu Tyr His Asp Gly Lys Asn Gln Pro Ser Lys Thr
145                 150                 155                 160

Tyr Pro Ala Phe Leu Glu Pro Asp Glu Thr Phe Ile Val Pro Asp Ser
                165                 170                 175

Phe Leu Val Ala Leu Asp Met Asp Asp Gly Thr Leu Ser Phe Ile Val
                180                 185                 190

Asp Gly Gln Tyr Met Gly Val Ala Phe Arg Gly Leu Lys Gly Lys Lys
            195                 200                 205

Leu Tyr Pro Val Val Ser Ala Val Trp Gly His Cys Glu Ile Arg Met
    210                 215                 220

Arg Tyr Leu Asn Gly Leu Asp Pro Glu Pro Leu Pro Leu Met Asp Leu
225                 230                 235                 240

Cys Arg Arg Ser Val Arg Leu Ala Leu Gly Lys Glu Arg Leu Gly Ala
                245                 250                 255

Ile Pro Ala Leu Pro Leu Pro Ala Ser Leu Lys Ala Tyr Leu Leu Tyr
                260                 265                 270

Gln
```

<210> SEQ ID NO 58
<211> LENGTH: 35
<212> TYPE: DNA

―continued

```
<213> ORGANISM: Artificial Sequence
<220> FEATURE:
<223> OTHER INFORMATION: Description of Artificial Sequence:
      Oligonucleotide no.3342

<400> SEQUENCE: 58
agctggcgcg ccagggtcag aaggtcacgg gaggg                              35

<210> SEQ ID NO 59
<211> LENGTH: 128
<212> TYPE: PRT
<213> ORGANISM: Mus musculus
<220> FEATURE:
<221> NAME/KEY: UNSURE
<222> LOCATION: (1)
<223> OTHER INFORMATION: Xaa is Leu, Ile, Val, Met, Ala or Pro
<221> NAME/KEY: UNSURE
<222> LOCATION: (2)
<223> OTHER INFORMATION: Xaa is any amino acid residue
<221> NAME/KEY: UNSURE
<222> LOCATION: (3)
<223> OTHER INFORMATION: Xaa is Pro, Thr or Ser
<221> NAME/KEY: UNSURE
<222> LOCATION: (4)
<223> OTHER INFORMATION: Xaa is Leu, Ile, Val, Met, Ala or Pro
<221> NAME/KEY: UNSURE
<222> LOCATION: (5)
<223> OTHER INFORMATION: Xaa is any amino acid
<221> NAME/KEY: UNSURE
<222> LOCATION: (6)
<223> OTHER INFORMATION: Xaa is any amino acid
<221> NAME/KEY: UNSURE
<222> LOCATION: (7)
<223> OTHER INFORMATION: Xaa is Leu, Ile, Val, Met, Ala, Phe, Tyr or Trp
<221> NAME/KEY: UNSURE
<222> LOCATION: (8)
<223> OTHER INFORMATION: Xaa is Cys, Thr or Ser
<221> NAME/KEY: UNSURE
<222> LOCATION: (9)
<223> OTHER INFORMATION: Xaa is Arg, Lys or His
<221> NAME/KEY: UNSURE
<222> LOCATION: (10)
<223> OTHER INFORMATION: Xaa is any amino acid
<221> NAME/KEY: UNSURE
<222> LOCATION: (11)
<223> OTHER INFORMATION: Xaa is any amino acid
<221> NAME/KEY: UNSURE
<222> LOCATION: (12)
<223> OTHER INFORMATION: Xaa is Leu, Ile, Val, Met, Ala or Pro
<221> NAME/KEY: UNSURE
<222> LOCATION: (13)
<223> OTHER INFORMATION: Xaa is any amino acid
<221> NAME/KEY: UNSURE
<222> LOCATION: (14)
<223> OTHER INFORMATION: Xaa is any amino acid
<221> NAME/KEY: UNSURE
<222> LOCATION: (15)
<223> OTHER INFORMATION: Xaa is any amino acid
<221> NAME/KEY: UNSURE
<222> LOCATION: (16)
<223> OTHER INFORMATION: Xaa is Leu, Ile, Val, Met, Ala, Pro, Gly, Cys,
      Thr or Ser
<221> NAME/KEY: UNSURE
<222> LOCATION: (17)..(66)
<223> OTHER INFORMATION: Xaa can be any amino acid or no amino acid.
      Position 17-66 can be 1-50 amino acids.
<221> NAME/KEY: UNSURE
<222> LOCATION: (67)
<223> OTHER INFORMATION: Xaa is Leu, Ile, Val, Met, Ala or Pro
<221> NAME/KEY: UNSURE
<222> LOCATION: (68)
<223> OTHER INFORMATION: Xaa is any amino acid
<221> NAME/KEY: UNSURE
<222> LOCATION: (69)
<223> OTHER INFORMATION: Xaa is any amino acid
<221> NAME/KEY: UNSURE
<222> LOCATION: (70)
```

```
<223> OTHER INFORMATION: Xaa is Leu, Ile, Val, Met, Ala or Pro
<221> NAME/KEY: UNSURE
<222> LOCATION: (72)
<223> OTHER INFORMATION: Xaa is Leu, Ile, Val, Met, Ala, Pro or Gly
<221> NAME/KEY: UNSURE
<222> LOCATION: (73)
<223> OTHER INFORMATION: Xaa is Pro or Asn
<221> NAME/KEY: UNSURE
<222> LOCATION: (74)..(123)
<223> OTHER INFORMATION: Xaa can be any amino acid or no amino acid.
      Position 74-123 can be 0-50 amino acids.
<221> NAME/KEY: UNSURE
<222> LOCATION: (124)
<223> OTHER INFORMATION: Xaa is Leu, Ile, Val, Met, Ala or Pro
<221> NAME/KEY: UNSURE
<222> LOCATION: (125)..(128)
<223> OTHER INFORMATION: Xaa is any amino acid

<400> SEQUENCE: 59

Xaa Xaa Xaa Xaa Xaa Xaa Xaa Xaa Xaa Xaa Xaa Xaa Xaa Xaa Xaa
 1               5                   10                  15

Xaa Xaa Xaa Xaa Xaa Xaa Xaa Xaa Xaa Xaa Xaa Xaa Xaa Xaa Xaa
             20                  25                  30

Xaa Xaa Xaa Xaa Xaa Xaa Xaa Xaa Xaa Xaa Xaa Xaa Xaa Xaa Xaa
         35                  40                  45

Xaa Xaa Xaa Xaa Xaa Xaa Xaa Xaa Xaa Xaa Xaa Xaa Xaa Xaa Xaa
     50                  55                  60

Xaa Xaa Xaa Xaa Xaa Xaa Pro Xaa Xaa Xaa Xaa Xaa Xaa Xaa Xaa
 65                  70                  75                  80

Xaa Xaa Xaa Xaa Xaa Xaa Xaa Xaa Xaa Xaa Xaa Xaa Xaa Xaa Xaa
             85                  90                  95

Xaa Xaa Xaa Xaa Xaa Xaa Xaa Xaa Xaa Xaa Xaa Xaa Xaa Xaa Xaa
            100                 105                 110

Xaa Xaa Xaa Xaa Xaa Xaa Xaa Xaa Xaa Xaa Xaa Xaa Xaa Xaa
            115                 120                 125

<210> SEQ ID NO 60
<211> LENGTH: 1611
<212> TYPE: DNA
<213> ORGANISM: Mouse
<220> FEATURE:
<221> NAME/KEY: CDS
<222> LOCATION: (1)..(1611)

<400> SEQUENCE: 60 atg gat aaa gtg ggg aaa atg tgg aac aac tta aaa tac aga tgc cag      48
Met Asp Lys Val Gly Lys Met Trp Asn Asn Leu Lys Tyr Arg Cys Gln
 1               5                   10                  15 aat ctc ttc agc cac gag gga gga agc cgt aat gag aac gtg gag atg      96
Asn Leu Phe Ser His Glu Gly Gly Ser Arg Asn Glu Asn Val Glu Met
             20                  25                  30 aac ccc aac aga tgt ccg tct gtc aaa gag aaa agc atc agt ctg gga     144
Asn Pro Asn Arg Cys Pro Ser Val Lys Glu Lys Ser Ile Ser Leu Gly
         35                  40                  45 gag gca gct ccc cag caa gag agc agt ccc tta aga gaa aat gtt gcc     192
Glu Ala Ala Pro Gln Gln Glu Ser Ser Pro Leu Arg Glu Asn Val Ala
     50                  55                  60 tta cag ctg gga ctg agc cct tcc aag acc ttt tcc agg cgg aac caa     240
Leu Gln Leu Gly Leu Ser Pro Ser Lys Thr Phe Ser Arg Arg Asn Gln
 65                  70                  75                  80 aac tgt gcc gca gag atc cct caa gtg gtt gaa atc agc atc gag aaa     288
Asn Cys Ala Ala Glu Ile Pro Gln Val Val Glu Ile Ser Ile Glu Lys
             85                  90                  95
```

```
gac agt gac tcg ggt gcc acc cca gga acg agg ctt gca cgg aga gac      336
Asp Ser Asp Ser Gly Ala Thr Pro Gly Thr Arg Leu Ala Arg Arg Asp
            100                 105                 110 tcc tac tcg cgg cac gcc ccg tgg gga gga aag aag aaa cat tcc tgt      384
Ser Tyr Ser Arg His Ala Pro Trp Gly Gly Lys Lys Lys His Ser Cys
        115                 120                 125 tcc aca aag acc cag agt tca ttg gat acc gag aaa aag ttt ggt aga      432
Ser Thr Lys Thr Gln Ser Ser Leu Asp Thr Glu Lys Lys Phe Gly Arg
130                 135                 140 act cga agc ggc ctt cag agg cga gag cgc tat gga gtc agc tcc          480
Thr Arg Ser Gly Leu Gln Arg Arg Glu Arg Arg Tyr Gly Val Ser Ser
145                 150                 155                 160 atg cag gac atg gac agc gtt tct agc cgc acg gtc ggg agc cgc tcc      528
Met Gln Asp Met Asp Ser Val Ser Ser Arg Thr Val Gly Ser Arg Ser
                165                 170                 175 ctg agg cag agg ctc cag gac acg gtg ggt ttg tgt ttt ccc atg aga      576
Leu Arg Gln Arg Leu Gln Asp Thr Val Gly Leu Cys Phe Pro Met Arg
            180                 185                 190 act tac agc aag cag tca aag cca ctc ttt tcc aat aaa aga aaa ata      624
Thr Tyr Ser Lys Gln Ser Lys Pro Leu Phe Ser Asn Lys Arg Lys Ile
        195                 200                 205 cat ctt tct gaa tta atg ctg gag aaa tgc cct ttt cct gct ggc tcg      672
His Leu Ser Glu Leu Met Leu Glu Lys Cys Pro Phe Pro Ala Gly Ser
210                 215                 220 gat tta gca caa aag tgg cat ttg att aaa cag cat acc gcc cct gtg      720
Asp Leu Ala Gln Lys Trp His Leu Ile Lys Gln His Thr Ala Pro Val
225                 230                 235                 240 agc cca cac tca aca ttt ttt gat aca ttt gat cca tca ctg gtg tct      768
Ser Pro His Ser Thr Phe Phe Asp Thr Phe Asp Pro Ser Leu Val Ser
                245                 250                 255 aca gaa gat gaa gaa gat agg ctt cgc gag aga aga cgg ctt agt atc      816
Thr Glu Asp Glu Glu Asp Arg Leu Arg Glu Arg Arg Arg Leu Ser Ile
            260                 265                 270 gaa gaa ggg gtg gat ccc cct ccc aac gca caa ata cac acc ttt gaa      864
Glu Glu Gly Val Asp Pro Pro Pro Asn Ala Gln Ile His Thr Phe Glu
        275                 280                 285 gct act gca cag gtc aac cca ttg tat aag ctg gga cca aag tta gct      912
Ala Thr Ala Gln Val Asn Pro Leu Tyr Lys Leu Gly Pro Lys Leu Ala
290                 295                 300 cct ggg atg aca gag ata agt gga gat ggt tct gca att cca caa acg      960
Pro Gly Met Thr Glu Ile Ser Gly Asp Gly Ser Ala Ile Pro Gln Thr
305                 310                 315                 320 aat tgt gac tca gaa gag gat tca acc acc cta tgt ctg cag tca cgg     1008
Asn Cys Asp Ser Glu Glu Asp Ser Thr Thr Leu Cys Leu Gln Ser Arg
                325                 330                 335 agg cag aag cag cgc cag gtg tcc ggg gac agc cac gcg cac gtt agc     1056
Arg Gln Lys Gln Arg Gln Val Ser Gly Asp Ser His Ala His Val Ser
            340                 345                 350 aga cag gga gct tgg aaa gtt cat acg cag atc gat tac ata cac tgc     1104
Arg Gln Gly Ala Trp Lys Val His Thr Gln Ile Asp Tyr Ile His Cys
        355                 360                 365 ctc gtg cca gat ttg ctt cag atc aca ggg aat ccc tgt tac tgg ggc     1152
Leu Val Pro Asp Leu Leu Gln Ile Thr Gly Asn Pro Cys Tyr Trp Gly
370                 375                 380 gtg atg gac cga tac gag gcc gaa gcc ctt cta gaa ggg aaa ccg gaa     1200
Val Met Asp Arg Tyr Glu Ala Glu Ala Leu Leu Glu Gly Lys Pro Glu
385                 390                 395                 400 ggc acg ttc ttg ctc agg gac tct gca cag gag gac tac ctc ttc tct     1248
Gly Thr Phe Leu Leu Arg Asp Ser Ala Gln Glu Asp Tyr Leu Phe Ser
                405                 410                 415
```

-continued

```
gtg agc ttc cgc cgc tac aac agg tct ctg cac gcc cgg atc gag cag    1296
Val Ser Phe Arg Arg Tyr Asn Arg Ser Leu His Ala Arg Ile Glu Gln
        420                 425                 430 tgg aac cac aac ttc agc ttc gat gcc cat gac ccc tgc gtg ttt cac    1344
Trp Asn His Asn Phe Ser Phe Asp Ala His Asp Pro Cys Val Phe His
            435                 440                 445 tcc tcc aca gtc acg ggg ctt ctc gaa cac tat aaa gac ccc agc tct    1392
Ser Ser Thr Val Thr Gly Leu Leu Glu His Tyr Lys Asp Pro Ser Ser
    450                 455                 460 tgc atg ttt ttt gaa ccg ttg cta acg ata tca ctg aat aga act ttc    1440
Cys Met Phe Phe Glu Pro Leu Leu Thr Ile Ser Leu Asn Arg Thr Phe
465                 470                 475                 480 cct ttc agc ctg cag tat atc tgc cgc gca gtg atc tgc aga tgc act    1488
Pro Phe Ser Leu Gln Tyr Ile Cys Arg Ala Val Ile Cys Arg Cys Thr
                485                 490                 495 acg tat gat ggg att gac ggg ctc ccg cta ccg tcg atg tta cag gat    1536
Thr Tyr Asp Gly Ile Asp Gly Leu Pro Leu Pro Ser Met Leu Gln Asp
            500                 505                 510 ttt tta aaa gag tat cat tat aaa caa aaa gtt agg gtt cgc tgg tta    1584
Phe Leu Lys Glu Tyr His Tyr Lys Gln Lys Val Arg Val Arg Trp Leu
        515                 520                 525 gaa cga gag cca gtc aaa gca aag taa                                1611
Glu Arg Glu Pro Val Lys Ala Lys
    530                 535
```

<210> SEQ ID NO 61
<211> LENGTH: 536
<212> TYPE: PRT
<213> ORGANISM: Mouse

<400> SEQUENCE: 61

```
Met Asp Lys Val Gly Lys Met Trp Asn Asn Leu Lys Tyr Arg Cys Gln
  1               5                  10                  15

Asn Leu Phe Ser His Glu Gly Gly Ser Arg Asn Glu Asn Val Glu Met
                 20                  25                  30

Asn Pro Asn Arg Cys Pro Ser Val Lys Glu Lys Ser Ile Ser Leu Gly
             35                  40                  45

Glu Ala Ala Pro Gln Gln Glu Ser Ser Pro Leu Arg Glu Asn Val Ala
         50                  55                  60

Leu Gln Leu Gly Leu Ser Pro Ser Lys Thr Phe Ser Arg Arg Asn Gln
 65                  70                  75                  80

Asn Cys Ala Ala Glu Ile Pro Gln Val Val Glu Ile Ser Ile Glu Lys
                 85                  90                  95

Asp Ser Asp Ser Gly Ala Thr Pro Gly Thr Arg Leu Ala Arg Arg Asp
            100                 105                 110

Ser Tyr Ser Arg His Ala Pro Trp Gly Gly Lys Lys His Ser Cys
        115                 120                 125

Ser Thr Lys Thr Gln Ser Ser Leu Asp Thr Glu Lys Lys Phe Gly Arg
    130                 135                 140

Thr Arg Ser Gly Leu Gln Arg Arg Glu Arg Tyr Gly Val Ser Ser
145                 150                 155                 160

Met Gln Asp Met Asp Ser Val Ser Ser Arg Thr Val Gly Ser Arg Ser
                165                 170                 175

Leu Arg Gln Arg Leu Gln Asp Thr Val Gly Leu Cys Phe Pro Met Arg
            180                 185                 190

Thr Tyr Ser Lys Gln Ser Lys Pro Leu Phe Ser Asn Lys Arg Lys Ile
        195                 200                 205
```

```
His Leu Ser Glu Leu Met Leu Glu Lys Cys Pro Phe Pro Ala Gly Ser
    210                 215                 220

Asp Leu Ala Gln Lys Trp His Leu Ile Lys Gln His Thr Ala Pro Val
225                 230                 235                 240

Ser Pro His Ser Thr Phe Phe Asp Thr Phe Asp Pro Ser Leu Val Ser
                    245                 250                 255

Thr Glu Asp Glu Asp Arg Leu Arg Glu Arg Arg Leu Ser Ile
                260                 265                 270

Glu Glu Gly Val Asp Pro Pro Asn Ala Gln Ile His Thr Phe Glu
            275                 280                 285

Ala Thr Ala Gln Val Asn Pro Leu Tyr Lys Leu Gly Pro Lys Leu Ala
    290                 295                 300

Pro Gly Met Thr Glu Ile Ser Gly Asp Gly Ser Ala Ile Pro Gln Thr
305                 310                 315                 320

Asn Cys Asp Ser Glu Glu Asp Ser Thr Thr Leu Cys Leu Gln Ser Arg
                325                 330                 335

Arg Gln Lys Gln Arg Gln Val Ser Gly Asp Ser His Ala His Val Ser
                340                 345                 350

Arg Gln Gly Ala Trp Lys Val His Thr Gln Ile Asp Tyr Ile His Cys
            355                 360                 365

Leu Val Pro Asp Leu Leu Gln Ile Thr Gly Asn Pro Cys Tyr Trp Gly
    370                 375                 380

Val Met Asp Arg Tyr Glu Ala Glu Ala Leu Leu Glu Gly Lys Pro Glu
385                 390                 395                 400

Gly Thr Phe Leu Leu Arg Asp Ser Ala Gln Glu Asp Tyr Leu Phe Ser
                405                 410                 415

Val Ser Phe Arg Arg Tyr Asn Arg Ser Leu His Ala Arg Ile Glu Gln
                420                 425                 430

Trp Asn His Asn Phe Ser Phe Asp Ala His Asp Pro Cys Val Phe His
            435                 440                 445

Ser Ser Thr Val Thr Gly Leu Leu Glu His Tyr Lys Asp Pro Ser Ser
450                 455                 460

Cys Met Phe Phe Glu Pro Leu Leu Thr Ile Ser Leu Asn Arg Thr Phe
465                 470                 475                 480

Pro Phe Ser Leu Gln Tyr Ile Cys Arg Ala Val Ile Cys Arg Cys Thr
                485                 490                 495

Thr Tyr Asp Gly Ile Asp Gly Leu Pro Leu Pro Ser Met Leu Gln Asp
                500                 505                 510

Phe Leu Lys Glu Tyr His Tyr Lys Gln Lys Val Arg Val Arg Trp Leu
            515                 520                 525

Glu Arg Glu Pro Val Lys Ala Lys
    530                 535

<210> SEQ ID NO 62
<211> LENGTH: 1601
<212> TYPE: DNA
<213> ORGANISM: Mouse
<220> FEATURE:
<221> NAME/KEY: CDS
<222> LOCATION: (1)..(1599)

<400> SEQUENCE: 62 atg aag aaa atc agt ctg aag acc ttc agg aaa tct ttt aac ctg agt      48
Met Lys Lys Ile Ser Leu Lys Thr Phe Arg Lys Ser Phe Asn Leu Ser
  1               5                  10                  15
```

-continued

| | | |
|---|---|---|
| aaa agc aaa gac gaa act gag ttc atg gtg gtt cag ccc cag tcc ctt<br>Lys Ser Lys Asp Glu Thr Glu Phe Met Val Val Gln Pro Gln Ser Leu<br>20                  25                  30 | 96 |
| gct ggt gac ttc gtg aaa gat gac tct tta ttc ggg agc tgt tat ggc<br>Ala Gly Asp Phe Val Lys Asp Asp Ser Leu Phe Gly Ser Cys Tyr Gly<br>    35                  40                  45 | 144 |
| aaa gac atg gcc agt tgt gac att ggc agc gag gat gag aaa ggg aag<br>Lys Asp Met Ala Ser Cys Asp Ile Gly Ser Glu Asp Glu Lys Gly Lys<br>50                  55                  60 | 192 |
| aac aga tcc aaa agc gag agc ctg atg ggc act ttg aag agg cgg ttg<br>Asn Arg Ser Lys Ser Glu Ser Leu Met Gly Thr Leu Lys Arg Arg Leu<br>65                  70                  75                  80 | 240 |
| tcc gcc aag cag aag acc aag ggc aag ggc ggc act gcg tct aca gat<br>Ser Ala Lys Gln Lys Thr Lys Gly Lys Gly Gly Thr Ala Ser Thr Asp<br>                85                  90                  95 | 288 |
| gag gac acc ttc tcc tca gct tca gct cct ggt ggg ctc aag gat gtg<br>Glu Asp Thr Phe Ser Ser Ala Ser Ala Pro Gly Gly Leu Lys Asp Val<br>            100                 105                 110 | 336 |
| cgt gct ccg cgg ccc atc cgc tcc aca tca ctg aga agc cac cat tat<br>Arg Ala Pro Arg Pro Ile Arg Ser Thr Ser Leu Arg Ser His His Tyr<br>        115                 120                 125 | 384 |
| agc ccc acg ccc tgg ccg ctg cgt ccc acc agc tcg gag gag acg tgc<br>Ser Pro Thr Pro Trp Pro Leu Arg Pro Thr Ser Ser Glu Glu Thr Cys<br>    130                 135                 140 | 432 |
| atc aag atg gag atg cga gtg aaa gca ctg gtg cat gct gcc agc cca<br>Ile Lys Met Glu Met Arg Val Lys Ala Leu Val His Ala Ala Ser Pro<br>145                 150                 155                 160 | 480 |
| gga cca gtc aac ggt gtg cgc aag gat ctg cgg gag cta cag ccc agg<br>Gly Pro Val Asn Gly Val Arg Lys Asp Leu Arg Glu Leu Gln Pro Arg<br>                165                 170                 175 | 528 |
| gag ctg cga gac ctg cag cca gag ccg cgc cct gag tcc cgc tgc agc<br>Glu Leu Arg Asp Leu Gln Pro Glu Pro Arg Pro Glu Ser Arg Cys Ser<br>            180                 185                 190 | 576 |
| ccc agc tca ccc ggg gac ctg agc ctc cac ctg gag gaa cac gtg cct<br>Pro Ser Ser Pro Gly Asp Leu Ser Leu His Leu Glu Glu His Val Pro<br>        195                 200                 205 | 624 |
| gta gta atc gga ctc atg tct cag gac tac ctt cag tac acc gtg cct<br>Val Val Ile Gly Leu Met Ser Gln Asp Tyr Leu Gln Tyr Thr Val Pro<br>    210                 215                 220 | 672 |
| tta gat gac ggg atg tgc cct ctt gaa ggg ccg cgc agc tgc tgc ctg<br>Leu Asp Asp Gly Met Cys Pro Leu Glu Gly Pro Arg Ser Cys Cys Leu<br>225                 230                 235                 240 | 720 |
| gat acg tct tct ccc atg gag gtg tca gcc gta ccc ctg ccg ggg gcg<br>Asp Thr Ser Ser Pro Met Glu Val Ser Ala Val Pro Leu Pro Gly Ala<br>                245                 250                 255 | 768 |
| agt ggt gcc ttc tcc gaa gac gac agt cat gtg gac cag gac ctg gtt<br>Ser Gly Ala Phe Ser Glu Asp Asp Ser His Val Asp Gln Asp Leu Val<br>            260                 265                 270 | 816 |
| gta ggc cca gag atc ctt gtg gat tca tca gtg aac aat ttg ttg att<br>Val Gly Pro Glu Ile Leu Val Asp Ser Ser Val Asn Asn Leu Leu Ile<br>        275                 280                 285 | 864 |
| ggc acc aca gga gtc atg ttg cag agc cct aga gga ggt cat gat gac<br>Gly Thr Thr Gly Val Met Leu Gln Ser Pro Arg Gly Gly His Asp Asp<br>    290                 295                 300 | 912 |
| gcc cct ccc ctc tca cca ttg cta cct cca atg cag aat aac cca atc<br>Ala Pro Pro Leu Ser Pro Leu Leu Pro Pro Met Gln Asn Asn Pro Ile<br>305                 310                 315                 320 | 960 |
| caa agg aac ttc agt ggc ctc tcg ggc cca gac ttg cac atg gcc gaa<br>Gln Arg Asn Phe Ser Gly Leu Ser Gly Pro Asp Leu His Met Ala Glu<br>                325                 330                 335 | 1008 |

```
agt gtt cgc tgt cat ttg aat ttc gat ccc aac tct gcg cct ggg gtt     1056
Ser Val Arg Cys His Leu Asn Phe Asp Pro Asn Ser Ala Pro Gly Val
        340                 345                 350 gct aga gtt tat gac tcg gtg caa agt agt ggc ccc atg gtt gtt aca     1104
Ala Arg Val Tyr Asp Ser Val Gln Ser Ser Gly Pro Met Val Val Thr
            355                 360                 365 agt ctt acg gag gag ctg aag aag ctt gca aaa cag ggg tgg tat tgg     1152
Ser Leu Thr Glu Glu Leu Lys Lys Leu Ala Lys Gln Gly Trp Tyr Trp
370                 375                 380 ggc ccc atc aca cgc tgg gag gca gag ggg aag ttg gca aat gtg cca     1200
Gly Pro Ile Thr Arg Trp Glu Ala Glu Gly Lys Leu Ala Asn Val Pro
385                 390                 395                 400 gat ggt tct ttt ctt gta agg gat agt tct gat gac cgt tac ctt tta     1248
Asp Gly Ser Phe Leu Val Arg Asp Ser Ser Asp Asp Arg Tyr Leu Leu
                405                 410                 415 agc ctg agc ttt cgt tcc cat ggt aaa aca ctt cac act aga att gag     1296
Ser Leu Ser Phe Arg Ser His Gly Lys Thr Leu His Thr Arg Ile Glu
            420                 425                 430 cac tca aat ggt aga ttc agc ttt tat gaa cag cca gat gtg gaa ggg     1344
His Ser Asn Gly Arg Phe Ser Phe Tyr Glu Gln Pro Asp Val Glu Gly
        435                 440                 445 cat aca tct ata gtt gac tta atc gag cat tca atc agg gac tct gaa     1392
His Thr Ser Ile Val Asp Leu Ile Glu His Ser Ile Arg Asp Ser Glu
    450                 455                 460 aat gga gca ttt tgt tat tca aga tct cga ttg cct gga tca gca act     1440
Asn Gly Ala Phe Cys Tyr Ser Arg Ser Arg Leu Pro Gly Ser Ala Thr
465                 470                 475                 480 tac cca gtc aga ctg acc aat cca gtg tca cga ttc atg cag gtg cgc     1488
Tyr Pro Val Arg Leu Thr Asn Pro Val Ser Arg Phe Met Gln Val Arg
                485                 490                 495 tcg ctg cag tac ctg tgc cgc ttt gtt atc cgt cag tac acc aga ata     1536
Ser Leu Gln Tyr Leu Cys Arg Phe Val Ile Arg Gln Tyr Thr Arg Ile
            500                 505                 510 gac tta att cag aaa ctg cct ttg cca aac aaa atg aag gat tat ttg     1584
Asp Leu Ile Gln Lys Leu Pro Leu Pro Asn Lys Met Lys Asp Tyr Leu
        515                 520                 525 cag gag aag cac tac tg                                              1601
Gln Glu Lys His Tyr
    530

<210> SEQ ID NO 63
<211> LENGTH: 533
<212> TYPE: PRT
<213> ORGANISM: Mouse

<400> SEQUENCE: 63

Met Lys Lys Ile Ser Leu Lys Thr Phe Arg Lys Ser Phe Asn Leu Ser
 1               5                  10                  15

Lys Ser Lys Asp Glu Thr Glu Phe Met Val Val Gln Pro Gln Ser Leu
            20                  25                  30

Ala Gly Asp Phe Val Lys Asp Asp Ser Leu Phe Gly Ser Cys Tyr Gly
        35                  40                  45

Lys Asp Met Ala Ser Cys Asp Ile Gly Ser Glu Asp Glu Lys Gly Lys
    50                  55                  60

Asn Arg Ser Lys Ser Glu Ser Leu Met Gly Thr Leu Lys Arg Arg Leu
65                  70                  75                  80

Ser Ala Lys Gln Lys Thr Lys Gly Lys Gly Gly Thr Ala Ser Thr Asp
            85                  90                  95
```

-continued

```
Glu Asp Thr Phe Ser Ala Ser Ala Pro Gly Gly Leu Lys Asp Val
            100                 105                 110

Arg Ala Pro Arg Pro Ile Arg Ser Thr Ser Leu Arg Ser His His Tyr
            115                 120                 125

Ser Pro Thr Pro Trp Pro Leu Arg Pro Thr Ser Glu Glu Thr Cys
            130                 135                 140

Ile Lys Met Glu Met Arg Val Lys Ala Leu Val His Ala Ala Ser Pro
145                 150                 155                 160

Gly Pro Val Asn Gly Val Arg Lys Asp Leu Arg Glu Leu Gln Pro Arg
                165                 170                 175

Glu Leu Arg Asp Leu Gln Pro Glu Pro Arg Pro Glu Ser Arg Cys Ser
            180                 185                 190

Pro Ser Ser Pro Gly Asp Leu Ser Leu His Leu Glu Glu His Val Pro
            195                 200                 205

Val Val Ile Gly Leu Met Ser Gln Asp Tyr Leu Gln Tyr Thr Val Pro
            210                 215                 220

Leu Asp Asp Gly Met Cys Pro Leu Glu Gly Pro Arg Ser Cys Cys Leu
225                 230                 235                 240

Asp Thr Ser Ser Pro Met Glu Val Ser Ala Val Pro Leu Pro Gly Ala
                245                 250                 255

Ser Gly Ala Phe Ser Glu Asp Asp Ser His Val Asp Gln Asp Leu Val
            260                 265                 270

Val Gly Pro Glu Ile Leu Val Asp Ser Ser Val Asn Asn Leu Leu Ile
            275                 280                 285

Gly Thr Thr Gly Val Met Leu Gln Ser Pro Arg Gly Gly His Asp Asp
            290                 295                 300

Ala Pro Pro Leu Ser Pro Leu Leu Pro Met Gln Asn Asn Pro Ile
305                 310                 315                 320

Gln Arg Asn Phe Ser Gly Leu Ser Gly Pro Asp Leu His Met Ala Glu
            325                 330                 335

Ser Val Arg Cys His Leu Asn Phe Asp Pro Asn Ser Ala Pro Gly Val
            340                 345                 350

Ala Arg Val Tyr Asp Ser Val Gln Ser Ser Gly Pro Met Val Val Thr
            355                 360                 365

Ser Leu Thr Glu Glu Leu Lys Lys Leu Ala Lys Gln Gly Trp Tyr Trp
            370                 375                 380

Gly Pro Ile Thr Arg Trp Glu Ala Glu Gly Lys Leu Ala Asn Val Pro
385                 390                 395                 400

Asp Gly Ser Phe Leu Val Arg Asp Ser Ser Asp Arg Tyr Leu Leu
            405                 410                 415

Ser Leu Ser Phe Arg Ser His Gly Lys Thr Leu His Thr Arg Ile Glu
            420                 425                 430

His Ser Asn Gly Arg Phe Ser Phe Tyr Glu Gln Pro Asp Val Glu Gly
            435                 440                 445

His Thr Ser Ile Val Asp Leu Ile Glu His Ser Ile Arg Asp Ser Glu
            450                 455                 460

Asn Gly Ala Phe Cys Tyr Ser Arg Ser Arg Leu Pro Gly Ser Ala Thr
465                 470                 475                 480

Tyr Pro Val Arg Leu Thr Asn Pro Val Ser Arg Phe Met Gln Val Arg
                485                 490                 495

Ser Leu Gln Tyr Leu Cys Arg Phe Val Ile Arg Gln Tyr Thr Arg Ile
            500                 505                 510

Asp Leu Ile Gln Lys Leu Pro Leu Pro Asn Lys Met Lys Asp Tyr Leu
```

```
                515                 520                 525
Gln Glu Lys His Tyr
    530

<210> SEQ ID NO 64
<211> LENGTH: 34
<212> TYPE: PRT
<213> ORGANISM: Mus musculus or Rattus norvegicus

<400> SEQUENCE: 64

Val Arg Pro Leu Gln Glu Leu Cys Arg Gln Arg Ile Val Ala Ala Val
  1               5                  10                  15

Gly Arg Glu Asn Leu Ala Arg Ile Pro Leu Asn Pro Val Leu Arg Asp
             20                  25                  30

Tyr Leu

<210> SEQ ID NO 65
<211> LENGTH: 32
<212> TYPE: PRT
<213> ORGANISM: Mus musculus

<400> SEQUENCE: 65

Ala Pro Thr Leu Gln His Phe Cys Arg Leu Ala Ile Asn Lys Cys Thr
  1               5                  10                  15

Gly Thr Ile Trp Gly Leu Pro Leu Pro Thr Arg Leu Lys Asp Tyr Leu
             20                  25                  30

<210> SEQ ID NO 66
<211> LENGTH: 33
<212> TYPE: PRT
<213> ORGANISM: Mus musculus

<400> SEQUENCE: 66

Val Ala Thr Leu Gln His Leu Cys Arg Lys Thr Val Asn Gly His Leu
  1               5                  10                  15

Asp Ser Tyr Glu Lys Val Thr Gln Leu Pro Gly Pro Ile Arg Glu Phe
             20                  25                  30

Leu

<210> SEQ ID NO 67
<211> LENGTH: 34
<212> TYPE: PRT
<213> ORGANISM: Homo sapiens

<400> SEQUENCE: 67

Val Arg Pro Leu Gln Glu Leu Cys Arg Gln Arg Ile Val Ala Thr Val
  1               5                  10                  15

Gly Arg Glu Asn Leu Ala Arg Ile Pro Leu Asn Pro Val Leu Arg Asp
             20                  25                  30

Tyr Leu

<210> SEQ ID NO 68
<211> LENGTH: 34
<212> TYPE: PRT
<213> ORGANISM: Mus musculus

<400> SEQUENCE: 68

Val Pro Ser Leu Gln His Ile Cys Arg Met Ser Ile Arg Arg Val Met
  1               5                  10                  15

Ser Thr Gln Glu Val Gln Lys Leu Pro Val Pro Ser Lys Ile Leu Ala
```

-continued

```
                20                  25                  30

Phe Leu

<210> SEQ ID NO 69
<211> LENGTH: 34
<212> TYPE: PRT
<213> ORGANISM: Mus musculus

<400> SEQUENCE: 69

Pro Phe Ser Leu Gln Tyr Ile Cys Arg Ala Val Ile Cys Arg Cys Thr
 1               5                  10                  15

Thr Tyr Asp Gly Ile Asp Gly Leu Pro Leu Pro Ser Met Leu Gln Asp
                20                  25                  30

Phe Leu

<210> SEQ ID NO 70
<211> LENGTH: 37
<212> TYPE: PRT
<213> ORGANISM: Mus musculus

<400> SEQUENCE: 70

Pro Arg Thr Leu Leu Ser Leu Cys Arg Val Ala Val Arg Arg Ala Leu
 1               5                  10                  15

Gly Lys Tyr Arg Leu His Leu Val Pro Ser Leu Pro Leu Pro Asp Pro
                20                  25                  30

Ile Lys Lys Phe Leu
                35

<210> SEQ ID NO 71
<211> LENGTH: 37
<212> TYPE: PRT
<213> ORGANISM: Mus musculus

<400> SEQUENCE: 71

Pro Arg Ser Leu Gln His Leu Cys Arg Cys Ala Leu Arg Ser His Leu
 1               5                  10                  15

Glu Gly Cys Leu Pro His Ala Leu Pro Arg Leu Pro Leu Pro Pro Arg
                20                  25                  30

Met Leu Arg Phe Leu
                35

<210> SEQ ID NO 72
<211> LENGTH: 34
<212> TYPE: PRT
<213> ORGANISM: Homo sapiens

<400> SEQUENCE: 72

Val Arg Ser Leu Gln Tyr Leu Cys Arg Phe Val Ile Cys Gln Tyr Thr
 1               5                  10                  15

Arg Ile Asp Leu Ile Gln Lys Leu Pro Leu Pro Asn Lys Met Lys Asp
                20                  25                  30

Tyr Leu

<210> SEQ ID NO 73
<211> LENGTH: 37
<212> TYPE: PRT
<213> ORGANISM: Mus musculus

<400> SEQUENCE: 73

Pro Arg Pro Leu Ala His Leu Cys Arg Leu Arg Val Arg Lys Ala Ile
```

```
                1               5              10              15
          Gly Lys Tyr Arg Ile Lys Leu Leu Asp Thr Leu Pro Leu Pro Gly Arg
                              20              25              30

Leu Ile Arg Tyr Leu
                      35

<210> SEQ ID NO 74
<211> LENGTH: 34
<212> TYPE: PRT
<213> ORGANISM: Homo sapiens

<400> SEQUENCE: 74

Val Lys Ser Leu Gln His Leu Cys Arg Phe Arg Ile Arg Gln Tyr Thr
 1               5              10              15

Arg Ile Asp His Ile Pro Asp Leu Pro Leu Pro Lys Pro Leu Ile Ser
                20              25              30

Tyr Ile

<210> SEQ ID NO 75
<211> LENGTH: 40
<212> TYPE: PRT
<213> ORGANISM: Mus musculus

<400> SEQUENCE: 75

Val Pro Ser Leu Thr His Leu Cys Arg Leu Glu Ile Arg Ala Ser Leu
 1               5              10              15

Lys Ala Glu His Leu His Ser Asp Ile Phe Ile His Gln Leu Pro Leu
                20              25              30

Pro Arg Ser Leu Gln Asn Tyr Leu
            35              40

<210> SEQ ID NO 76
<211> LENGTH: 37
<212> TYPE: PRT
<213> ORGANISM: Mus musculus

<400> SEQUENCE: 76

Pro Leu Pro Leu Met Asp Leu Cys Arg Arg Ser Val Arg Leu Ala Leu
 1               5              10              15

Gly Lys Glu Arg Leu Gly Ala Ile Pro Ala Leu Pro Leu Pro Ala Ser
                20              25              30

Leu Lys Ala Tyr Leu
            35

<210> SEQ ID NO 77
<211> LENGTH: 34
<212> TYPE: PRT
<213> ORGANISM: Mus musculus

<400> SEQUENCE: 77

Pro Phe Ser Leu Gln His Ile Cys Arg Thr Val Ile Cys Asn Cys Thr
 1               5              10              15

Thr Tyr Asp Gly Ile Asp Ala Leu Pro Ile Pro Ser Pro Met Lys Leu
                20              25              30

Tyr Leu

<210> SEQ ID NO 78
<211> LENGTH: 37
<212> TYPE: PRT
<213> ORGANISM: Mus musculus
```

```
<400> SEQUENCE: 78

Pro Gln Ser Leu Leu His Leu Ser Arg Leu Cys Val Arg His Ala Leu
 1               5                  10                  15

Gly Asp Thr Arg Leu Gly Gln Ile Ser Thr Leu Pro Leu Pro Pro Ala
                20                  25                  30

Met Lys Arg Tyr Leu
            35

<210> SEQ ID NO 79
<211> LENGTH: 37
<212> TYPE: PRT
<213> ORGANISM: Homo sapiens

<400> SEQUENCE: 79

Pro His Ser Leu Leu His Leu Ser Arg Leu Cys Val Arg His Asn Leu
 1               5                  10                  15

Gly Asp Thr Arg Leu Gly Gln Val Ser Ala Leu Pro Leu Pro Pro Ala
                20                  25                  30

Met Lys Arg Tyr Leu
            35

<210> SEQ ID NO 80
<211> LENGTH: 34
<212> TYPE: PRT
<213> ORGANISM: Mus musculus

<400> SEQUENCE: 80

Leu Ser Ser Leu Lys His Leu Cys Arg Lys Ala Leu Arg Ser Phe Leu
 1               5                  10                  15

Thr Thr Tyr Gln Val Leu Ala Leu Pro Ile Pro Lys Lys Met Lys Glu
                20                  25                  30

Phe Leu

<210> SEQ ID NO 81
<211> LENGTH: 34
<212> TYPE: PRT
<213> ORGANISM: Mouse

<400> SEQUENCE: 81

Val Arg Ser Leu Gln Tyr Leu Cys Arg Phe Val Ile Arg Gln Tyr Thr
 1               5                  10                  15

Arg Ile Asp Leu Ile Gln Lys Leu Pro Leu Pro Asn Lys Met Lys Asp
                20                  25                  30

Tyr Leu
```

What is claimed is:

1. An isolated nucleic acid molecule which encodes a protein, wherein said protein
   (i) comprises a SOCS box, wherein the SOCS box comprises an amino acid sequence having at least 70% identity to SEQ ID NO: 8;
   (ii) comprises at least one protein:protein or protein:DNA interacting domain in a region N-terminal of the SOCS box; and
   (iii) modulates signal transduction mediated by at least one cytokine selected from the group consisting of granulocyte colony stimulatory factor (G-CSF), interleukin 6 (IL-6) and leukemia inhibitory factor (LIF).

2. The isolated nucleic acid molecule of claim 1, wherein said SOCS box comprises the sequence as set forth in SEQ ID NO: 8.

3. An isolated nucleic acid molecule which encodes a protein, wherein said protein
   (i) comprises a SOCS box, wherein the SOCS box comprises an amino acid sequence having at least 70% identity to SEQ ID NO: 66;
   (ii) comprises at least one protein:protein or protein:DNA interacting domain in a region N-terminal of the SOCS box; and
   (iii) modulates signal transduction mediated by at least one cytokine selected from the group consisting of granulocyte colony stimulatory factor (G-CSF), interleukin 6 (IL-6) and leukemia inhibitory factor (LIF).

4. The isolated nucleic acid molecule of claim 3, wherein said SOCS box comprises the sequence as set forth in SEQ ID NO: 66.

5. A nucleic acid molecule according to claim 1 or 3 wherein the signal transduction is mediated by IL-6.

6. An isolated nucleic acid molecule encoding a protein which comprises the sequence as set forth in SEQ ID NO: 8.

* * * * *